(12) United States Patent
Buchwald et al.

(10) Patent No.: US 10,117,948 B2
(45) Date of Patent: Nov. 6, 2018

(54) SELECTIVE ARYLATION OF DICHALCOGENIDES IN BIOMOLECULES

(71) Applicant: Massachusetts Institute of Technology, Cambridge, MA (US)

(72) Inventors: Stephen L. Buchwald, Newton, MA (US); Bradley L. Pentelute, Cambridge, MA (US); Daniel T. Cohen, Brighton, MA (US); Chi Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/187,169

(22) Filed: Jun. 20, 2016

(65) Prior Publication Data

US 2016/0367693 A1 Dec. 22, 2016

Related U.S. Application Data

(60) Provisional application No. 62/182,146, filed on Jun. 19, 2015.

(51) Int. Cl.
  *A61K 38/14* (2006.01)
  *A61K 47/64* (2017.01)
  (Continued)

(52) U.S. Cl.
  CPC ........ *A61K 47/48246* (2013.01); *A61K 38/14* (2013.01); *A61K 47/64* (2017.08);
  (Continued)

(58) Field of Classification Search
  CPC ...... A61K 38/14; A61K 47/54; A61K 47/545; A61K 47/552; A61K 47/64; C07K 1/1075; C07K 1/1077; C07K 1/13; C07K 9/008
  See application file for complete search history.

(56) References Cited

U.S. PATENT DOCUMENTS

2014/0113871 A1 4/2014 Pentelute et al.

FOREIGN PATENT DOCUMENTS

| JP | 2004/277387 A | 10/2004 |
| WO | WO-2015/175941 A1 | 11/2015 |
| WO | WO-2016/011107 A2 | 1/2016 |

OTHER PUBLICATIONS

Leem et al. Purification and Characterization of N-beta-5-S-glutathionyl-3,4-dihydroxyphenylalanine, a Novel Antibacterial Substance . . . The Journal of Biological Chemistry. Jun. 7, 1996. vol. 271, No. 23, pp. 13573-13577.*

(Continued)

*Primary Examiner* — Jeffrey E. Russel
(74) *Attorney, Agent, or Firm* — Foley Hoag LLP

(57) ABSTRACT

Disclosed are chemical transformations for the conjugation of unprotected peptide biomolecules. The disclosed chemical transformations relate to methods of selective cysteine and selenocysteine functionalization of unprotected peptide and protein molecules. The processes feature several significant advantages over existing methods of peptide modification, including specificity towards selenocysteine over other nucleophiles (e.g., amines, hydroxyls), excellent functional group tolerance, and mild reaction conditions. Also disclosed are syntheses of arylated cysteine and arylated selenocysteine peptide compounds.

10 Claims, 35 Drawing Sheets
Specification includes a Sequence Listing.

(51) Int. Cl.
    C07K 1/113    (2006.01)
    C07K 9/00     (2006.01)
    A61K 47/48    (2006.01)
    C07K 1/107    (2006.01)
    C07K 1/13     (2006.01)
    C07K 14/47    (2006.01)
    A61K 47/68    (2017.01)

(52) U.S. Cl.
    CPC ........ *A61K 47/6851* (2017.08); *C07K 1/1075* (2013.01); *C07K 1/1077* (2013.01); *C07K 1/13* (2013.01); *C07K 9/008* (2013.01); *C07K 14/47* (2013.01)

(56) References Cited

OTHER PUBLICATIONS

Matsumoto et al. Design and synthesis of antifungal lactoferricin derivatives. Peptide Science—Present and Future. Proceedings of the International Peptide Symposium, 1$^{st}$. 1999, pp. 697-698.*
Cohen et al. An Umpolung Approach for the Chemoselective Arylation of Selenocysteine in Unprotected Peptides. Journal of the American Chemical Society. Jul. 30, 2015, vol. 137, pp. 9784-9787.*
Lam et al. Reduction of Benzoquinones to Hydroquinones via Spontaneous Reaction with Glutathione . . . Biochemistry. 2012, vol. 41, pp. 5014-5021.*
Mason et al. Characterization of Benzoquinone-Peptide Adducts by Electrospray Mass Spectrometry. Chemical Research in Toxicology. 2000, vol. 13, No. 10, pp. 976-982.*
Wrona et al. Oxidation of Serotonin by Superoxide Radical . . . Chemical Research in Toxicology. 1998, vol. 11, No. 6, pp. 639-650.*
Andreadou et al., "Comparative Cytotoxicity of 14 Novel Selenocysteine Se-conjugates in Rat Renal Proximal Tubular Cells," Toxicol Appl Pharm, 141(1): 278-287 (Aug. 1, 1996).
Andreadou et al., "Synthesis of Novel Se-Substituted Selenocysteine Derivatives as Potential Kidney Selective Prodrugs of Biologically Active Selenol Compounds: Evaluation of Kinetics of Beta-Elimination Reactions in Rat Renal Cytosol," J Med Chem, 39:2040-2046 (Jan. 1, 1996).
Barton et al., "Synthesis of Novel Alpha-Amino-Acids and Derivatives Using Radical Chemistry: Synthesis of L- and D-Alpha-Amino-Adipics Acids, L-Alpha-Aminopimelic Acid and Appropriate Unsaturated Derivatives," Tetrahedron, 43(19): 4297-4308 (Jan. 1, 1987).
Barton et al., "The Free Radical Chemistry of Carboxylic Esters of 2-selenopyridine-N-oxide: A Convenient Synthesis of (L)-vinylglycine," Tetrahedron, 41(19): 4347-4357 (Jan. 1, 1985).
Beletskaya et al., "Transition-Metal-Catalyzed C-S, C-Se, and C-Te Bond Formation via Cross-Coupling and Atom-Economic Addition Reactions," Chem Rev, 111(3): 1596-1636 (Mar. 9, 2011).
Braga et al., "Chiral Seleno-Amines from Indium Selenolates. A Straightforward Synthesis of Selenocysteine Derivatives," J Org Chem, 71(11): 4305-4307 (May 1, 2006).
Braga et al., "One-Pot Indium Iodide Mediated Synthesis of Chiral [beta]-Seleno Amides and Selenocysteine Derivatives by Ring-Opening Reaction of 2-Oxazolines," Eur J Org Chem, 2007(32): 5327-5331 (Nov. 1, 2007).
Flemer Jr. et al., "Fmoc-Sec(Xan)-OH: Synthesis and Utility of Fmoc Selenocysteine SPPS Derivatives with Acid-Labile Sidechain Protection," J Pept Sci, 21(1): 53-59 (Dec. 11, 2014).
Gordon et al., "Chemistry of Isoprenylated Cysteinyl Containing Peptides. [2,3]. Sigmatropic Rearrangement of S-farnesylcysteinyl sulfoxides. Studies Toward a Mild Method of Deprenylating Lipopeties," J Am Chem Soc, 114(4): 1521-1523 (Feb. 1, 1992).
Herradura et al., "Copper-Mediated Cross-Coupling of Aryl Boronic Acids and Alkyl Thiols," Org Lett, 2(14): 2019-2022 (Jul. 1, 2000).
Jungheim et al., "Potent Human Immunodeficiency Virus Type 1 Protease Inhibitors That Utilize Noncoded D-Amino Acids as P2/P3 Ligands," J Med Chem, 39(1): 96-108 (Jan. 1, 1996).
Kondo et al., "S → N and N → S Reverse Rearrangement of S- and N-(2,4-dinitrophenyl)cysteines," J Org Chem, 46(7): 1333-1336 (Mar. 1, 1981).
Krouzelka et al., "Preparation of Arylmercapturic Acids by S-Arylation of N, N'-Diacetylcystine," Eur J Org Chem, 2009(36): 6336-6340 (Dec. 1, 2009).
Mason et al., "Characterization of Benzoquinone-Peptide Adducts by Electrospray Mass Spectrometry," Chem Res Toxicol, 13(10): 976-982 (Oct. 1, 2000).
Moreau et al., "Palladium Catalyzed Thiol Cross-Coupling of Cystein Derivatives with Aryl and Alkenyl Halides," J Organomet Chem, 687(2): 322-326 (Dec. 7, 2003).
Munroe et al., "Potent, Orally Bioavailable HIV-1 Protease Inhibitors Containing Noncoded D-amino acids," Bioorg Med Chem Lett, 5(23): 2897-2902 (Dec. 7, 1995).
Narayanaperumal et al., "Transition Metal Oxide Nanopowder and Ionic Liquid: An Efficient System for the Synthesis of Diorganyl Selenides, Selenocysteine and Derivatives," J Brazil Chem Soc, 21(11): 2079-2087 (Jan. 1, 2010).
Obi et al., "Novel Nikkomycin Analogues: Inhibitors of the Fungal Cell Wall Biosynthesis Enzyme Chitin Synthase," Bioorg Med Chem Lett, 10(13): 1451-1454 (Jul. 3, 2000).
Okeley et al., "Facile Chemoselective Synthesis of Dehydroalanine-containing Peptides," Org Lett, 2(23): 3603-3606 (Nov. 16, 2000).
Phadnis et al., "Internally Stabilized Selenocysteine Derivatives: Syntheses, 77Se NMR and Biomimetic Studies," Org Biomol Chem, 3(13): 2476-2481 (Jan. 1, 2005).
Schwab et al., "Straightforward Synthesis of Non-Natural Chalcogen Peptides Via Ring Opening of Aziridines," Tetrahedron, 68(51): 10449-10455 (Dec. 1, 2012).
Tamamura et al., "Reduction of Peptide Character of HIV Protease Inhibitor That Exhibit Nanomolar Potency Against Multidrug Resistant HIV-1 Strains," J Med Chem, 46(9): 1764-1768 (Apr. 1, 2003).
International Preliminary Report on Patentability in Application No. PCT/US2016/038372 dated Dec. 28, 2017.
International Search Report and Written Opinion for International Application No. PCT/US17/20438 dated Aug. 28, 2017.
Vinogradova et al., "Organometallic palladium reagents for cysteine bioconjugation," Nature, 526(7575): 687-691 (2015).

* cited by examiner

Figure 1
*Previous work:* Bioconjugation of Cysteine and Selenocysteine
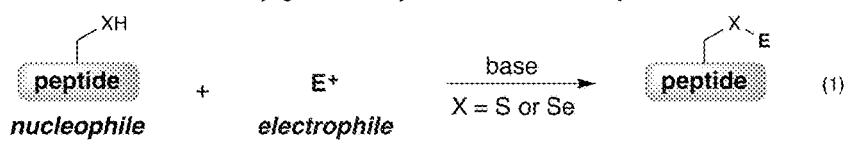
*This work:* Umpolung Bioconjugation of Selenocysteine
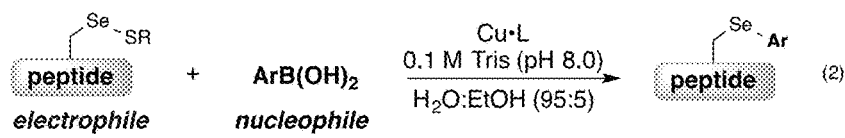
*Proposed Reaction Pathway*
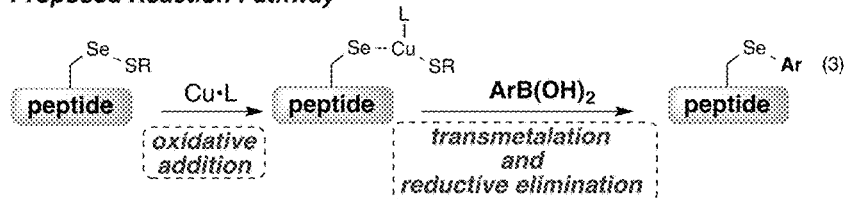

FIG. 3C
Biorelevant
L-phenylalanine
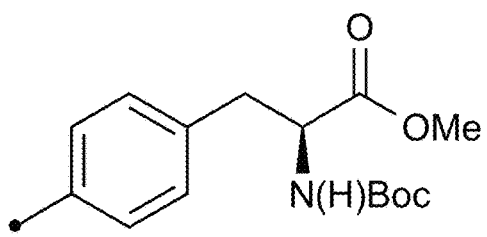
6a[d]
85% yield
coumarin
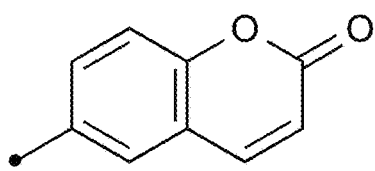
6b[d]
74% yield
tolfenamic ester
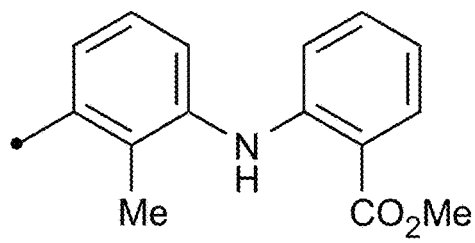
6c
57% yield
paracetamol
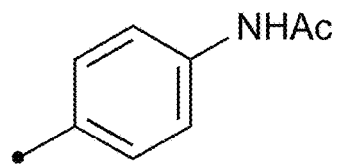
6d[d]
86% yield
estrone
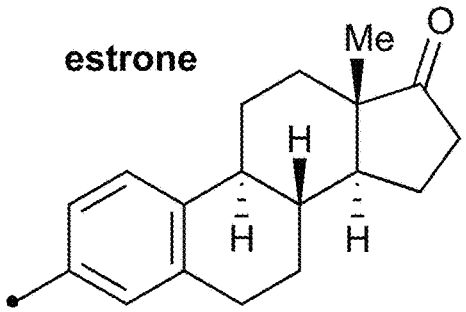
6e[e]
43% yield

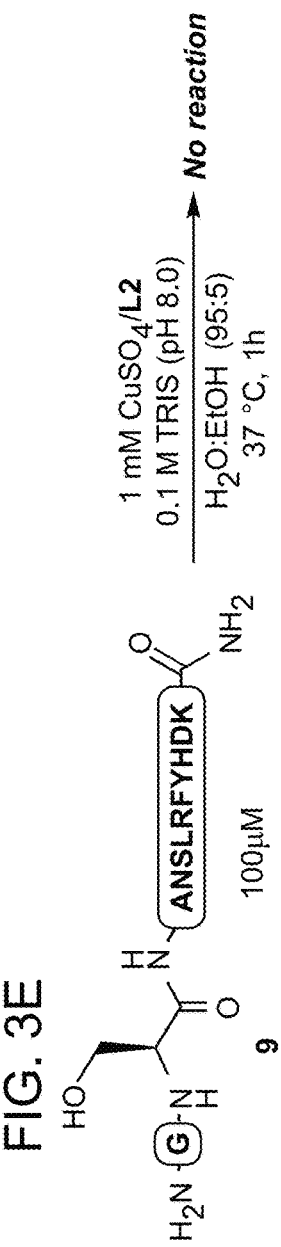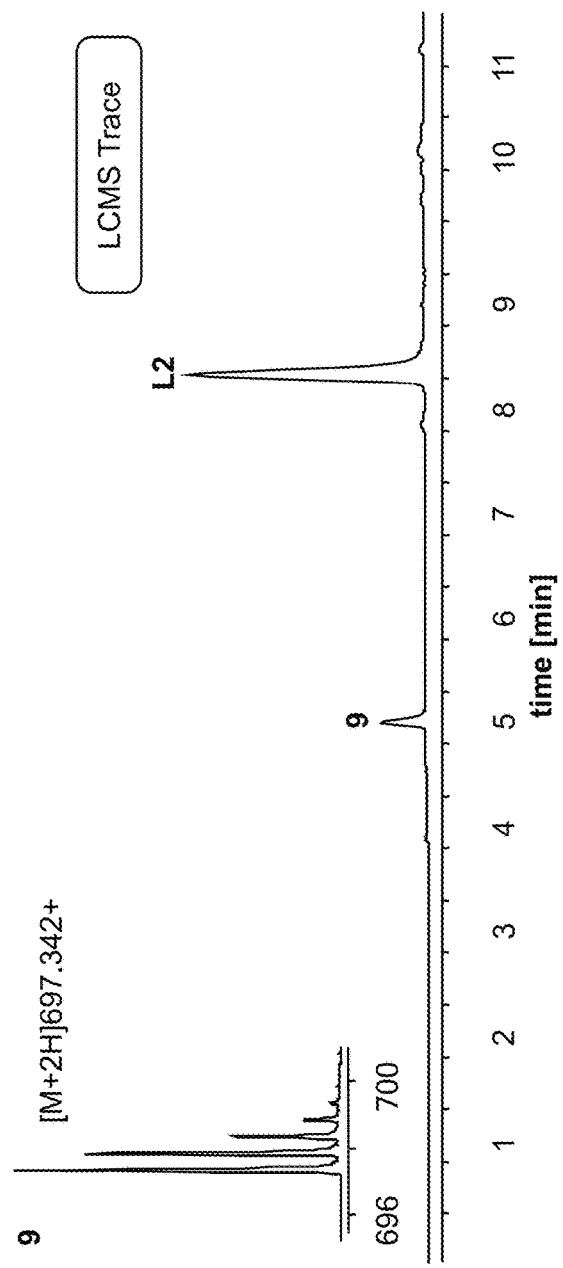
FIG. 3E

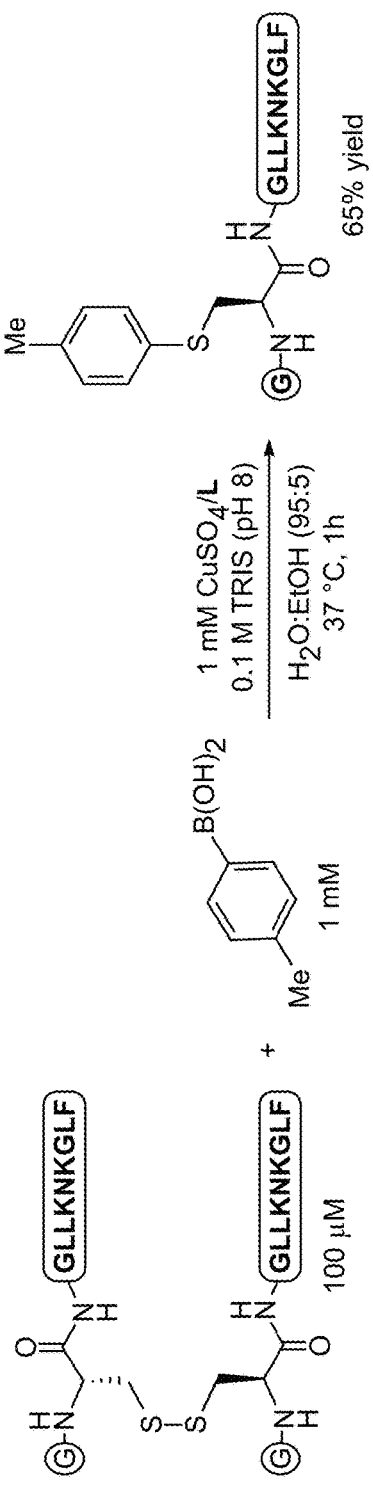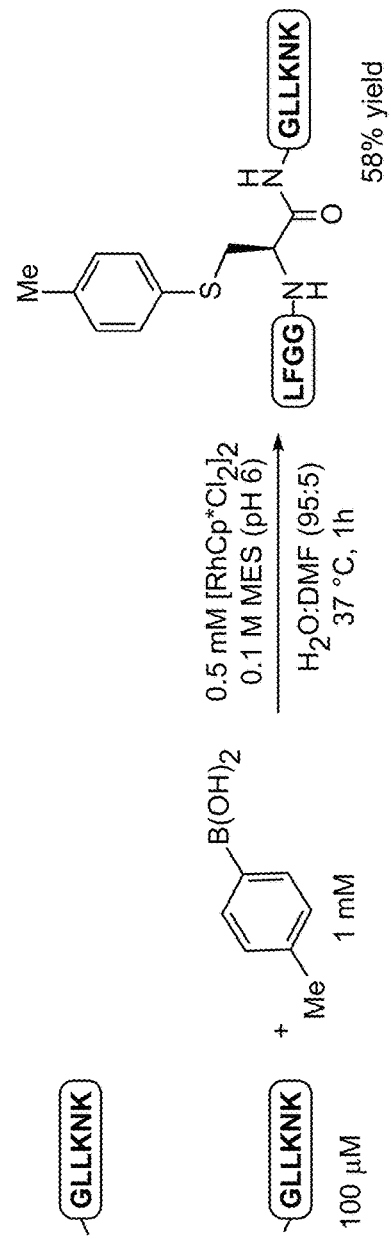
FIG. 17

Figure 21

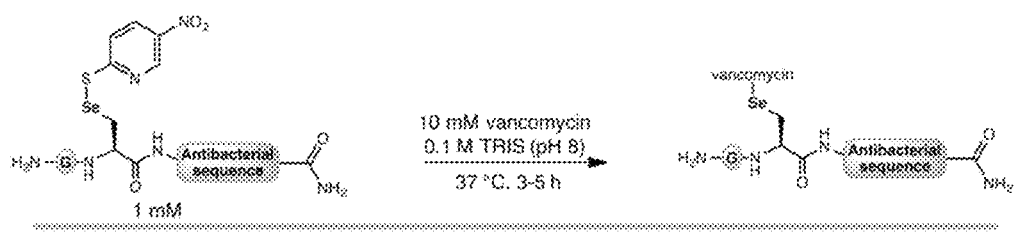

| Sample Name | Sequence | Name |
|---|---|---|
| DTC-09-167 | GUANSLRFYHDK (SEQ ID NO: 7) | None available |
| DTC-09-190 | LAGGUGLLKNK (SEQ ID NO: 15) | None available |
| DTC-09-235 | GUFRIRVRV (SEQ ID NO: 16) | Designated 1037 |
| DTC-09-255 | GUGNNRPVYIPQPRPPHPRL (SEQ ID NO: 17) | Apidaecin |
| DTC-09-256 | GURAGLQFPVGRVHRLLRK (SEQ ID NO: 18) | Buforin 2 (5-21) |
| DTC-09-262 | GUGIGKFLKKAKKFGKAFVKLLKK (SEQ ID NO: 19) | Pexiganin |
| DTC-09-263 | GUGWGSFFKKAAHVGKHVGKAALTHYL (SEQ ID NO: 20) | Pleurocidin |
| DTC-09-264 | GUALWKTLLKKVLKA (SEQ ID NO: 21) | K4-S4(1-13a) Dermaseptin |
| DTC-09-271 | GUGIKKFLKKAGKFGKAF (SEQ ID NO: 22) | Maginin II |
| DTC-09-272 | GUVDKPPYLPRPRPPPRRIYNR (SEQ ID NO: 23) | Oncocin |
| DTC-09-282 | GUV-Orn-L-DPhe-P-V-Orn-L-DPhe-P | Gramicidin S |
| DTC-09-283 | GUALYKKFKKKLLKSLKRLG (SEQ ID NO: 24) | Kinocidins Conger Peptide RP-1 |

*Model Peptide*

*HIV-1 capsid*

*Tyrosine/Histidine control*

Phallotoxins

Amatoxins

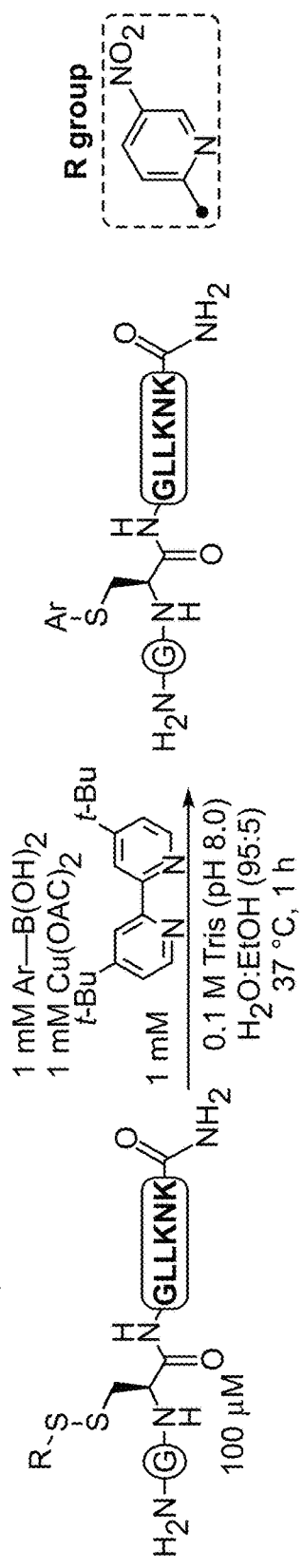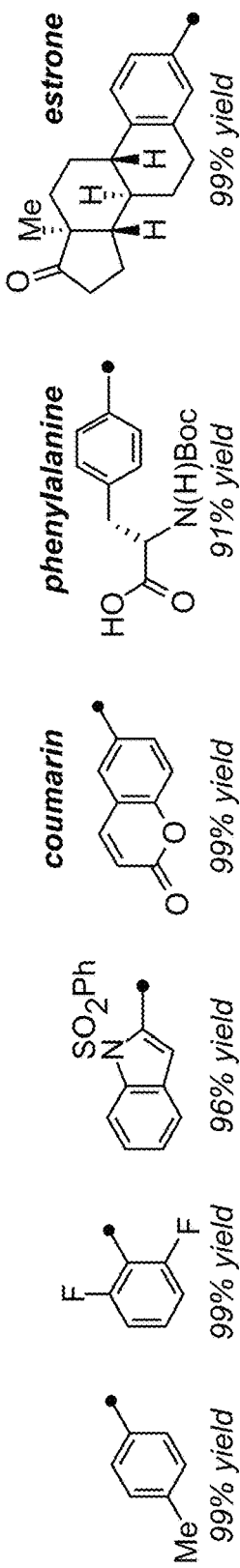
FIG. 32A

FIG. 32B
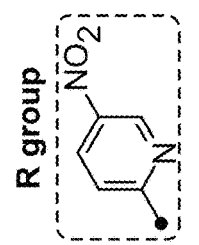
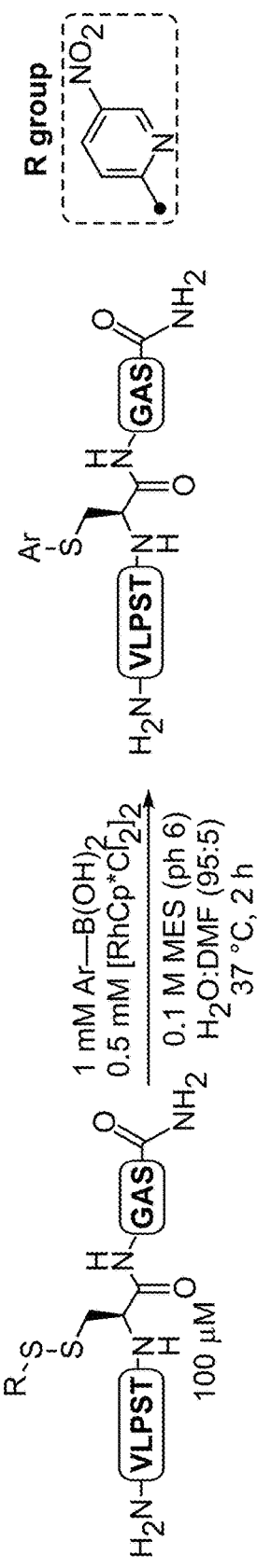
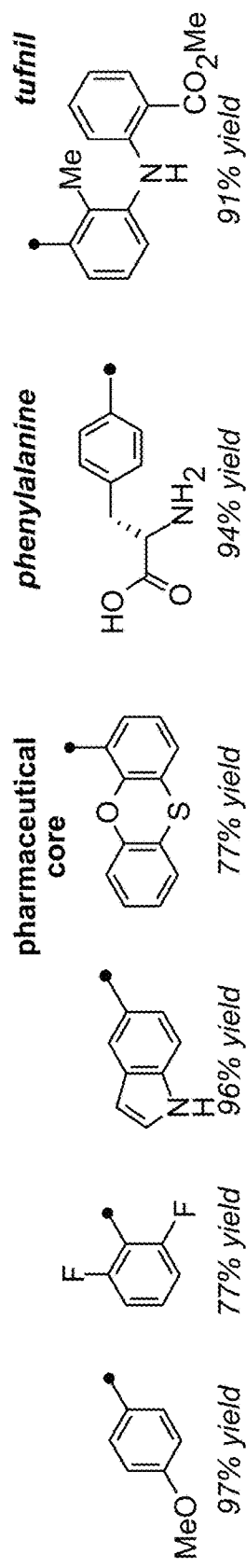

SEQUENCE LISTING

<160> NUMBER OF SEQ ID NOS: 41

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ile Lys Lys Phe Leu Lys Lys Ala Gly Lys Phe Gly Lys Ala Phe
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Selenocysteine

<400> SEQUENCE: 3

Leu Phe Gly Gly Xaa Gly Leu Leu Lys Asn Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Phe Gly Gly Ser Gly Leu Leu Lys Asn Lys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Phe Gly Gly Cys Gly Leu Leu Lys Asn Lys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Phe Gly Gly Met Gly Leu Leu Lys Asn Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 7

Gly Xaa Ala Asn Ser Leu Arg Phe Tyr His Asp Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Ala Asn Ser Leu Arg Phe Tyr His Asp Lys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Dehydroalanine

<400> SEQUENCE: 9

Leu Phe Gly Gly Ala Gly Leu Leu Lys Asn Lys
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Cys Gly Leu Leu Lys Asn Lys
1               5

```
<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Leu Pro Ser Thr Cys Gly Ala Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 12

Gly Xaa Gly Leu Leu Lys Asn Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Selenocysteine

<400> SEQUENCE: 13

Val Leu Pro Ser Thr Xaa Gly Ala Ser
1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Cys Gly Leu Leu Lys Asn Lys Gly Leu Phe
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Selenocysteine

<400> SEQUENCE: 15

Leu Ala Gly Gly Xaa Gly Leu Leu Lys Asn Lys
```

-continued

```
<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 16

Gly Xaa Phe Arg Ile Arg Val Arg Val
1               5

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 17

Gly Xaa Gly Asn Asn Arg Pro Val Tyr Ile Pro Gln Pro Arg Pro Pro
1               5                   10                  15

His Pro Arg Leu
            20

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 18

Gly Xaa Arg Ala Gly Leu Gln Phe Pro Val Gly Arg Val His Arg Leu
1               5                   10                  15

Leu Arg Lys

<210> SEQ ID NO 19
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 19

Gly Xaa Gly Ile Gly Lys Phe Leu Lys Lys Ala Lys Lys Phe Gly Lys
1               5                   10                  15
```

```
Ala Phe Val Lys Leu Leu Lys Lys
            20

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 20

Gly Xaa Gly Trp Gly Ser Phe Phe Lys Lys Ala Ala His Val Gly Lys
1               5                   10                  15

His Val Gly Lys Ala Ala Leu Thr His Tyr Leu
            20                  25

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 21

Gly Xaa Ala Leu Trp Lys Thr Leu Leu Lys Lys Val Leu Lys Ala
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 22

Gly Xaa Gly Ile Lys Lys Phe Leu Lys Lys Ala Gly Lys Phe Gly Lys
1               5                   10                  15

Ala Phe

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 23

Gly Xaa Val Asp Lys Pro Pro Tyr Leu Pro Arg Pro Arg Pro Pro Pro
1               5                   10                  15
```

Arg Arg Ile Tyr Asn Arg
            20

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 24

Gly Xaa Ala Leu Tyr Lys Lys Phe Lys Lys Leu Leu Lys Ser Leu
1               5                   10                  15

Lys Arg Leu Gly
            20

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Selenocysteine

<400> SEQUENCE: 25

Gly Gly Gly Gly Gly Lys Phe Leu Xaa Gly
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Pro Ser Thr Gly Gly
1               5

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Selenocysteine

<400> SEQUENCE: 27

Leu Pro Ser Thr Gly Gly Gly Gly Gly Lys Phe Leu Xaa Gly
1               5                   10

<210> SEQ ID NO 28
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Selenocysteine

<400> SEQUENCE: 28

Gly Gly Gly Gly Gly Lys Phe Leu Xaa Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Selenocysteine

<400> SEQUENCE: 29

Gly Xaa Gly Gly Gly Trp Leu Leu Lys Asn Lys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Selenocysteine

<400> SEQUENCE: 30

Ile Thr Phe Xaa Asp Leu Leu Trp Tyr Tyr Gly Lys Lys Lys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ile Thr Phe Cys Asp Leu Leu Trp Tyr Tyr Gly Lys Lys Lys
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Gly Cys Gly Leu Leu Lys Asn Lys
1               5
```

-continued

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Cys Gly Leu Leu Lys Asn Lys Gly Leu Phe
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Cys Gly Leu Leu Lys Asn Ala Gly Leu Phe
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Cys Gly Leu Leu Lys Ala Lys Gly Leu Phe
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Cys Gly Leu Leu Ala Asn Lys Gly Leu Phe
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Cys Gly Leu Leu Ala Ala Ala Gly Leu Phe
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Cys Gly Leu Leu Lys Asn Lys Gly Leu Phe
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Leu Gly Lys Asn Lys Leu Leu Gly Cys Gly
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Gly Cys Gly Leu Leu Lys Asn Lys Gly Leu Phe
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Ala Gly Cys Gly Leu Leu Lys Asn Lys Gly Leu Phe
1               5                   10
```

SELECTIVE ARYLATION OF DICHALCOGENIDES IN BIOMOLECULES

RELATED APPLICATIONS

This application claims the benefit of priority to U.S. Provisional Patent Application Ser. No. 62/182,146, filed Jun. 19, 2015, the contents of which are hereby incorporated by reference.

GOVERNMENT SUPPORT

This invention was made with Government support under Grant Nos. GM046059 and GM110535 awarded by the National Institutes of Health. The government has rights in this invention.

SEQUENCE LISTING

The instant application contains a Sequence Listing which has been submitted electronically in ASCII format and is hereby incorporated by reference in its entirety. Said ASCII copy, created on Aug. 9, 2016, is named MTV-154_01_SL.txt and is 12,287 bytes in size.

BACKGROUND

Peptide-based technologies have facilitated the elucidation of disease mechanisms and serve as novel and effective therapeutics. An emerging theme in biotechnology is to use peptide variants to disrupt protein-protein interactions because compared to small molecules they have a larger surface area for binding, can recognize targets with higher specificity/affinity, and can be generated in weeks by phage display. For this and other reasons, for many years researchers in the field of bioconjugate chemistry have needed well-defined ligation strategies that can be used for the at-will modification of biomolecules. Efficient bioconjugation strategies generally involve high levels of functional group tolerance, compatibility with water and other solvents, and efficient conversions (e.g., fast reaction times and high yields).

Selenocysteine (Sec or U), discovered by Stadtman in 1974, is the 21$^{st}$ proteinogenic amino acid. Selenocysteine is a structural analogue to cysteine with a selenol in place of the thiol. There are several other notable differences between cysteine and selenocysteine. The greater acidity of selenocysteine (pKa=5.47) versus cysteine (pK$_a$=8.14) causes it to be deprotonated under physiological pH and its lower reduction potential makes it an integral part of antioxidant proteins. Selenocysteine is essential for enzymatic activity in enzymes including glutathione peroxidases, iodothyronine deiodinases, formate dehydrogenases, and methionine-R-sulfoxide reductase. Mutation of the catalytic selenocysteine to cysteine in the aforementioned enzymes results in a decrease in activity of >100 fold.

The inherent nucleophilicity of selenols makes selenocysteine an appealing handle for chemoselective bioconjugation in peptides and proteins. Nevertheless, reports on bioconjugation with this amino acid have been sparse due to several challenges associated with its functionalization. Namely, a selenol is easily oxidized to the diselenide or seleninic acid. In addition, because selenium is highly polarizable, it can be eliminated to generate dehydroalanine. Reports of selenocysteine functionalization have paralleled methods to modify cysteine and relied upon alkylation and maleimide conjugate addition with the selenol group (FIG. 1, Panel (1)). In contrast to common cysteine conjugation methods, a reducing agent [i.e., tris(2-carboxyethyl)phosphine (TCEP)] and exclusion of oxygen are needed to generate the selenol in situ prior to reaction with the electrophile.

There exists a need for development of a direct, robust, and selective method for the functionalization of selenocysteine that overcomes these limitations and allow for site-selective modification of unprotected peptides.

SUMMARY

In certain embodiments, the invention relates to a compound comprising substructure I:

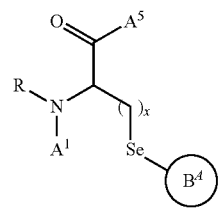

wherein, independently for each occurrence,

A$^1$ is H, an amine protecting group, a natural or unnatural amino acid, a peptide, an oligopeptide, a polypeptide, or a protein;

A$^5$ is OH, —O(carboxylate protecting group), a natural or unnatural amino acid, a peptide, an oligopeptide, a polypeptide, or a protein;

is a substituted or unsubstituted aryl or heteroaryl radical;
x is 0, 1, 2, 3, 4, 5, or 6; and
R is H or alkyl.

In certain embodiments, the invention relates to a compound comprising substructure II:

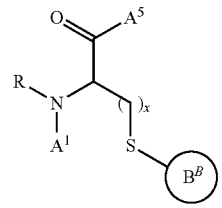

wherein, independently for each occurrence,

A$^1$ is H, an amine protecting group, a natural or unnatural amino acid, a peptide, an oligopeptide, a polypeptide, or a protein;

A$^5$ is OH, —O(carboxylate protecting group), a natural or unnatural amino acid, a peptide, an oligopeptide, a polypeptide, or a protein;

is a substituted or unsubstituted aryl or heteroaryl radical, provided

is not a perfluoroaryl radical;
x is 0, 1, 2, 3, 4, 5, or 6; and
R is H or alkyl.

In certain embodiments, the invention relates to a compound comprising substructure III:

III wherein, independently for each occurrence,
$A^1$ is H, an amine protecting group, a natural or unnatural amino acid, a peptide, an oligopeptide, a polypeptide, or a protein;
$A^2$, $A^3$, and $A^4$ are selected from the group consisting of a natural amino acid, an unnatural amino acid, and a plurality of natural amino acids or unnatural amino acids;
$A^5$ is OH, —O(carboxylate protecting group), a natural or unnatural amino acid, a peptide, an oligopeptide, a polypeptide, or a protein;
x is 0, 1, 2, 3, 4, 5, or 6;

is a substituted or unsubstituted aryl or heteroaryl diradical; and
R is H or alkyl.

In certain embodiments, the invention relates to a compound comprising substructure IV:

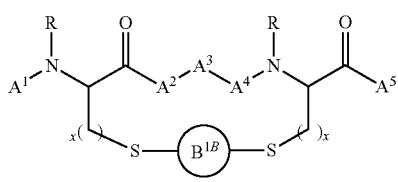

IV wherein, independently for each occurrence,
$A^1$ is H, an amine protecting group, a natural or unnatural amino acid, a peptide, an oligopeptide, a polypeptide, or a protein;
$A^2$, $A^3$, and $A^4$ are selected from the group consisting of a natural amino acid, an unnatural amino acid, and a plurality of natural amino acids or unnatural amino acids;
$A^5$ is OH, —O(carboxylate protecting group), a natural or unnatural amino acid, a peptide, an oligopeptide, a polypeptide, or a protein;
x is 0, 1, 2, 3, 4, 5, or 6;

is a substituted or unsubstituted aryl or heteroaryl diradical, provided

is not a perfluoroaryl diradical; and
R is H or alkyl.

In certain embodiments, the invention relates to a compound comprising substructure V or substructure VII:

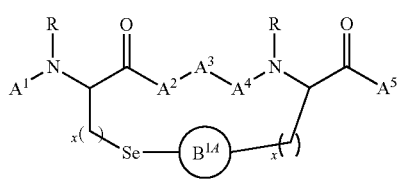

V

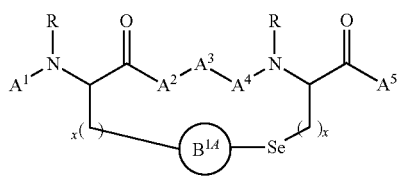

VII wherein, independently for each occurrence,
$A^1$ is H, an amine protecting group, a natural or unnatural amino acid, a peptide, an oligopeptide, a polypeptide, or a protein;
$A^2$, $A^3$, and $A^4$ are selected from the group consisting of a natural amino acid, an unnatural amino acid, and a plurality of natural amino acids or unnatural amino acids;
$A^5$ is OH, —O(carboxylate protecting group), a natural or unnatural amino acid, a peptide, an oligopeptide, a polypeptide, or a protein;
x is 0, 1, 2, 3, 4, 5, or 6;

is a substituted or unsubstituted aryl or heteroaryl diradical; and R is H or alkyl.

In certain embodiments, the invention relates to a compound comprising substructure VI or substructure VIII:

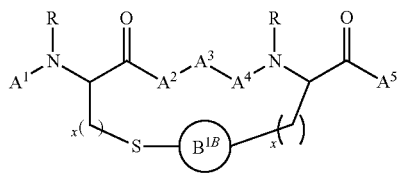

VI

-continued

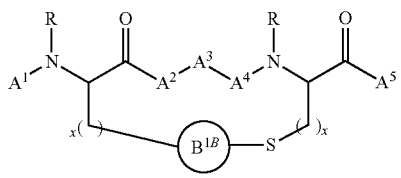
VIII wherein, independently for each occurrence,

A$^1$ is H, an amine protecting group, a natural or unnatural amino acid, a peptide, an oligopeptide, a polypeptide, or a protein;

A$^2$, A$^3$, and A$^4$ are selected from the group consisting of a natural amino acid, an unnatural amino acid, and a plurality of natural amino acids or unnatural amino acids;

A$^5$ is OH, —O(carboxylate protecting group), a natural or unnatural amino acid, a peptide, an oligopeptide, a polypeptide, or a protein;

x is 0, 1, 2, 3, 4, 5, or 6;

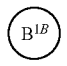

is a substituted or unsubstituted aryl or heteroaryl diradical, provided

is not a perfluoroaryl diradical; and

R is H or alkyl.

In certain embodiments, the invention relates to a hybrid composition, wherein the hybrid composition comprises a linker, any one of the aforementioned compounds, and a detectable moiety; and the linker links the compound to the detectable moiety.

In certain embodiments, the invention relates to a hybrid composition, wherein the hybrid composition comprises a linker, any one of the aforementioned compounds, and a biomolecule; and the linker links the compound to the biomolecule.

In certain embodiments, the invention relates to a peptide, an oligopeptide, a polypeptide, or a protein, wherein the peptide, oligopeptides, polypeptide, or protein comprises substructure I, substructure II, substructure III, substructure IV, substructure V, substructure VI, substructure VII, or substructure VIII.

In certain embodiments, the invention relates to an affibody comprising substructure I, substructure II, substructure III, substructure IV, substructure V, substructure VI, substructure VII, or substructure VIII.

In certain embodiments, the invention relates to a method according to Scheme 1:

Scheme 1a

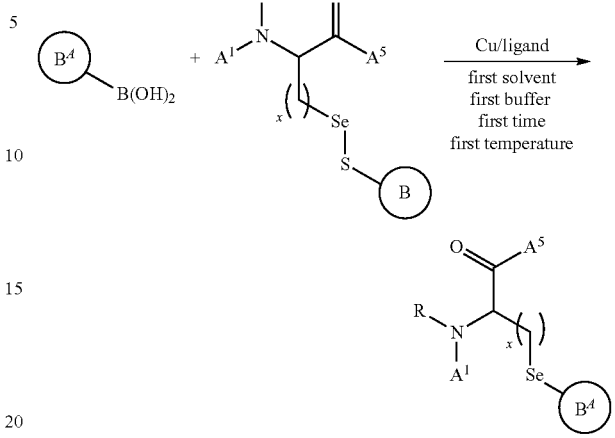

Scheme 1b

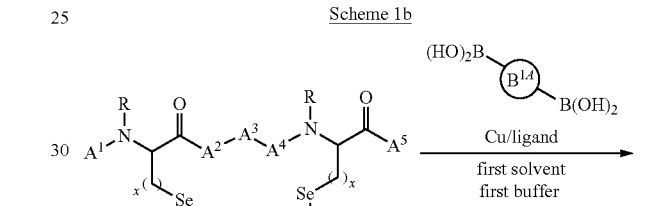

Scheme 1c

Scheme 1d

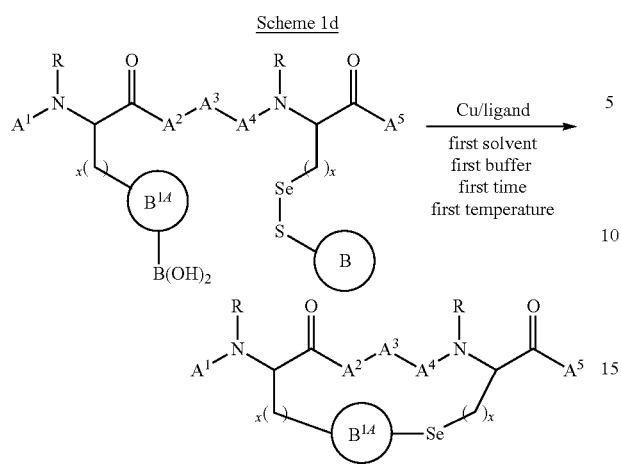

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

($B^A$)

is a substituted or unsubstituted aryl or heteroaryl radical;

($B^{1A}$)

is a substituted or unsubstituted aryl or heteroaryl diradical (B)

is a heteroaromatic moiety substituted with an electron withdrawing group;

x is 0, 1, 2, 3, 4, 5, or 6; and

R is H or alkyl.

In certain embodiments, the invention relates to a method according to Scheme 2:

Scheme 2a

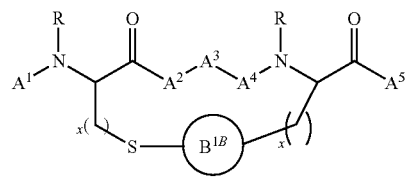

-continued

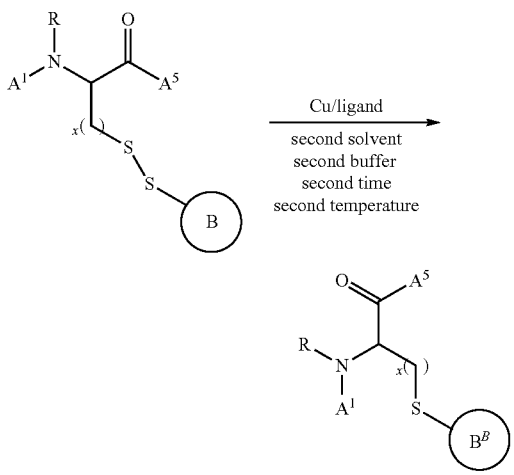

Scheme 2b

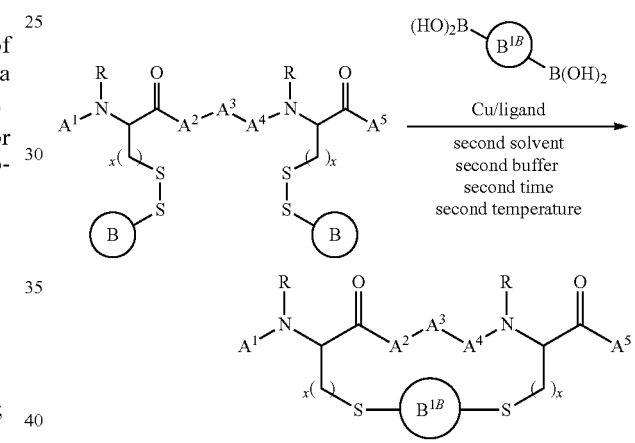

Scheme 2c

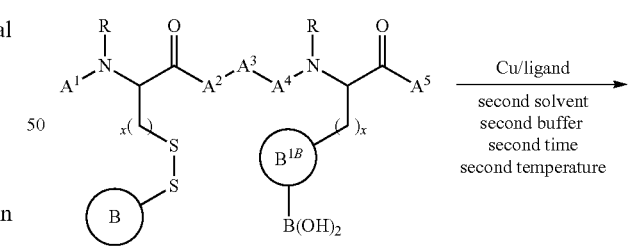

Scheme 2d

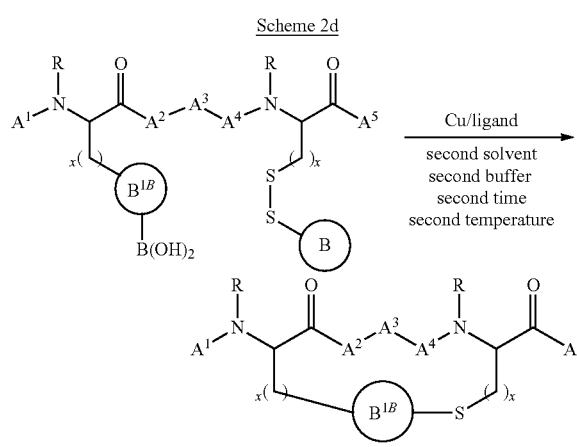

wherein, independently for each occurrence,

A¹ is H, an amine protecting group, a natural or unnatural amino acid, a peptide, an oligopeptide, a polypeptide, or a protein;

A², A³, and A⁴ are selected from the group consisting of a natural amino acid, an unnatural amino acid, and a plurality of natural amino acids or unnatural amino acids;

A⁵ is OH, —O(carboxylate protecting group), a natural or unnatural amino acid, a peptide, an oligopeptide, a polypeptide, or a protein;

x is 0, 1, 2, 3, 4, 5, or 6;

is a substituted or unsubstituted aryl or heteroaryl radical, provided

is not a perfluoroaryl radical;

is a substituted or unsubstituted aryl or heteroaryl diradical, provided

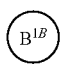

is not a perfluoroaryl radical;

is a heteroaromatic moiety substituted with an electron withdrawing group;

x is 0, 1, 2, 3, 4, 5, or 6; and

R is H or alkyl.

In certain embodiments, the invention relates to a method according to Scheme 3:

Scheme 3a

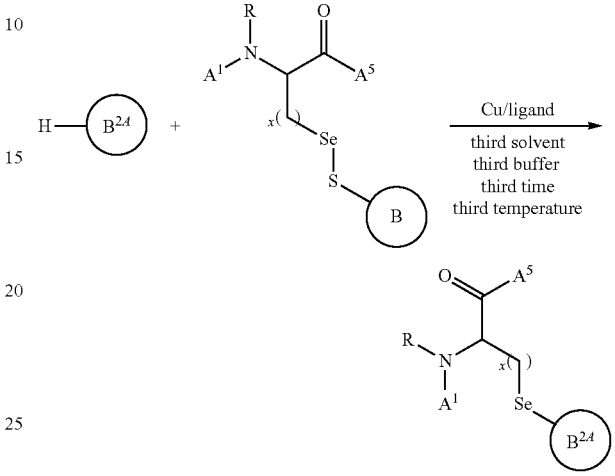

Scheme 3b

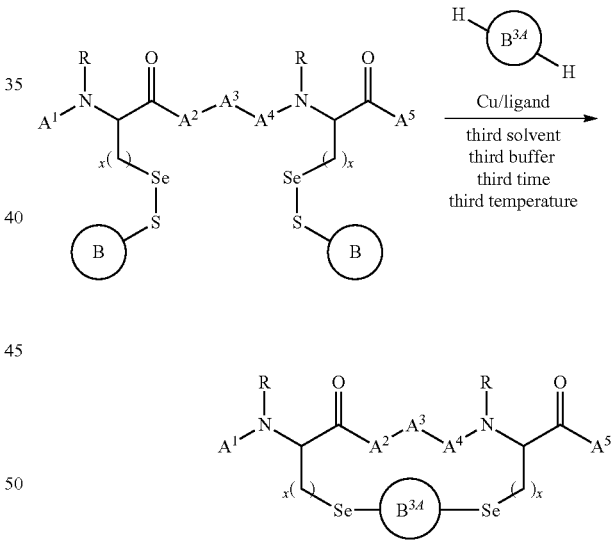

Scheme 3c

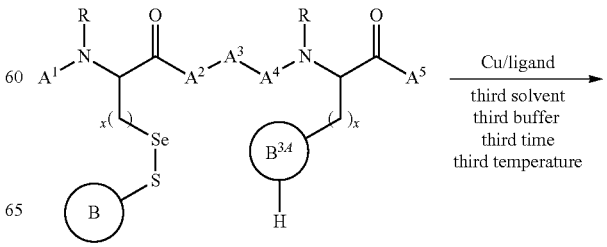

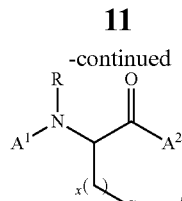

Scheme 3d

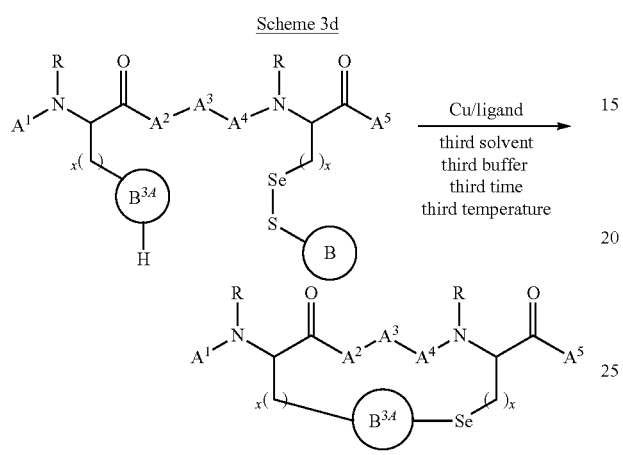

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is an aryl or heteroaryl radical substituted with at least one electron donating group;

is a substituted aryl or heteroaryl diradical substituted with at least one electron donating group;

is a heteroaromatic moiety substituted with an electron withdrawing group;

x is 0, 1, 2, 3, 4, 5, or 6; and

R is H or alkyl.

In certain embodiments, the invention relates to a method according to Scheme 4:

Scheme 4a

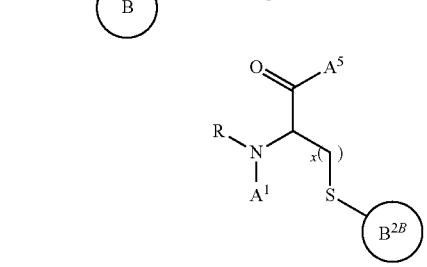

Scheme 4b

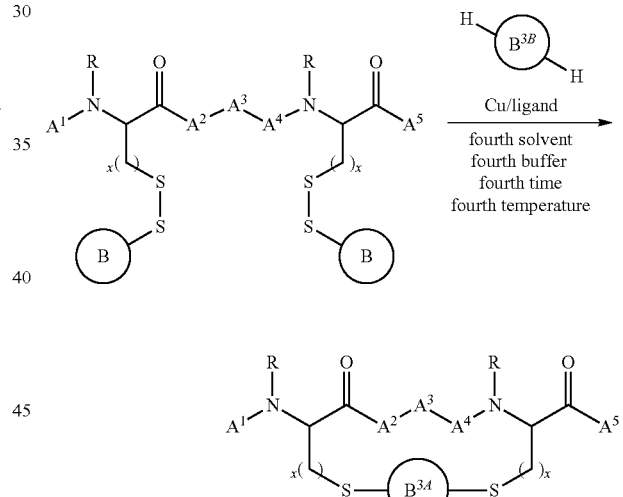

Scheme 4c

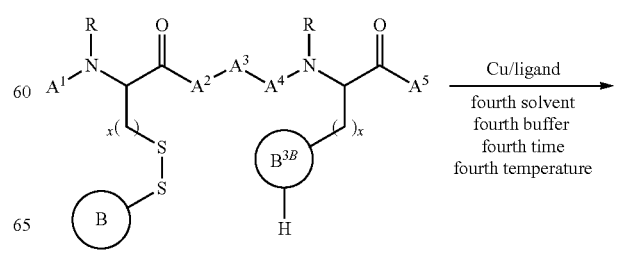

-continued

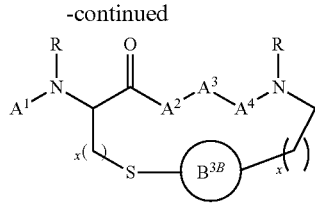

Scheme 4d

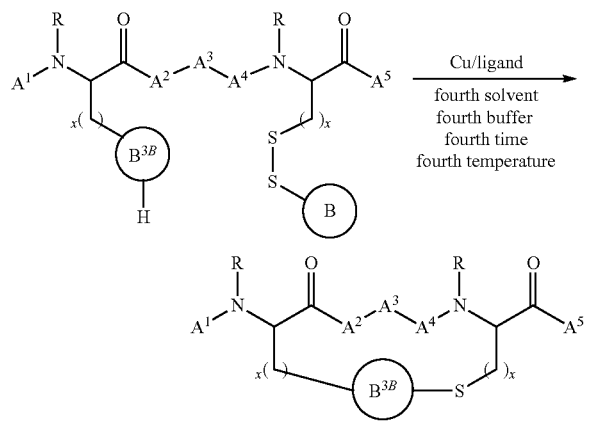

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is an aryl or heteroaryl radical substituted with at least one electron donating group, provided

is not a perfluoroaryl radical;

is an aryl or heteroaryl diradical substituted with at least one electron donating group, provided

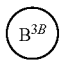

is not a perfluoroaryl radical;

is a heteroaromatic moiety substituted with an electron withdrawing group;

x is 0, 1, 2, 3, 4, 5, or 6; and

R is H or alkyl.

In certain embodiments, the invention relates to a method according to Scheme 5:

Scheme 5a

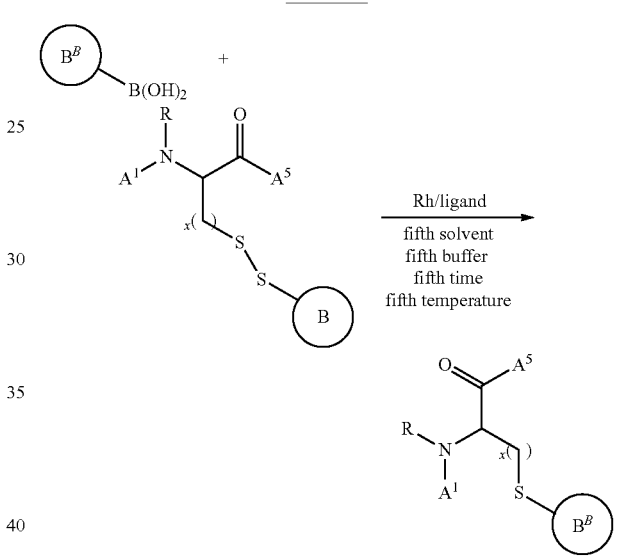

Scheme 5b

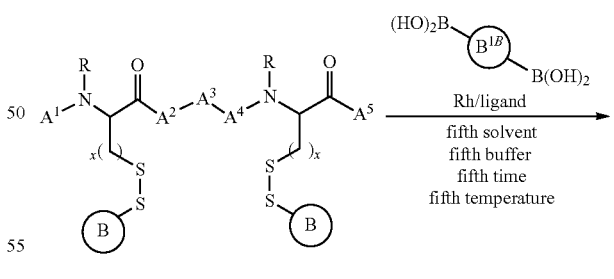

Scheme 5c

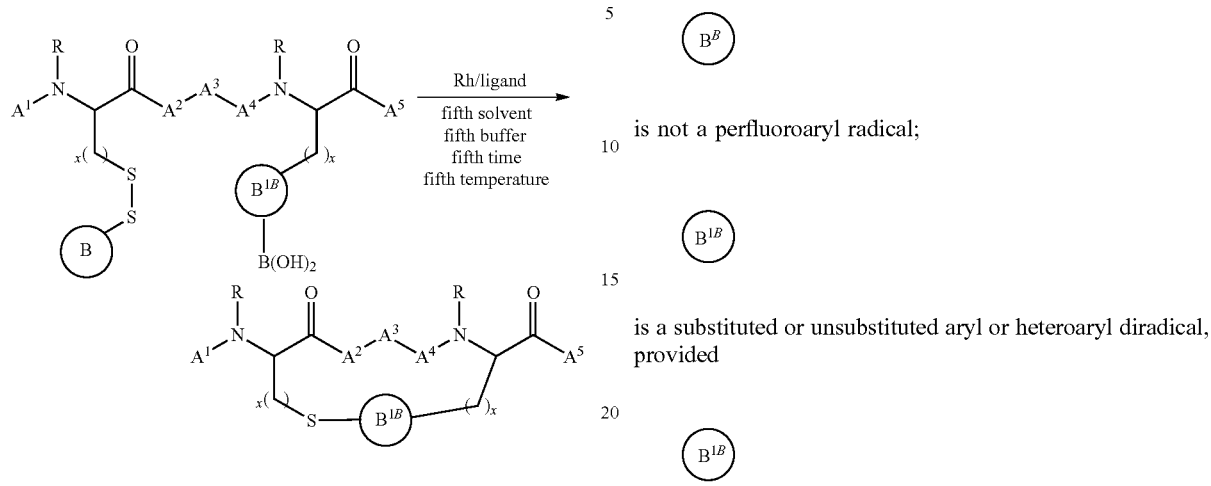

Scheme 5d

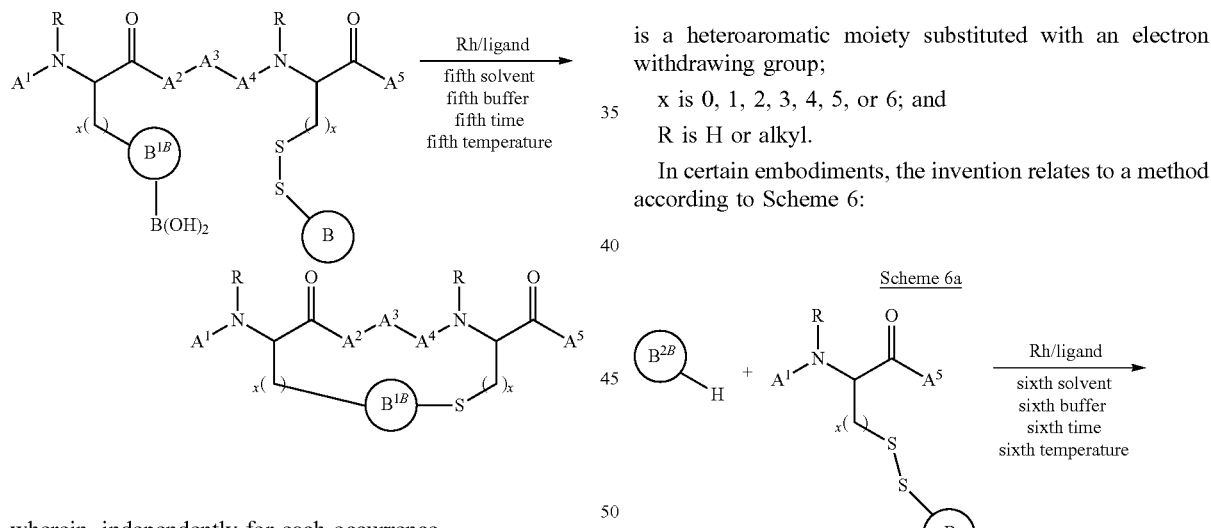

wherein, independently for each occurrence,
$A^1$ is H, an amine protecting group, a natural or unnatural amino acid, a peptide, an oligopeptide, a polypeptide, or a protein;
$A^2$, $A^3$, and $A^4$ are selected from the group consisting of a natural amino acid, an unnatural amino acid, and a plurality of natural amino acids or unnatural amino acids;
$A^5$ is OH, —O(carboxylate protecting group), a natural or unnatural amino acid, a peptide, an oligopeptide, a polypeptide, or a protein;
x is 0, 1, 2, 3, 4, 5, or 6;

$B^B$ is a substituted or unsubstituted aryl or heteroaryl radical, provided $B^B$ is not a perfluoroaryl radical;

$B^{1B}$ is a substituted or unsubstituted aryl or heteroaryl diradical, provided $B^{1B}$ is not a perfluoroaryl radical;

$B$ is a heteroaromatic moiety substituted with an electron withdrawing group;
x is 0, 1, 2, 3, 4, 5, or 6; and
R is H or alkyl.

In certain embodiments, the invention relates to a method according to Scheme 6:

Scheme 6a

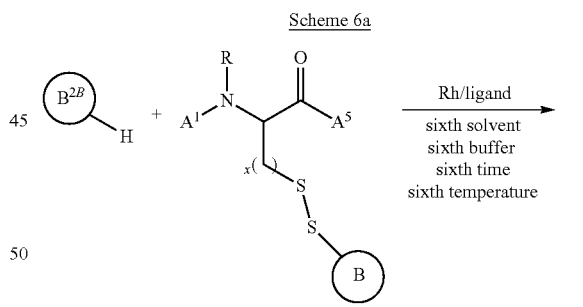

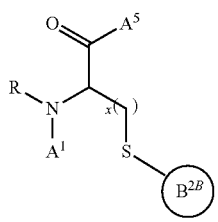

Scheme 6b

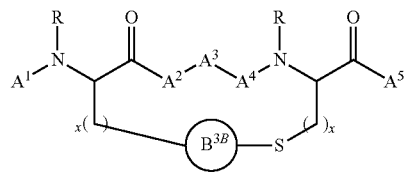
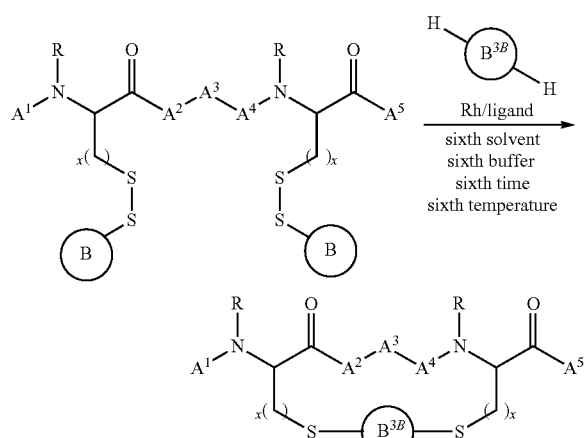

Scheme 6c

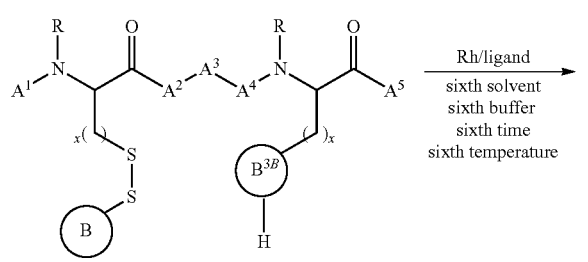

Scheme 6d

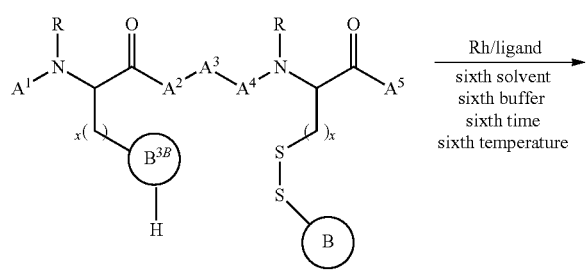

-continued wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

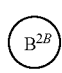

is an aryl or heteroaryl radical substituted with at least one electron donating group, provided

is not a perfluoroaryl radical;

is an aryl or heteroaryl diradical substituted with at least one electron donating group, provided

is not a perfluoroaryl radical;

is a heteroaromatic moiety substituted with an electron withdrawing group;

x is 0, 1, 2, 3, 4, 5, or 6; and

R is H or alkyl.

In certain embodiments, the invention relates to a method according to Scheme 7:

Scheme 7a

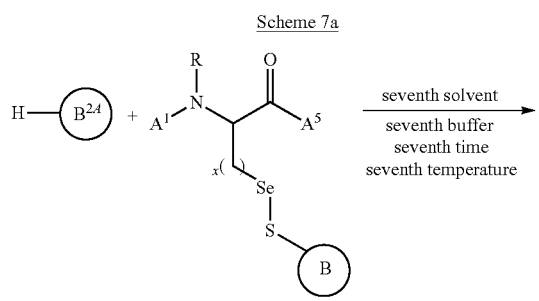

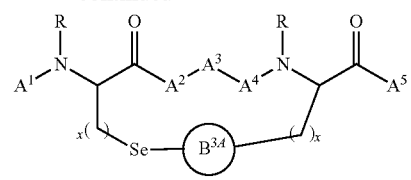

Scheme 7b

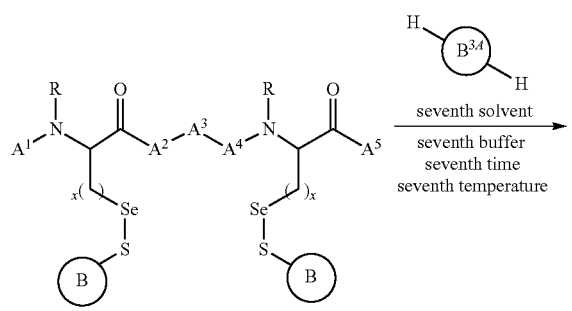

Scheme 7c

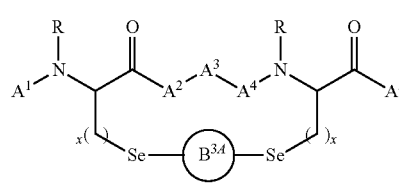

-continued

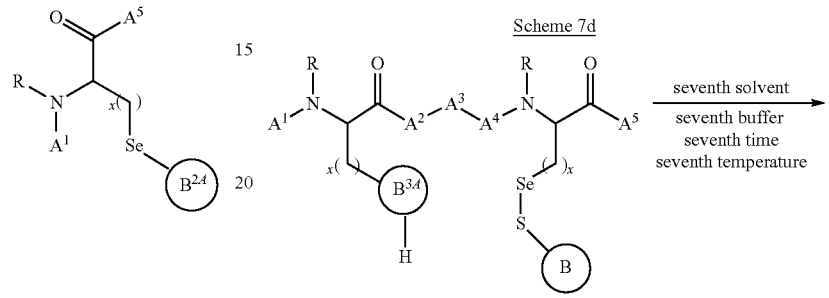

Scheme 7d

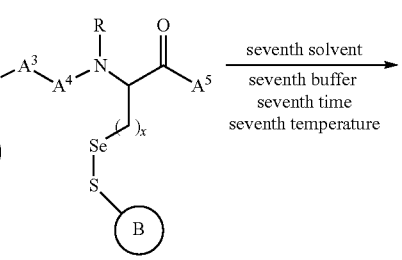

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

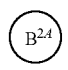

is an aryl or heteroaryl radical substituted with at least one electron donating group;

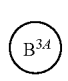

is a substituted aryl or heteroaryl diradical substituted with at least one electron donating group;

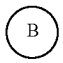

is a heteroaromatic moiety substituted with an electron withdrawing group;

x is 0, 1, 2, 3, 4, 5, or 6; and

R is H or alkyl.

In certain embodiments, the invention relates to a method according to Scheme 8:

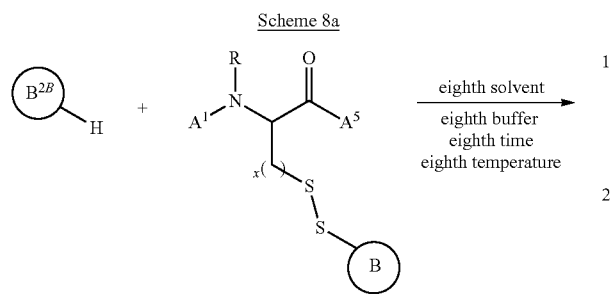

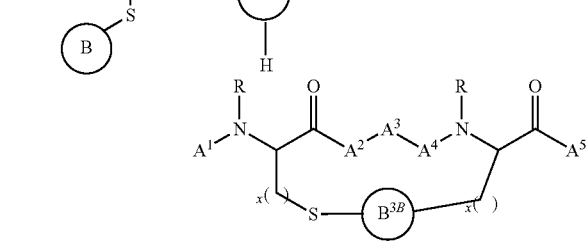

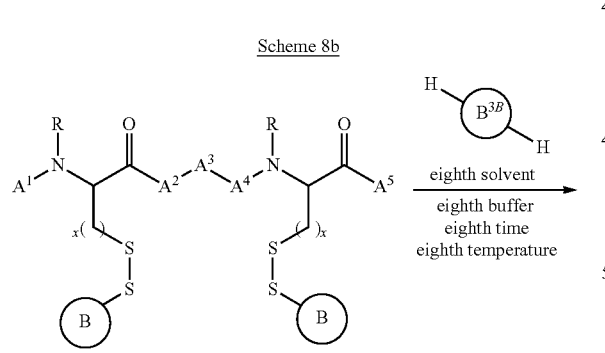

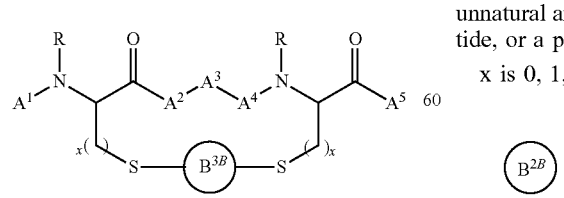

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

$B^{2B}$ is an aryl or heteroaryl radical substituted with at least one electron donating group, provided

is not a perfluoroaryl radical;

is an aryl or heteroaryl diradical substituted with at least one electron donating group, provided

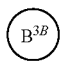

is not a perfluoroaryl radical;

is a heteroaromatic moiety substituted with an electron withdrawing group;

x is 0, 1, 2, 3, 4, 5, or 6; and

R is H or alkyl.

In certain embodiments, the invention relates to a method of killing or inhibiting the growth or proliferation of a bacterium, a fungus, a virus, or a parasite, comprising the step of:

contacting with the bacterium, fungus, virus, or parasite an effective amount of any one of the aforementioned compounds, thereby treating killing or inhibiting the growth or proliferation of the bacterium, fungus, virus, or parasite.

In certain embodiments, the invention relates to a method of treating a disease in a subject in need thereof comprising the step of:

administering to the subject an effective amount of any one of the aforementioned compounds, thereby treating the disease.

BRIEF DESCRIPTION OF THE FIGURES

FIG. 1 depicts three panels ((1)-(3)) showing reaction schemes comparing the bioconjugation of cysteine (panel (1)) and selenocysteine (panel (2)). The proposed reaction pathway of the reaction shown in panel (2) is shown in panel (3).

FIG. 3C shows the yields of peptides 6a-6e using various biorelevant aryl boronic acids. FIG. 3E shows a reaction scheme and an LCMS trace of starting material 9 in the product mixture.

FIG. 17 depicts (top) a reaction scheme showing the Cu-catalyzed arylation of symmetrically S—S-coupled peptides containing cysteine residues near their N-termini (SEQ ID NOS 14, 14 and 14, respectively, in order of appearance), and (bottom) a reaction scheme showing the Rh-catalyzed arylation of symmetrically S—S-coupled peptides containing cysteine residues in the middle of their sequences (SEQ ID NOS 5, 5 and 5, respectively, in order of appearance).

FIG. 21 depicts (top) a reaction scheme showing the conditions for conjugating vancomycin to an antibacterial peptide, and (bottom) a table of various peptide sequences (SEQ ID NOS 7, 15-23, the sequence for sample DTC-09-282, and SEQ ID NO: 24, respectively, in order of appearance) (note, the first two sequences are random sequences with no reported antibacterial activity) that have been conjugated to vancomycin and screened against the gram positive and gram negative bacteria in Table 3.

FIG. 32A depicts a reaction scheme and reactants for copper-mediated arylation of disulfide-containing peptides (SEQ ID NOS 10 and 10, respectively, in order of appearance).

FIG. 32B depicts a reaction scheme and reactants for rhodium-mediated arylation of disulfide-containing peptides (SEQ ID NOS 11 and 11, respectively, in order of appearance).

DETAILED DESCRIPTION

Overview

In certain embodiments, the invention relates to the discovery and subsequent development of a new chemical transformation for the conjugation of unprotected peptide biomolecules. This process features several significant advantages over existing methods of peptide modifications such as specificity towards selenocysteine over other nucleophiles (e.g., amines, hydroxyls), excellent functional group tolerance, and mild reaction conditions. While the reaction times normally vary depending on the concentration and chemical identity of the peptide, the reaction conditions usually can be optimized where full conversion is accomplished within 1-6 hours.

In certain embodiments, this method is employed for synthesis of functionalized peptides, "stapled" peptides, macrocyclized peptides, or heterocoupled peptide systems. In certain embodiments, this methodology is useful for producing hybrid biomaterials featuring other biomolecules such as DNA, RNA, PNA, proteins, oligosaccharides, and a combination of thereof. In certain embodiments, the hybrid biomaterials are useful for cell penetration and intracellular targeting. In certain embodiments, the invention relates to organic polymer-peptide conjugates, peptides decorated with functional small-molecules (such as fluorescent dye labels), natural products or small-molecule drugs (such as antibacterial agents, antifungal agents, antiviral agents, anticonvulsant agents, and antipsychotic agents), inorganic MRI, radio-contrast agents, and also various functionalized metal-based nanoparticle scaffolds.

In certain embodiments, the invention employs an Umpolung approach that utilizes the electrophilic character of the oxidized selenocysteine together with a copper, ligand, and nucleophilic boronic acid combination to provide the arylated selenocysteine in unprotected peptides (FIG. 1, Panel (2)). While not wishing to be bound by any particular theory, the proposed reaction pathway involves an initial oxidative addition of copper to the Se—S bond (FIG. 1, Panel (3)). A subsequent transmetalation with an arylboronic acid and reductive elimination furnishes the arylated selenocysteine. This method does not require oxygen-free conditions or a reducing agent and takes place in water rich media (e.g., 0.1 M Tris buffer (pH=8.0), 95:5 $H_2O$:EtOH). In certain embodiments, reaction yields are excellent for a wide range of substrates. In certain embodiments, this approach is selective for selenocysteine over cysteine.

Figure 2:
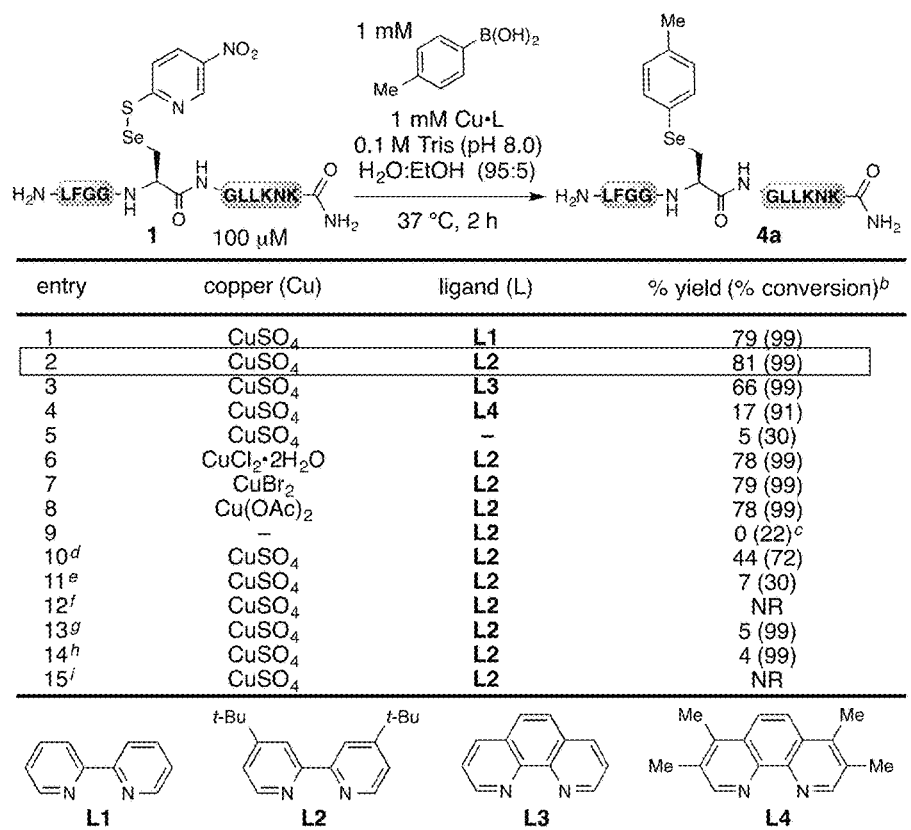
FIG. 2 depicts a table summarizing reaction conditions and % yield for various arylation reactions. $^a$Amino acids are shown in a one-letter code (SEQ ID NOS 3 and 3, respectively, in order of appearance). NR=no reaction. $^b$Yields determined by integration of total ion currents (TIC) from LC-MS analysis of the unpurified reaction mixture. $^c$Elimination and diselenide were the only observable products. $^d$0.5 mM $CuSO_4$, 0.5 mM L2, and 0.5 mM boronic acid were used. $^e$0.25 mM $CuSO_4$, 0.25 mM L2, and 0.25 mM boronic acid were used. $^f$Selenocysteine-TNP residue replaced with a serine. $^g$Selenocysteine-2-thiol-5-nitropyridine residue replaced with a cysteine. $^h$Selenocysteine-2-thiol-5-nitropyridine residue replaced with a cysteine-2-thiol-5-nitropyridine. $^i$Selenocysteine-2-thiol-5-nitropyridine residue replaced with a methionine.
Figure 6:
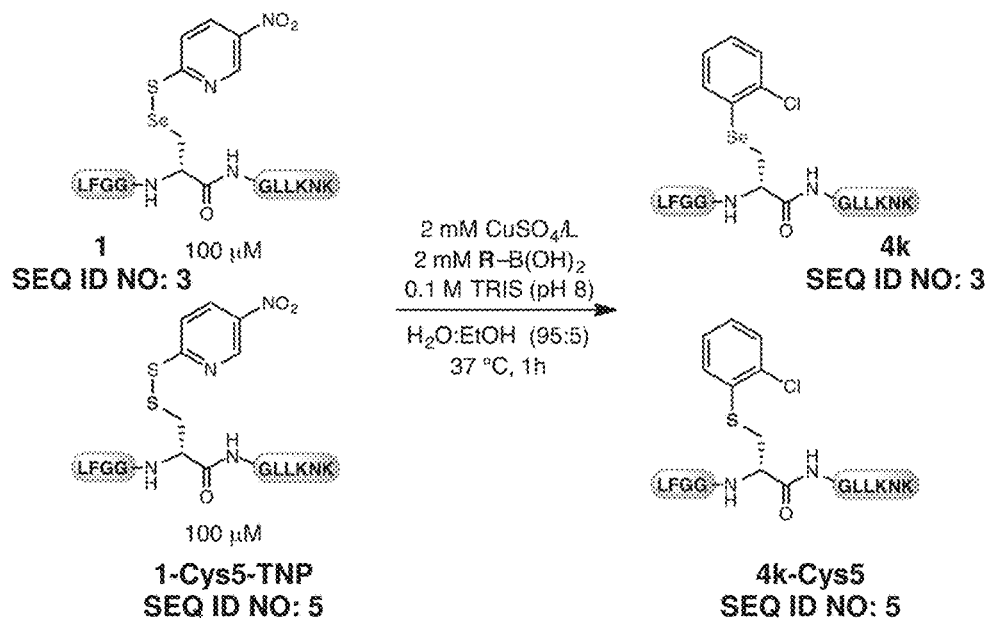
FIG. 6 depicts a reaction scheme showing a competition experiment between a functionalized selenocysteine-containing peptide (top starting material) (compound 1, SEQ ID NO: 3) and a functionalized cysteine-containing peptide (bottom starting material) (compound 1-Cys5-TNP, SEQ ID NO: 5). The mole ratio of product peptides is 90:10 Se:S. The Se product peptide is compound 4k (SEQ ID NO: 3), and the S product peptide is compound 4k-Cys5 (SEQ ID NO: 5).
Figure 7:
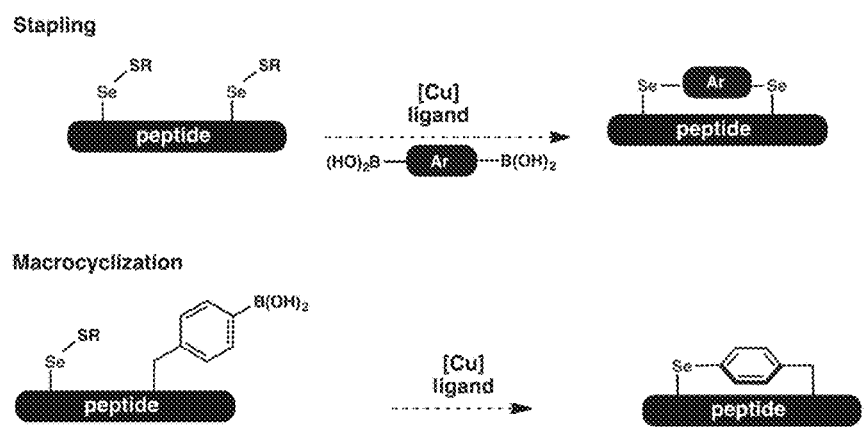
FIG. 7 depicts two applications of the various Cu-catalyzed reactions of the invention: peptide stapling with a bis-boronic acid (top) and macrocyclization (bottom).
Figure 8:
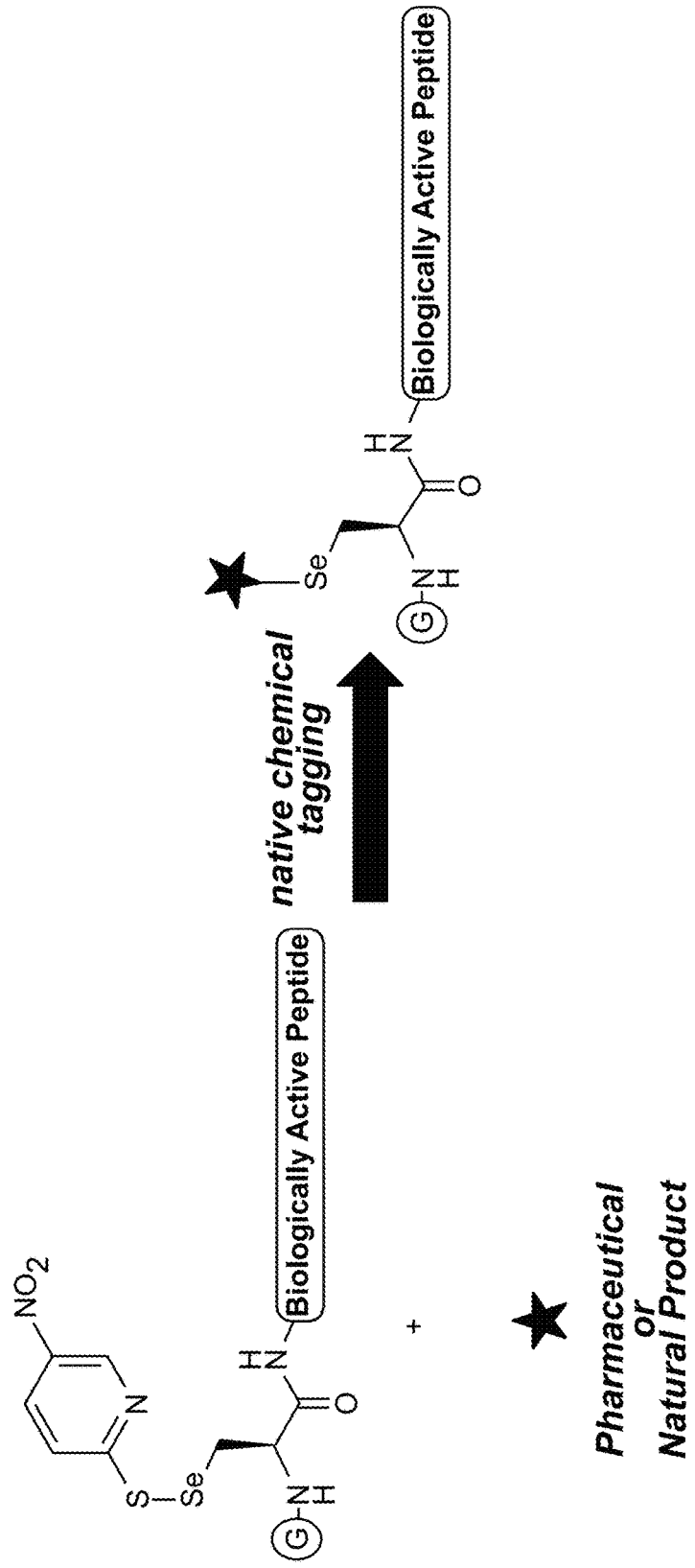
FIG. 8 depicts an application of the various reactions of the invention: tagging of a biologically active peptide with a pharmaceutical or natural product.
Figure 9:
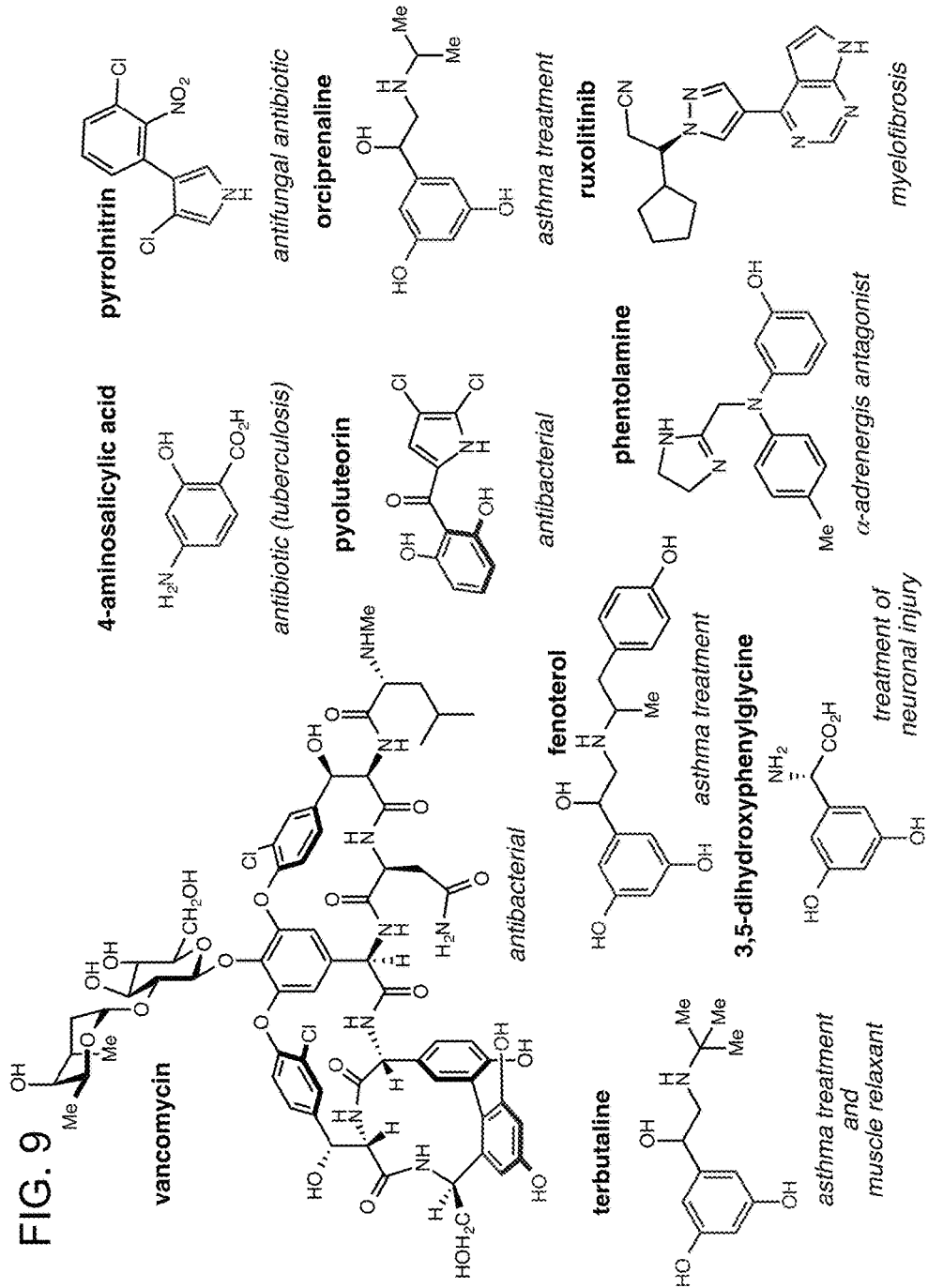
FIG. 9 depicts various pharmaceuticals and biologically active natural products containing electron-rich aromatic rings suitable for conjugation to a selenocysteine-containing peptide.
Figure 10:
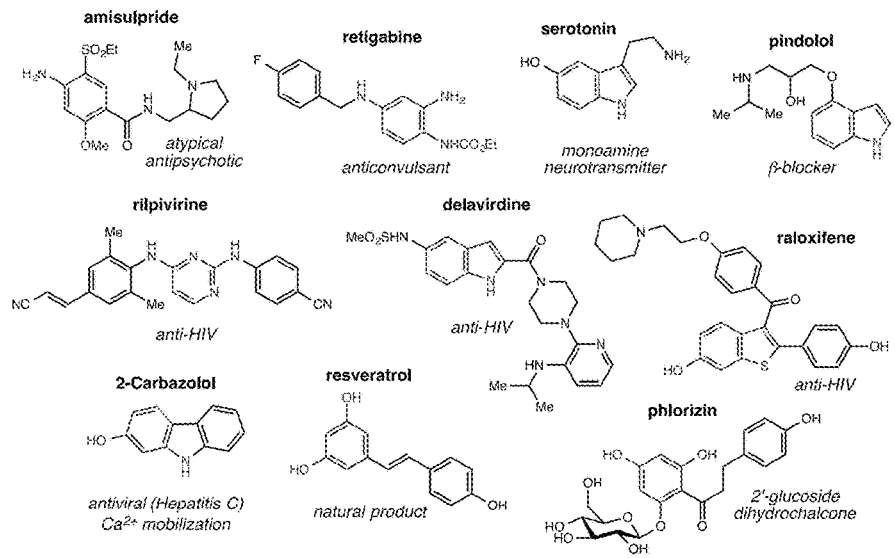
FIG. 10 depicts various pharmaceuticals and biologically active natural products containing electron-rich aromatic rings suitable for conjugation to a selenocysteine-containing peptide.
Figure 11:
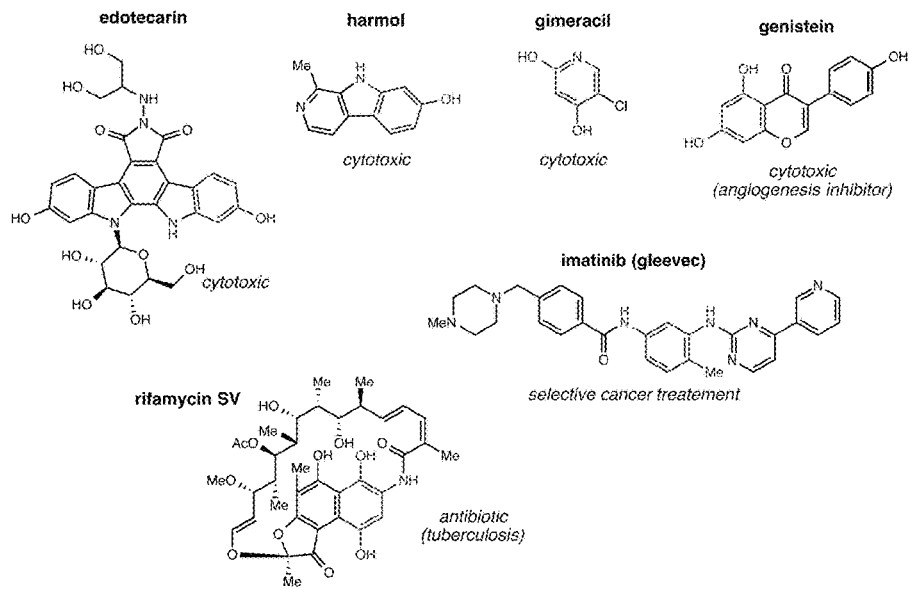
FIG. 11 depicts various pharmaceuticals and biologically active natural products containing electron-rich aromatic rings suitable for conjugation to a selenocysteine-containing peptide.
Figure 12:
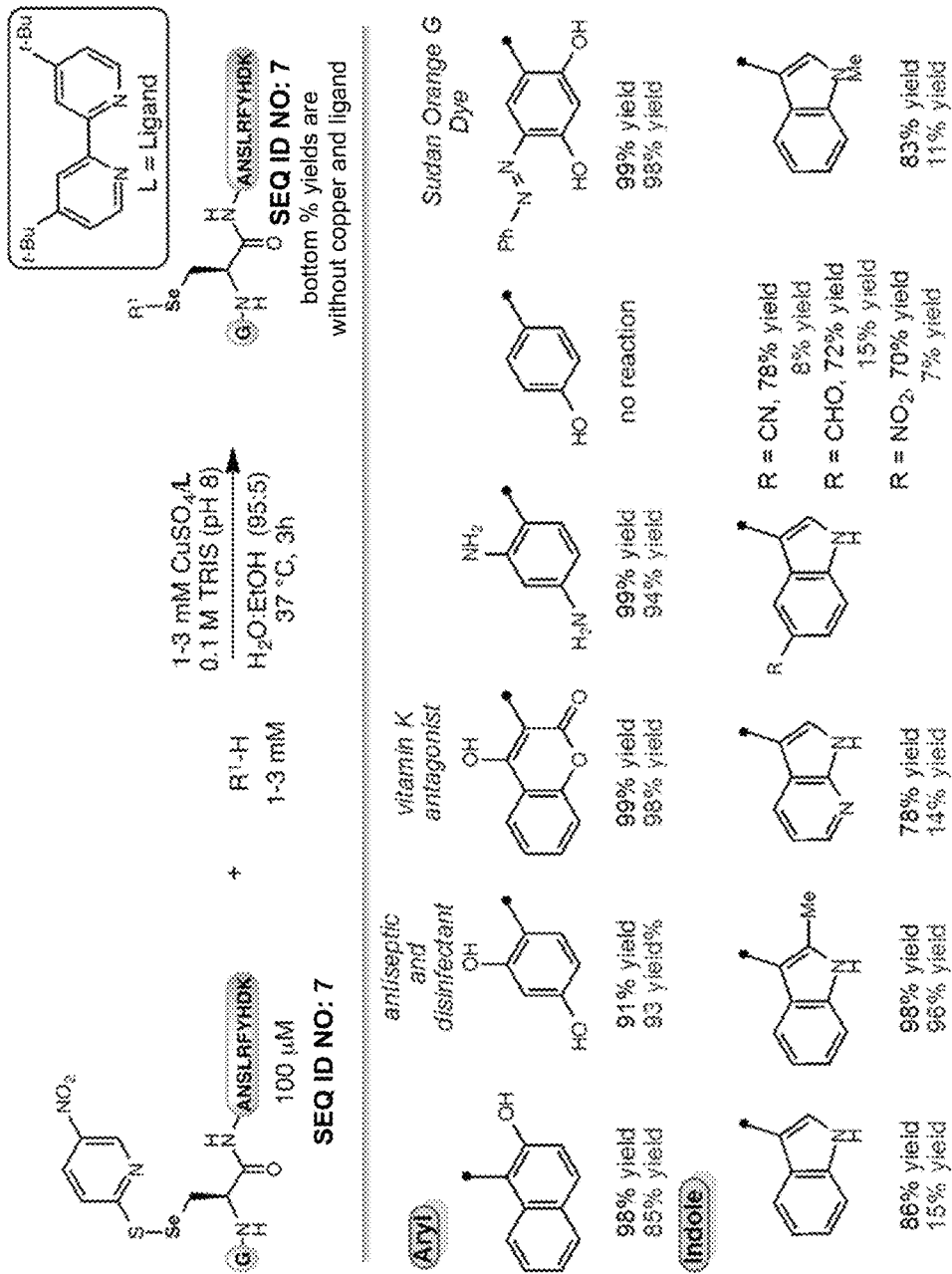
FIG. 12 depicts a reaction scheme and % yield for various arylation reactions using substituted aromatic groups or substituted or unsubstituted indoles in the presence of $CuSO_4$-catalyst (top yields), and in the absence of a metal catalyst and ligand (bottom yields) (peptides disclosed as SEQ ID NOS 7 and 7, respectively, in order of appearance).
Figure 13:
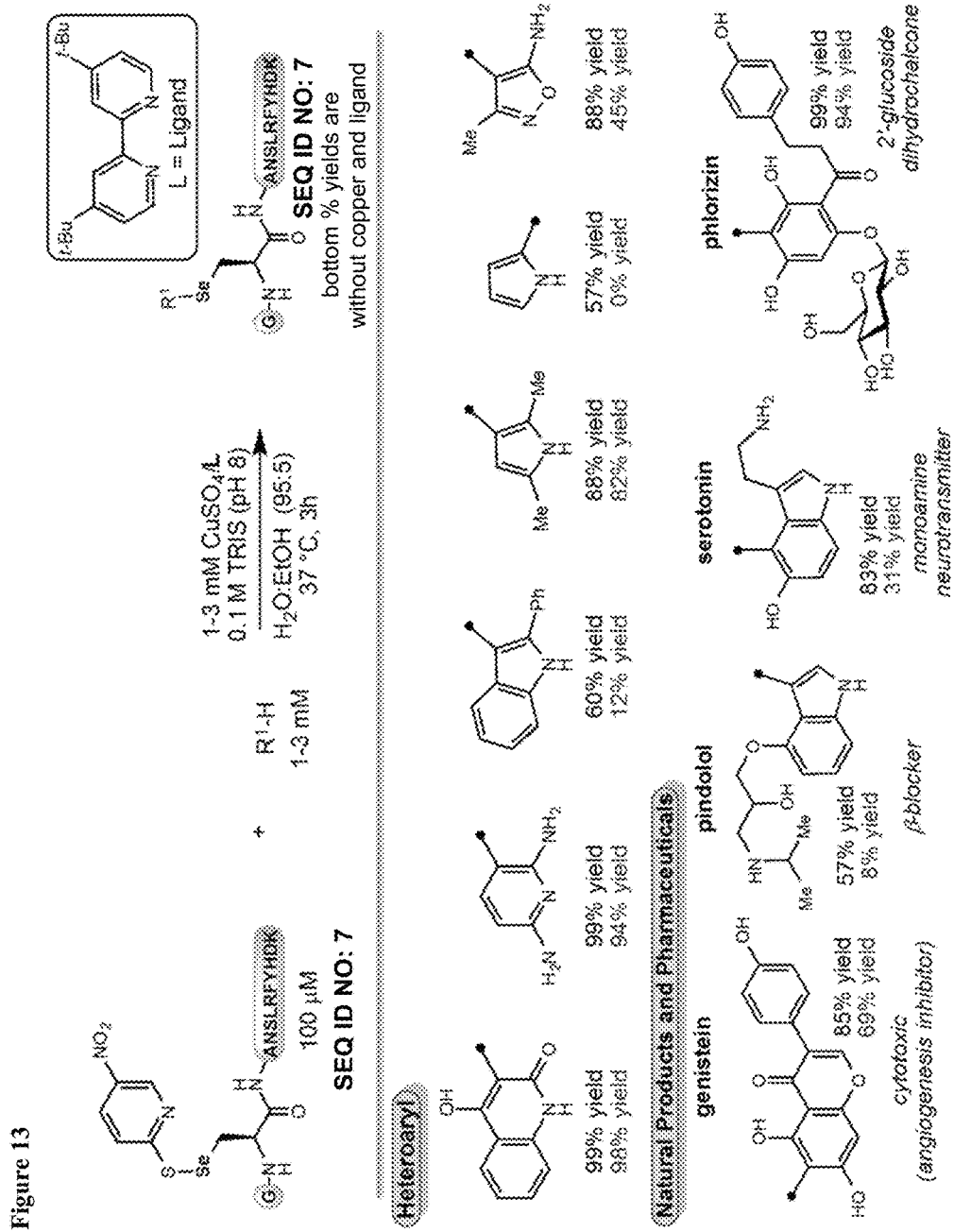
FIG. 13 depicts a reaction scheme and % yield for various arylation reactions using substituted or unsubstituted heteroaromatic groups, natural products, or pharmaceuticals in the presence of $CuSO_4$-catalyst (top yields), and in the absence of a metal catalyst and ligand (bottom yields) (peptides disclosed as SEQ ID NOS 7 and 7, respectively, in order of appearance).
Figure 14:
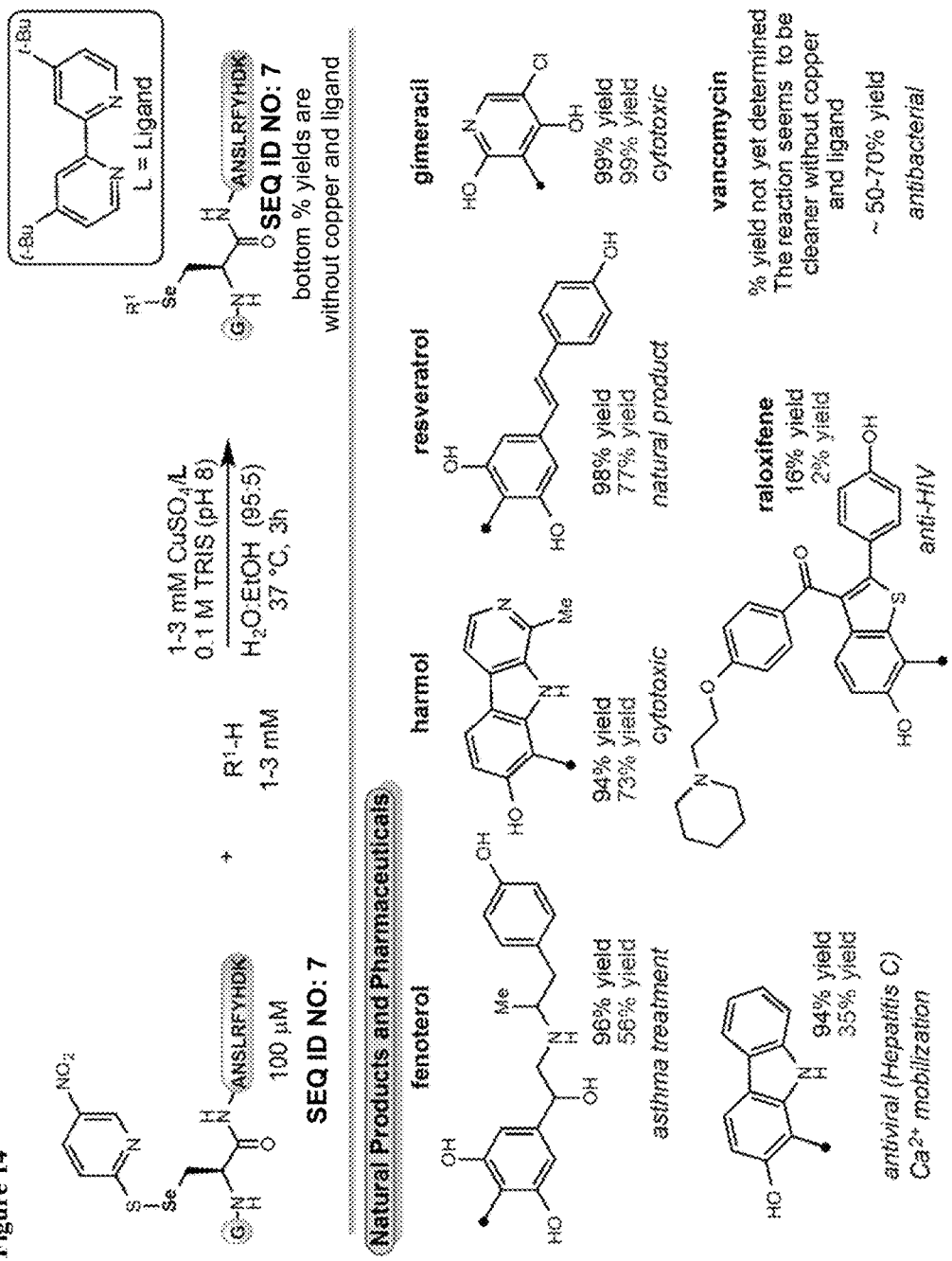
FIG. 14 depicts a reaction scheme and % yield for various arylation reactions using natural products or pharmaceuticals in the presence of CuSO$_4$-catalyst (top yields), and in the absence of a metal catalyst and ligand (bottom yields) (peptides disclosed as SEQ ID NOS 7 and 7, respectively, in order of appearance).
Figure 15:
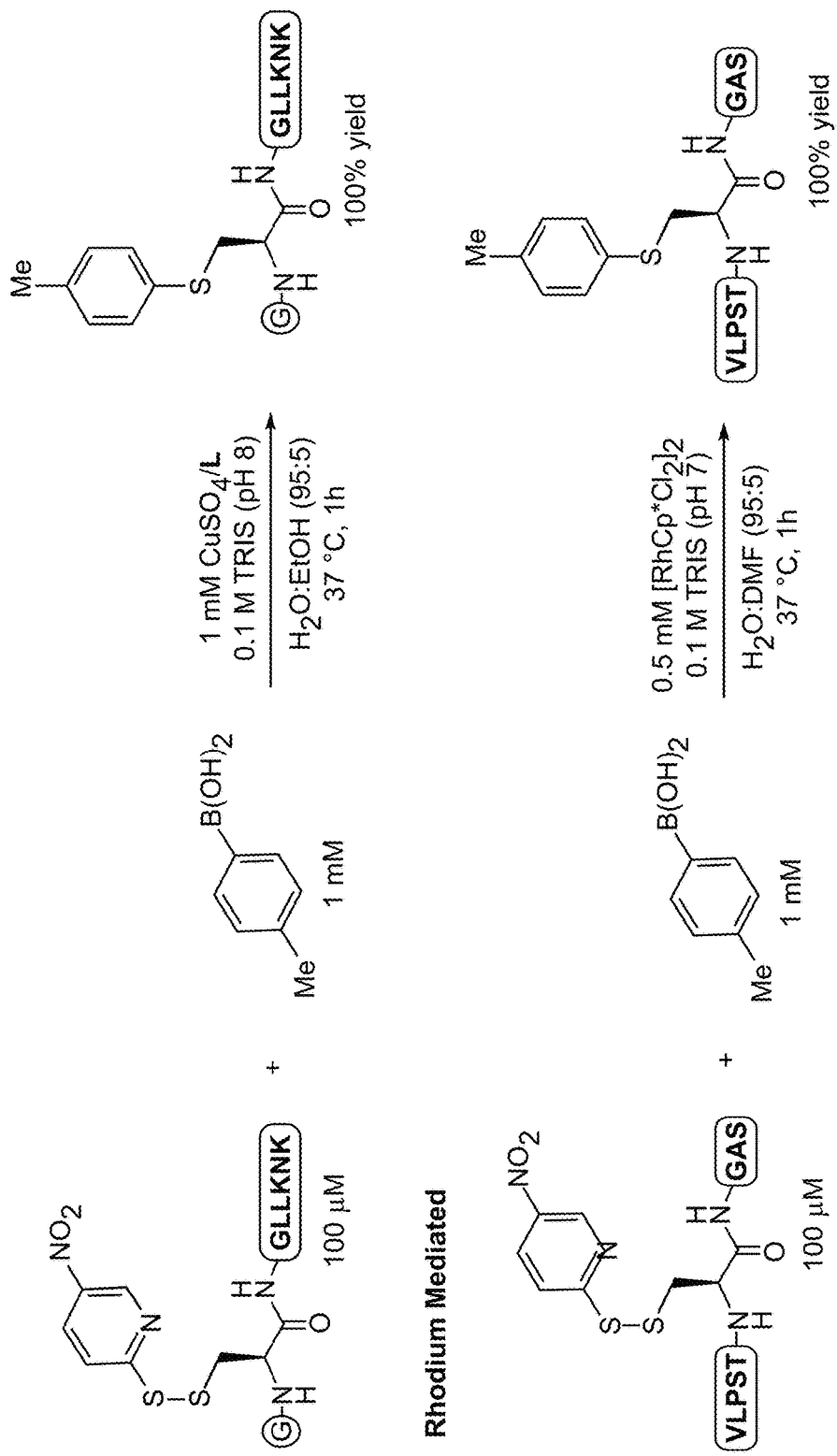
FIG. 15 depicts (top) a reaction scheme showing the Cu-catalyzed arylation of a peptide containing a protected cysteine residue near its N-terminus (SEQ ID NOS 10 and 10, respectively, in order of appearance), and (bottom) a reaction scheme showing the Rh-catalyzed arylation of a peptide containing a protected cysteine residue in the middle of its sequence (SEQ ID NOS 11 and 11, respectively, in order of appearance).
Figure 16:
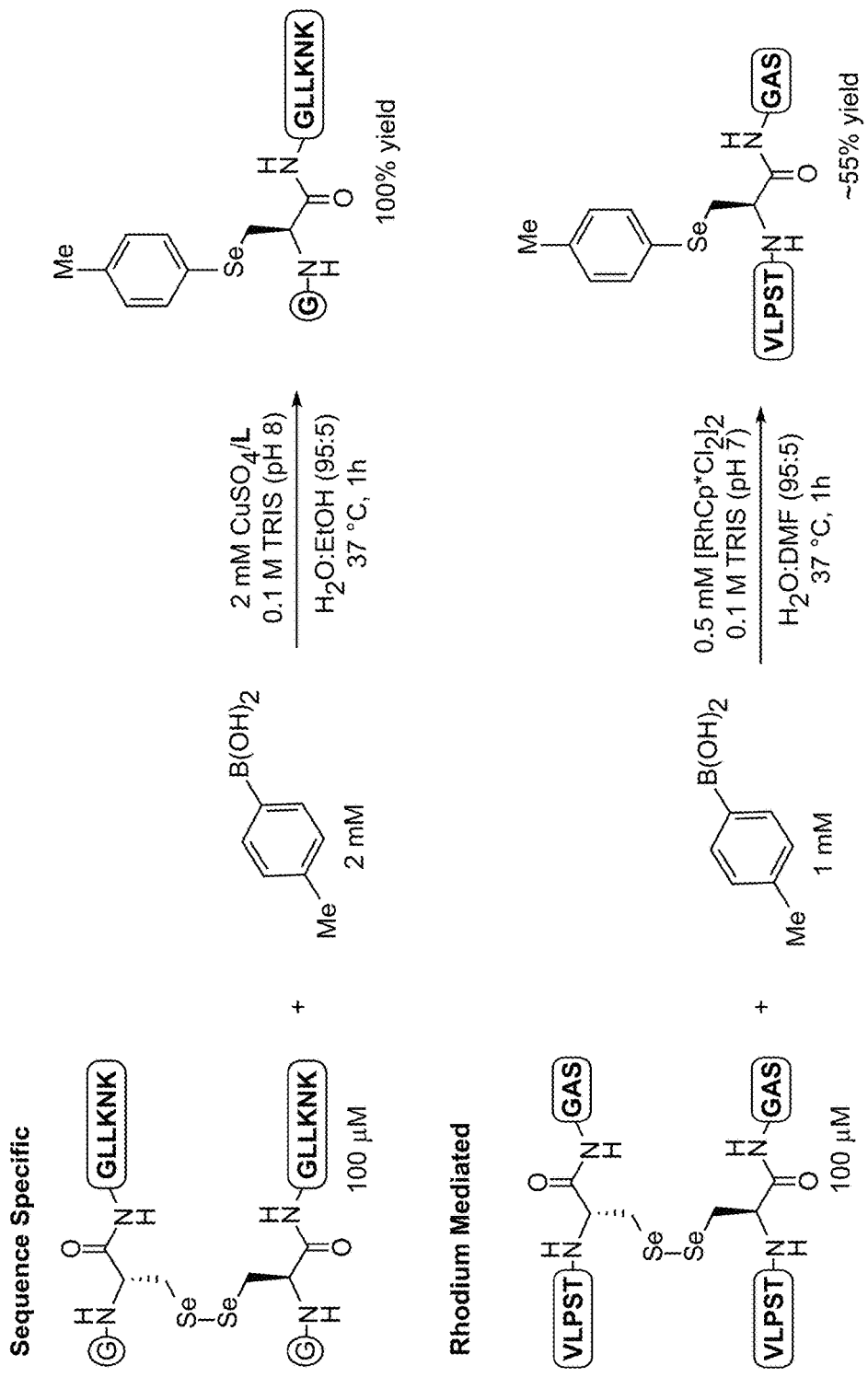
FIG. 16 depicts (top) a reaction scheme showing the Cu-catalyzed arylation of symmetrically Se—Se-coupled peptides containing selenocysteine residues near their N-termini (SEQ ID NOS 12, 12 and 12, respectively, in order of appearance), and (bottom) a reaction scheme showing the Rh-catalyzed arylation of symmetrically Se—Se-coupled peptides containing selenocysteine residues in the middle of their sequences (SEQ ID NOS 13, 13 and 13, respectively, in order of appearance).
Figure 18:
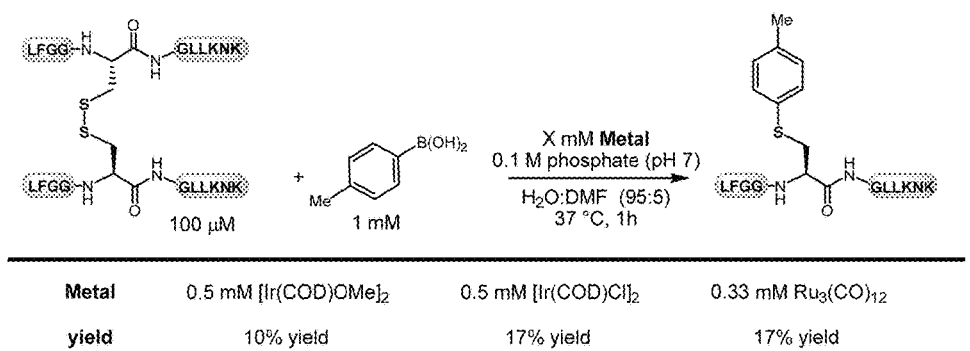
FIG. 18 depicts (top) a reaction scheme showing the metal-catalyzed arylation of symmetrically S—S-coupled peptides containing cysteine residues (SEQ ID NOS 5, 5 and 5, respectively, in order of appearance), and (bottom) the yields of these reactions in the presence of various Ir or Ru metal-catalysts.

In certain embodiments, the invention relates to the synthesis of arylated selenocysteine, which begins by combining unprotected peptide 1, p-tolylboronic acid, $CuSO_4$, and a ligand in buffered aqueous conditions [0.1 M Tris (pH=8.0), 95:5 $H_2O$:EtOH] at 37° C. In certain other embodiments, 2-thiol-5-nitropyridine protected selenocysteine (1) is used as a starting material, as it is the reaction product from the deprotection of p-methoxybenzyl protecting group in solid-phase peptide synthesis. In certain embodiments, different bipyridine and phenanthroline ligands (FIG. 2, entries 1-4) may be used. The formation of the diselenide, seleninic acid, and elimination to dehydroalanine (Dha) were the observed side products. In the absence of ligand, only 30% conversion of 1 and 5% arylation to 4a was observed (FIG. 2, entry 5). Other sources of copper provided similar yields (FIG. 2, entries 6-8). In the absence of copper, no arylation was observed (FIG. 2, entry 9). Lastly, decreasing the number of equivalents of copper, ligand, or boronic acid resulted in lower levels of conversion and increased side reactions (FIG. 2, entries 10-11). No product was observed in a control reaction with selenocysteine-to-serine variant (FIG. 2, entry 12), confirming that arylation occurs exclusively at selenium. To probe the reactivity of selenocysteine versus cysteine, two peptides in which the selenocysteine was replaced with cysteine (free thiol) or cysteine linked with a 2-thiol-5-nitropyridine as the masking agent (FIG. 2, entries 13-14) were examined. For both peptides we observed low conversion to the arylated cysteine, rather the starting material (1) was converted to the respective disulfide or sulfinic acid. This result demonstrates the enhanced reactivity of selenocysteine over cysteine toward copper-mediated arylation. See also FIG. 6. It also indicates cysteine is not compatible under these reaction conditions. Lastly, no oxidation was detected for the selenocysteine-to-methionine variant (FIG. 2, entry 15), which proves that this method could be applied to methionine containing peptides.

Figure 3:
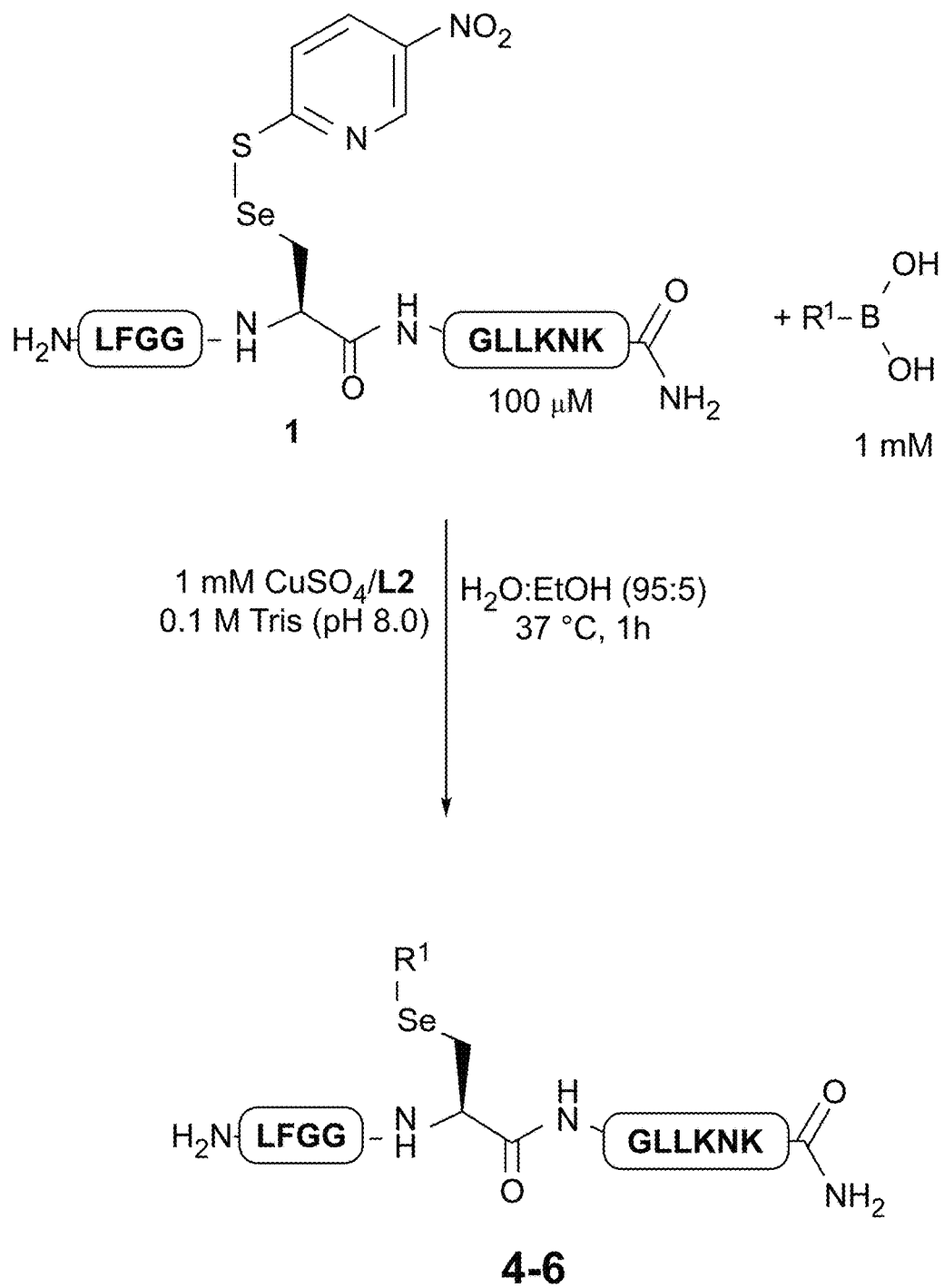
FIG. 3 summarizes reaction substrates, boronic acids, and yields for various arylation reactions. $^a$Amino acids are shown in a one-letter code (SEQ ID NOS 3, 3, 7 and 8, respectively, in order of appearance). $^b$Yields determined by integration of total ion currents (TIC) from LC-MS analysis of the unpurified reaction mixture (Average of two runs). $^b$2 h reaction time. $^c$1.5 h reaction time. $^d$2 mM $CuSO_4$, 2 mM L2, and 2 mM boronic acid were used. $^e$2 mM $CuSO_4$, 2 mM L2, 2 mM boronic acid, and $H_2O$:DMF (90:10) for 3 h.
Figure 3A:
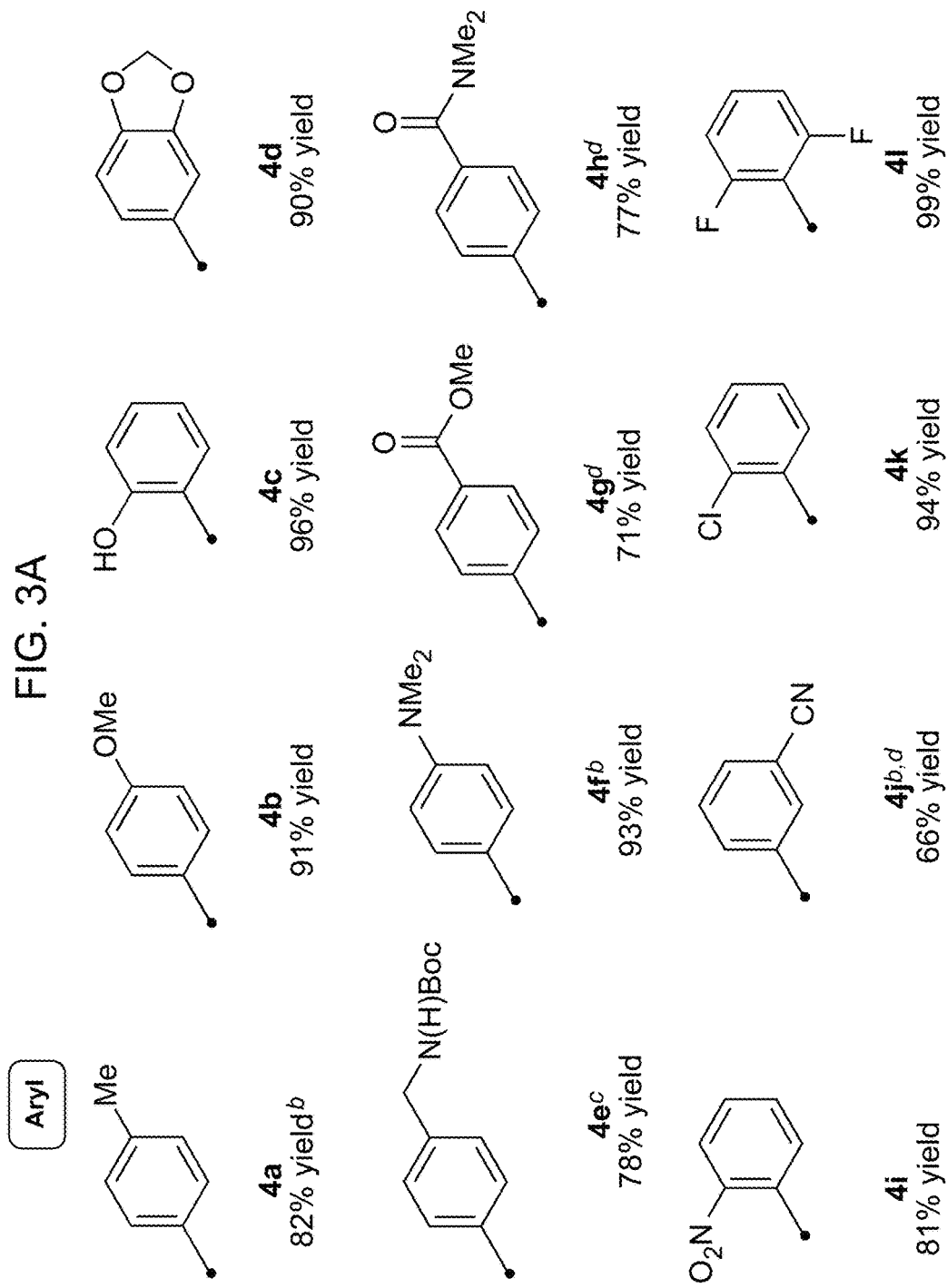
FIG. 3A shows the yield of peptides 4a-4l using aryl boronic acids.

In certain embodiments, the invention relates to a reaction methodology applicable to a wide variety of substrates. See FIG. 3. Aryl boronic acids with electron-donating functional groups were examined (FIG. 3A). Methoxy (4b), orthophenol (4c), dioxolane (4d), —$CH_2N(H)Boc$ (4e), and para-dimethylamine (4f) groups were readily tolerated. Under these reaction conditions, Boc deprotection was not observed (4e), thus demonstrating the mild conditions needed to achieve the arylation.

In certain embodiments, the invention relates to a method of functionalizing a selenocysteine residue using an aryl boronic acid having an electron-withdrawing functional group (FIG. 3A). Despite the decreased nucleophilicity of these electron-poor boronic acids, the corresponding selenium conjugates were formed in good to excellent yield. In some cases, the number of equivalents of the Cu/L and boronic acid needed to be increased to provide full conversion to product while suppressing side reactions. Ester (4g), amide (4h), nitro (4i), nitrile (4j), and halogen (4k and 4l) functional groups were compatible with these conditions. Peptide 4l was formed quantitatively despite 2,6-difluorophenyl boronic acid having the tendency to undergo protodeboronation under basic conditions.

Figure 3B:
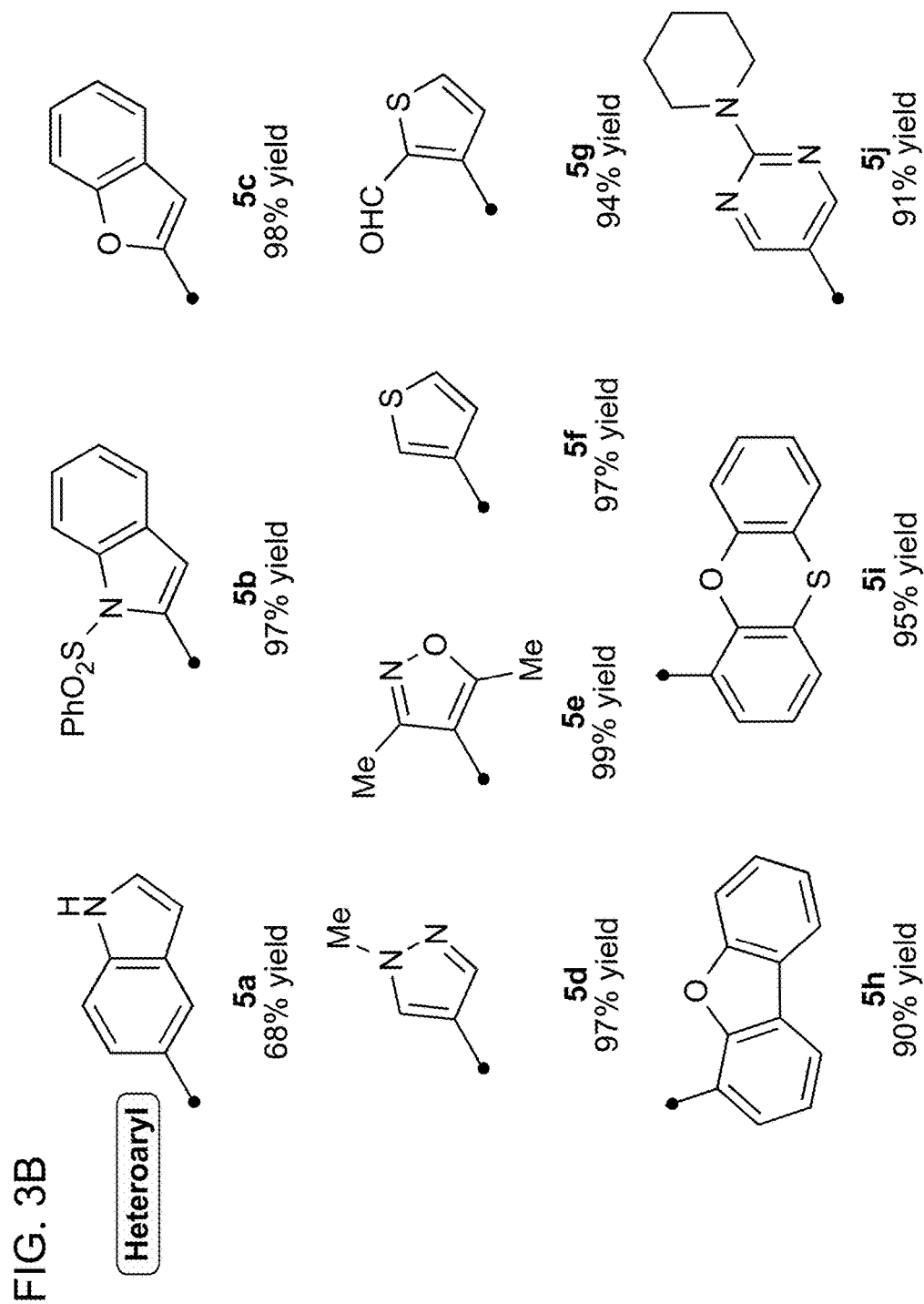
FIG. 3B shows the yield of peptides 5a-5j using heteroaryl boronic acids.

In certain embodiments, the invention relates to a method of functionalizing a selenocysteine residue using a heteroaryl boronic acid (FIG. 3B). Known bioactivities comprising heterocycles makes heterocycles an important class of molecules for conjugation to selenocysteine. The arylation of five-membered heterocycles such as indole (5a and 5b), benzofuran (5c), pyrazole (5d), 2,5-disubstituted isoxazole (5e), and thiophene (5f and 5g) proceeded with excellent yields. Six-membered heterocycles, such as dibenzofuran (5h), phenoxathiine (5i), and pyrimidine (5j) likewise furnished the corresponding conjugate in greater than 90% yield.

In certain embodiments, the invention relates to the functionalization of selenocysteine-containing peptides with biorelevant molecules (FIG. 3C). The linking of protected phenylalanine and coumarin proceeded in good yield (6a and 6b respectively). The boronic acids of anti-inflammatory drugs tolfenamic ester and paracetamol furnished the corresponding conjugates in moderate to good yields (6c and 6d respectively). Lastly, estrone was coupled to selenium in moderate yield (6e).

Figure 3D:
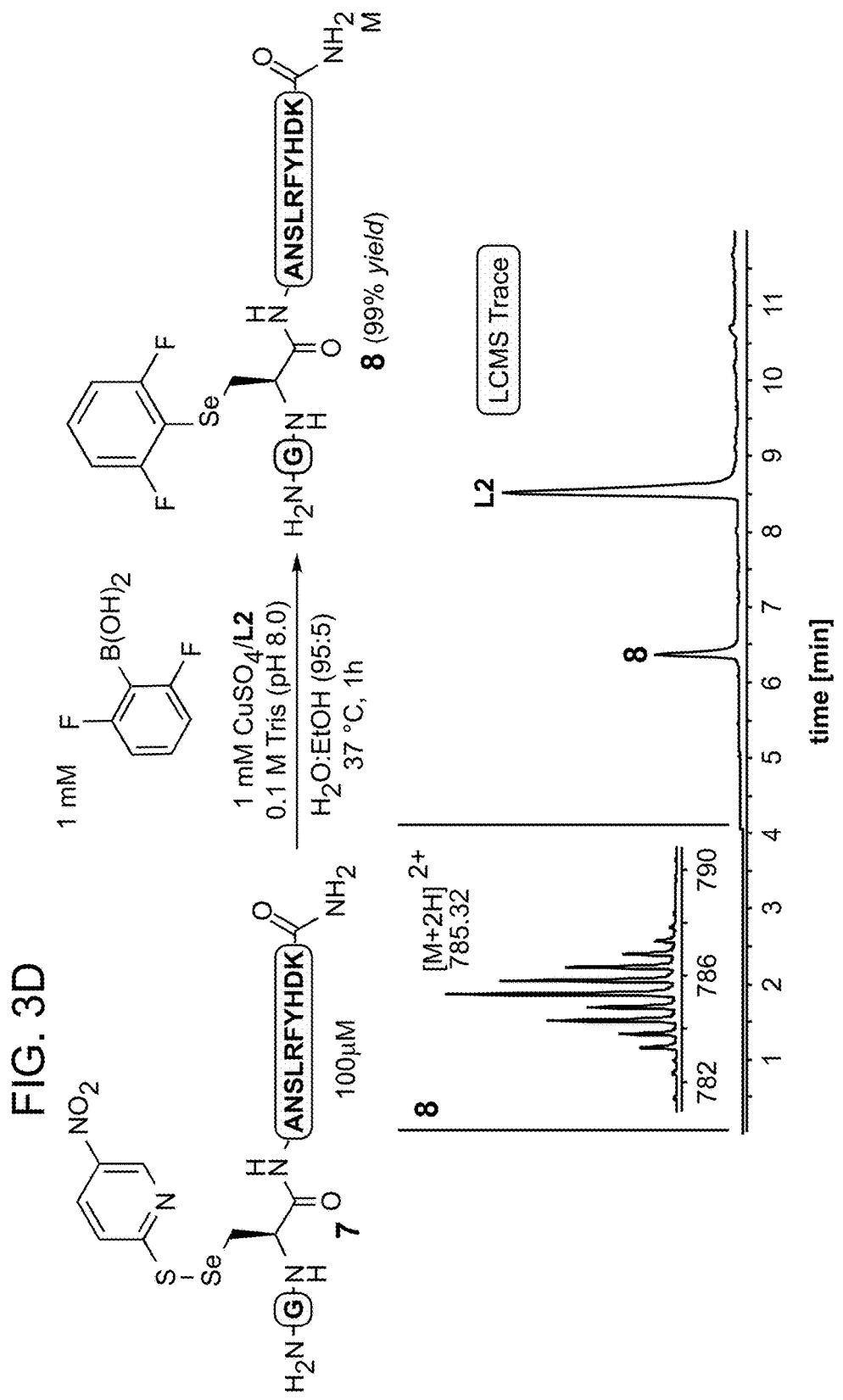
FIG. 3D shows a reaction scheme and an LCMS trace of arylated peptide 8 in the product mixture.

In certain embodiments, the invention relates to a robust, selective reaction. As an example, peptide 7 was prepared; peptide 7 contains most of the key functional groups found in polyamides (e.g., histidine, arginine, aspartic acid, tyrosine, and asparagine) excluding sulfur-based amino acids (FIG. 3D). Exposure of 7 to 2,6-difluorophenyl boronic acid under reaction conditions provided the corresponding arylated product (8) in quantitative yield based on LC-MS analysis. No other peptidic species were observed (see LC-MS trace, FIG. 3D). The arylation occurred exclusively on the selenocysteine as a selenocysteine-to-serine control variant (9) provided no product under identical reaction conditions (FIG. 3E).

Figure 5A:
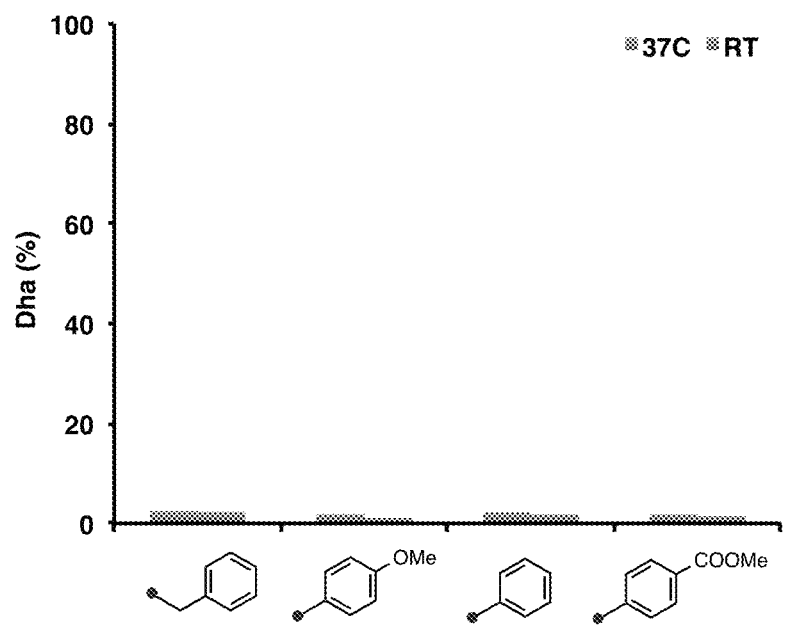
FIG. 5A depicts the yield of Dha elimination product (%) at pH 8.0 for various selenocysteine peptides at 37° C. (left bar) and at room temperature (about 23° C.) (right bar).
Figure 5B:
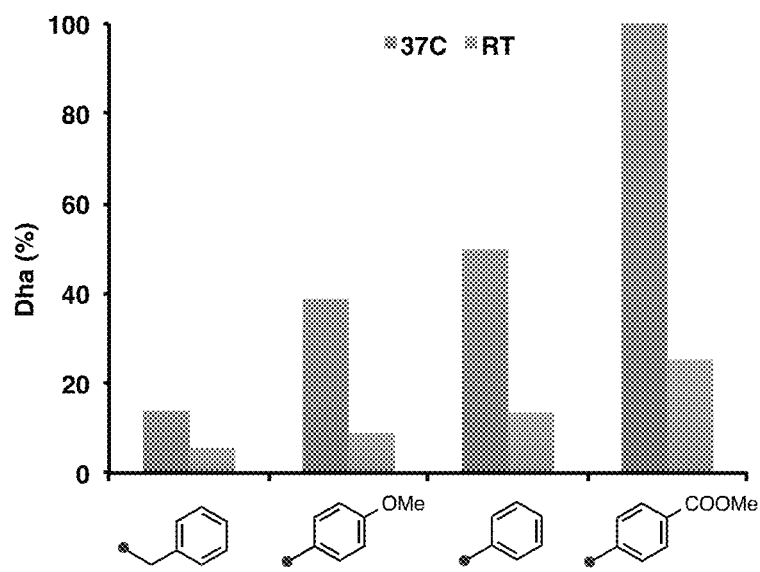
FIG. 5B depicts the yield of Dha elimination product (%) at pH 10.0 for various selenocysteine peptides at 37° C. (left bar) and at room temperature (about 23° C.) (right bar).

In certain embodiments, the invention relates to peptides comprising aryl-functionalized selenocysteine. The stability of these aryl conjugates relative to the corresponding benzylated variant under basic conditions was investigated. In a pH 8.0 buffered solution at room temperature or 37° C., neither the arylated nor alkylated selenocysteine peptide underwent elimination to dehydroalanine (1a, Dha) even after 11 hours. FIG. 5A. However, in a buffered solution at pH 10.0, appreciable amounts of elimination were observed for both the alkylated and arylated derivatives depending on the substituent on the selenium. FIG. 5B.

Figure 4:
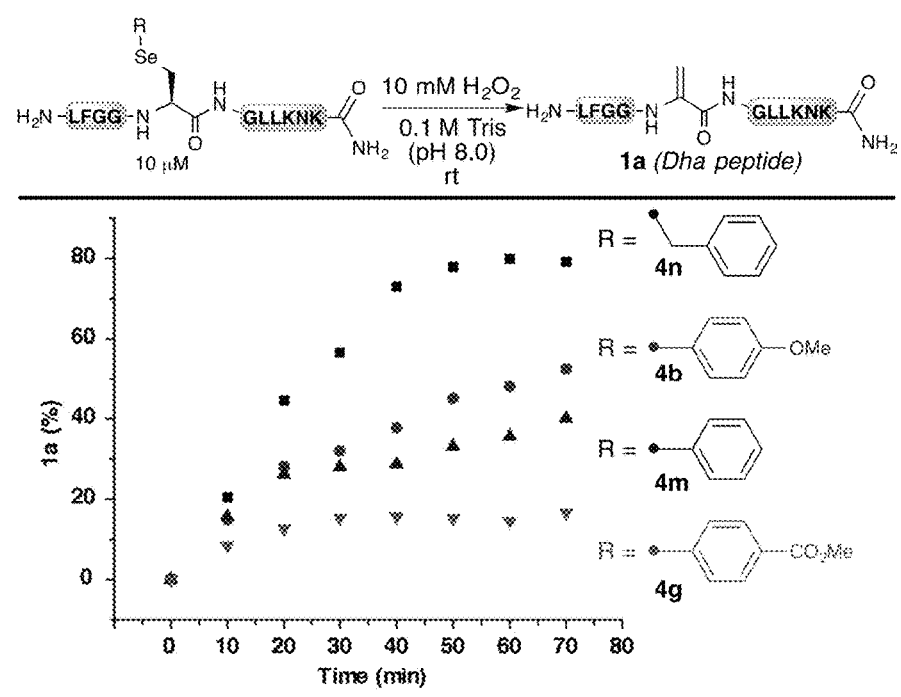
FIG. 4 depicts data from a stability study of functionalized selenocysteine in peptides (SEQ ID NOS 3 and 9, respectively, in order of appearance). % yields determined by integration of total ion currents (TIC) from LC-MS analysis of the unpurified reaction mixture.

In certain embodiments, the invention relates to peptides comprising aryl-functionalized selenocysteine that are relatively stable under oxidative conditions. Exposure of these peptide derivatives to a large excess of H$_2$O$_2$ (10 mM) at room temperature lead to the formation of varying amounts of dehydroalanine (1a) depending on the R-group on the selenocysteine (FIG. 4). In general, the arylated selenocysteine derivatives were less prone to oxidation/elimination than the benzylated selenocysteine (4n). This result is in agreement with previous reports that alkylated or arylated selenocysteine can be readily converted to dehydroalanine (1a) even under mildly oxidative conditions. With regards to the different arenes, the more electron deficient the aryl ring on the selenium, the slower formation of Dha, 1a. So, in certain embodiments, the invention relates to the ability to stabilize the arylated selenocysteine by modulating the electronic nature of the arene substituent.

Exemplary Functionalized Compounds

In certain embodiments, the invention relates to a compound comprising substructure I:

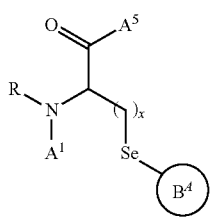

wherein, independently for each occurrence,

A$^1$ is H, an amine protecting group, a natural or unnatural amino acid, a peptide, an oligopeptide, a polypeptide, or a protein;

A$^5$ is OH, —O(carboxylate protecting group), a natural or unnatural amino acid, a peptide, an oligopeptide, a polypeptide, or a protein;

is a substituted or unsubstituted aryl or heteroaryl radical;
x is 0, 1, 2, 3, 4, 5, or 6; and
R is H or alkyl.

In certain embodiments, the invention relates to a compound comprising substructure II:

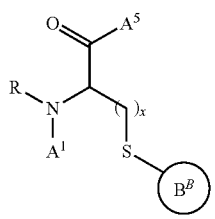

wherein, independently for each occurrence,

A$^1$ is H, an amine protecting group, a natural or unnatural amino acid, a peptide, an oligopeptide, a polypeptide, or a protein;

A$^5$ is OH, —O(carboxylate protecting group), a natural or unnatural amino acid, a peptide, an oligopeptide, a polypeptide, or a protein;

is a substituted or unsubstituted aryl or heteroaryl radical, provided

is not a perfluoroaryl radical;
x is 0, 1, 2, 3, 4, 5, or 6; and
R is H or alkyl.

In certain embodiments, the invention relates to any one of the aforementioned compounds, wherein the compound is depicted in the Figures.

In certain embodiments, the invention relates to any one of the aforementioned compounds, wherein

is a substituted aryl radical. In certain embodiments, the invention relates to any one of the aforementioned compounds, wherein

is a substituted phenyl radical.

In certain embodiments, the invention relates to any one of the aforementioned compounds, wherein (B^A)

is an unsubstituted aryl radical.

In certain embodiments, the invention relates to any one of the aforementioned compounds, wherein (B^A)

is a substituted heteroaryl radical. In certain embodiments, the invention relates to any one of the aforementioned compounds, wherein (B^A)

is a substituted indole, pyrazolo, thiophene, pyrimidine, benzofuran, or isoxazole radical.

In certain embodiments, the invention relates to any one of the aforementioned compounds, wherein (B^A)

is an unsubstituted heteroaryl radical. In certain embodiments, the invention relates to any one of the aforementioned compounds, wherein (B^A)

is an unsubstituted indole, pyrazolo, thiophene, pyrimidine, benzofuran, or isoxazole radical.

In certain embodiments, the invention relates to any one of the aforementioned compounds, wherein

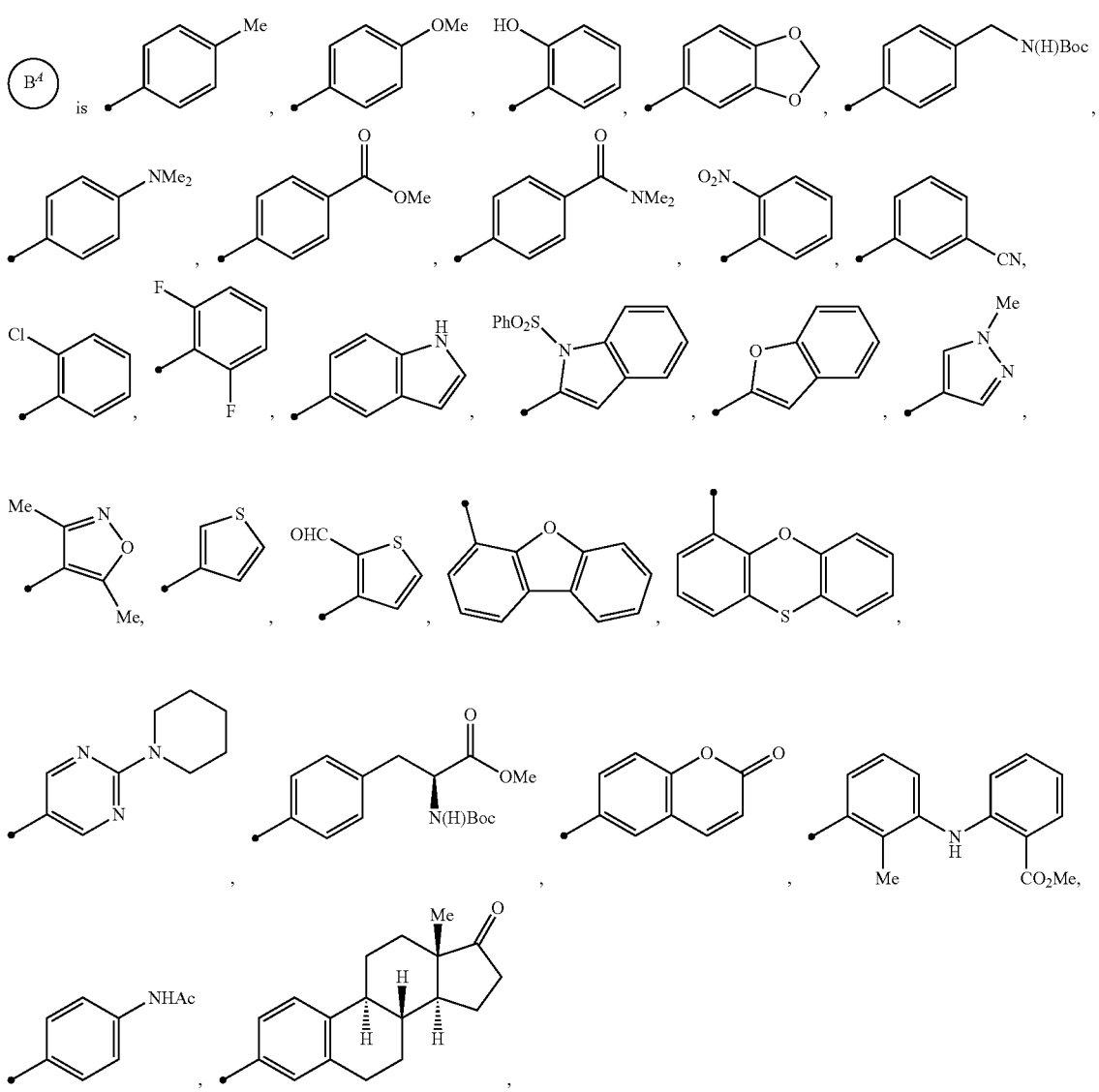

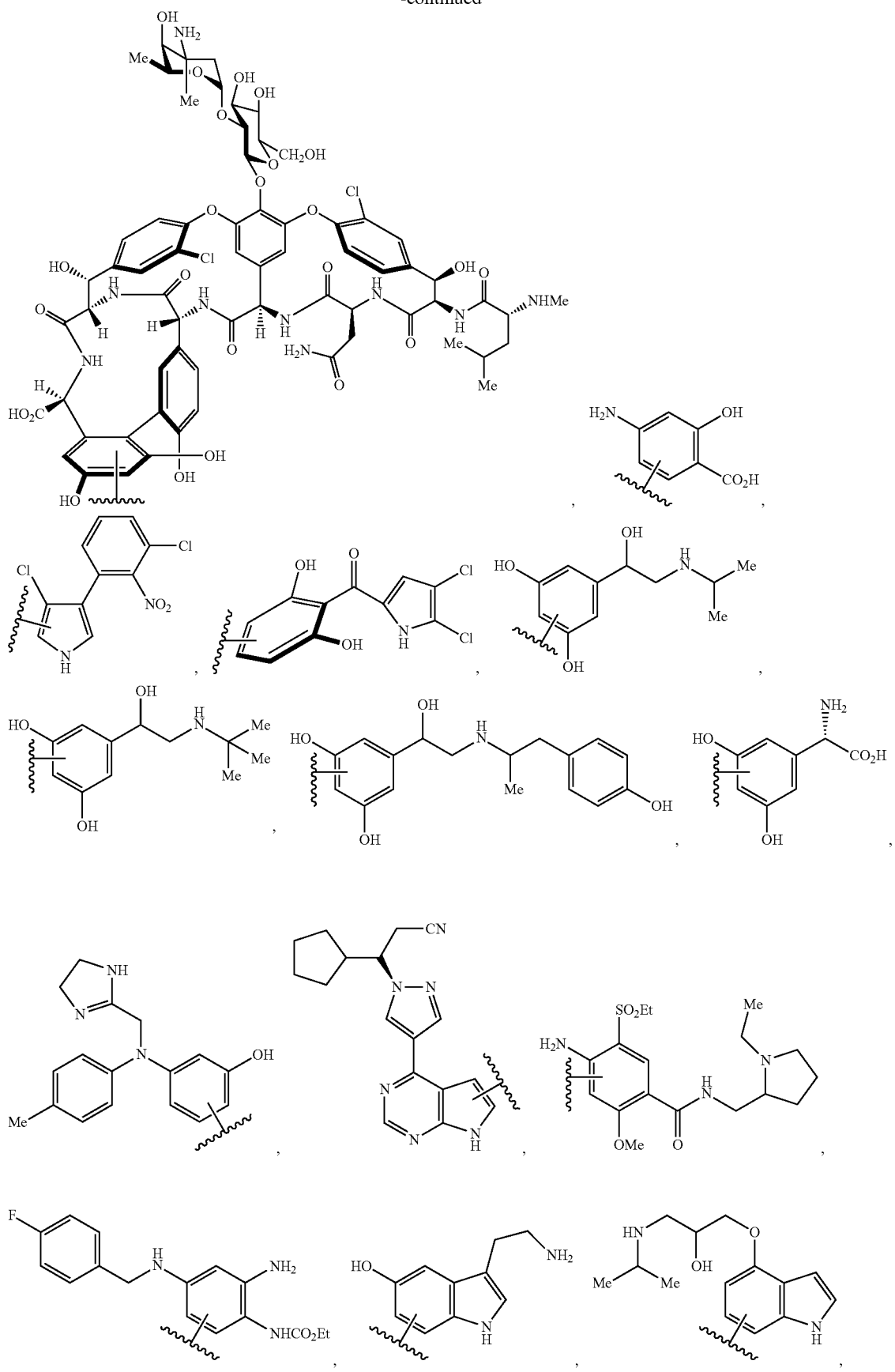

35
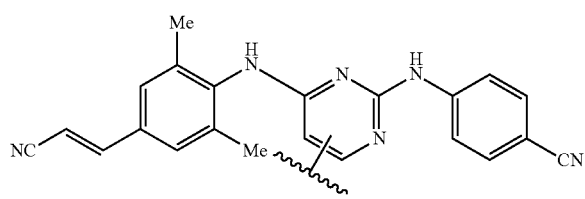
36
-continued
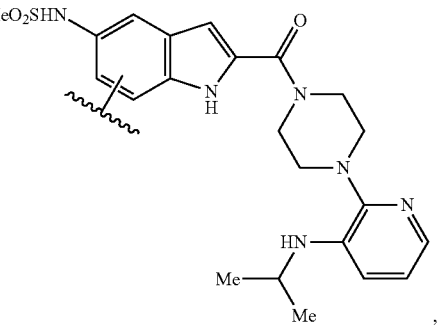
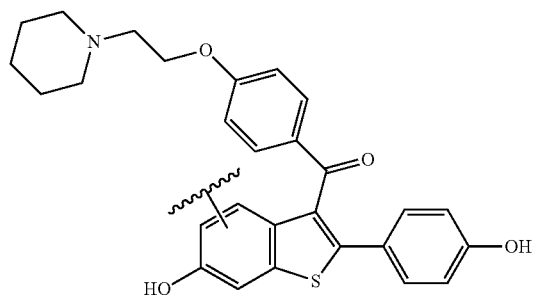, 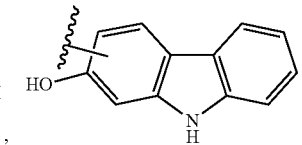,
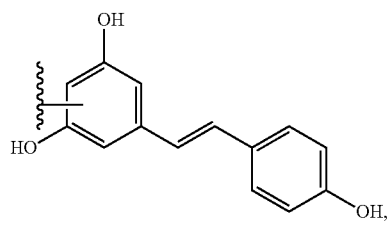, 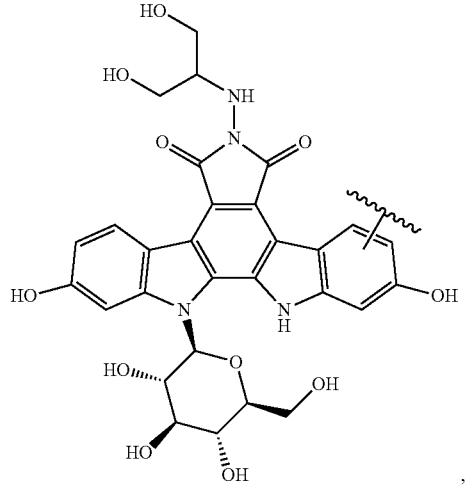
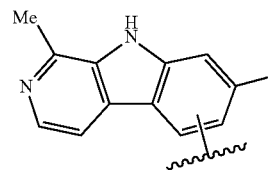, 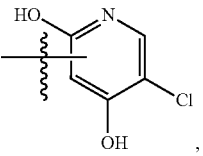,
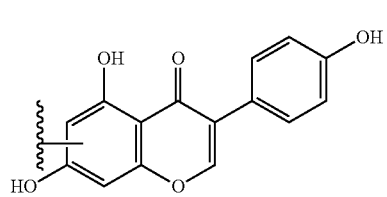, 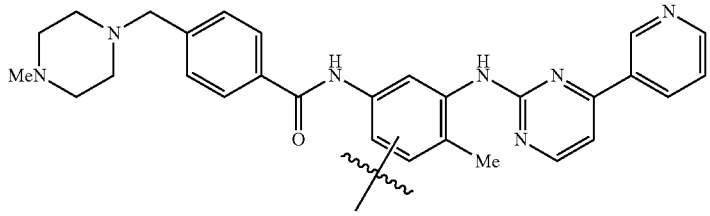,

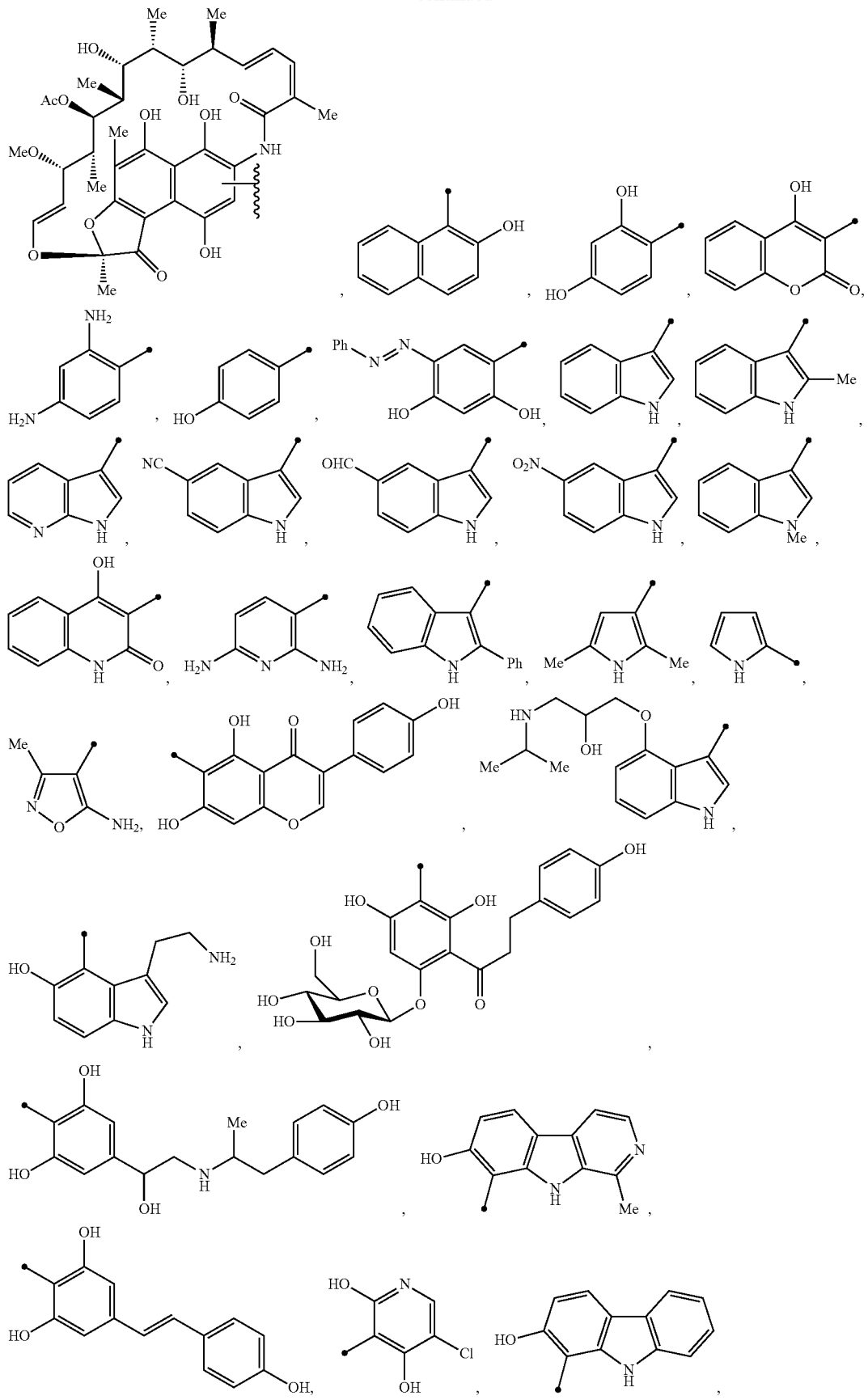

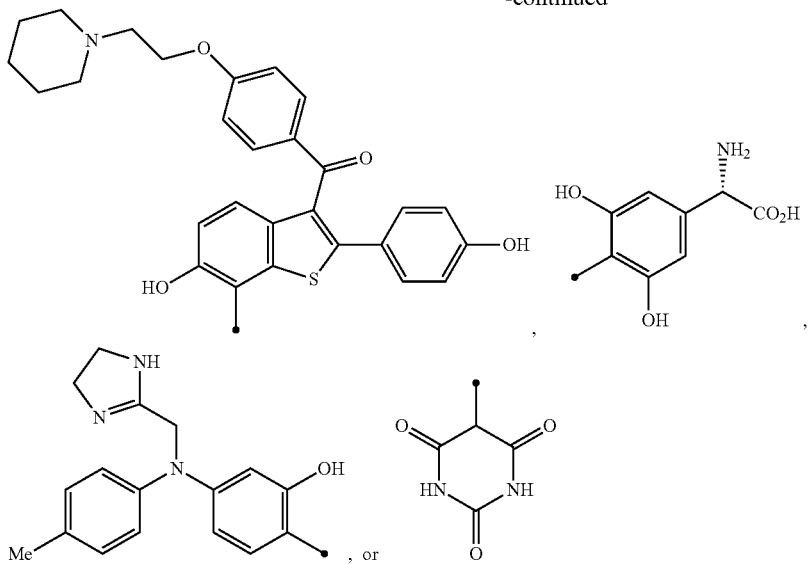
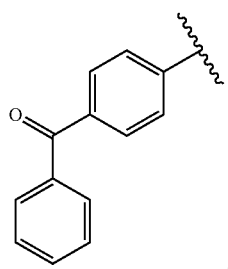
, or
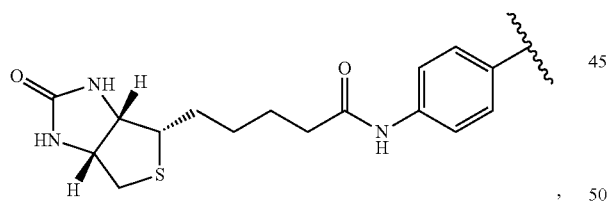
or a regioisomer or stereoisomer thereof. In certain embodiments,
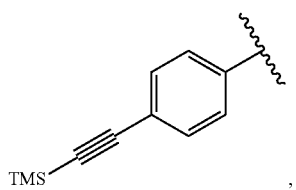
is any of the aforementioned moieties, wherein the moiety is further substituted.
In certain embodiments, the invention relates to any one of the aforementioned compounds, wherein
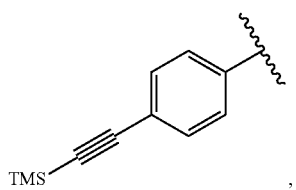 is
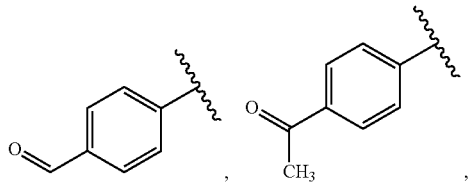
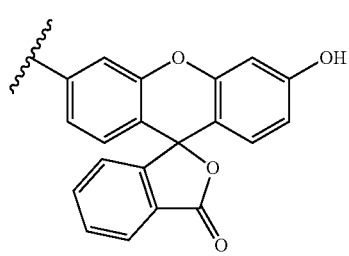
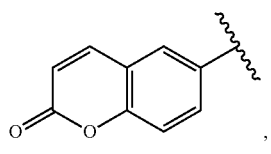
-continued
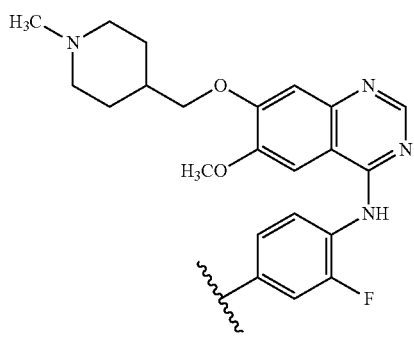
, -continued

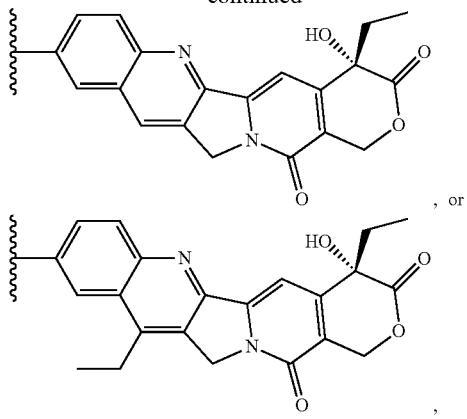

, or or a regioisomer or stereoisomer thereof. In certain embodiments,

is any of the aforementioned moieties, wherein the moiety is further substituted.

In certain embodiments, the invention relates to any one of the aforementioned compounds, wherein

is a substituted aryl radical. In certain embodiments, the invention relates to any one of the aforementioned compounds, wherein

is a substituted phenyl radical.

In certain embodiments, the invention relates to any one of the aforementioned compounds, wherein

is an unsubstituted aryl radical.

In certain embodiments, the invention relates to any one of the aforementioned compounds, wherein

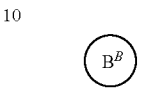

is a substituted heteroaryl radical. In certain embodiments, the invention relates to any one of the aforementioned compounds, wherein

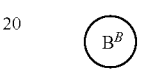

is a substituted indole, pyrazolo, thiophene, pyrimidine, benzofuran, or isoxazole radical.

In certain embodiments, the invention relates to any one of the aforementioned compounds, wherein

is an unsubstituted heteroaryl radical. In certain embodiments, the invention relates to any one of the aforementioned compounds, wherein

is an unsubstituted indole, pyrazolo, thiophene, pyrimidine, benzofuran, or isoxazole radical.

In certain embodiments, the invention relates to any one of the aforementioned compounds, wherein

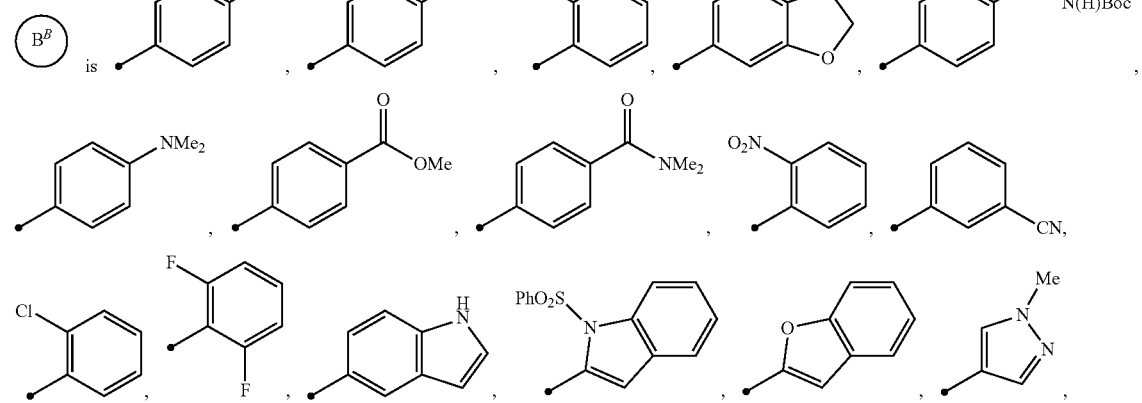

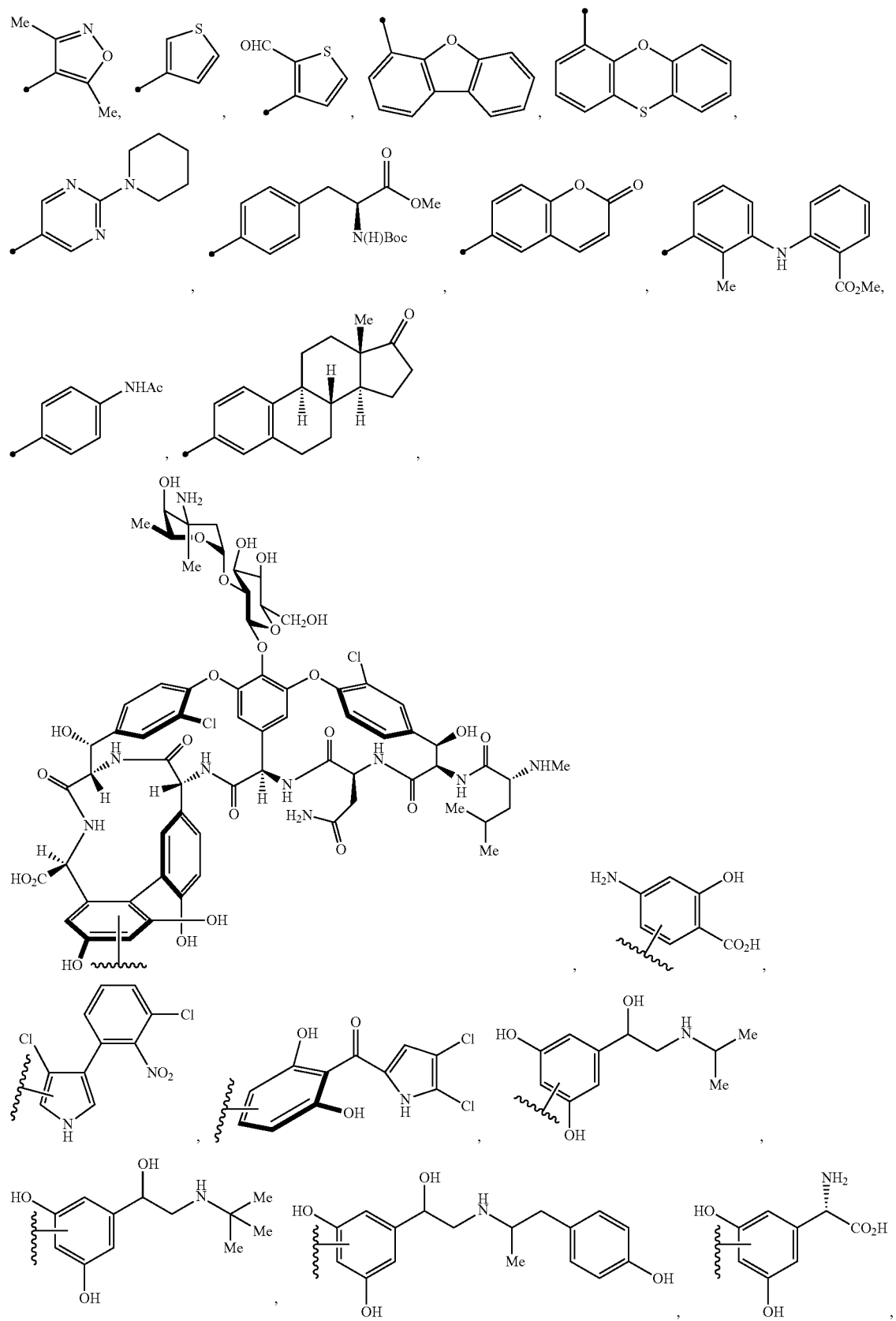

-continued
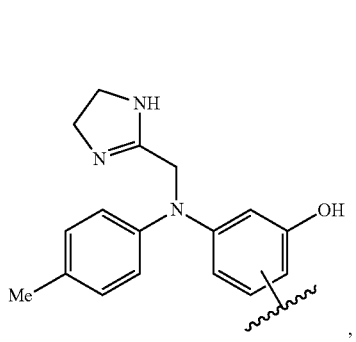 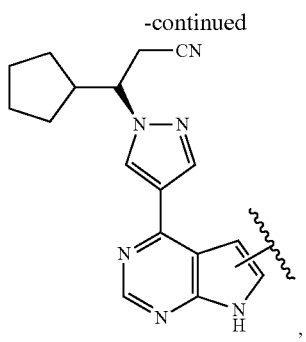 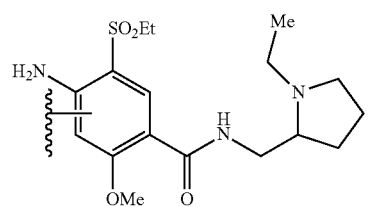
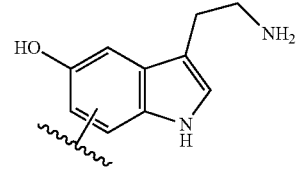 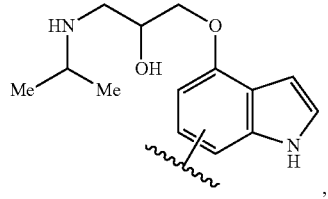
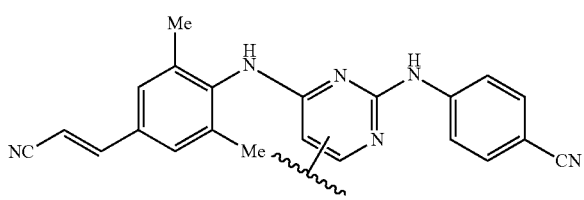 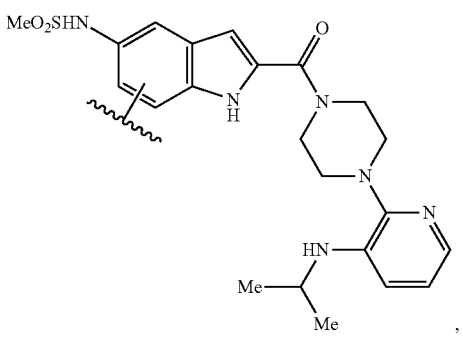
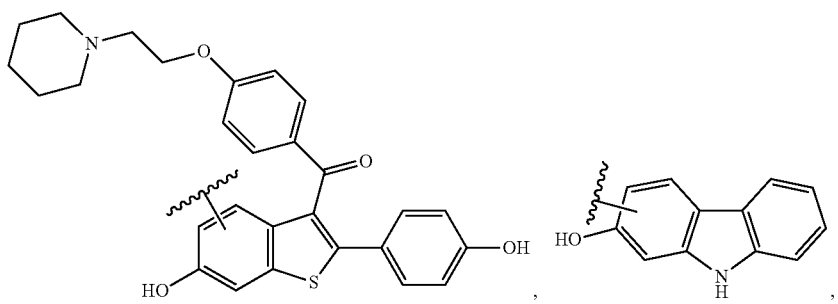
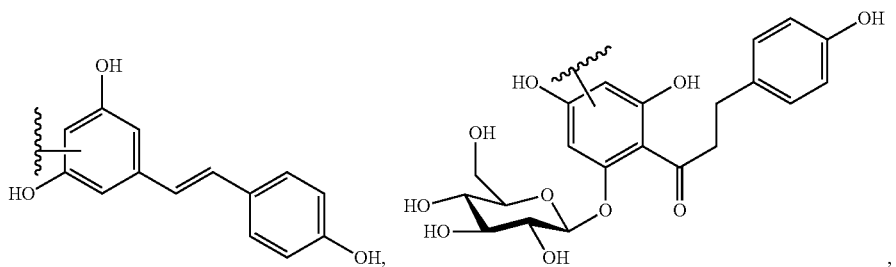

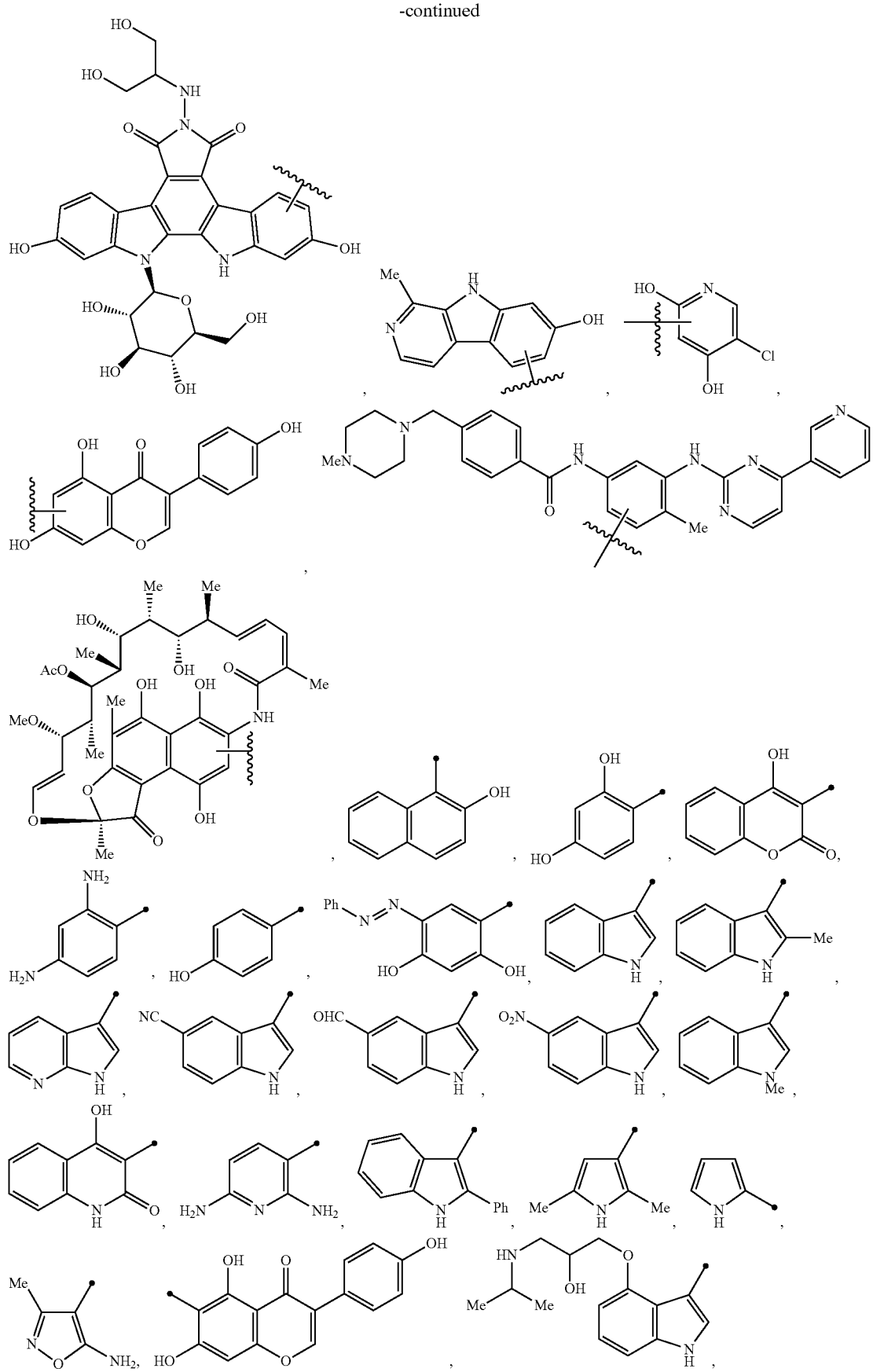

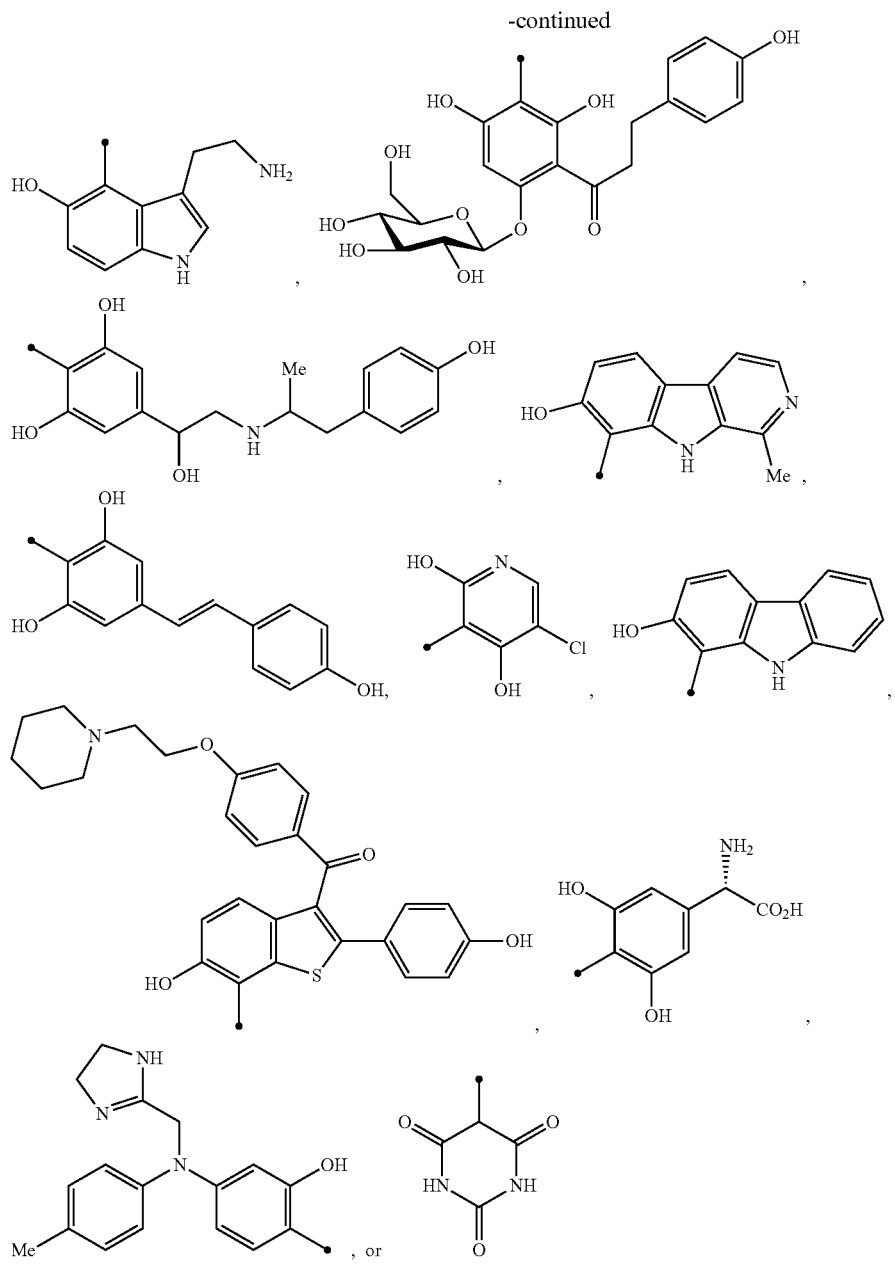
or a regioisomer or stereoisomer thereof. In certain embodiments,
B^B
is any of the aforementioned moieties, wherein the moiety is further substituted.
In certain embodiments, the invention relates to any one of the aforementioned compounds, wherein
B^B is
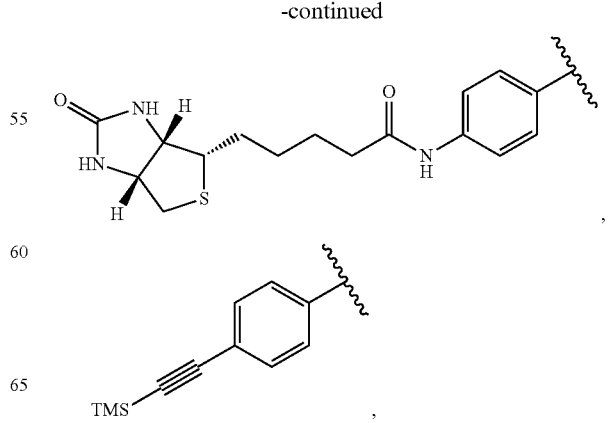

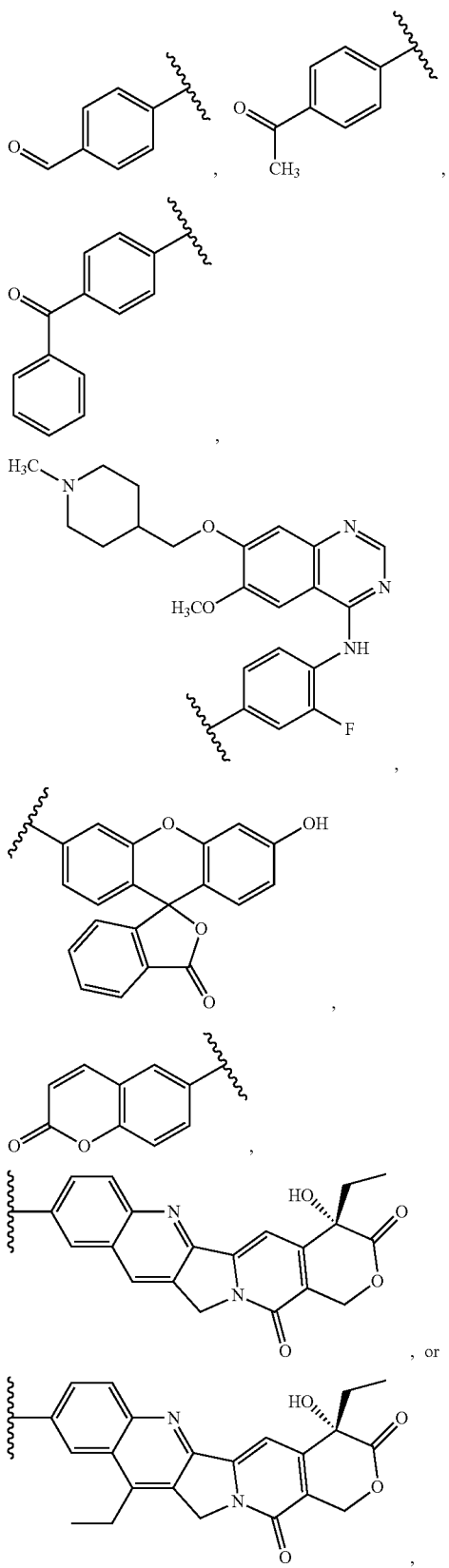

or a regioisomer or stereoisomer thereof. In certain embodiments, $B^B$ is any of the aforementioned moieties, wherein the moiety is further substituted.

In certain embodiments, the invention relates to any one of the aforementioned compounds, wherein the compound is a compound comprising substructure I; and none of $A^1$ and $A^5$ comprises selenocysteine.

In certain embodiments, the invention relates to any one of the aforementioned compounds, wherein the compound is a compound comprising substructure I; and one or more of $A^1$ and $A^5$ comprises arginine, cysteine, histidine, lysine, aspartic acid, glutamic acid, serine, threonine, asparagine, glutamine, glycine, proline, alanine, valine, isoleucine, leucine, methionine, phenylalanine, tyrosine, or tryptophan.

In certain embodiments, the invention relates to any one of the aforementioned compounds, wherein the compound is a compound comprising substructure II; and none of $A^1$ and $A^5$ comprises cysteine.

In certain embodiments, the invention relates to any one of the aforementioned compounds, wherein the compound is a compound comprising substructure II; and one or more of $A^1$ and $A^5$ comprises arginine, histidine, lysine, aspartic acid, glutamic acid, serine, threonine, asparagine, glutamine, glycine, proline, alanine, valine, isoleucine, leucine, methionine, phenylalanine, tyrosine, or tryptophan.

In certain embodiments, the invention relates to any one of the aforementioned compounds, wherein $A^1$ is an amine protecting group selected from the group consisting of an N,O-acetal, allyloxycarbonyl (Aloe), benzyl (Bn), benzyloxycarbonyl (Cbz), benzyloxymethyl (BOM), t-butoxycarbonyl (Boc), t-butyldimethylsilyl (TBDMS), t-butyldiphenylsilyl (TBDPS), diphenylmethyl, diphenylmethylenc, cthoxycarbonyl, 9-fluorenylmethoxycarbonyl (Fmoc), p-methoxybenzyl (PMB), methoxycarbonyl, methoxymethyl (MOM), p-methoxyphenyl (PMP), p-nitrocinnamyloxycarbonyl (Noc), tosyl (Ts), 2-tosylethoxycarbonyl (Tsoc), 2,2,2-trichloroethoxycarbonyl (Troc), trifluoroacetyl, triisopropylsilyl (TIPS), trimethylsilyl (TMS), 2-(trimethylsilyl)ethoxycarbonyl (Teoc), 2-(trimethylsilyl)ethoxymethyl (SEM), or trityl (Tr).

In certain embodiments, the invention relates to any one of the aforementioned compounds, wherein $A^5$ is —O(carboxylate protecting group), wherein the carboxylate protecting group is selected from the group consisting of allyl, benzyl, benzyloxymethyl (BOM), t-Bu, t-butyldimethylsilyl (TBDMS), t-butyldiphenylsilyl (TBDPS), diphenylmethyl, 9-fluorenylmethyl (Fm), 2-methoxyethoxymethyl (MEM), methoxymethyl (MOM), p-nitrobenzyl (PNB), an ester, a 1,3-oxazoline, pivaloyloxymethyl (Pom), 2-tosylethyl (TSE), 2,2,2-trichloroethyl (TCE), triethylsilyl (TES), trimethylsilyl (TMS), 2-(trimethylsilyl)ethoxymethyl (SEM), or 2-(trimethylsilyl)ethyl (TMSE).

In certain embodiments, the invention relates to any one of the aforementioned compounds, wherein $A^1$ or $A^5$ is an antimicrobial peptide, such as a compound comprising magainin/pexiganan (a 22-amino acid linear peptide that may be isolated from the skin of the African clawed frog (*Xenopus laevis*)), omiganan (a cationic peptide that may be derived from indolicidin), OP-145 (a 24-mer peptide that may be derived from LL-37 that may bind to lipopolysaccharides or lipoteichoic acid), novexatin (a cyclic cationic peptide of 1093 Da), LTX-109 (Lytixar, a membrane-degrading peptide), NVB302 (a class B lantibiotic), MU1140

(a lantibiotic), arenicin (a 21-mer that is rich in arginine and hydrophobic amino acids), avidocin (a R-type bacteriocin that may be derived from *Pseudomanas aeruginosa*), purocin (a R-type bacteriocin that may be derived from *Pseudomanas aeruginosa*), IMX924 (a 5-mer with defense regulation capabilities), GIGKFLHSAKKFGKAFVGEIMNS (SEQ ID NO: 1), or GIKKFLKKAGKFGKAF (SEQ ID NO: 2). In certain embodiments, $A^1$ or $A^5$ is an antimicrobial peptide described in Fox, J. L. *Nature Biotechnology* 2013, 31, 5, 379 or Arnusch, C. J. et al. *PLoS ONE* 2012, 7(6), e39768.

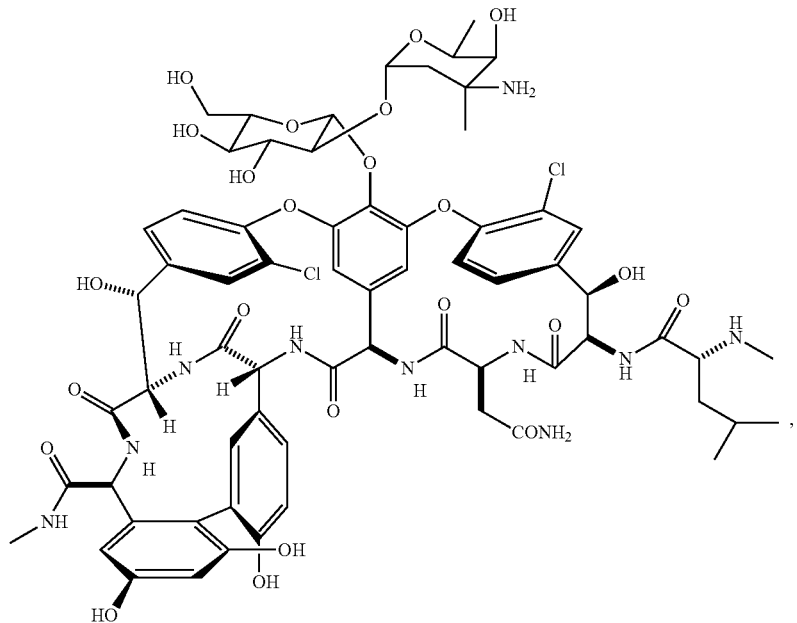

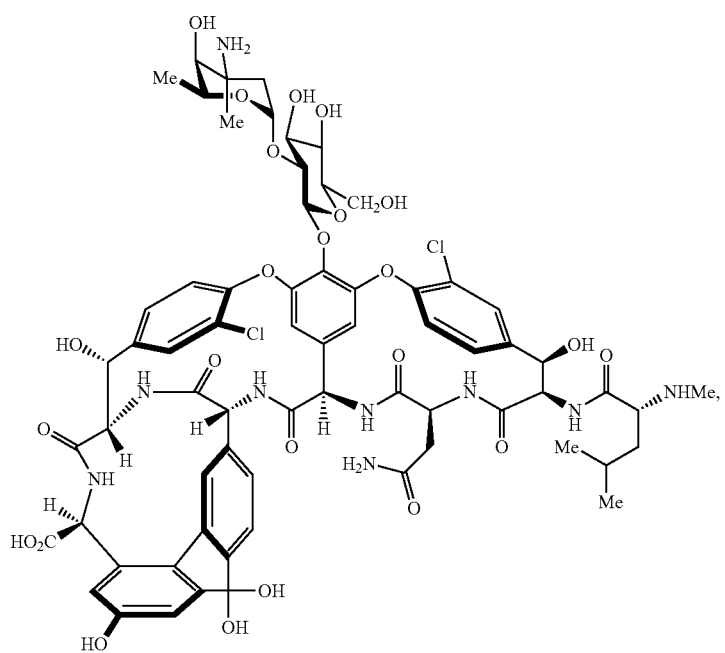

In certain embodiments, the invention relates to any one of the aforementioned compounds, wherein R is H.

In certain embodiments, the invention relates to any one of the aforementioned compounds, wherein x is 1, 2, or 3. In certain embodiments, the invention relates to any one of the aforementioned compounds, wherein x is 1.

In certain embodiments, the invention relates to any one of the compounds described herein.

Exemplary Stapled or Macrocyclized Compounds

In certain embodiments, the invention relates to a compound comprising substructure III:

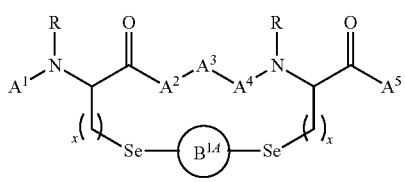

III wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is a substituted or unsubstituted aryl or heteroaryl diradical; and

R is H or alkyl.

In certain embodiments, the invention relates to a compound comprising substructure IV:

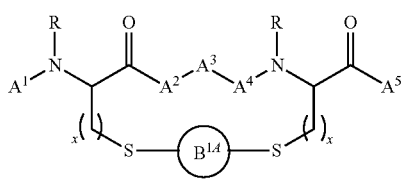

IV wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is a substituted or unsubstituted aryl or heteroaryl diradical, provided

is not a perfluoroaryl diradical; and

R is H or alkyl.

In certain embodiments, the invention relates to a compound comprising substructure V or substructure VII:

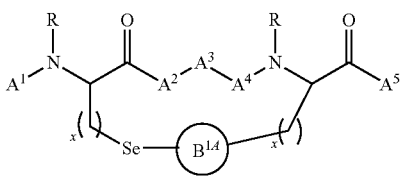

V

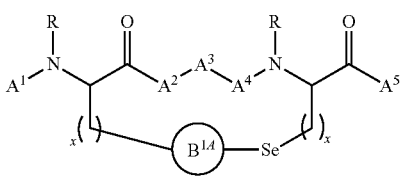

VII wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is a substituted or unsubstituted aryl or heteroaryl diradical; and

R is H or alkyl.

In certain embodiments, the invention relates to a compound comprising substructure VI or substructure VIII:

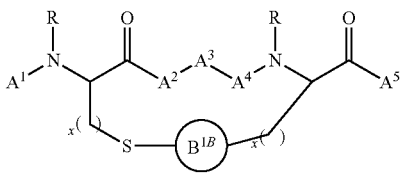

VI

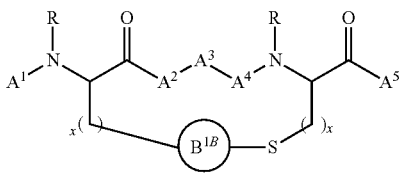

VIII wherein, independently for each occurrence,

A¹ is H, an amine protecting group, a natural or unnatural amino acid, a peptide, an oligopeptide, a polypeptide, or a protein;

A², A³, and A⁴ are selected from the group consisting of a natural amino acid, an unnatural amino acid, and a plurality of natural amino acids or unnatural amino acids;

A⁵ is OH, —O(carboxylate protecting group), a natural or unnatural amino acid, a peptide, an oligopeptide, a polypeptide, or a protein;

x is 0, 1, 2, 3, 4, 5, or 6;

$\text{B}^{1B}$ is a substituted or unsubstituted aryl or heteroaryl diradical, provided $\text{B}^{1B}$ is not a perfluoroaryl diradical; and R is H or alkyl.

In certain embodiments, the invention relates to any one of the aforementioned compounds, wherein the compound is depicted in the Figures.

In certain embodiments, the invention relates to any one of the aforementioned compounds, wherein A², A³, and A⁴ are natural or unnatural amino acids.

In certain embodiments, the invention relates to any one of the aforementioned compounds, wherein A² represents one natural or unnatural amino acid. In certain embodiments, the invention relates to any one of the aforementioned compounds, wherein A³ represents one natural or unnatural amino acid. In certain embodiments, the invention relates to any one of the aforementioned compounds, wherein A⁴ represents one natural or unnatural amino acid.

In certain embodiments, the invention relates to any one of the aforementioned compounds, wherein A² represents two natural or unnatural amino acids. In certain embodiments, the invention relates to any one of the aforementioned compounds, wherein A³ represents two natural or unnatural amino acids. In certain embodiments, the invention relates to any one of the aforementioned compounds, wherein A⁴ represents two natural or unnatural amino acids.

In certain embodiments, the invention relates to any one of the aforementioned compounds, wherein A² represents three natural or unnatural amino acids. In certain embodiments, the invention relates to any one of the aforementioned compounds, wherein A³ represents three natural or unnatural amino acids. In certain embodiments, the invention relates to any one of the aforementioned compounds, wherein A⁴ represents three natural or unnatural amino acids.

In certain embodiments, the invention relates to any one of the aforementioned compounds, wherein the compound is a compound comprising substructure III, V, or VII; and none of A¹, A², A³, A⁴, and A⁵ comprises selenocysteine.

In certain embodiments, the invention relates to any one of the aforementioned compounds, wherein the compound is a compound comprising substructure III, V, or VII; and one or more of A¹, A², A³, A⁴, and A⁵ comprises arginine, cysteine, histidine, lysine, aspartic acid, glutamic acid, serine, threonine, asparagine, glutamine, glycine, proline, alanine, valine, isoleucine, leucine, methionine, phenylalanine, tyrosine, or tryptophan.

In certain embodiments, the invention relates to any one of the aforementioned compounds, wherein the compound is a compound comprising substructure IV, VI, or VIII; and none of A¹, A², A³, A⁴, and A⁵ comprises cysteine.

In certain embodiments, the invention relates to any one of the aforementioned compounds, wherein the compound is a compound comprising substructure IV, VI, or VIII; and one or more of A¹, A², A³, A⁴, and A⁵ comprises arginine, histidine, lysine, aspartic acid, glutamic acid, serine, threonine, asparagine, glutamine, glycine, proline, alanine, valine, isoleucine, leucine, methionine, phenylalanine, tyrosine, or tryptophan.

In certain embodiments, the invention relates to any one of the aforementioned compounds, wherein A¹ is an amine protecting group selected from the group consisting of an N,O-acetal, allyloxycarbonyl (Aloc), benzyl (Bn), benzyloxycarbonyl (Cbz), benzyloxymethyl (BOM), t-butoxycarbonyl (Boc), t-butyldimethylsilyl (TBDMS), t-butyldiphenylsilyl (TBDPS), diphenylmethyl, diphenylmethylene, ethoxycarbonyl, 9-fluorenylmethoxycarbonyl (Fmoc), p-methoxybenzyl (PMB), methoxycarbonyl, methoxymethyl (MOM), p-methoxyphenyl (PMP), p-nitrocinnamyloxycarbonyl (Noc), tosyl (Ts), 2-tosylethoxycarbonyl (Tsoc), 2,2,2-trichloroethoxycarbonyl (Troc), trifluoroacetyl, triisopropylsilyl (TIPS), trimethylsilyl (TMS), 2-(trimethylsilyl)ethoxycarbonyl (Teoc), 2-(trimethylsilyl)ethoxymethyl (SEM), or trityl (Tr).

In certain embodiments, the invention relates to any one of the aforementioned compounds, wherein A⁵ is —O(carboxylate protecting group); and the carboxylate protecting group is selected from the group consisting of allyl, benzyl, benzyloxymethyl (BOM), t-Bu, t-butyldimethylsilyl (TBDMS), 1-butyldiphenylsilyl (TBDPS), diphenylmethyl, 9-fluorenylmethyl (Fm), 2-methoxycthoxymethyl (MEM), methoxymethyl (MOM), p-nitrobenzyl (PNB), an ester, a 1,3-oxazoline, pivaloyloxymethyl (Pom), 2-tosylethyl (TSE), 2,2,2-trichloroethyl (TCE), triethylsilyl (TES), trimethylsilyl (TMS), 2-(trimethylsilyl)ethoxymethyl (SEM), or 2-(trimethylsilyl)ethyl (TMSE).

In certain embodiments, the invention relates to any one of the aforementioned compounds, wherein A¹ or A⁵ is an antimicrobial peptide, such as a compound comprising magainin/pexiganan (a 22-amino acid linear peptide that may be isolated from the skin of the African clawed frog (*Xenopus laevis*)), omiganan (a cationic peptide that may be derived from indolicidin), OP-145 (a 24-mer peptide that may be derived from LL-37 that may bind to lipopolysaccharides or lipoteichoic acid), novexatin (a cyclic cationic peptide of 1093 Da), LTX-109 (Lytixar, a membrane-degrading peptide), NVB302 (a class B lantibiotic), MU1140 (a lantibiotic), arenicin (a 21-mer that is rich in arginine and hydrophobic amino acids), avidocin (a R-type bacteriocin that may be derived from *Pseudomanas aeruginosa*), purocin (a R-type bacteriocin that may be derived from *Pseudomanas aeruginosa*), IMX924 (a 5-mer with defense regulation capabilities),

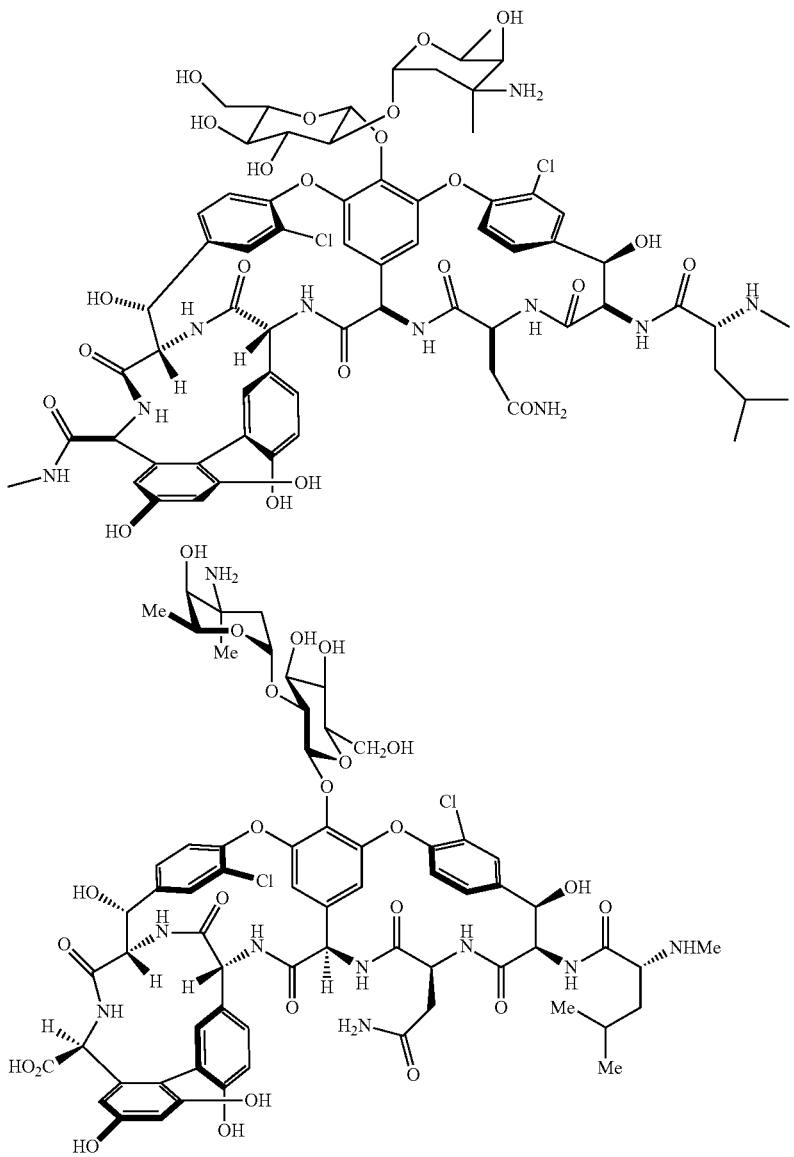

GIGKFLHSAKKFGKAFVGEIMNS (SEQ ID NO: 1), or GIKKFLKKAGKFGKAF (SEQ ID NO: 2). In certain embodiments, $A^1$ or $A^5$ is an antimicrobial peptide described in Fox, J. L. *Nature Biotechnology* 2013, 31, 5, 379 or Arnusch, C. J. et al. *PLoS ONE* 2012, 7(6), e39768.

In certain embodiments, the invention relates to any one of the aforementioned compounds, wherein (B1,4)

is a substituted aryl diradical. In certain embodiments, the invention relates to any one of the aforementioned compounds, wherein (B1,4)

is a substituted phenyl diradical.

In certain embodiments, the invention relates to any one of the aforementioned compounds, wherein (B1,4)

is an unsubstituted aryl diradical.

In certain embodiments, the invention relates to any one of the aforementioned compounds, wherein

is a substituted heteroaryl diradical. In certain embodiments, the invention relates to any one of the aforementioned compounds, wherein

is a substituted indole, pyrazolo, thiophene, pyrimidine, benzofuran, or isoxazole diradical.

In certain embodiments, the invention relates to any one of the aforementioned compounds, wherein

is an unsubstituted heteroaryl diradical. In certain embodiments, the invention relates to any one of the aforementioned compounds, wherein

is an unsubstituted indole, pyrazolo, thiophene, pyrimidine, benzofuran, or isoxazole diradical.

In certain embodiments, the invention relates to any one of the aforementioned compounds, wherein

is a substituted aryl diradical. In certain embodiments, the invention relates to any one of the aforementioned compounds, wherein

is a substituted phenyl diradical.

In certain embodiments, the invention relates to any one of the aforementioned compounds, wherein

is 1,4-disubstituted phenylene, 1,4-disubstituted-2,5-dimethylphenylene, 1,3-disubstituted-5-fluorophenylene, 1,4-disubstituted-2,5-difluorophenylene, 1,4-disubstituted-2,5-bis(trifluoromethyl)phenylene, 4,4'-disubstituted-1,1'-biphenylene, 4,4'-disubstituted-oxy(1,1'-bisphenylene), or 4,4'-disubstituted-oxy(1,1'-bis(3-methylphenylene)).

In certain embodiments, the invention relates to any one of the aforementioned compounds, wherein

is an unsubstituted aryl diradical.

In certain embodiments, the invention relates to any one of the aforementioned compounds, wherein

is a substituted heteroaryl diradical. In certain embodiments, the invention relates to any one of the aforementioned compounds, wherein

is a substituted indole, pyrazolo, thiophene, pyrimidine, benzofuran, or isoxazole diradical.

In certain embodiments, the invention relates to any one of the aforementioned compounds, wherein

is an unsubstituted heteroaryl diradical. In certain embodiments, the invention relates to any one of the aforementioned compounds, wherein

is an unsubstituted indole, pyrazolo, thiophene, pyrimidine, benzofuran, or isoxazole diradical.

In certain embodiments, the invention relates to any one of the aforementioned compounds, wherein R is H.

In certain embodiments, the invention relates to any one of the aforementioned compounds, wherein x is 1, 2, or 3. In certain embodiments, the invention relates to any one of the aforementioned compounds, wherein x is 1.

In certain embodiments, the invention relates to any one of the compounds described herein.

Exemplary Conjugated Compounds

In certain embodiments, the invention relates to a hybrid composition, wherein the hybrid composition comprises a linker, any one of the aforementioned compounds, and a detectable moiety; and the linker links the compound to the detectable moiety.

In certain embodiments, the invention relates to any one of the aforementioned hybrid compositions, wherein the detectable moiety is a fluorescent moiety, a dye moiety, a radionuclide, or an MRI contrast agent.

In certain embodiments, the invention relates to a hybrid composition, wherein the hybrid composition comprises a linker, any one of the aforementioned compounds, and a biomolecule; and the linker links the compound to the biomolecule.

In certain embodiments, the invention relates to any one of the aforementioned hybrid compositions, wherein the biomolecule is a protein.

In certain embodiments, the invention relates to any one of the aforementioned hybrid compositions, wherein the biomolecule is DNA or RNA.

In certain embodiments, the invention relates to any one of the aforementioned hybrid compositions, wherein the biomolecule is siRNA.

In certain embodiments, the invention relates to any one of the hybrid compositions described herein.

Exemplary Peptides, Oligopeptides, Polypeptides, and Proteins

In certain embodiments, the invention relates to a peptide, an oligopeptide, a polypeptide, or a protein, wherein the peptide, oligopeptides, polypeptide, or protein comprises substructure I, substructure II, substructure III, substructure IV, substructure V, substructure VI, substructure VII, or substructure VIII.

In certain embodiments, the invention relates to a peptide, an oligopeptide, a polypeptide, or a protein, wherein the peptide, oligopeptides, polypeptide, or protein comprises a plurality of substructures selected from the group consisting of substructure I, substructure II, substructure III, substructure IV, substructure V, substructure VI, substructure VII, or substructure VIII.

In certain embodiments, the invention relates to any one of the peptides, oligopeptides, polypeptides, or proteins described herein.

Exemplary Affibodies

In certain embodiments, the invention relates to an affibody comprising substructure I, substructure II, substructure III, substructure IV, substructure V, substructure VI, substructure VII, or substructure VIII.

In certain embodiments, the invention relates to an affibody comprising a plurality of substructures selected from the group consisting of substructure I, substructure II, substructure III, substructure IV, substructure V, substructure VI, substructure VII, or substructure VIII.

As used herein the term "affibody" refers to a small protein composed of alpha helices. In certain embodiments, the affibody is engineered to bind a target protein or target peptide with high affinity. In certain embodiments, affibodies are antibody mimetics. In certain embodiments, affibodies lack disulfide bridges. In certain embodiments, the affibody comprises a three-helix bundle. In certain embodiments, the affibody has a molar mass of less than about 8 kDa. In certain embodiments, the affibody has a molar mass of about 6 kDa.

In certain embodiments, the invention relates to any one of the affibodies described herein.

Exemplary Methods

In certain embodiments, the invention relates to a method according to Scheme 1:

Scheme 1a

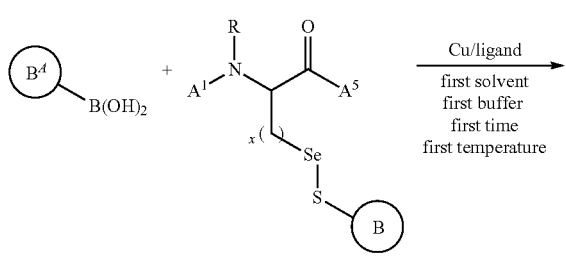

-continued

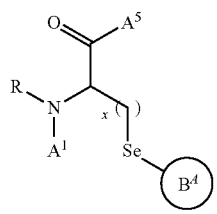

Scheme 1b

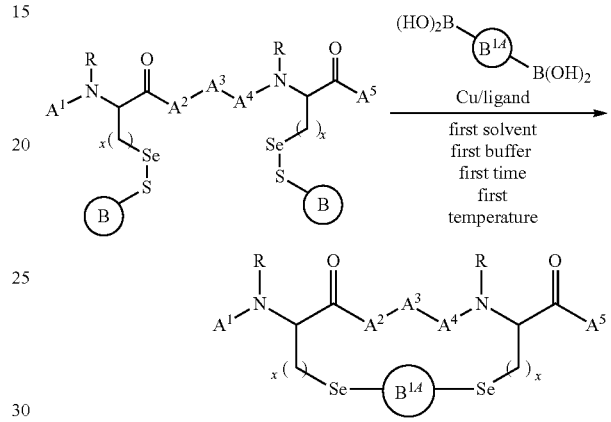

Scheme 1c

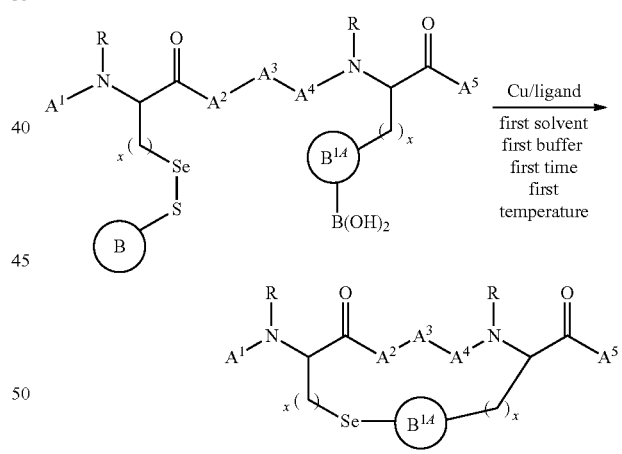

Scheme 1d

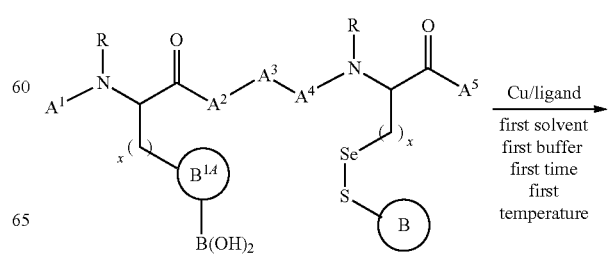

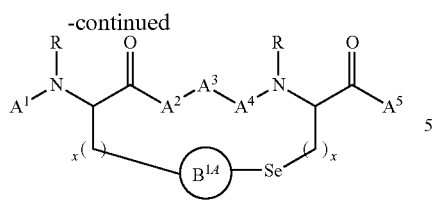

wherein, independently for each occurrence,

A$^1$ is H, an amine protecting group, a natural or unnatural amino acid, a peptide, an oligopeptide, a polypeptide, or a protein;

A$^2$, A$^3$, and A$^4$ are selected from the group consisting of a natural amino acid, an unnatural amino acid, and a plurality of natural amino acids or unnatural amino acids;

A$^5$ is OH, —O(carboxylate protecting group), a natural or unnatural amino acid, a peptide, an oligopeptide, a polypeptide, or a protein;

x is 0, 1, 2, 3, 4, 5, or 6;

is a substituted or unsubstituted aryl or heteroaryl radical;

is a substituted or unsubstituted aryl or heteroaryl diradical

is a heteroaromatic moiety substituted with an electron withdrawing group;

x is 0, 1, 2, 3, 4, 5, or 6; and

R is H or alkyl.

In certain embodiments, the invention relates to a method according to Scheme 2:

Scheme 2a

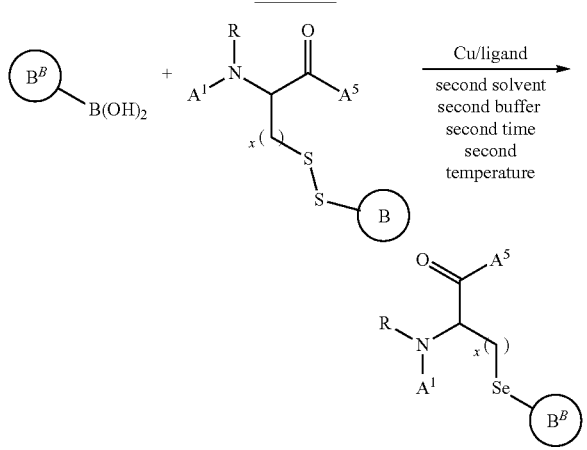

Scheme 2b

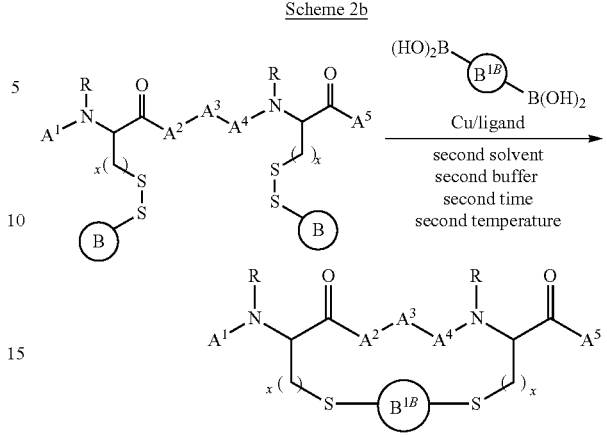

Scheme 2c

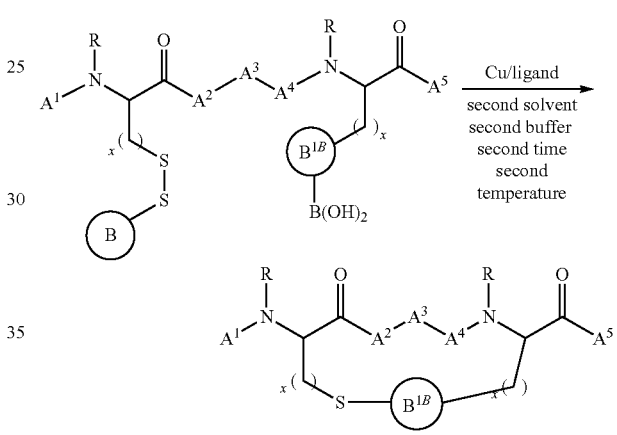

Scheme 2d

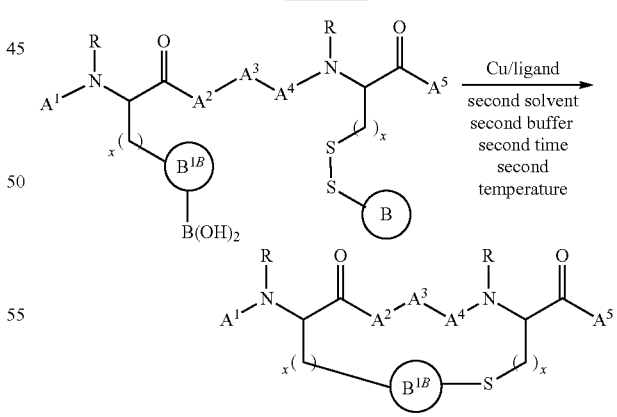

wherein, independently for each occurrence,

A$^1$ is H, an amine protecting group, a natural or unnatural amino acid, a peptide, an oligopeptide, a polypeptide, or a protein;

A$^2$, A$^3$, and A$^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is a substituted or unsubstituted aryl or heteroaryl radical, provided

is not a perfluoroaryl radical;

is a substituted or unsubstituted aryl or heteroaryl diradical, provided

is not a perfluoroaryl radical;

is a heteroaromatic moiety substituted with an electron withdrawing group;

x is 0, 1, 2, 3, 4, 5, or 6; and

R is H or alkyl.

In certain embodiments, the invention relates to a method according to Scheme 3:

Scheme 3a

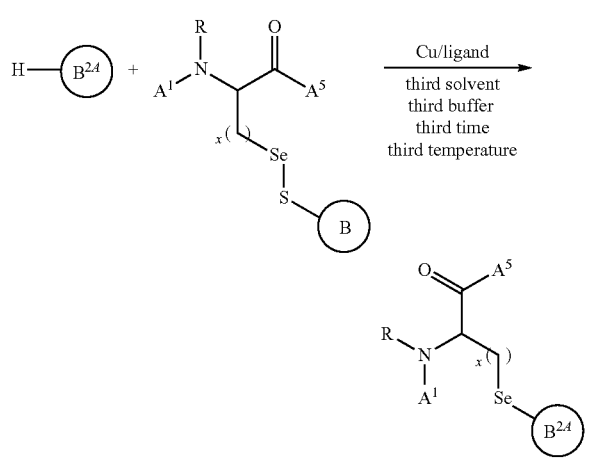

Scheme 3b

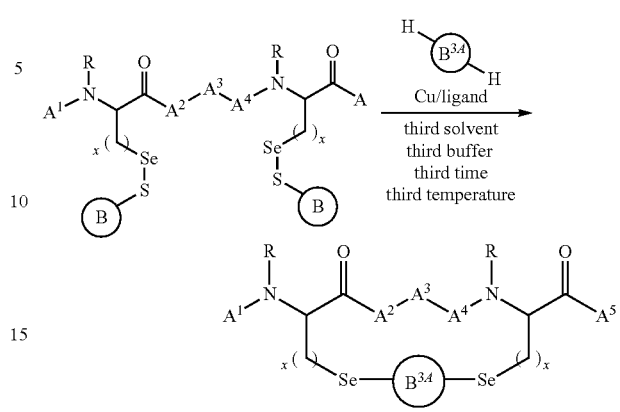

Scheme 3c

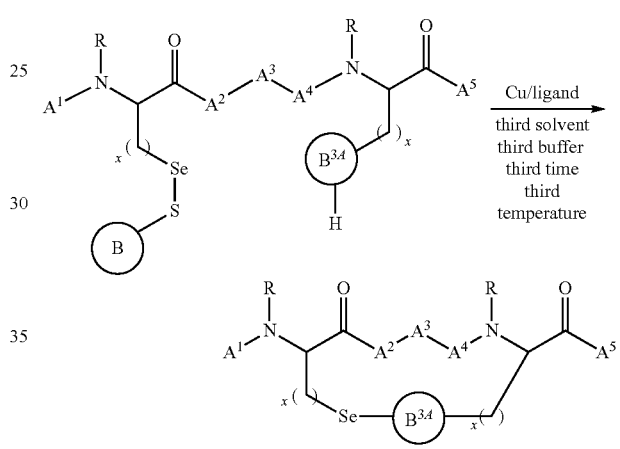

Scheme 3d

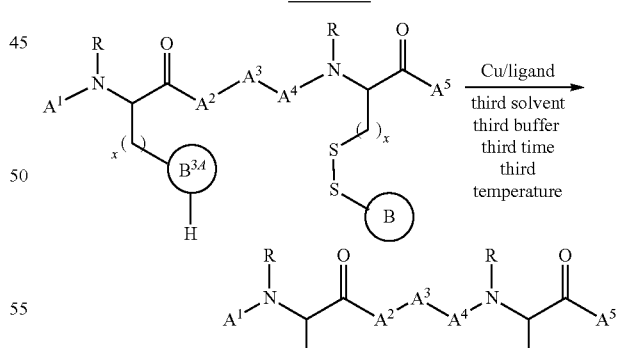

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

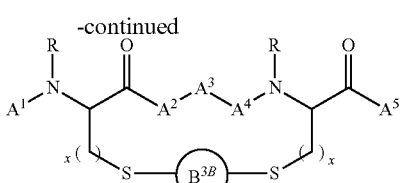

is an aryl or heteroaryl radical substituted with at least one electron donating group;

is a substituted aryl or heteroaryl diradical substituted with at least one electron donating group;

is a heteroaromatic moiety substituted with an electron withdrawing group;

x is 0, 1, 2, 3, 4, 5, or 6; and

R is H or alkyl.

In certain embodiments, the invention relates to a method according to Scheme 4:

Scheme 4a

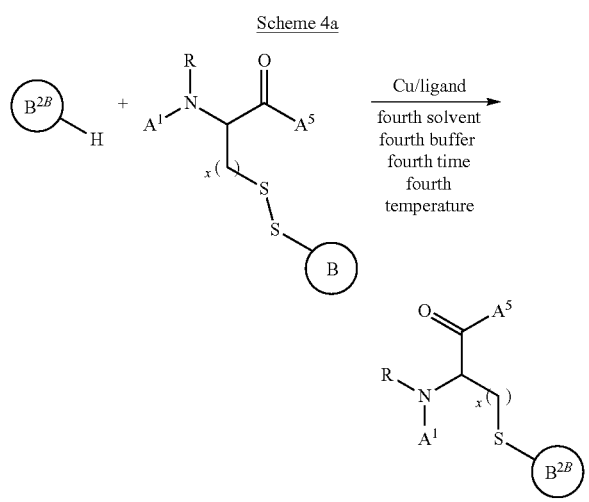

Scheme 4b

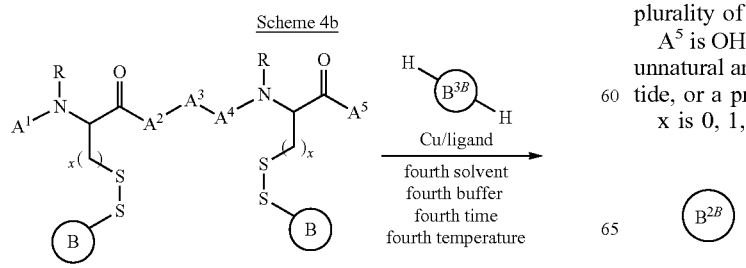

Scheme 4c

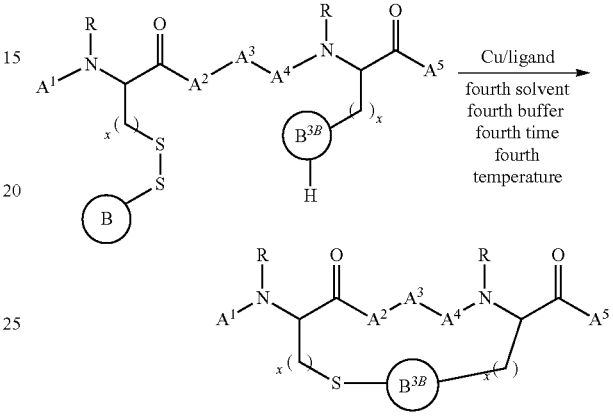

Scheme 4d

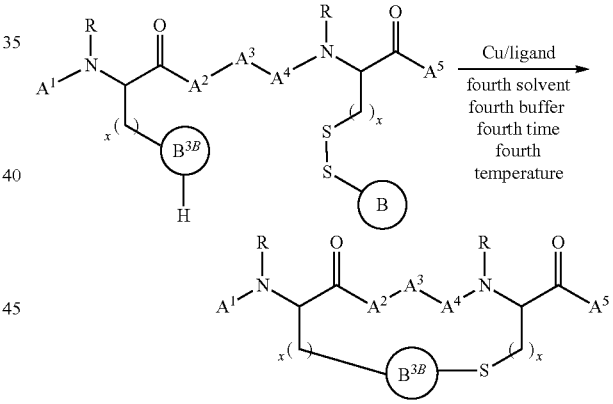

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is an aryl or heteroaryl radical substituted with at least one electron donating group, provided

is not a perfluoroaryl radical;

is an aryl or heteroaryl diradical substituted with at least one electron donating group, provided

is not a perfluoroaryl radical;

is a heteroaromatic moiety substituted with an electron withdrawing group;

x is 0, 1, 2, 3, 4, 5, or 6; and

R is H or alkyl.

In certain embodiments, the invention relates to a method according to Scheme 5:

Scheme 5a

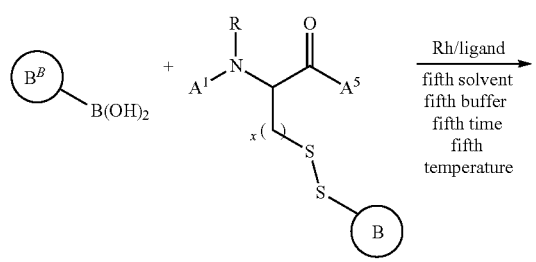

Scheme 5b

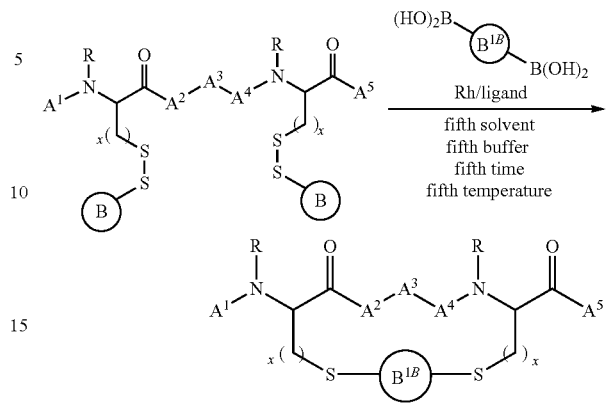

Scheme 5c

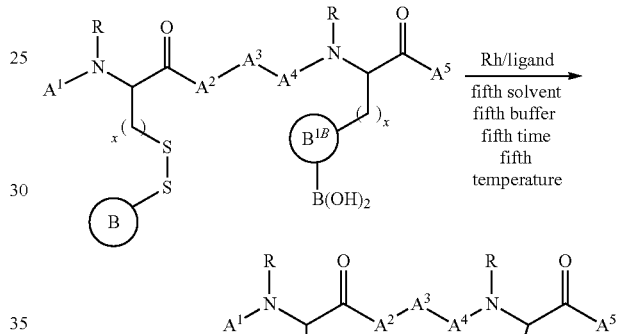

Scheme 5d

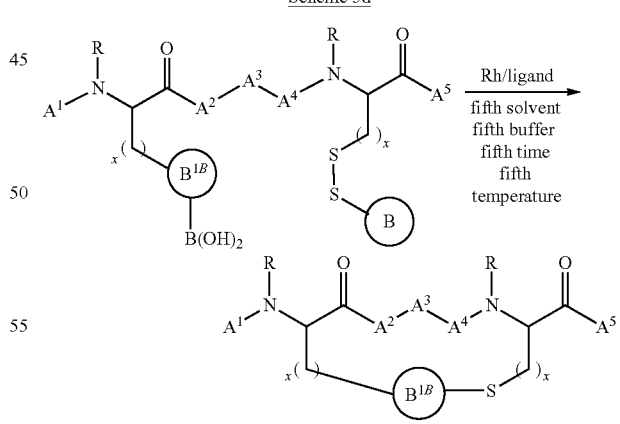

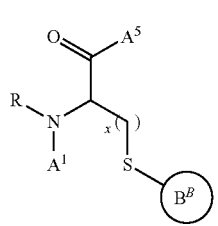

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is a substituted or unsubstituted aryl or heteroaryl radical, provided

is not a perfluoroaryl radical;

is a substituted or unsubstituted aryl or heteroaryl diradical, provided

is not a perfluoroaryl radical;

is a heteroaromatic moiety substituted with an electron withdrawing group;

x is 0, 1, 2, 3, 4, 5, or 6; and

R is H or alkyl.

In certain embodiments, the invention relates to a method according to Scheme 6:

Scheme 6a

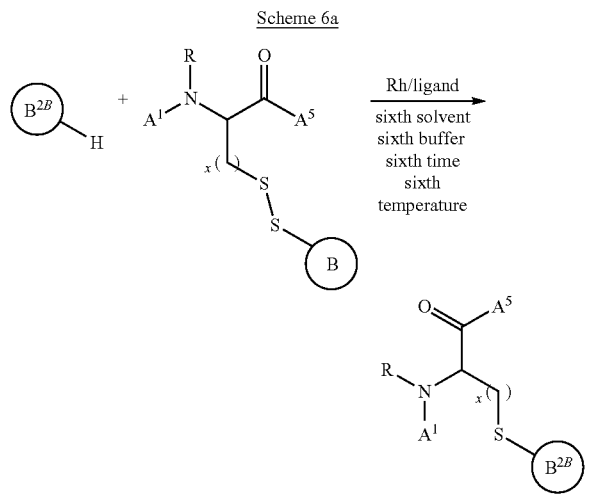

Scheme 6b

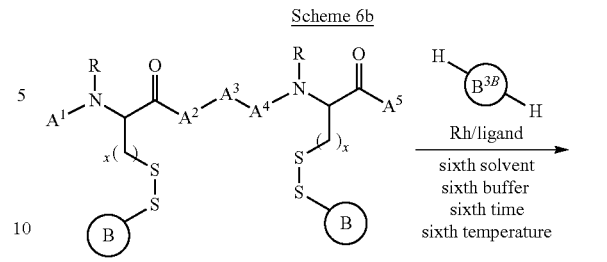

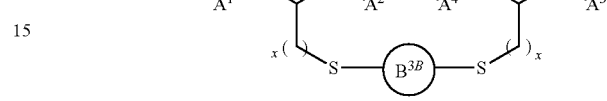

Scheme 6c

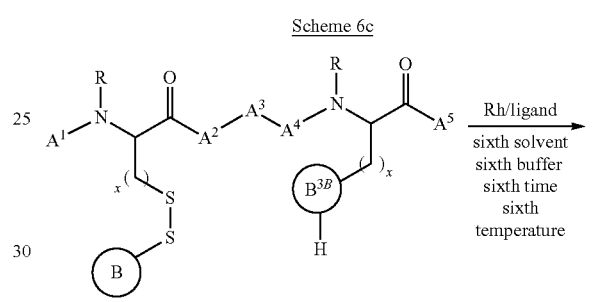

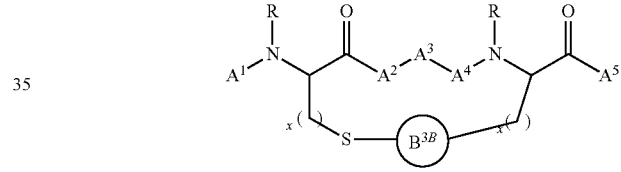

Scheme 6d

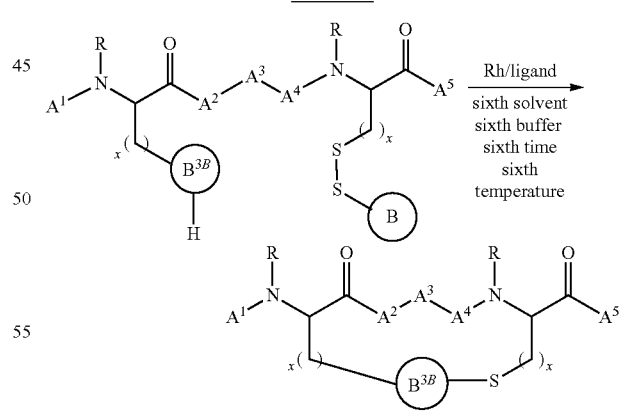

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is an aryl or heteroaryl radical substituted with at least one electron donating group, provided

is not a perfluoroaryl radical;

is an aryl or heteroaryl diradical substituted with at least one electron donating group, provided

is not a perfluoroaryl radical;

is a heteroaromatic moiety substituted with an electron withdrawing group;

x is 0, 1, 2, 3, 4, 5, or 6; and

R is H or alkyl.

In certain embodiments, the invention relates to a method according to Scheme 7:

Scheme 7a

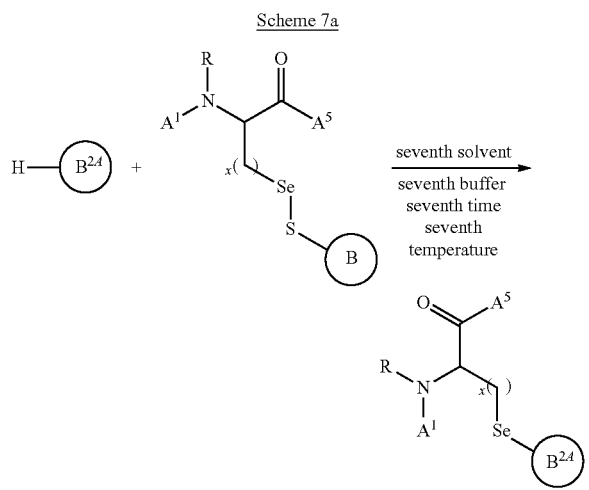

Scheme 7b

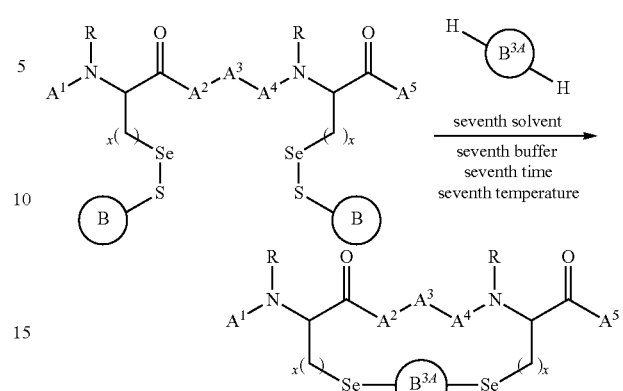

Scheme 7c

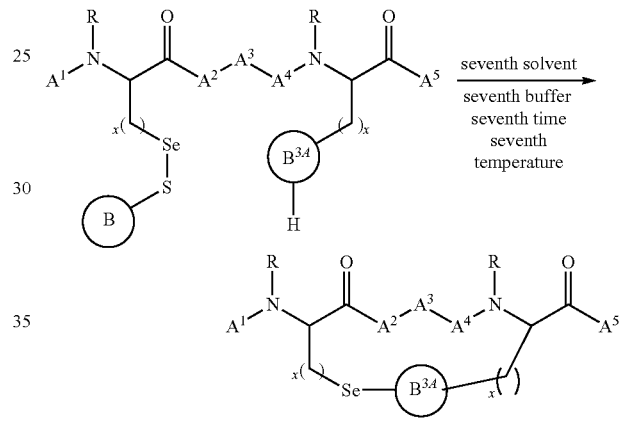

Scheme 7d

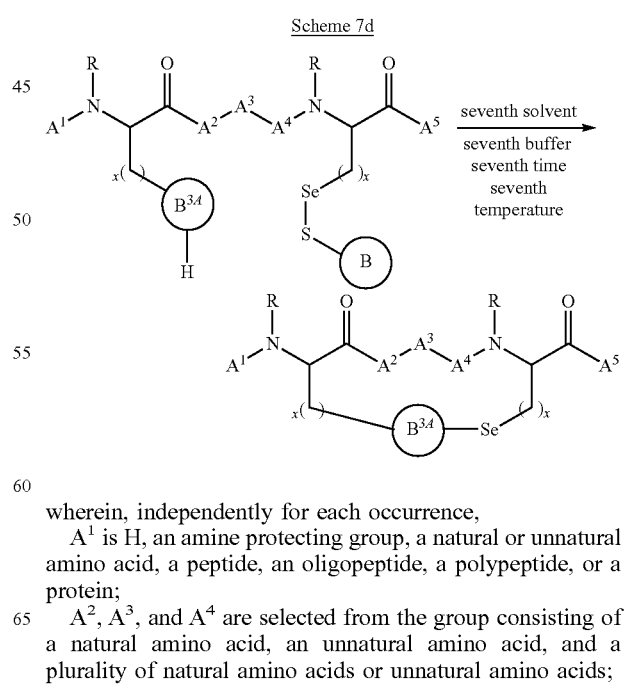

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is an aryl or heteroaryl radical substituted with at least one electron donating group;

is a substituted aryl or heteroaryl diradical substituted with at least one electron donating group;

is a heteroaromatic moiety substituted with an electron withdrawing group;

x is 0, 1, 2, 3, 4, 5, or 6; and

R is H or alkyl.

In certain embodiments, the invention relates to a method according to Scheme 8:

Scheme 8a

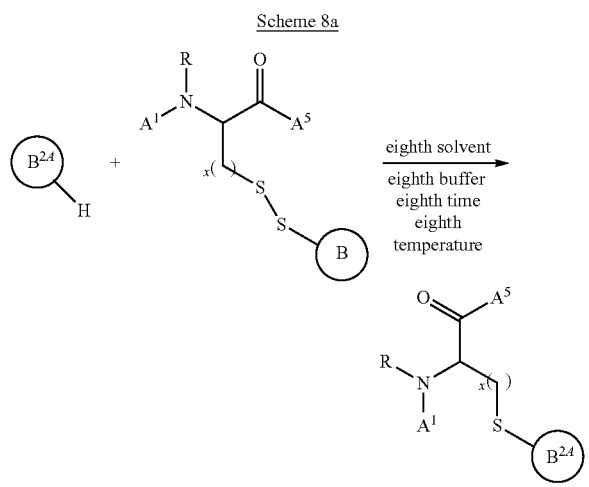

Scheme 8b

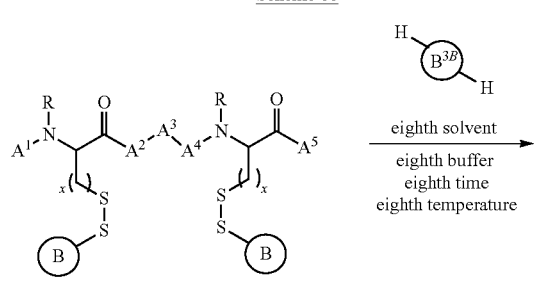

-continued

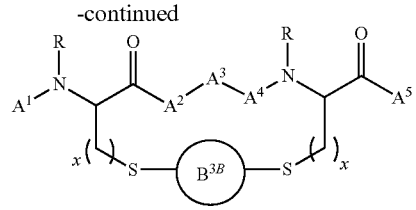

Scheme 8c

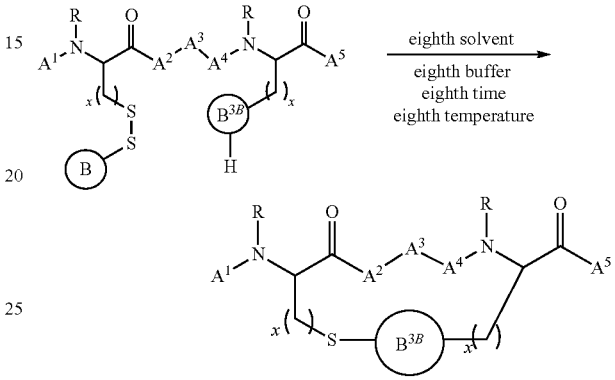

Scheme 8d

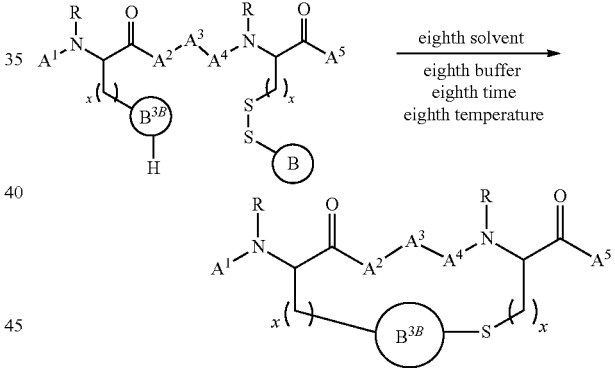

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

x is 0, 1, 2, 3, 4, 5, or 6;

is an aryl or heteroaryl radical substituted with at least one electron donating group, provided

is not a perfluoroaryl radical;

is an aryl or heteroaryl diradical substituted with at least one electron donating group, provided

is not a perfluoroaryl radical;

is a heteroaromatic moiety substituted with an electron withdrawing group;
x is 0, 1, 2, 3, 4, 5, or 6; and
R is H or alkyl.

In certain embodiments, the invention relates to any one of the aforementioned methods, wherein the product is a hybrid biopolymer.

In certain embodiments, the invention relates to any one of the aforementioned methods, wherein

is a substituted aryl radical. In certain embodiments, the invention relates to any one of the aforementioned methods, wherein

is a substituted phenyl radical.

In certain embodiments, the invention relates to any one of the aforementioned methods, wherein

is an unsubstituted aryl radical.

In certain embodiments, the invention relates to any one of the aforementioned methods, wherein

is a substituted heteroaryl radical. In certain embodiments, the invention relates to any one of the aforementioned methods, wherein

is a substituted indole, pyrazolo, thiophene, pyrimidine, benzofuran, or isoxazole radical.

In certain embodiments, the invention relates to any one of the aforementioned methods, wherein

is an unsubstituted heteroaryl radical. In certain embodiments, the invention relates to any one of the aforementioned methods, wherein

is an unsubstituted indole, pyrazolo, thiophene, pyrimidine, benzofuran, or isoxazole radical.

In certain embodiments, the invention relates to any one of the aforementioned methods, wherein

81
-continued
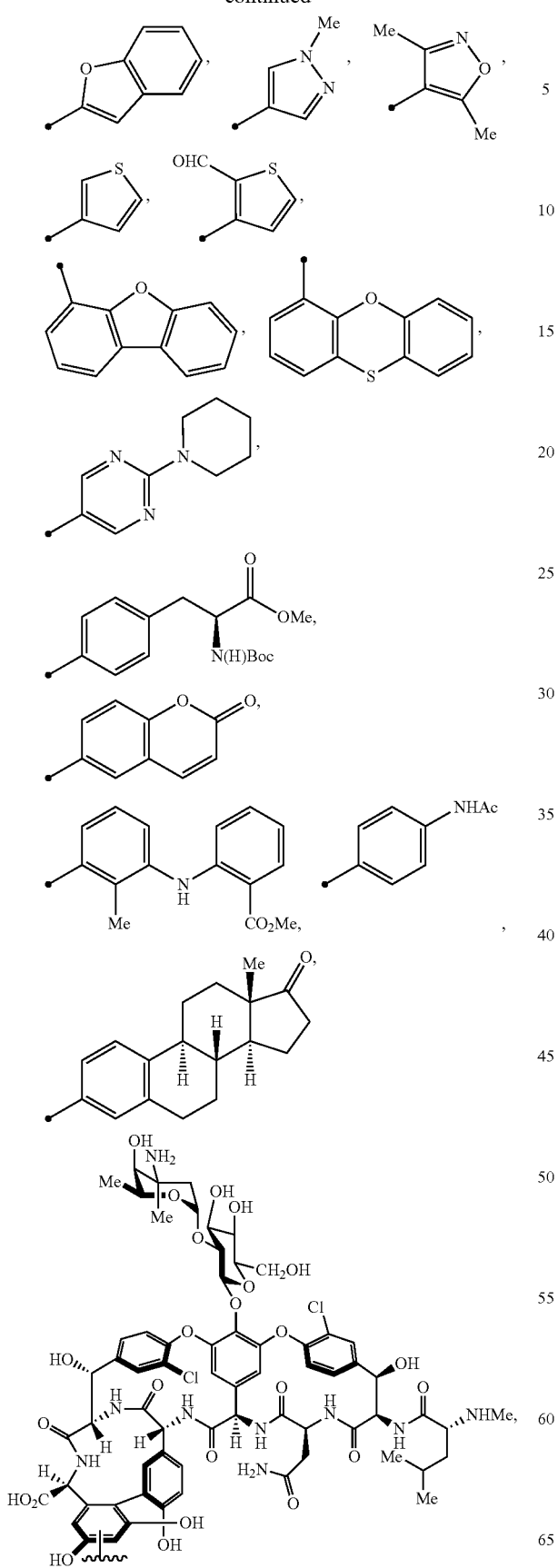
82
-continued
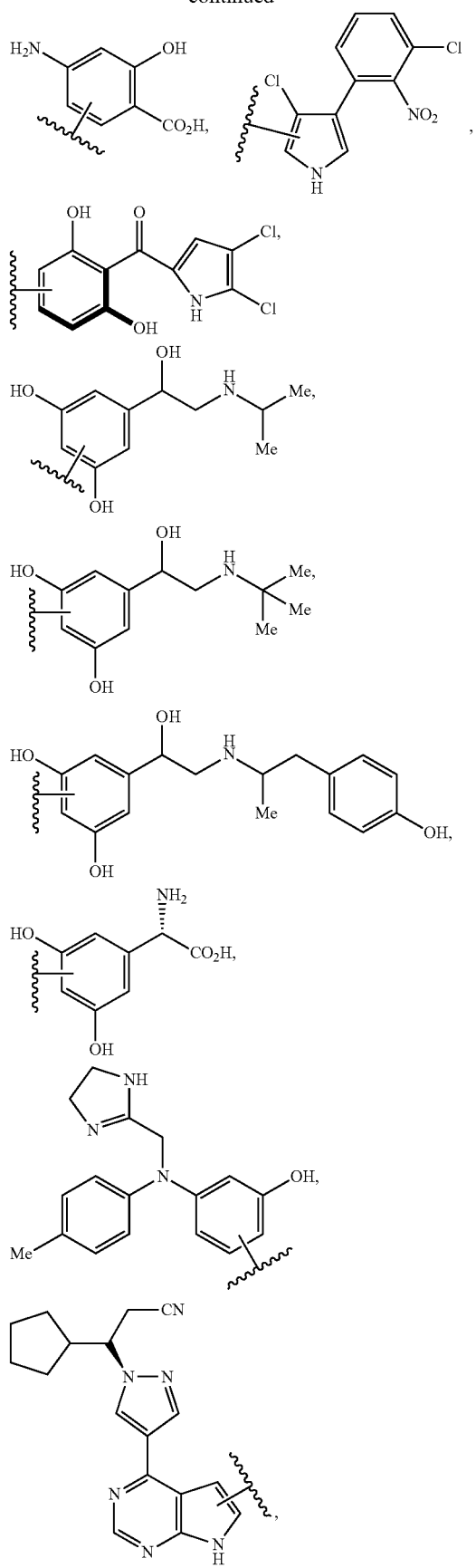

-continued
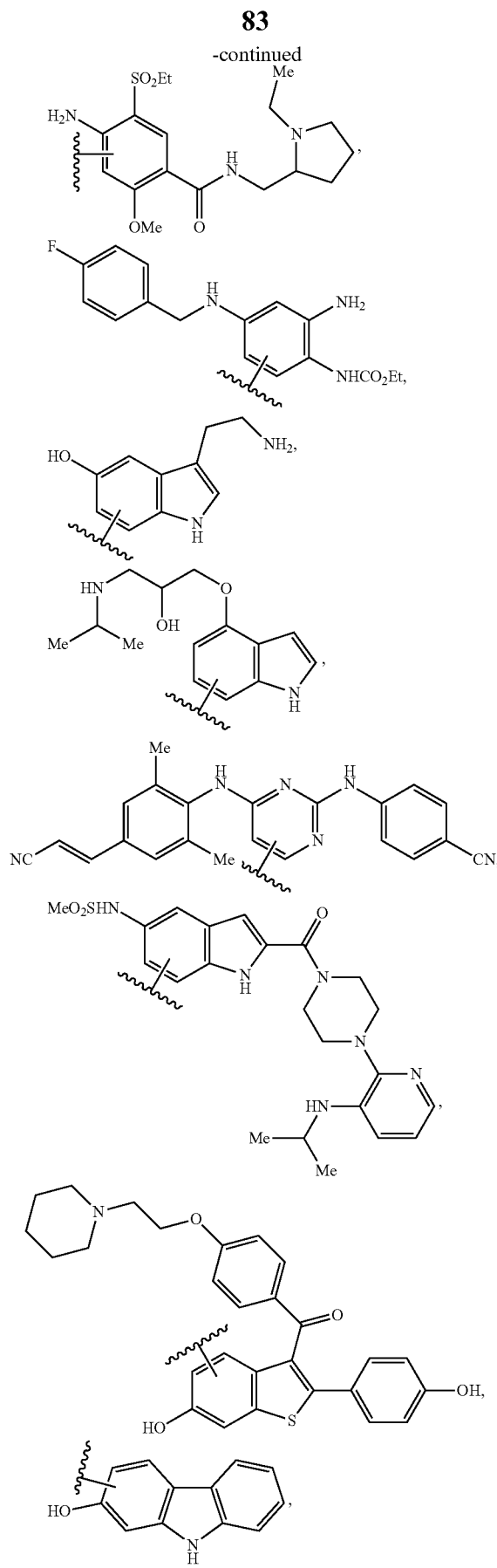
-continued
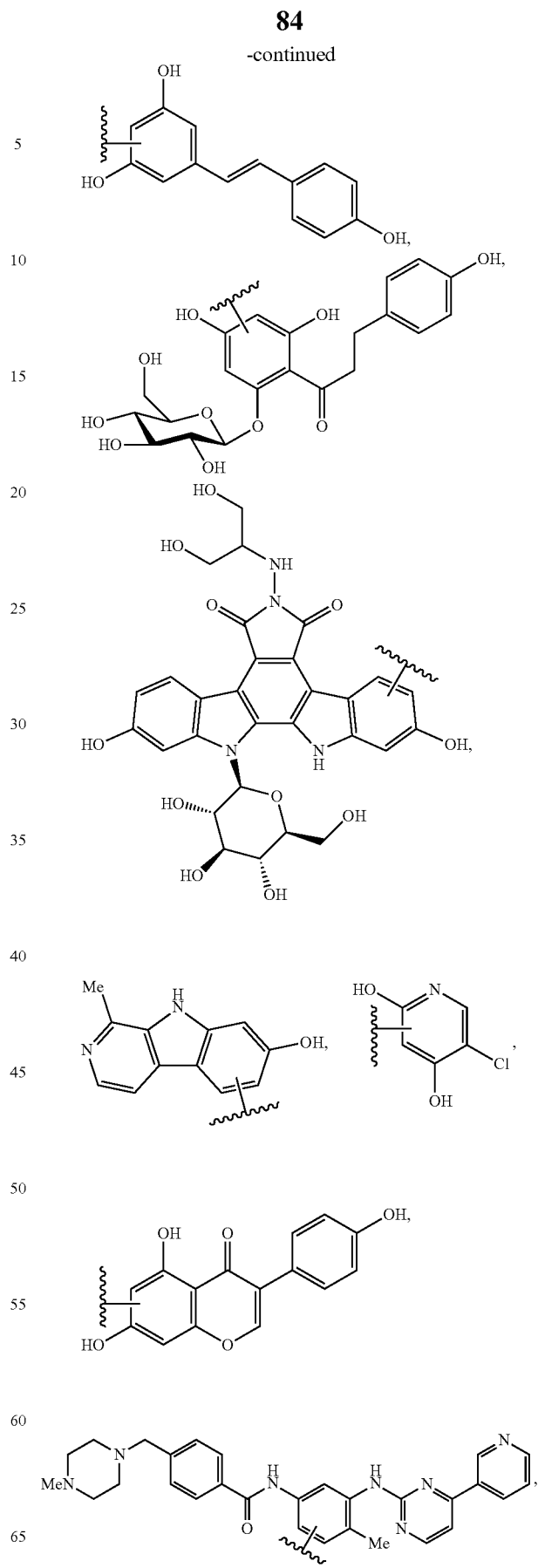

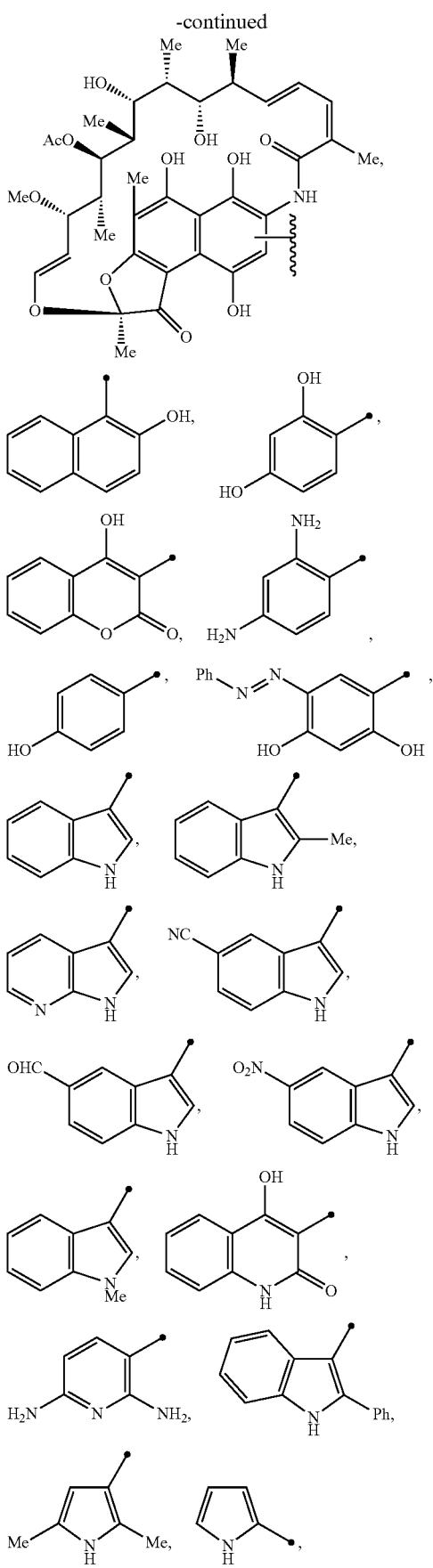
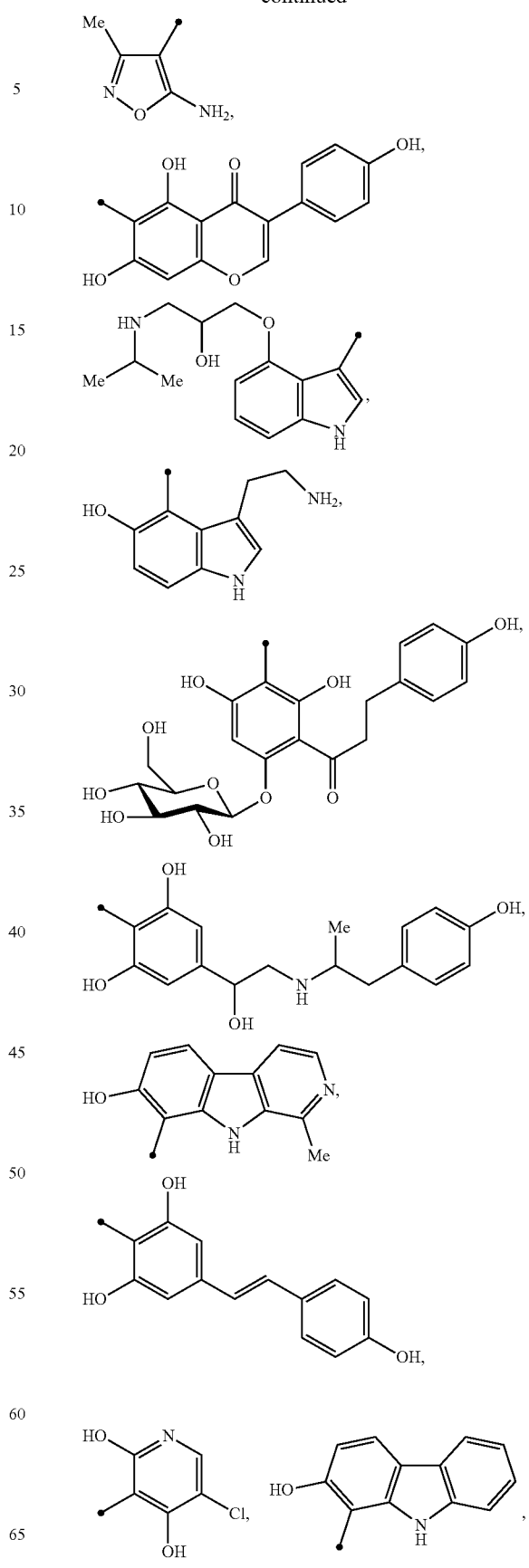

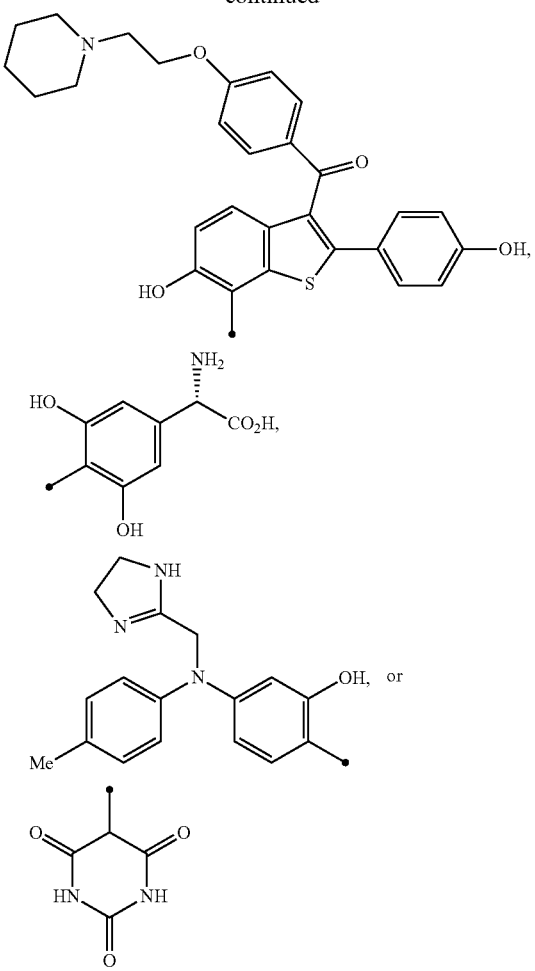

or a regioisomer or stereoisomer thereof. In certain embodiments,

B^A is any of the aforementioned moieties, wherein the moiety is further substituted.

In certain embodiments, the invention relates to any one of the aforementioned methods, wherein

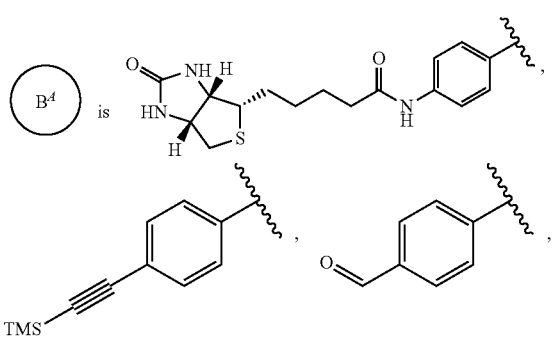

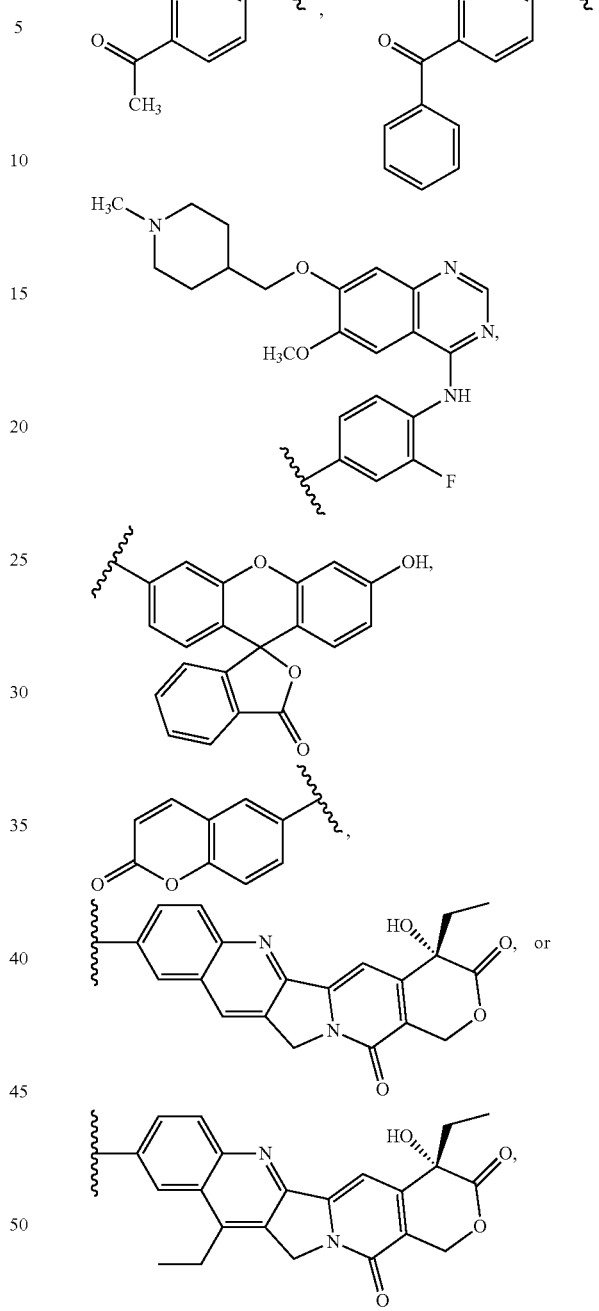

or a regioisomer or stereoisomer thereof. In certain embodiments,

B^A is any of the aforementioned moieties, wherein the moiety is further substituted.

In certain embodiments, the invention relates to any one of the aforementioned methods, wherein $B^B$ is a substituted aryl radical. In certain embodiments, the invention relates to any one of the aforementioned methods, wherein $B^B$ is a substituted phenyl radical.
In certain embodiments, the invention relates to any one of the aforementioned methods, wherein $B^B$ is an unsubstituted aryl radical.
In certain embodiments, the invention relates to any one of the aforementioned methods, wherein $B^B$ is a substituted heteroaryl radical. In certain embodiments, the invention relates to any one of the aforementioned methods, wherein $B^B$ is a substituted indole, pyrazolo, thiophene, pyrimidine, benzofuran, or isoxazole radical.
In certain embodiments, the invention relates to any one of the aforementioned methods, wherein $B^B$ is an unsubstituted heteroaryl radical. In certain embodiments, the invention relates to any one of the aforementioned methods, wherein $B^B$ is an unsubstituted indole, pyrazolo, thiophene, pyrimidine, benzofuran, or isoxazole radical.
In certain embodiments, the invention relates to any one of the aforementioned methods, wherein

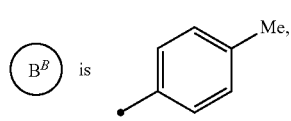

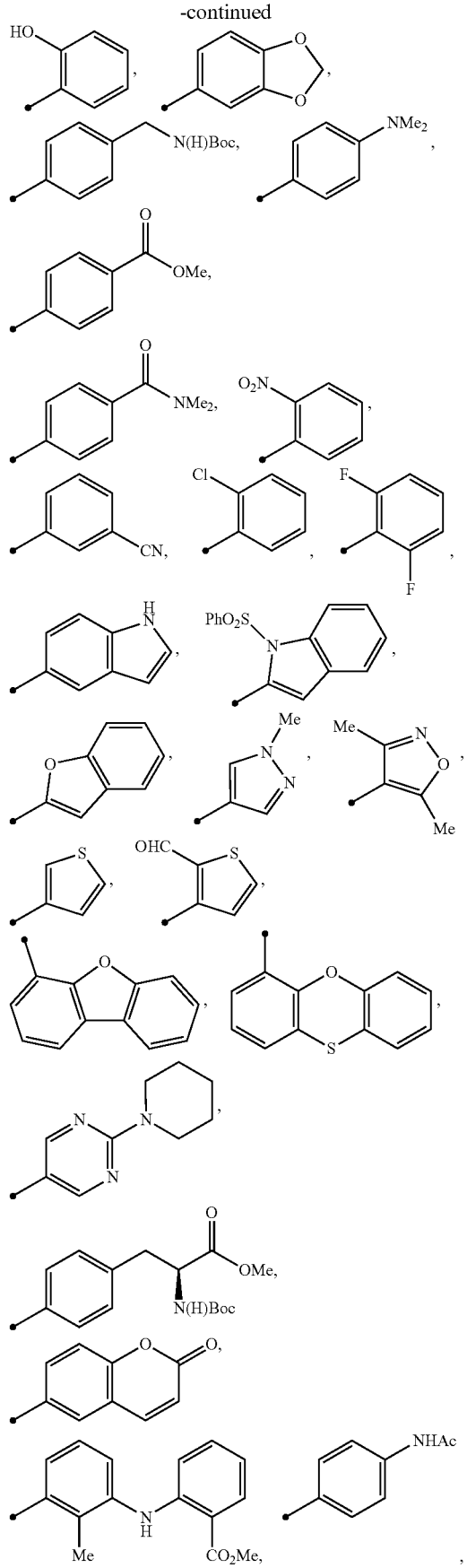

91
-continued
92
-continued
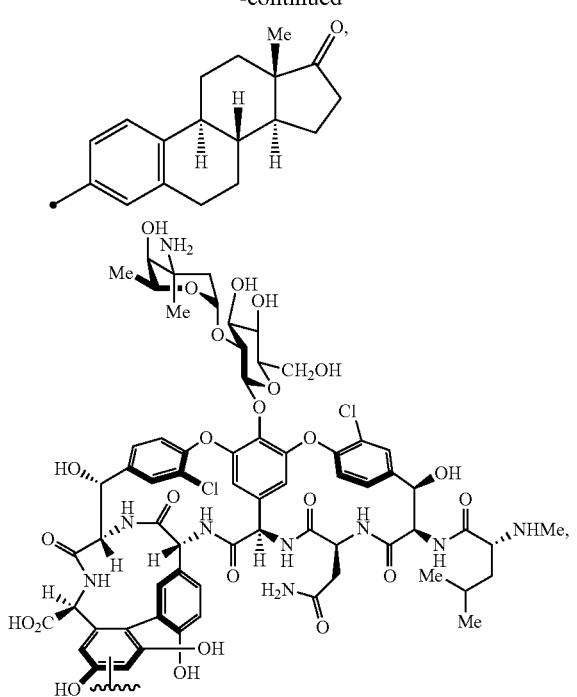
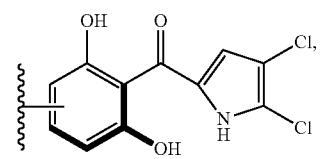
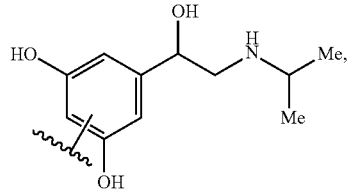
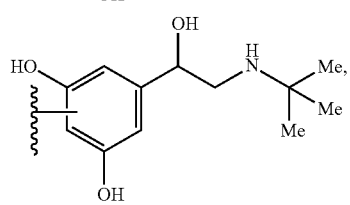
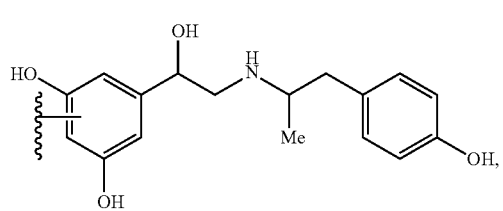
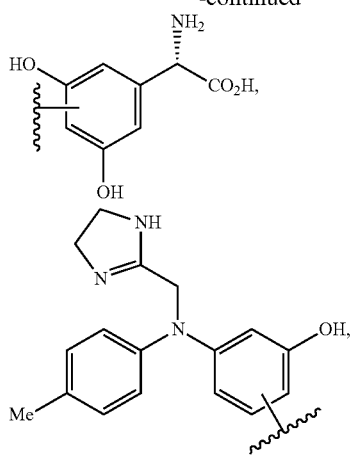
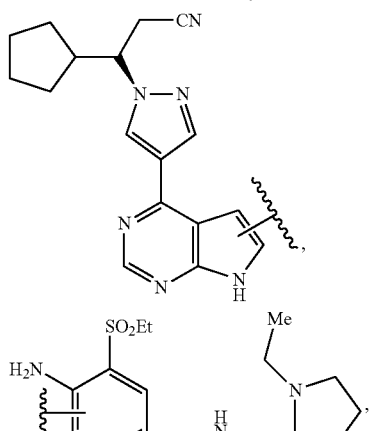
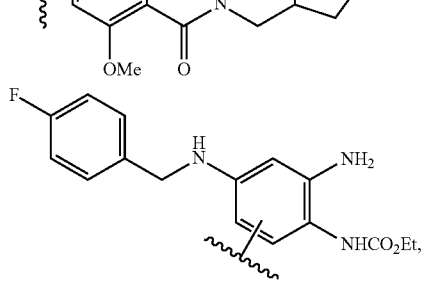
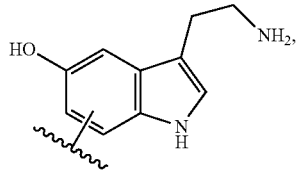
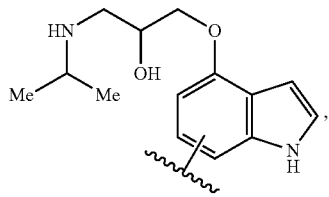
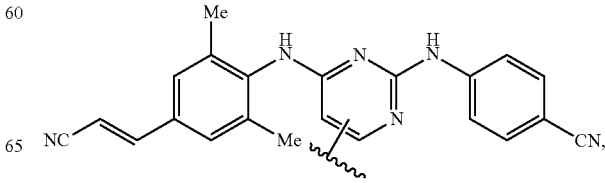

93
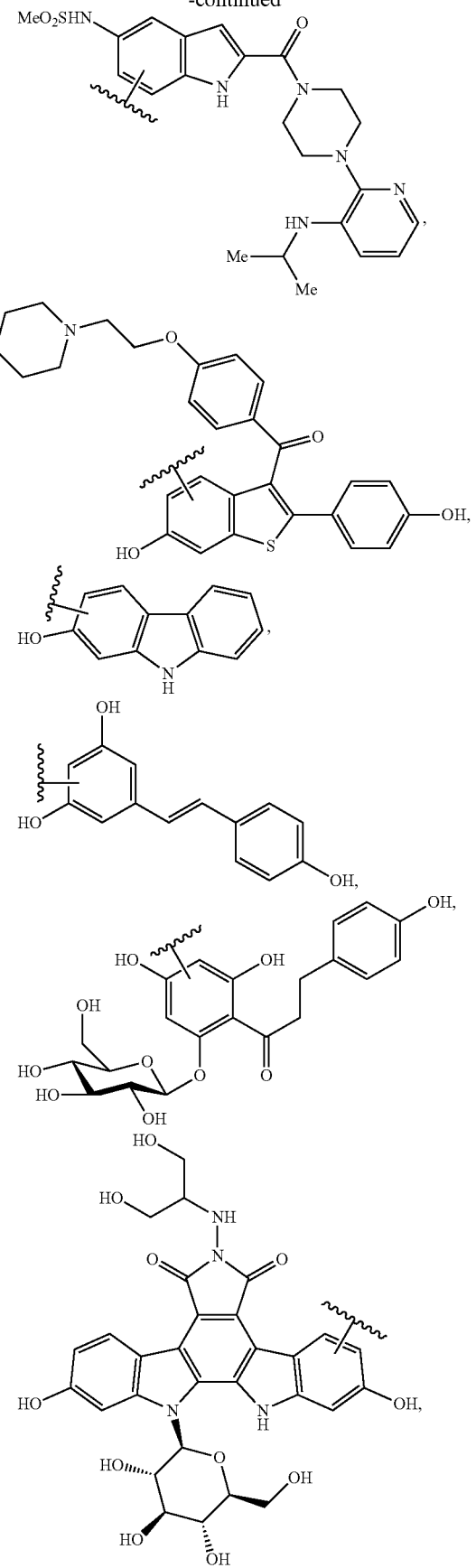
94
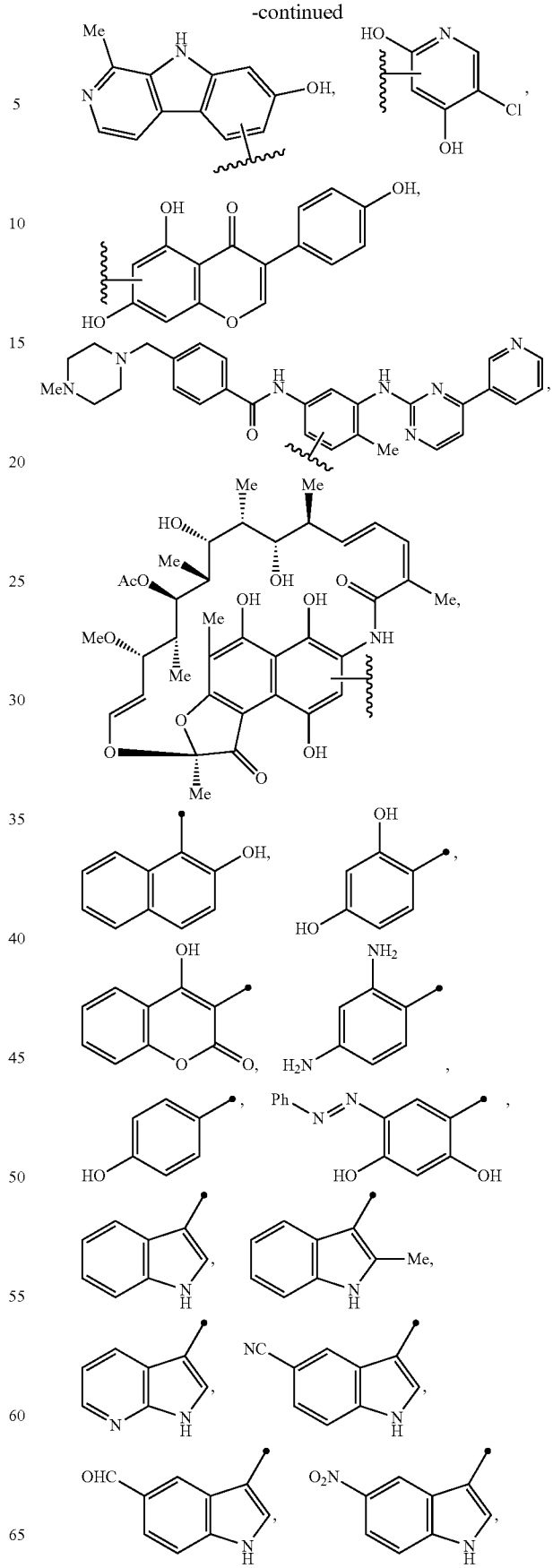

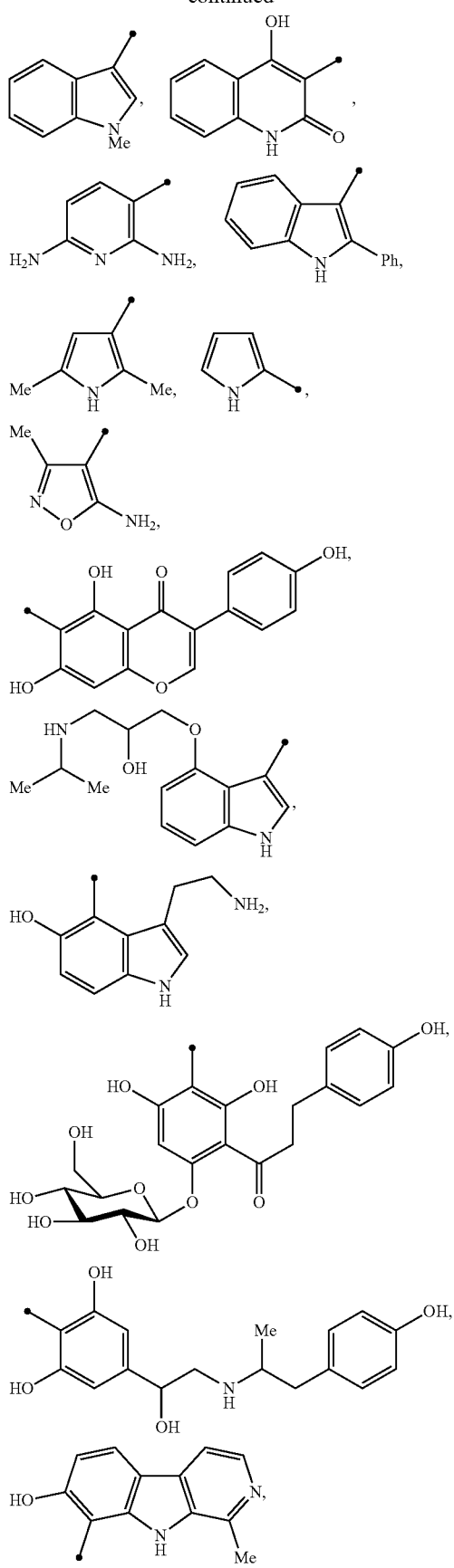
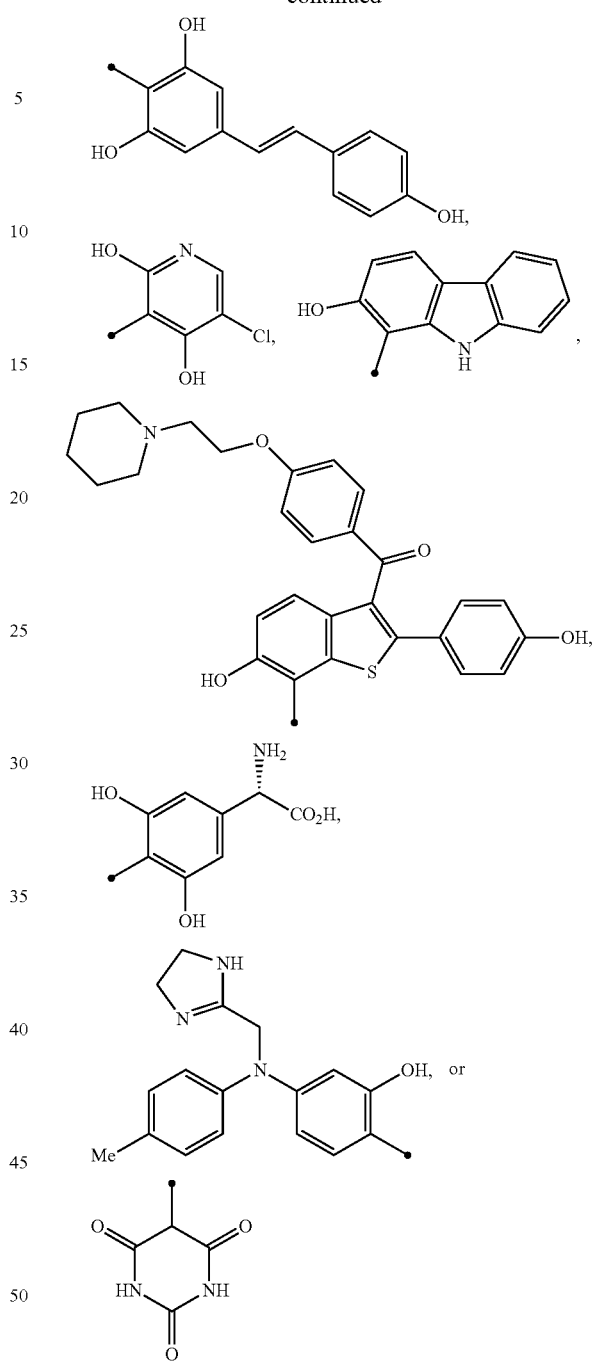
or a regioisomer or stereoisomer thereof. In certain embodiments,
$B^B$
is any of the aforementioned moieties, wherein the moiety is further substituted.
In certain embodiments, the invention relates to any one of the aforementioned methods, wherein

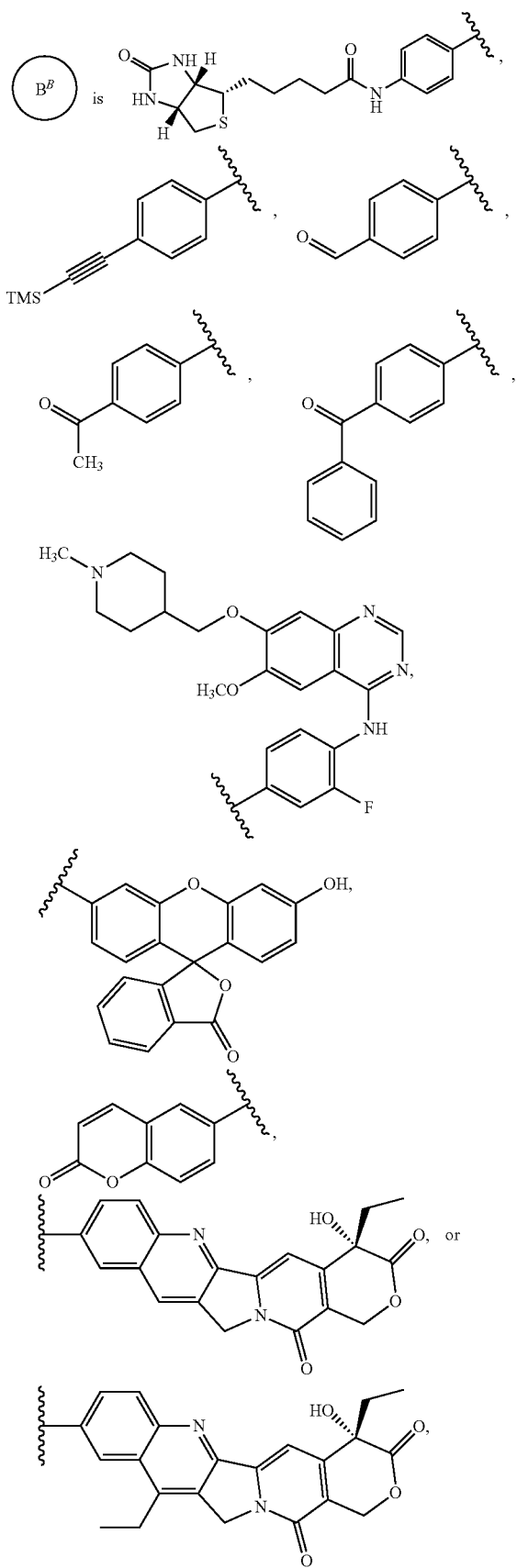

or a regioisomer or stereoisomer thereof. In certain embodiments,

is any of the aforementioned moieties, wherein the moiety is further substituted.

In certain embodiments, the invention relates to any one of the aforementioned methods, wherein

is a substituted aryl radical. In certain embodiments, the invention relates to any one of the aforementioned methods, wherein

is a substituted phenyl radical.

In certain embodiments, the invention relates to any one of the aforementioned methods, wherein

is a substituted heteroaryl radical. In certain embodiments, the invention relates to any one of the aforementioned methods, wherein

is a substituted indole, pyrazolo, thiophene, pyrimidine, benzofuran, or isoxazole radical.

In certain embodiments, the invention relates to any one of the aforementioned methods, wherein

 is 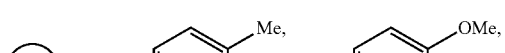

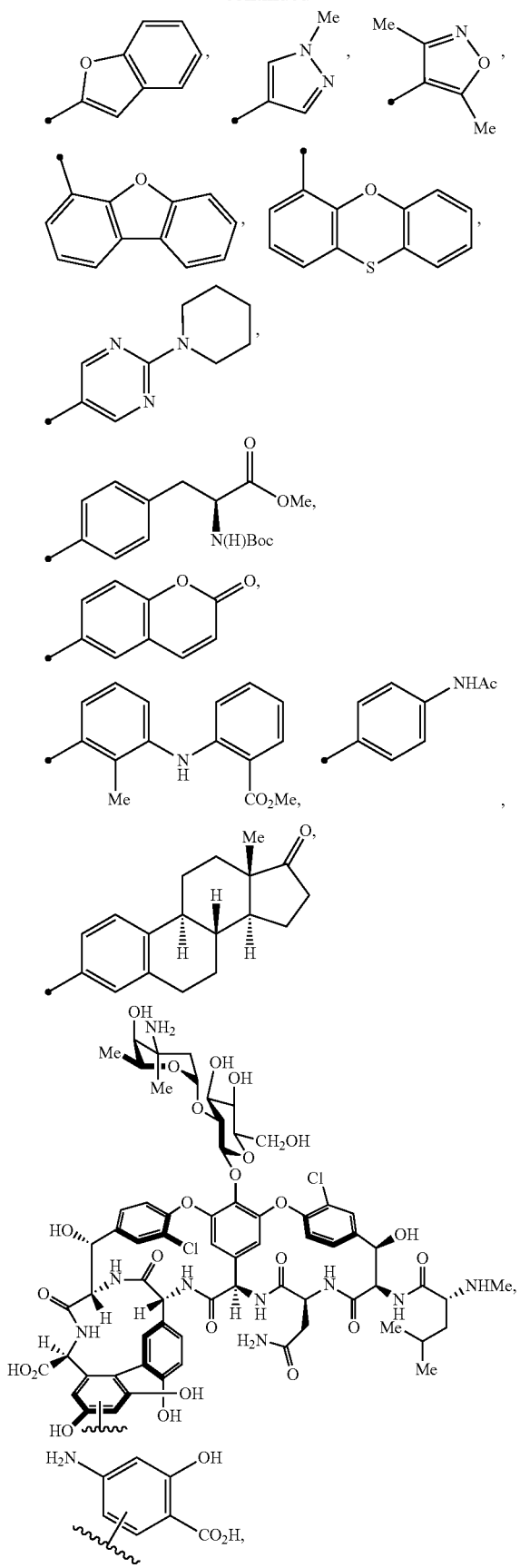
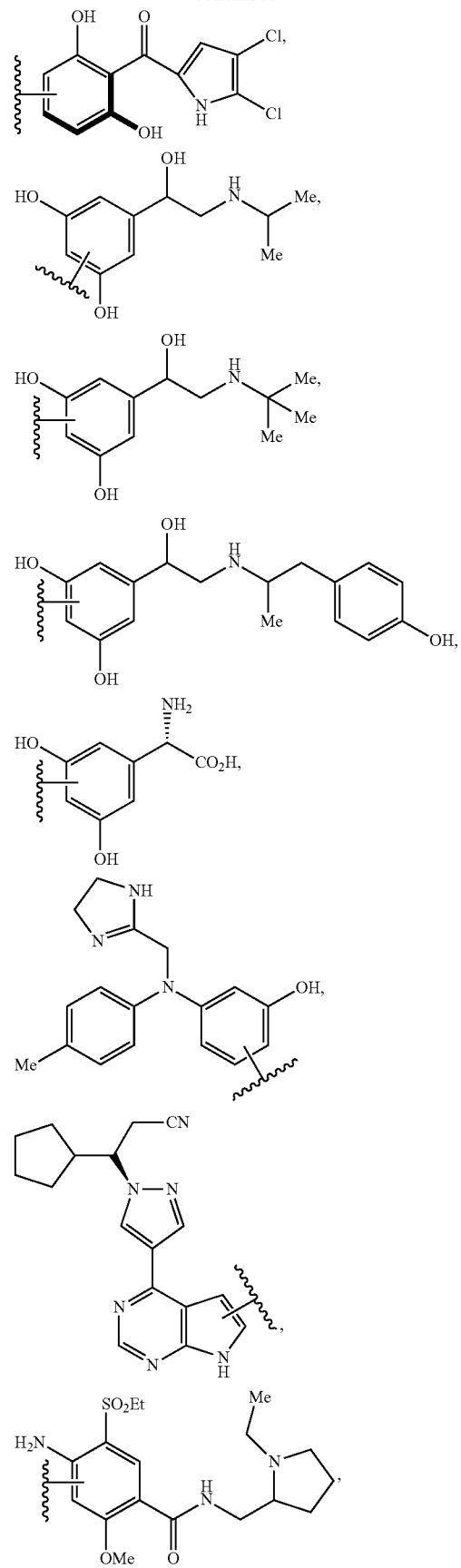

101
-continued
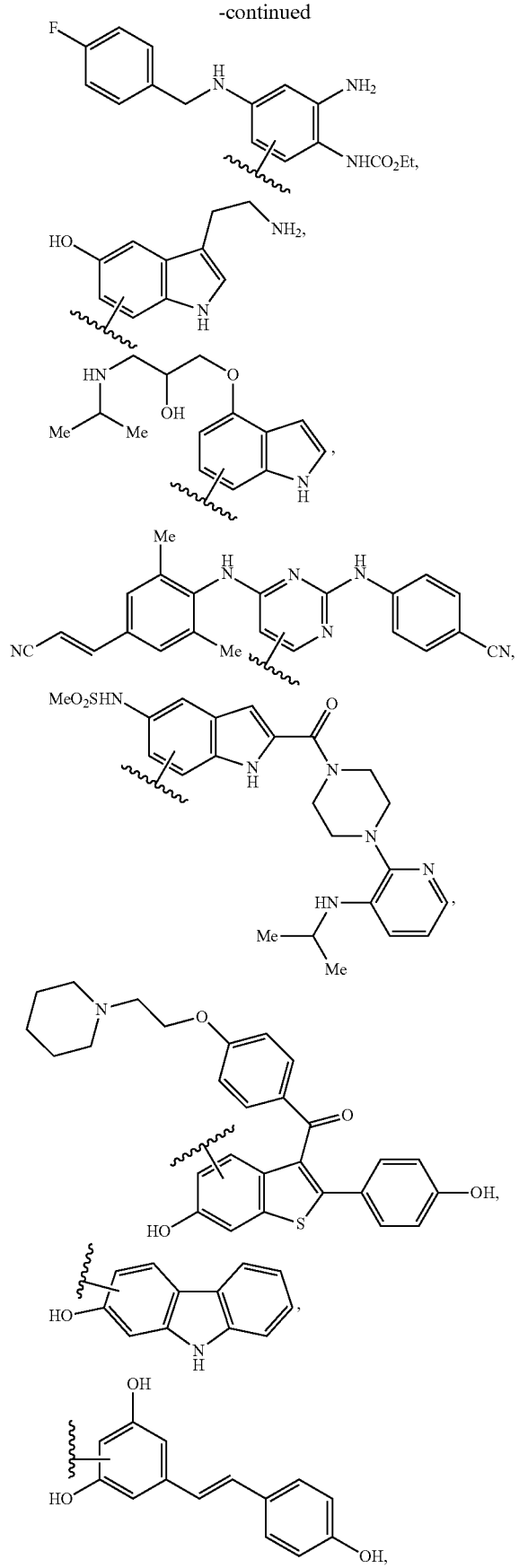
102
-continued
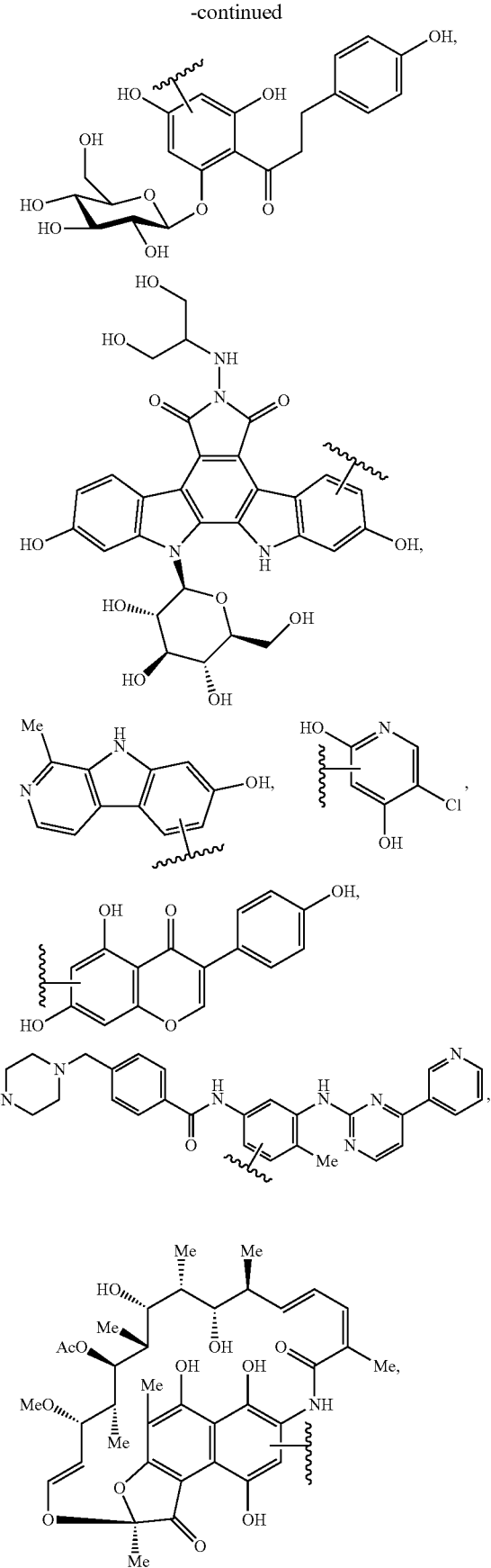

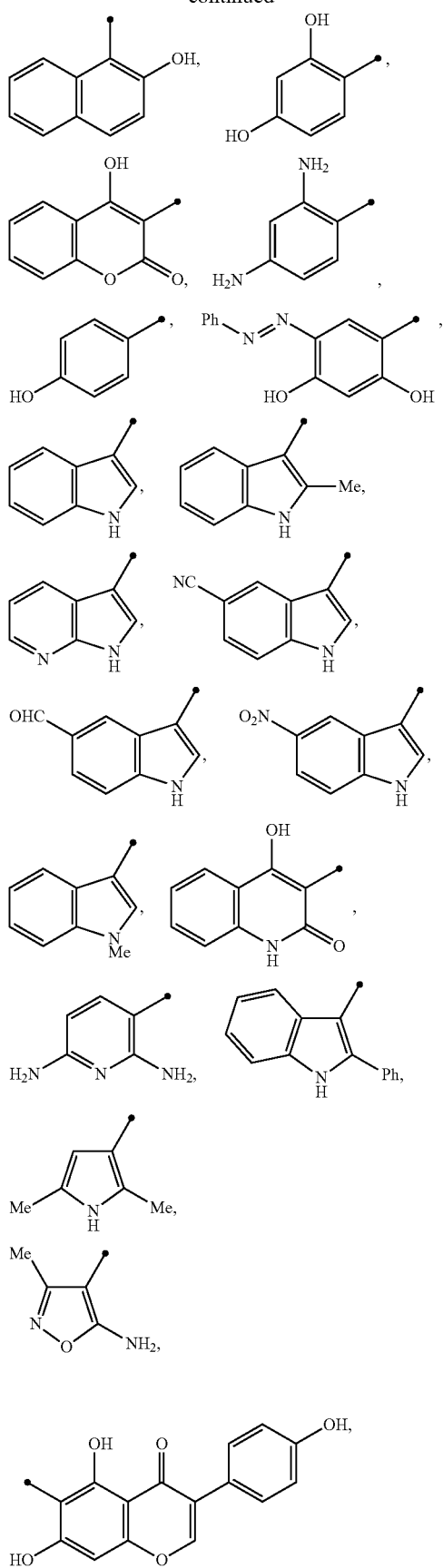
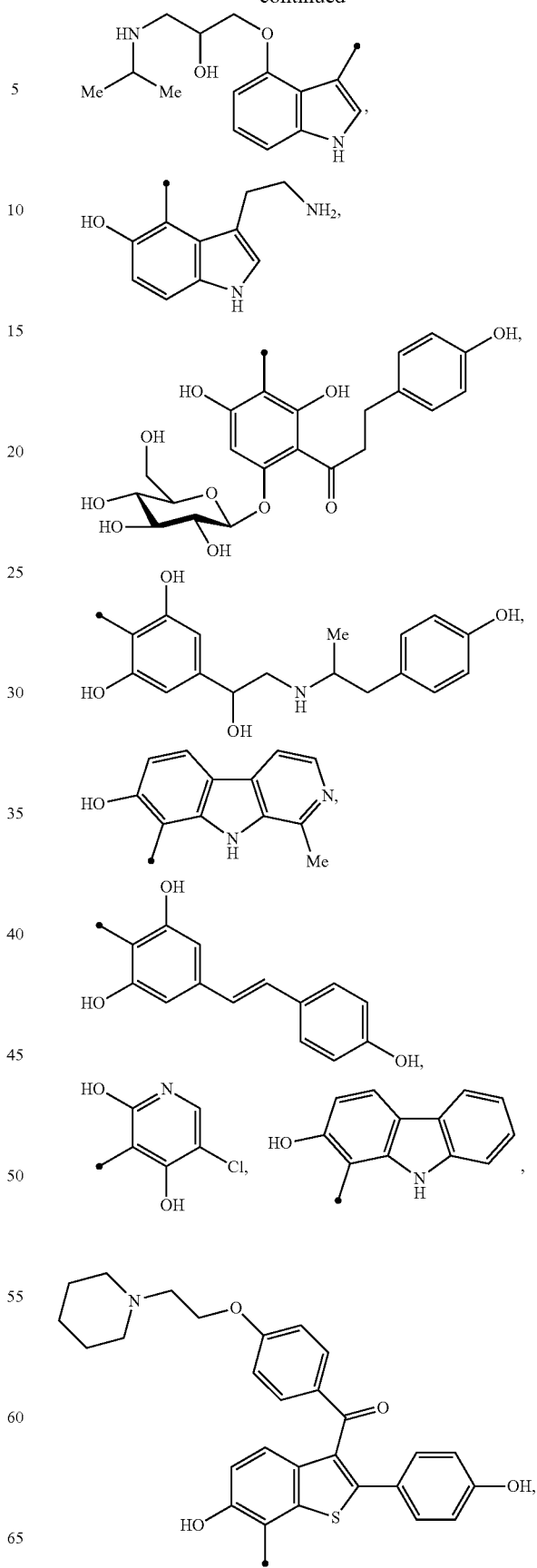

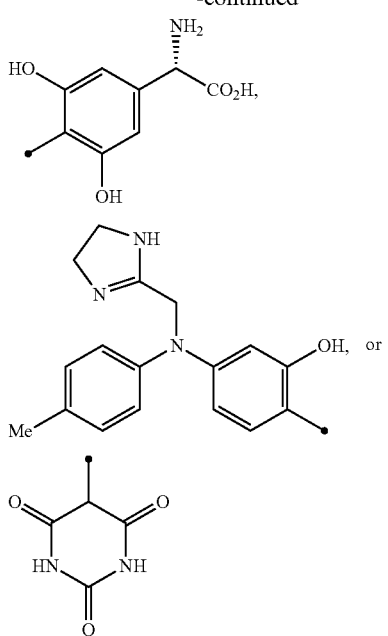

or a regioisomer or stereoisomer thereof. In certain embodiments,

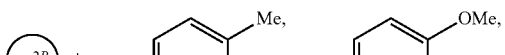

is any of the aforementioned moieties, wherein the moiety is further substituted.

In certain embodiments, the invention relates to any one of the aforementioned methods, wherein

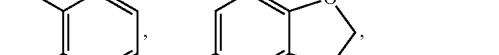

is a substituted aryl radical. In certain embodiments, the invention relates to any one of the aforementioned methods, wherein

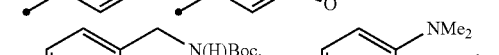

is a substituted phenyl radical.

In certain embodiments, the invention relates to any one of the aforementioned methods, wherein

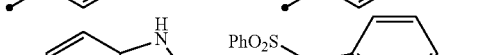

is a substituted heteroaryl radical. In certain embodiments, the invention relates to any one of the aforementioned methods, wherein

is a substituted indole, pyrazolo, thiophene, pyrimidine, benzofuran, or isoxazole radical.

In certain embodiments, the invention relates to any one of the aforementioned methods, wherein

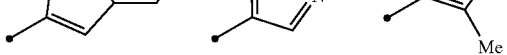 is

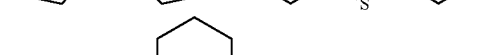

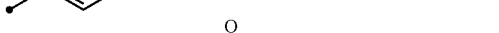

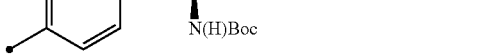

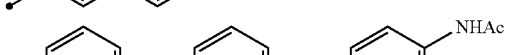

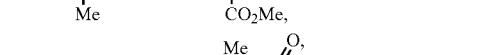

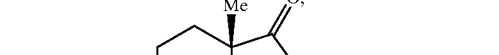

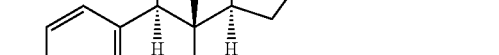

107
-continued
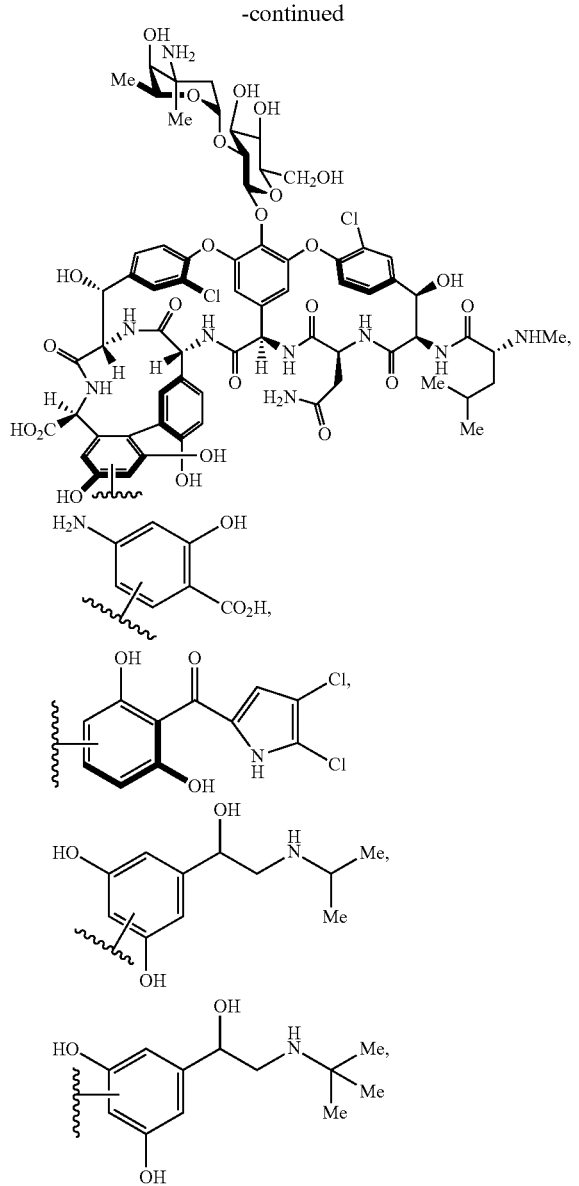
108
-continued
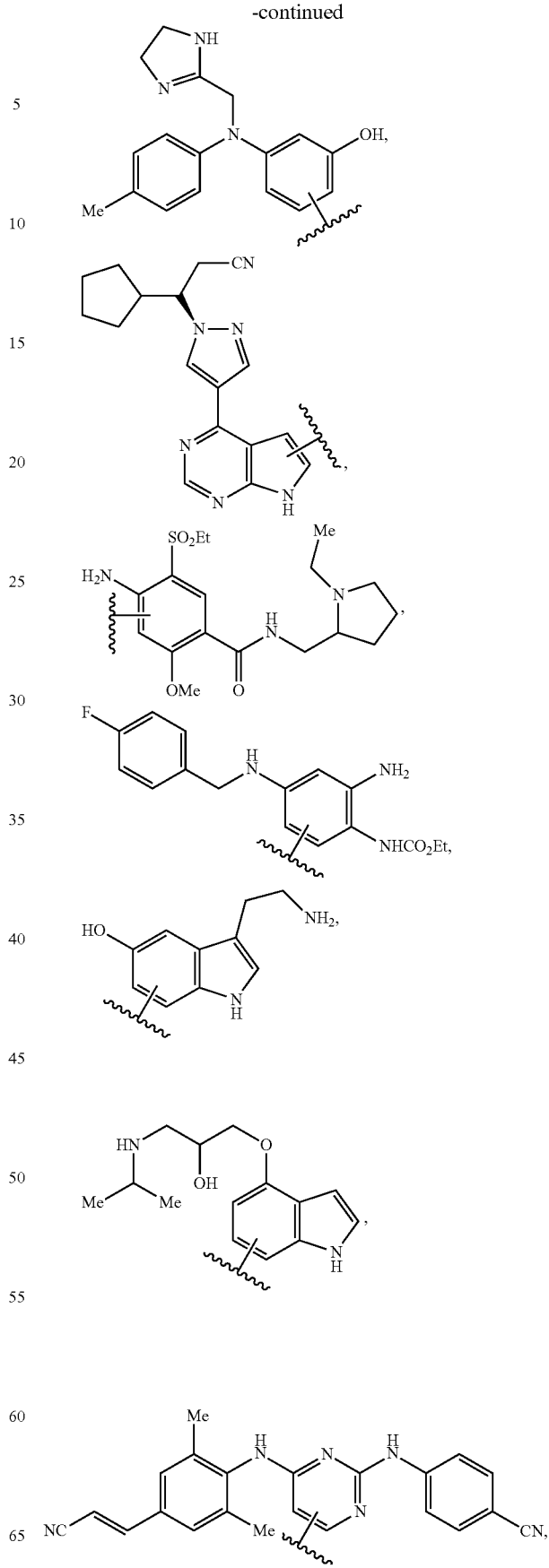

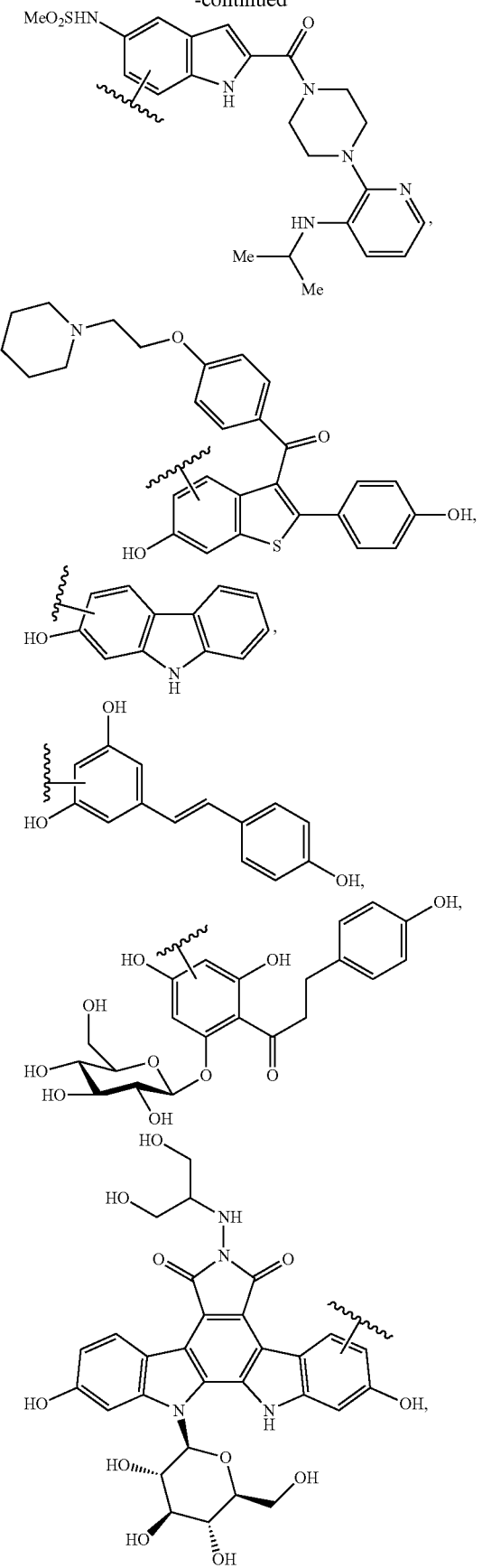
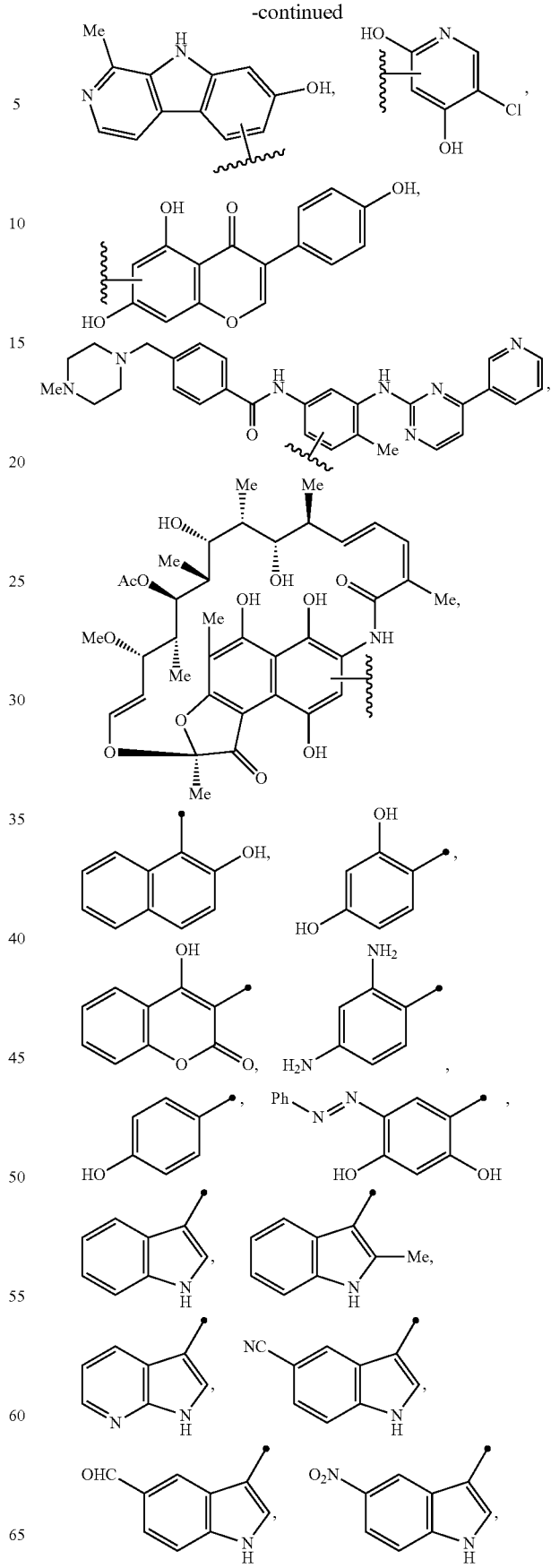

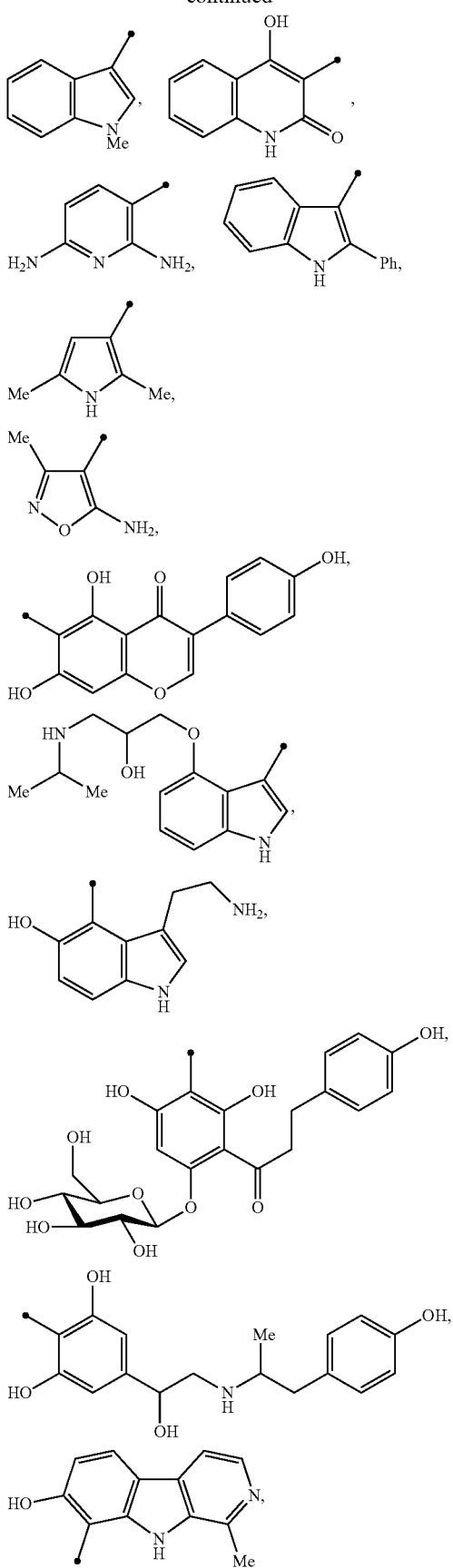
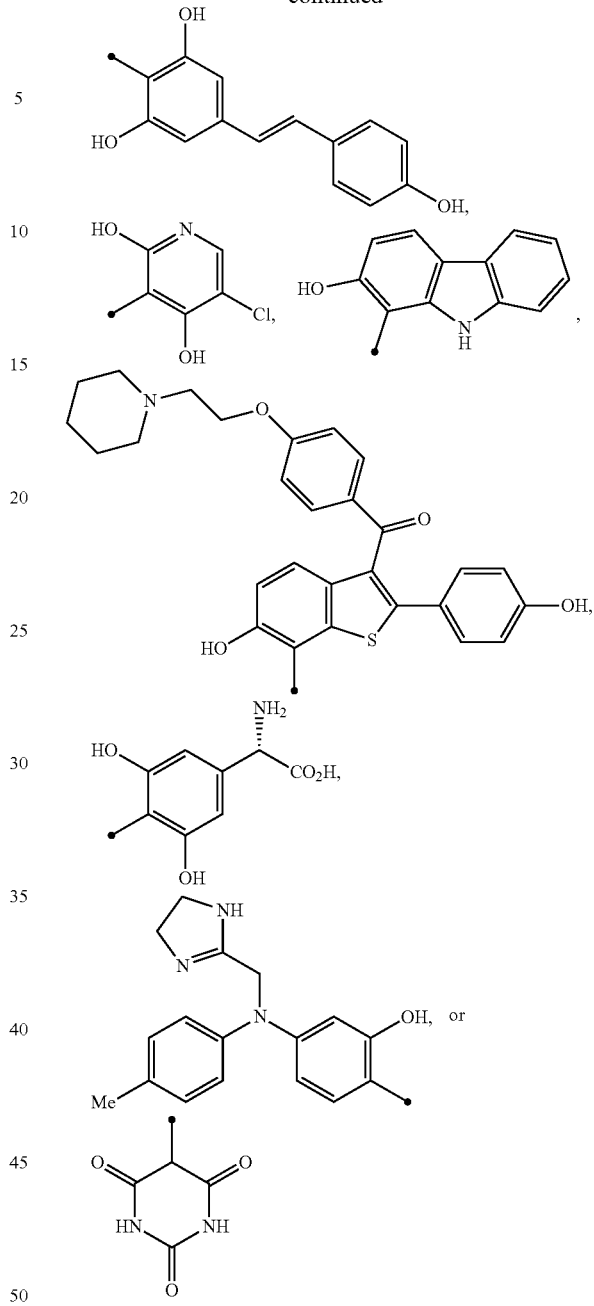

or a regioisomer or stereoisomer thereof. In certain embodiments, $B^{2B}$ is any of the aforementioned moieties, wherein the moiety is further substituted.

In certain embodiments, the invention relates to any one of the aforementioned methods, wherein $A^2$, $A^3$, and $A^4$ are natural or unnatural amino acids.

In certain embodiments, the invention relates to any one of the aforementioned methods, wherein $A^2$ represents one natural or unnatural amino acid. In certain embodiments, the invention relates to any one of the aforementioned methods, wherein $A^3$ represents one natural or unnatural amino acid. In certain embodiments, the invention relates to any one of the aforementioned methods, wherein $A^4$ represents one natural or unnatural amino acid.

In certain embodiments, the invention relates to any one of the aforementioned methods, wherein $A^2$ represents two natural or unnatural amino acids. In certain embodiments, the invention relates to any one of the aforementioned methods, wherein $A^3$ represents two natural or unnatural amino acids. In certain embodiments, the invention relates to any one of the aforementioned methods, wherein $A^4$ represents two natural or unnatural amino acids.

In certain embodiments, the invention relates to any one of the aforementioned methods, wherein $A^2$ represents three natural or unnatural amino acids. In certain embodiments, the invention relates to any one of the aforementioned methods, wherein $A^3$ represents three natural or unnatural amino acids. In certain embodiments, the invention relates to any one of the aforementioned methods, wherein $A^4$ represents three natural or unnatural amino acids.

In certain embodiments, the invention relates to any one of the aforementioned methods, wherein the first solvent, the second solvent, the third solvent, the fourth solvent, the fifth solvent, the sixth solvent, the seventh solvent, or the eighth solvent is water, DMF, $CH_3CN$, $CH_3CH_2OH$, $CH_3OH$, DMSO, tris(2-carboxyethyl)phosphine (TCEP), dibutyl ether, tetrahydrofuran (THF), 1,4-dioxane, DME, dichloromethane, dichloroethane, acetone, diethyl ether, hexanes, or a mixture thereof.

In certain embodiments, the invention relates to any one of the aforementioned methods, wherein the first buffer, the second buffer, the third buffer, the fourth buffer, the fifth buffer, the sixth buffer, the seventh buffer, or the eighth buffer comprises $Na_3PO_4$, MES, or tris(hydroxymethyl) aminomethane (TRIS).

In certain embodiments, the invention relates to any one of the aforementioned methods, wherein the first time, the second time, the third time, the fourth time, the fifth time, the sixth time, the seventh time, or the eighth time is from about 30 min to about 24 h. In certain embodiments, the invention relates to any one of the aforementioned methods, wherein the first time, the second time, the third time, the fourth time, the fifth time, the sixth time, the seventh time, or the eighth time is about 30 min, about 40 min, about 50 min, about 1 h, about 2 h, about 3 h, about 4 h, about 5 h, about 6 h, about 7 h, about 8 h, about 9 h, about 10 h, about 11 h, about 12 h, about 13 h, about 14 h, or about 15 h.

In certain embodiments, the invention relates to any one of the aforementioned methods, wherein $A^1$ is an amine protecting group selected from the group consisting of an N,O-acetal, allyloxycarbonyl (Aloe), benzyl (Bn), benzyloxycarbonyl (Cbz), benzyloxymethyl (BOM), t-butoxycarbonyl (Boc), t-butyldimethylsilyl (TBDMS), t-butyldiphenylsilyl (TBDPS), diphenylmethyl, diphenylmethylene, ethoxycarbonyl, 9-fluorenylmethoxycarbonyl (Fmoc), p-methoxybenzyl (PMB), methoxycarbonyl, methoxymethyl (MOM), p-methoxyphenyl (PMP), p-nitrocinnamyloxycarbonyl (Noc), tosyl (Ts), 2-tosylethoxycarbonyl (Tsoc), 2,2,2-trichloroethoxycarbonyl (Trot), trifluoroacetyl, triisopropylsilyl (TIPS), trimethylsilyl (TMS), 2-(trimethylsilyl)ethoxycarbonyl (Teoc), 2-(trimethylsilyl)ethoxymethyl (SEM), or trityl (Tr).

In certain embodiments, the invention relates to any one of the aforementioned methods, wherein $A^5$ is —O(carboxylate protecting group); and the carboxylate protecting group is selected from the group consisting of allyl, benzyl, benzyloxymethyl (BOM), t-Bu, t-butyldimethylsilyl (TBDMS), t-butyldiphenylsilyl (TBDPS), diphenylmethyl, 9-fluorenylmethyl (Fm), 2-methoxyethoxymethyl (MEM), methoxymethyl (MOM), p-nitrobenzyl (PNB), an ester, a 1,3-oxazoline, pivaloyloxymethyl (Pom), 2-tosylethyl (TSE), 2,2,2-trichloroethyl (TCE), triethylsilyl (TES), trimethylsilyl (TMS), 2-(trimethylsilyl)ethoxymethyl (SEM), or 2-(trimethylsilyl)ethyl (TMSE).

In certain embodiments, the invention relates to any one of the aforementioned methods, wherein R is H.

In certain embodiments, the invention relates to any one of the aforementioned methods, wherein x is 1, 2, or 3. In certain embodiments, the invention relates to any one of the aforementioned methods, wherein x is 1.

In certain embodiments, the invention relates to any one of the aforementioned methods, wherein the first, second, third, fourth, fifth, sixth, seventh, or eighth temperature is between about 10° C. and about 50° C. In certain embodiments, the invention relates to any one of the aforementioned methods, wherein the first, second, third, fourth, fifth, sixth, seventh, or eighth temperature is about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C.

In certain embodiments, the invention relates to any one of the aforementioned methods, wherein the Cu/ligand comprises $CuSO_4$. In certain embodiments, the invention relates to any one of the aforementioned methods, wherein the Cu/ligand comprises a substituted or unsubstituted hipyridine ligand or a substituted or unsubstituted phenanthroline ligand. In certain embodiments, the invention relates to any one of the aforementioned methods, wherein the Cu/ligand comprises 4,4'-di-tert-butyl-2,2'-bipy.

In certain embodiments, the invention relates to any one of the aforementioned methods, wherein the Rh/ligand comprises $[RhCp*Cl_2]_2$.

In certain embodiments, the invention relates to any one of the aforementioned methods, wherein the catalytic metal is not Cu or Rh or absent, but comprises Fe, Co, Ni, Au, Pd, Pt, Ru, or Ir. In certain embodiments, the invention relates to any one of the aforementioned methods, wherein the catalytic metal is not Cu or Rh or absent, but is selected from the group consisting of Fe, Co, Ni, Au, Pd, Pt, Ru, and Ir.

The reactions typically proceed at mild temperatures and pressures to give high yields of the product. Thus, yields of desired products greater than 45%, greater than 75%, greater than 80%, greater than 85%, greater than 90%, or greater than 95% may be obtained from reactions at mild temperatures according to the invention.

In certain embodiments, the reactions take place under an inert atmosphere of a gas such as nitrogen or argon.

The reaction processes of the invention can be conducted in continuous, semi-continuous or batch fashion and may involve a liquid recycle operation as desired. The processes of this invention are preferably conducted in batch fashion. Likewise, the manner or order of addition of the reaction ingredients, base, and solvent are not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. When complete conversion is not desired or not obtainable, the starting materials can be separated from the product and then recycled back into the reaction zone.

The processes may be conducted in glass lined, stainless steel, fluoropolymer coated (e.g., Teflon coated) or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized on or incorporated into a polymer or other insoluble matrix by, for example, derivatization with one or more of the substituents of the aryl group or an amino acid residue.

The ability to provide synthesis schemes for the compounds of the invention that can be carried out under mild conditions has broad application.

In addition, the subject methods can be used as part of combinatorial synthesis schemes to yield libraries of compounds. Accordingly, another aspect of the invention relates to use of the subject method to generate variegated libraries of compounds, and to the libraries themselves. The libraries can be soluble or linked to insoluble supports, e.g., through a substituent of a reactant (prior to carrying out a reaction of the invention).

Further, the methods of the invention can be used to produce synthetic intermediates that, after being subjected to additional methods known in the art, are transformed to desired end products.

Exemplary Therapeutic Methods

In certain embodiments, the invention relates to a method of killing or inhibiting the growth or proliferation of a bacterium, a fungus, a virus, or a parasite, comprising the step of:

contacting with the bacterium, fungus, virus, or parasite an effective amount of any one of the aforementioned compounds, thereby treating killing or inhibiting the growth or proliferation of the bacterium, fungus, virus, or parasite.

In certain embodiments, the invention relates to a method of treating a disease in a subject in need thereof comprising the step of:

administering to the subject an effective amount of any one of the aforementioned compounds, thereby treating the disease.

In certain embodiments, the invention relates to any one of the aforementioned methods, wherein the disease is an infection, for example, a bacterial infection, a fungal infection, a viral infection, or a parasitic infection.

In certain embodiments, the invention relates to any one of the aforementioned methods, wherein the disease is cancer. In one group of embodiments, the invention relates to any one of the aforementioned methods, wherein the disease is selected from the group consisting of breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer being treated is metastatic. In other embodiments, the cancer being treated is resistant to anti-cancer agents.

In certain embodiments, the invention relates to any one of the aforementioned methods, further comprising the step of: monitoring the cell or the subject by $^{19}$F NMR.

A subject in need thereof (or a mammal in need thereof) may include, for example, a subject who has been diagnosed with any one of the aforementioned diseases, or a subject who has been treated for any one of the aforementioned diseases, including subjects that have been refractory to the previous treatment.

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active agent will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of the subject agent may be determined by reference to the plasma concentrations of the agent. For example, the maximum plasma concentration ($C_{max}$) and the area under the plasma concentration-time curve from time 0 to infinity (AUC (0-4)) may be used. Dosages for the present invention include those that produce the above values for $C_{max}$ and AUC (0-4) and other dosages resulting in larger or smaller values for those parameters.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents of the invention employed in the pharmaceutical composition at levels lower than that required in order to achieve the desired therapeutic effect and gradually increase the dosage until the desired effect is achieved.

In general, a suitable daily dose of an agent of the invention will be that amount of the agent which is the lowest dose effective to produce a therapeutic effect. Such an effective dose will generally depend upon the factors described above.

If desired, the effective daily dose of the agent may be administered as two, three, four, five, six or more sub-doses administered separately at appropriate intervals throughout the day, optionally, in unit dosage forms.

The precise time of administration and amount of any particular agent that will yield the most effective treatment in a given patient will depend upon the activity, pharmacokinetics, and bioavailability of a particular agent, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the subject may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained. In addition, the combined use an agent that modulates an autotrophy-associated gene product and a second agent, e.g., another agent useful for the treatment of the autophagy-related disease, may reduce the required dosage for any individual agent because the onset and duration of effect of the different compounds and/or agents may be complimentary.

In one aspect of the invention, a compound of the invention, or a pharmaceutically acceptable salt thereof, can be used alone or in combination with another therapeutic agent to treat diseases such cancer. It should be understood that the compounds of the invention can be used alone or in combination with an additional agent, e.g., a therapeutic agent, said additional agent being selected by the skilled artisan for its intended purpose. For example, the additional agent can be a therapeutic agent that is art-recognized as being useful to treat the disease or condition being treated by the compound of the present invention. The additional agent also can be an agent that imparts a beneficial attribute to the therapeutic composition e.g., an agent that affects the viscosity of the composition.

The combination therapy contemplated by the invention includes, for example, administration of a compound of the invention, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

It should further be understood that the combinations included within the invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

In certain embodiments, the co-administration of two or more therapeutic agents (e.g., a pharmaceutical and a peptide) achieves a synergistic effect, i.e., a therapeutic effect that is greater than the sum of the therapeutic effects of the individual components of the combination. The term "synergistic" refers to a combination which is more effective than the additive effects of any two or more single agents. A synergistic effect permits the effective treatment of a disease using lower amounts (doses) of individual therapy. The lower doses result in lower toxicity without reduced efficacy. In addition, a synergistic effect can result in improved efficacy. Finally, synergy may result in an improved avoidance or reduction of disease as compared to any single therapy. Combination therapy can allow for the product of lower doses of the first therapeutic or the second therapeutic agent (referred to as "apparent one-way synergy" herein), or lower doses of both therapeutic agents (referred to as "two-way synergy" herein) than would normally be required when either drug is used alone.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "arylalkoxy" and "heteroalkoxy" as used herein, means an aryl group or heteroaryl group, as defined herein, appended to the parent molecular moiety through an alkoxy group, as defined herein.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "amino" as used herein, refers to radicals of both unsubstituted and substituted amines appended to the parent molecular moiety through a nitrogen atom. The two groups are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group. The aryl groups of the invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "arylene," is art-recognized, and as used herein, pertains to a bidentate moiety obtained by removing two hydrogen atoms of an aryl ring, as defined above.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkoxy" or "arylalkyloxy" as used herein, means an arylalkyl group, as defined herein, appended to the parent molecular moiety through an oxygen. The term "heteroarylalkoxy" as used herein, means an heteroarylalkyl group, as defined herein, appended to the parent molecular moiety through an oxygen.

The term "arylalkylthio" as used herein, means an arylalkyl group, as defined herein, appended to the parent molecular moiety through an sulfur. The term "heteroarylalkylthio" as used herein, means an heteroarylalkyl group, as defined herein, appended to the parent molecular moiety through an sulfur.

The term "arylalkenyl" as used herein, means an aryl group, as defined herein, appended to the parent molecular moiety through an alkenyl group. A representative example is phenylethylenyl.

The term "arylalkynyl" as used herein, means an aryl group, as defined herein, appended to the parent molecular moiety through an alkynyl group. A representative example is phenylethynyl.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein, means an arylcarbonyl group, as defined herein, bound to the parent molecule through an alkyl group, as defined herein.

The term "arylcarbonylalkoxy" as used herein, means an arylcarbonylalkyl group, as defined herein, bound to the parent molecule through an oxygen.

The term "aryloxy" as used herein, means an aryl group, as defined herein, appended to the parent molecular moiety through an oxygen. The term "heteroaryloxy" as used herein, means a heteroaryl group, as defined herein, appended to the parent molecular moiety through an oxygen.

The term "carbonyl" as used herein, means a —C(=O)— group.

The term "carboxy" as used herein, means a —CO$_2$H group.

The term "cycloalkyl" as used herein, means monocyclic or multicyclic (e.g., bicyclic, tricyclic) hydrocarbons containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkoxy" as used herein, means a cycloalkyl group, as defined herein, appended to the parent molecular moiety through an oxygen.

The term "cyano" as used herein, means a —CN group.

The term "formyl" as used herein, means a —C(=O)H group.

The term "halo" or "halogen" means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroarylene," is art-recognized, and as used herein, pertains to a bidentate moiety obtained by removing two hydrogen atoms of a heteroaryl ring, as defined above.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "phosphinyl" as used herein includes derivatives of the H$_3$P— group, wherein the hydrogens are independently replaced with alkyl, adamantyl, fluoroalkyl, cycloalkyl, aryl, heteroaryl, heterocyclyl, aryloxy, or heteroaryloxy groups.

The term "silyl" as used herein includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

Certain compounds contained in compositions of the invention may exist in particular geometric or stereoisomeric forms. In addition, polymers of the invention may also be optically active. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

A "polar solvent" means a solvent which has a dielectric constant (c) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred polar solvents are DMF, DME, NMP, and acetonitrile.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

A "polar, aprotic solvent" means a polar solvent as defined above which has no available hydrogens to exchange with the compounds of this invention during reaction, for example DMF, acetonitrile, diglyme, DMSO, or THF.

A "hydroxylic solvent" means a solvent that comprises a hydroxyl moiety; for example, water, methanol, ethanol, tert-butanol, and ethylene glycol are hydroxylic solvents.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The invention now being generally described, it will be more readily understood by reference to the following examples, which are included merely for purposes of illustration of certain aspects and embodiments of the invention, and are not intended to limit the invention.

Example 1: Copper-Catalyzed Arylation of Selenocysteine in Unprotected Peptides

Materials
1. Chemicals
Tris(2-carboxyethyl)phosphine hydrochloride (TCEP-HCl) was purchased from Hampton Research (Aliso Viejo, Calif.). 1-[Bis(dimethylamino)methylene]-1H-1,2,3-triazolo[4,5-b]pyridinium 3-oxid hexafluorophosphate (HATU), Fmoc-L-Gly-OH, Fmoc-L-Leu-OH, Fmoc-L-Lys(Boc)-OH, Fmoc-L-Ala-OH, Fmoc-L-Cys(Trt)-OH, Fmoc-L-Asn(Trt)-OH, Fmoc-L-Asp(tBu)-OH, Fmoc-L-Arg(Pbf)-OH, Fmoc-L-Phe-OH, Fmoc-L-Ser(tBu)-OH, Fmoc-L-Tyr(tBu)-OH, Fmoc-Ser-OH, and Fmoc-L-His(Trt)-OH were purchased from Chem-Impex International (Wood Dale, Ill.). Fmoc-L-4-methoxybenzyl-selenocysteine (Fmoc-L-Sec(Pmb)-OH) was prepared from Fmoc-Ser-OH using standard literature procedure. Schroll, A. L.; Hondal, R. J.; Flemer, S. *J. Pept. Sci.* 2012, 18, 155. Peptide synthesis-grade N, N-dimethylformamide (DMF), dichloromethane (DCM), diethyl ether, HPLC-grade acetonitrile, and guanidine hydrochloride were obtained from VWR International (Philadelphia, Pa.). All reactions were set up on the bench top open to air. Water was deionized and used as is. Ethanol, copper, ligands were purchased from commercial sources and used as received. Boronic acids were purchase from commercial sources or prepared according to standard literature procedure. Ishiyama, T.; Murata, M.; Miyaura, N. *J. Org. Chem.*, 1995, 60, 7508.

2. Reaction Vessels
a) 0.6 mL Axygen Tubes (For 100 μM reaction)—Axygen Cat. No. MCT-060-L-C
b) Scintillation Vials (For 1 mM scale-up reactions)—VWR Cat. No. VW74510-20

Methods for LC-MS Analysis
LC-MS chromatograms and associated mass spectra were acquired using Agilent 6520 ESI-Q-TOF mass spectrometer unless noted. Mobile phases are: 0.1% formic acid in water (solvent C) and 0.1% formic acid in acetonitrile (solvent D) Following LC-MS methods were used:

Method A—LC conditions: Zorbax SB 3 column: 2.1× 150 mm, 5 μm, column temperature: 40° C., gradient: 0-2 minutes 1% D, 2-11 minutes 1-61% D, 11-12 minutes 61% D, flow rate: 0.8 mL/min. MS conditions: positive electrospray ionization (ESI) extended dynamic mode in mass range 300-3000 m/z, temperature of drying gas=350° C., flow rate of drying gas=11 L/min, pressure of nebulizer gas=60 psi, the capillary, fragmentor, and octupole rf voltages were set at 4000, 175, and 750, respectively.

Method B—LC conditions: Zorbax SB C3 column: 2.1× 150 mm, 5 μm, column temperature: 40° C., gradient: 0-1 minutes 5-25% D, 1-5 minutes 25-75% D, flow rate: 0.8 mL/min. 5-6 minutes 75-95% D, flow rate: 1.5 mL/min. MS conditions are same as Method A.

Method C—LC conditions: Zorbax SB C3 column: 2.1× 150 mm, 5 μm, column temperature: 40° C., gradient: 0-2 minutes 1% D, 2-23 minutes 1-61% D, 23-24 minutes 61% D, flow rate: 0.8 mL/min. MS conditions are same as Method A.

Method D—LC conditions: Zorbax SB C18 column: 2.1×150 mm, μm, column temperature: 40° C., gradient: 0-2 minutes 1% D, 2-11 minutes 1-61% D, 11-12 minutes 61% D, flow rate: 0.8 mL/min. MS conditions are same as Method A.

All reactions for peptide stability studies were analyzed by Agilent 6550 ESI-Q-TOF mass spectrometer. Mobile phases are: 0.1% formic acid in water (solvent C) and 0.1% formic acid in acetonitrile (solvent D). Following LC-MS method was used:

Method E—LC conditions: EclipsePlus C18 column: 2.1×50 mm, RRHD 1.8 μm, column temperature: 40° C., gradient: 0-1 minutes 5% D, 1-6 minutes 5-50% D, 6-8 minutes 50-95% D, 8-10 minutes 95% D, flow rate: 0.5 mL/min. MS conditions: positive electrospray ionization (ESI) extended dynamic mode in mass range 300-3000 m/z, temperature of drying gas=200° C., flow rate of drying gas=17 L/min, pressure of nebulizer gas=35 psi, the capillary, fragmentor, and nozzle voltages were set at 3500, 380, and 500, respectively.

All data were processed using Agilent MassHunter software package. Y-axis in all chromatograms shown represents total ion current (TIC) unless noted; mass spectrum corresponds to the integration of the TIC peak unless noted.

All yields reported were determined by integrating TIC spectra. First, using Agilent MassHunter software package, the peak areas for all relevant peptidic species on the chromatogram were integrated. Then the yield was calculated as following: % yield=$S_p/S_{all}$ where $S_p$ is the peak area of the desired product, and $S_{all}$ is sum of the peak areas of all peptidic species.

General Method for Preparation of Peptides
1) Fast-Flow Peptide Synthesis

All peptide sequences C-terminal to selenocysteine were synthesized on a 0.2-mmol scale using manual Fmoc-SPPS (Solid phase peptide synthesis) chemistry under flow using a 3-minute cycle for each amino acid. Simon, M. D.; et al., *ChemBioChem* 2014, 15, 713. Specifically, all reagents and solvents are delivered to a stainless steel reactor containing resins at a constant flow rate using an HPLC pump; temperature of the reactor was maintained at 60° C. during the synthesis using a water bath. The procedure for each amino acid coupling cycle included a 30 second coupling with 1 mmol Fmoc-protected amino acid, 1 mmol HATU, and 500 μL of diisopropyl ethyl amine (DIEA) in 2.5 mL of DMF at a flow rate of 6 mL/min (note that for the coupling of cysteine and histidine, 190 μL of DIEA was used to prevent racemization); 1 min wash with DMF at a flow rate of 20 mL/min; 20 second deprotection with 20% (v/v) piperidine in DMF at a flow rate of 20 mL/min; and 1 minute wash with DMF at a flow rate of 20 mL/min. After completion of the fast-flow synthesis, the resins are washed with DCM (3×) and dried under vacuum. The dried resins are used in batch synthesis for coupling of selenocysteine and the rest of the peptide sequence.

TABLE 1

Peptide Sequences. Amino acids were incorporated through fast-flow SPPS except for those underlined, which were synthesized through batch SPPS.

| Peptide | Sequence |
|---|---|
| 1 | NH$_2$-Leu-Phe-Gly-Gly-Sec(TNP)-Gly-Leu-Leu-Lys-Asn-Lys-CONH$_2$ (SEQ ID NO: 3) |
| 1-Ser5 | NH$_2$-Leu-Phe-Gly-Gly-Ser-Gly-Leu-Leu-Lys-Asn-Lys-CONH$_2$ (SEQ ID NO: 4) |
| 1-Cys5 | NH$_2$-Leu-Phe-Gly-Gly-Cys-Gly-Leu-Leu-Lys-Asn-Lys-CONH$_2$ (SEQ ID NO: 5) |
| 1-Cys5-TNP | NH$_2$-Leu-Phe-Gly-Gly-Cys(TNP)-Gly-Leu-Leu-Lys-Asn-Lys-CONH$_2$ (SEQ ID NO: 5) |
| 1-Met5 | NH$_2$-Leu-Phe-Gly-Gly-Met-Gly-Leu-Leu-Lys-Asn-Lys-CONH$_2$ (SEQ ID NO: 6) |
| 7 | NH$_2$-Gly-Sec(TNP)-Ala-Asn-Ser-Leu-Arg-Phe-Tyr-His-Asp-Lys-CONH$_2$ (SEQ ID NO: 7) |
| 9 | NH$_2$-Gly-Ser-Ala-Asn-Ser-Leu-Arg-Phe-Tyr-His-Asp-Lys-CONH$_2$ (SEQ ID NO: 8) |

2) Solid-Phase Peptide Synthesis (SPPS) in Batch

Selenocysteine and amino acids N-terminal to selenocysteine were coupled to the resin under batch SPPS conditions on a 0.2-mmol scale. Each amino acid was incorporated into the peptide sequence through a cycle of coupling, washing, deprotection, and washing steps. Procedure for the coupling of selenocysteine included a 20 min coupling with 0.4 mmol Fmoc-L-Sec(Pmb)-OH, 0.4 mmol HATU, and 38 μL of DIEA in 2 mL of DMF. For other amino acids, coupling was performed for 10 min with 1 mmol Fmoc-protected amino acids, 1 mmol HATU, 500 μL of DIEA in 2.5 mL of DMF. After coupling, the resin was washed with DMF (3×). Piperidine (20% (v/v) in DMF) was added to the resin for 2×5 min each. The resin was washed with DMF (3×) and then subjected to coupling of the next amino acid.

Peptide sequences synthesized using batch SPPS are underlined in Table 1.

3) Peptide Cleavage and Deprotection

Peptides containing selenocysteine were cleaved from the resin and the side-chain was simultaneously deprotected by treatment with 5% (v/v) water, 95% (v/v) trifluoroacetic acid (TFA), 0.4 M 2,2'-dithiobis(5-nitropyridine) (DTNP) for 7 min at 60° C. 5 mL of cleavage cocktail was used for 0.2 mmol of peptide. The resulting solution was triturated and washed with cold diethyl ether (pre-chilled in −80° C. freezer) this was repeated a total of three times. The obtained solids were dissolved in 50% H$_2$O: 50% acetonitrile containing 0.1% TFA and lyophilized. These same solvent compositions were used in the majority of experiments and will be referred to as A: 0.1% TFA in H$_2$O and B: 0.1% TFA in acetonitrile.

Peptides without selenocysteine were cleaved from the resin and the side-chain was simultaneously deprotected by treatment with 2.5% (v/v) water, 2.5% (v/v) 1,2-ethanedithiol (EDT), 1% (v/v) triisopropylsilane (TIPS) in neat TFA for 7 min at 60° C., 5 mL of cleavage cocktail was used for 0.2 mmol of peptide. The resulting solution was triturated and washed with cold ether (pre-chilled in −80° C. freezer). The trituration was repeated a total of three times. The obtained solids were dissolved in 50% A and 50% B and lyophilized.

Peptide containing methionine was cleaved from the resin and the side-chain was simultaneously deprotected by treatment with 1% (v/v) triisopropylsilane (TIPS), 2.5% (v/v) water, 2.5% (v/v) 1,2-ethanedithiol (EDT), 2% (v/v) methyl disulfide, 92% (v/v) trifluoroacetic acid (TFA), and saturated ammonium iodide for 8 min at 60° C. 5 mL of this cleavage cocktail was used for 0.2 mmol of peptide. The resulting solution was triturated and washed with cold diethyl ether (pre-chilled in −80° C. freezer) this was repeated a total of three times. The obtained solids were dissolved in 50% $H_2O$: 50% acetonitrile containing 0.1% TFA and lyophilized.

4) RP-HPLC Purification of Peptides

The crude peptide was dissolved in 95% A: 5% B with 6 M guanidinium hydrochloride and purified by semi-preparative RP-HPLC (Agilent Zorbax SB C18 column: 21.2×250 mm, 7 um, linear gradient: 5-50% B over 90 min, flow rate: 5 mL/min). 1 µL of each HPLC fraction was mixed with 1 µL of α-cyano-4-hydroxycinnamic acid (CHCA) matrix in 75% A: 25% B, spotted with MALDI, and checked for fractions with desired molecular mass. The purity of fractions was confirmed by analytical RP-HPLC (Agilent Zorbax SB C3 column: 2.1×150 mm, 5 um, gradient: 0-2 minutes 5% B, 2-11 minutes 5-65% B, 11-12 minutes 65% B, flow rate: 0.8 mL/min). HPLC fractions containing only product materials were confirmed by LC-MS analysis, combined, and then lyophilized. Peptides purified by RP-HPLC are listed in Table 1.

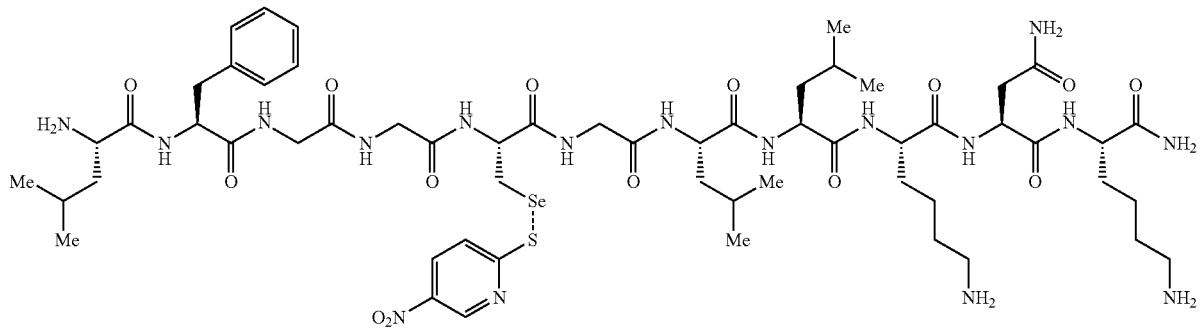

Peptide 1: LCMS Analysis Method A. HRMS (ESI) Mass. calcd. for $C_{57}H_{92}N_{17}O_{14}SSe$ $[M+H]^+$, 1350.58. Found $[M+H]^+$, 1350.58.

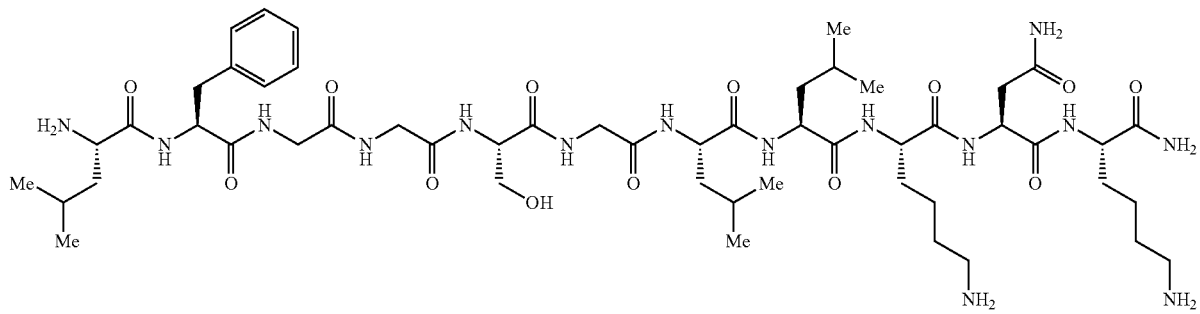 [SMILES: CC(C)C[C@H](NC(=O)CNC(=O)[C@H](CO)NC(=O)CNC(=O)CNC(=O)[C@H](Cc1ccccc1)NC(=O)[C@@H](N)CC(C)C)C(=O)N[C@@H](CC(C)C)C(=O)N[C@@H](CCCCN)C(=O)N[C@@H](CC(N)=O)C(=O)N[C@@H](CCCCN)C(N)=O]

Peptide 1-Ser5: LCMS Analysis Method A. HRMS (ESI) Mass. calcd. for $C_{52}H_{90}N_{15}O_{13}$ $[M+H]^+$, 1132.68. Found $[M+H]^+$, 1132.67.

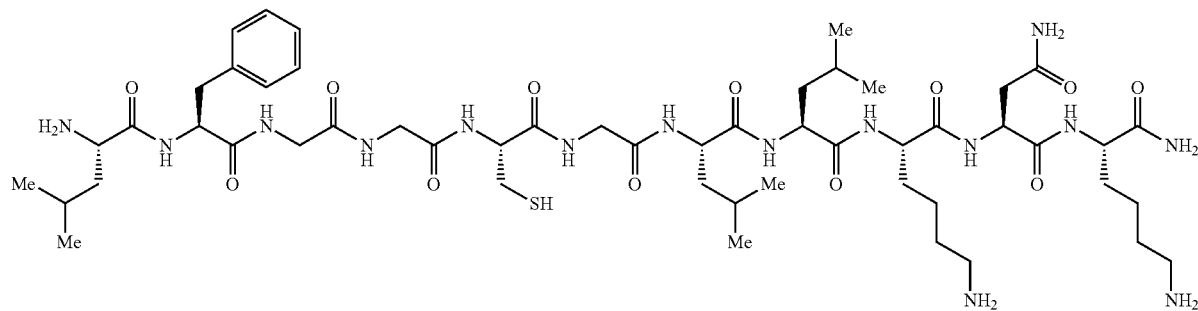 [SMILES: CC(C)C[C@H](NC(=O)CNC(=O)[C@H](CS)NC(=O)CNC(=O)CNC(=O)[C@H](Cc1ccccc1)NC(=O)[C@@H](N)CC(C)C)C(=O)N[C@@H](CC(C)C)C(=O)N[C@@H](CCCCN)C(=O)N[C@@H](CC(N)=O)C(=O)N[C@@H](CCCCN)C(N)=O]

Peptide 1-Cys5: LCMS Analysis Method A. HRMS (ESI) Mass. calcd. for $C_{52}H_{90}H_{15}O_{12}S$ $[M+H]^+$, 1148.66. Found $[M+H]^+$, 1148.67.

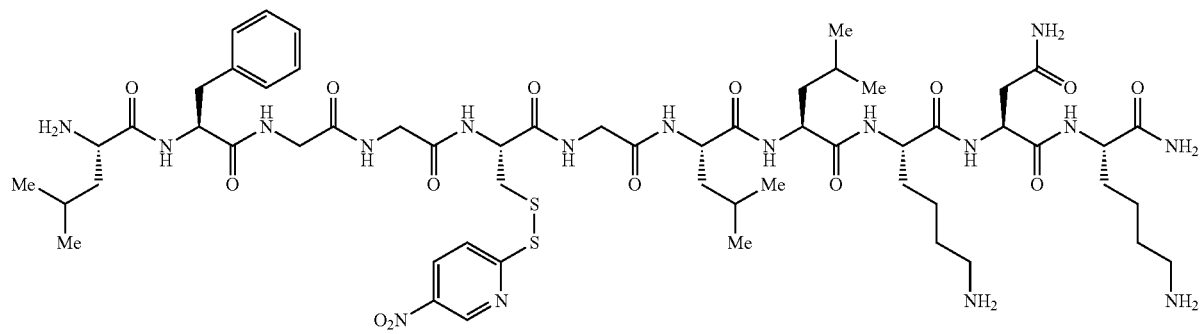 [SMILES: CC(C)C[C@H](NC(=O)CNC(=O)[C@H](CSSc1ccc([N+](=O)[O-])cn1)NC(=O)CNC(=O)CNC(=O)[C@H](Cc1ccccc1)NC(=O)[C@@H](N)CC(C)C)C(=O)N[C@@H](CC(C)C)C(=O)N[C@@H](CCCCN)C(=O)N[C@@H](CC(N)=O)C(=O)N[C@@H](CCCCN)C(N)=O]

Peptide 1-Cys5-TNP: Peptide was synthesized using fast-flow peptide synthesis procedure. The TNP protecting group was installed using cleavage cocktail: 5% (v/v) H$_2$O, 95% (v/v) TFA, 0.4 M DTNP, at 60° C. for 5 minutes. LCMS Analysis Method A. HRMS (ESI) Mass. calcd. for $C_{57}H_{91}H_{17}O_{14}S_2$ $[M+H]^+$, 1302.64. Found $[M+H]^+$, 1302.64.

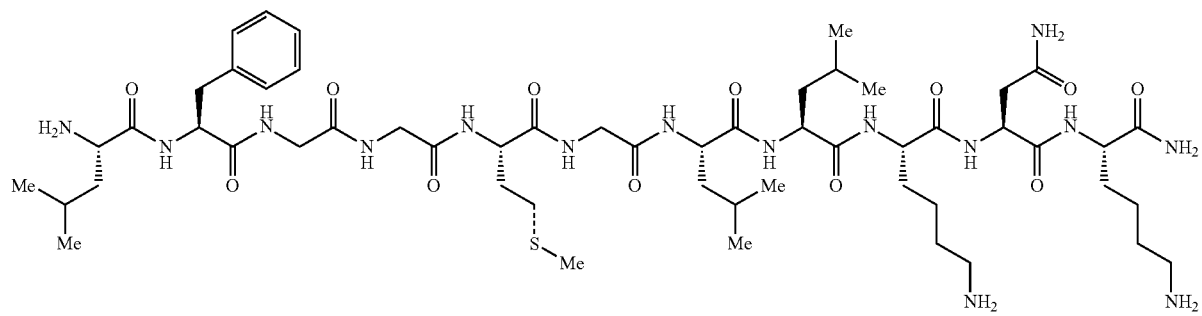

Peptide 1-Met5: LCMS Analysis Method A. HRMS (ESI) Mass. calcd. for $C_{54}H_{94}H_{15}O_{12}S$ $[M+H]^+$, 1176.69. Found $[M+H]^+$, 1176.73.

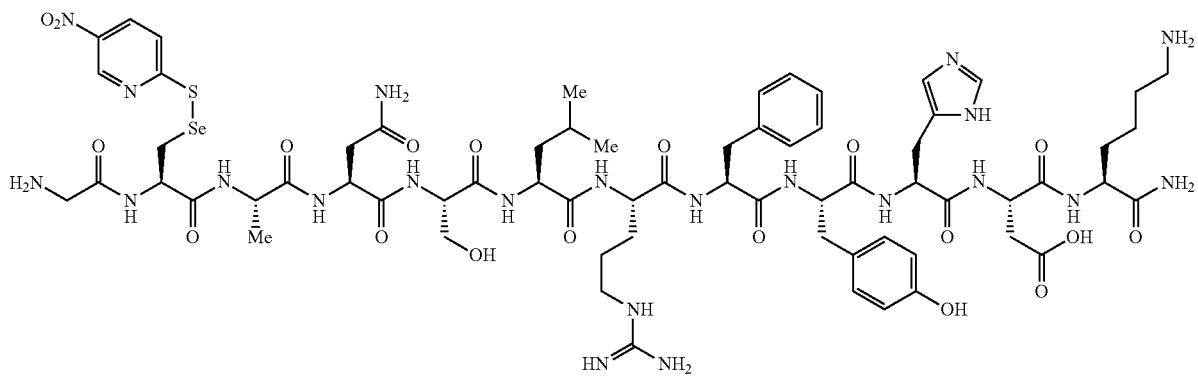 [SMILES: CC(C)C[C@H](NC(=O)[C@H](CO)NC(=O)[C@H](CC(N)=O)NC(=O)[C@H](C)NC(=O)[C@H](C[Se]Sc1ccc([N+](=O)[O-])cn1)NC(=O)CN)C(=O)N[C@@H](CCCNC(=N)N)C(=O)N[C@@H](Cc1ccccc1)C(=O)N[C@@H](Cc1ccc(O)cc1)C(=O)N[C@@H](Cc1cnc[nH]1)C(=O)N[C@@H](CC(=O)O)C(=O)N[C@@H](CCCCN)C(N)=O]

Peptide 7: LCMS Analysis Method A. HRMS (ESI) Mass. calcd. for $C_{66}H_{95}N_{22}O_{19}SSe$ $[M+H]^+$, 1611.60. Found $[M+H]^+$, 1611.60.

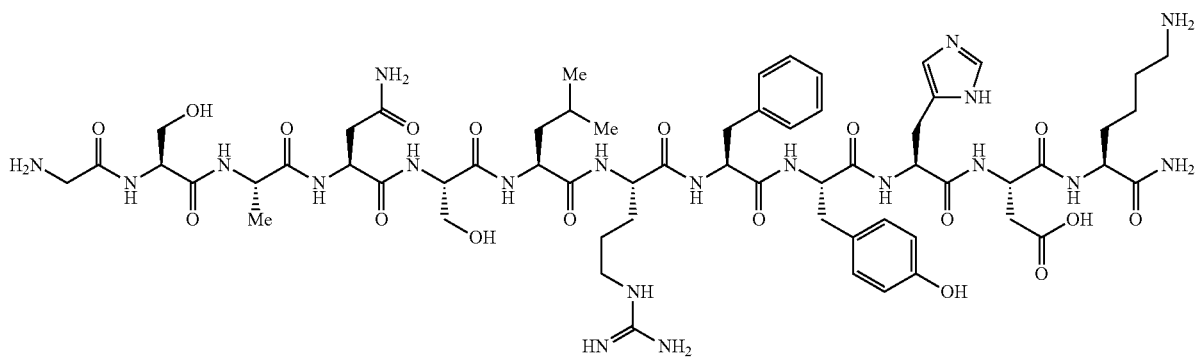 [SMILES: CC(C)C[C@H](NC(=O)[C@H](CO)NC(=O)[C@H](CC(N)=O)NC(=O)[C@H](C)NC(=O)[C@H](CO)NC(=O)CN)C(=O)N[C@@H](CCCNC(=N)N)C(=O)N[C@@H](Cc1ccccc1)C(=O)N[C@@H](Cc1ccc(O)cc1)C(=O)N[C@@H](Cc1cnc[nH]1)C(=O)N[C@@H](CC(=O)O)C(=O)N[C@@H](CCCCN)C(N)=O]

Peptide 9: LCMS Analysis Method A. HRMS (ESI) Mass. calcd. for $C_{61}H_{93}N_{20}O_{18}$ $[M+H]^+$, 1393.69. Found $[M+H]^+$, 1393.72.

General Procedure (A) for the Synthesis of Arylated Selenocysteine

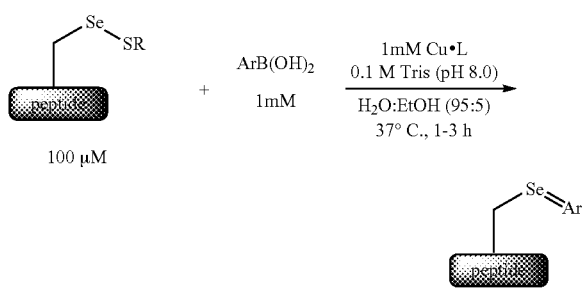

A 0.6 mL Eppendorf tube was charged with 75 μL of deionized $H_2O$, 10 μL of 1.0 M Tris Buffer (pH=8.0), 10 μL of peptide (1 mM stock solution in $H_2O$). A separate 1.7 mL Eppendorf tube was charged with copper (20 μmol), ligand (20 μmol), arylboronic acid (20 μmol), and 1 mL or 0.5 mL of 200 proof EtOH (making a 20 or 40 mM stock solution, respectively). The heterogeneous solution was subjected to sonication for 1 min, vortexed for 30 sec, and 5 μL of the resulting solution was added to the peptide solution in the 0.6 mL Eppendorf tube. The resulting reaction mixture was capped, vortexed for 30 seconds, and placed in a 37° C. water bath for the indicated time (1-3 h). The reaction mixture was quenched with 5 μL of EDTA (200 mM in $H_2O$) and 100 μL of 50% A: 50% B. The quenched reaction mixture was subjected to LC-MS analysis.

Optimization Table

Selenopeptide Arylation Optimization (Peptides Disclosed as SEQ ID NOS 3, 9, 3, 3, 3 and 3, Respectively, in Order of Appearance)

TABLE 2
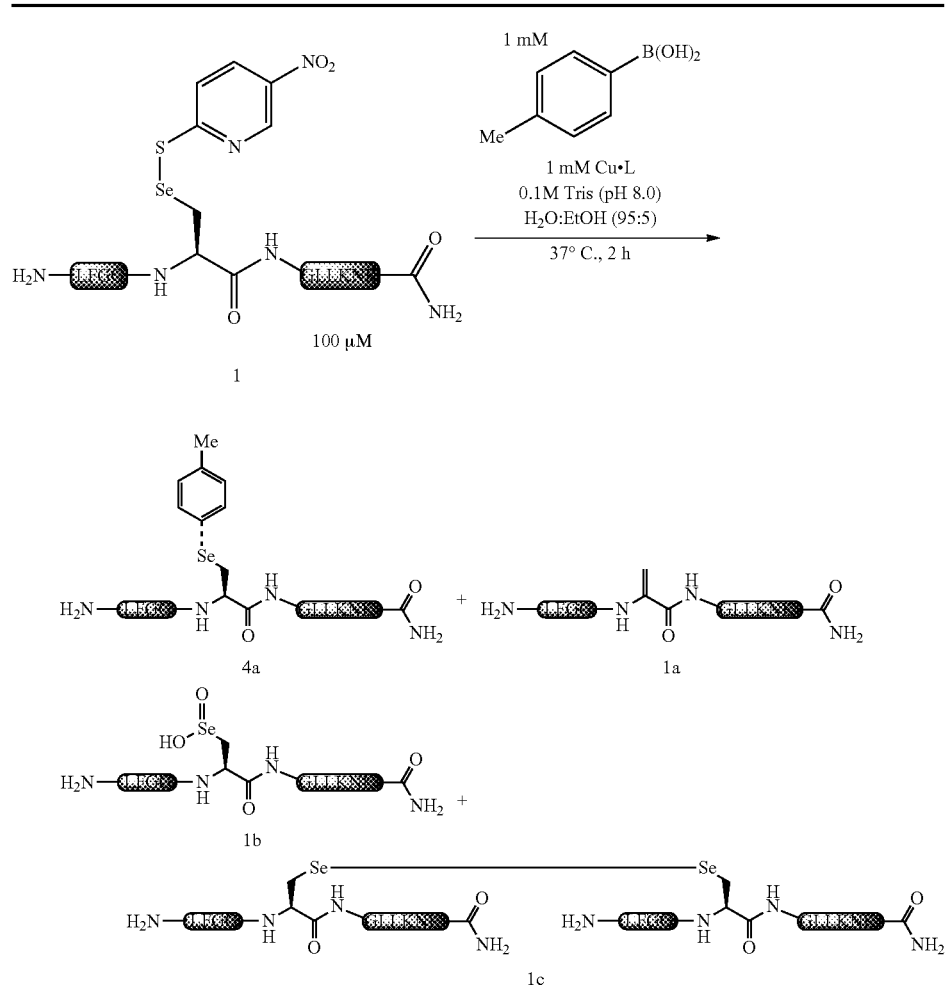
| entry | copper (Cu) | ligand (L) | % conversions[b] | % yield of 4a[a] | % yield of 1a[a] | % yield of 1b[a] | % yield of 1c[a] |
|---|---|---|---|---|---|---|---|
| 1 | CuSO$_4$ | L1 | 100 | 78 | 12 | 6 | 3 |
| 2 | CuSO$_4$ | L2 | 100 | 82 | 10 | 6 | 3 |
| 3 | CuSO$_4$ | L3 | 100 | 66 | 19 | 12 | 4 |
| 4 | CuSO$_4$ | L4 | 91 | 17 | 30 | 27 | 17 |
| 5[b] | CuSO$_4$ | — | 30 | 5 | 9 | 8 | 9 |
| 6 | CuCl$_2$·2H$_2$O | L2 | 100 | 78 | 13 | 6 | 2 |
| 7 | CuBr$_2$ | L2 | 100 | 79 | 13 | 6 | 2 |
| 8 | Cu(OAc)$_2$ | L2 | 100 | 78 | 14 | 6 | 2 |
| 9 | — | L2 | 22 | 0 | 5 | 0 | 16 |
| 10[d] | CuSO$_4$ | L2 | 73 | 44 | 13 | 8 | 8 |
| 11[e] | CuSO$_4$ | L2 | 28 | 7 | 8 | 3 | 10 |
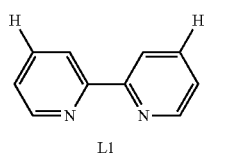 [SMILES: c1ccc(-c2ccccn2)nc1]
L1
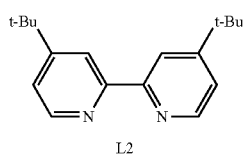 [SMILES: CC(C)(C)c1ccnc(-c2cc(C(C)(C)C)ccn2)c1]
L2

TABLE 2-continued

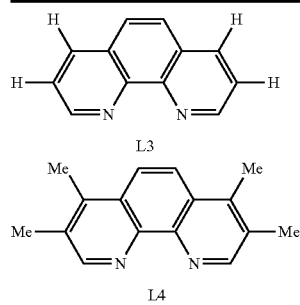

L3

L4

[a] Conversion and yields were determined by measuring the total ion currents (TIC) of LC-MS using Method A.
[b] Reaction run without any ligand.
[c] Reaction run without any copper.
[d] 0.5 mM CuSO$_4$, 0.5 mM L2, and 0.5 mM boronic acid were used.
[e] 0.25 mM CuSO$_4$, 0.25 mM L2, and 0.25 mM boronic acid were used.

[a] Conversion and yields were determined by measuring the total ion currents (TIC) of LC-MS using Method A. [b] Reaction run without any ligand. [c] Reaction run without any copper. [d] 0.5 mM CuSO$_4$, 0.5 mM L2, and 0.5 mM boronic acid were used. [e] 0.25 mM CuSO$_4$, 0.25 mM L2, and 0.25 mM boronic acid were used.

Serine Control Reaction (SEQ ID NO: 4)

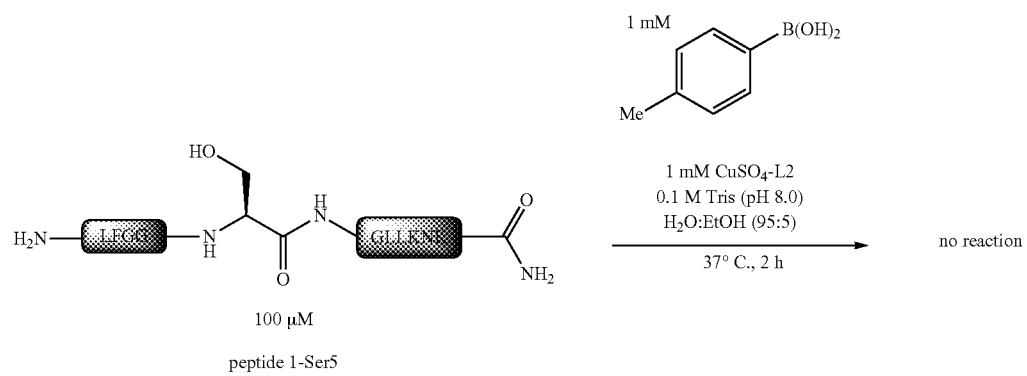

Cysteine Control Reaction (all Peptides Disclosed as SEQ ID NO: 5)

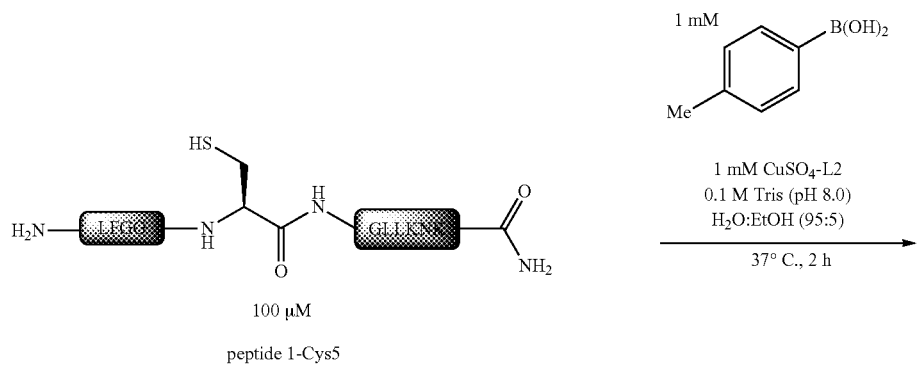

-continued
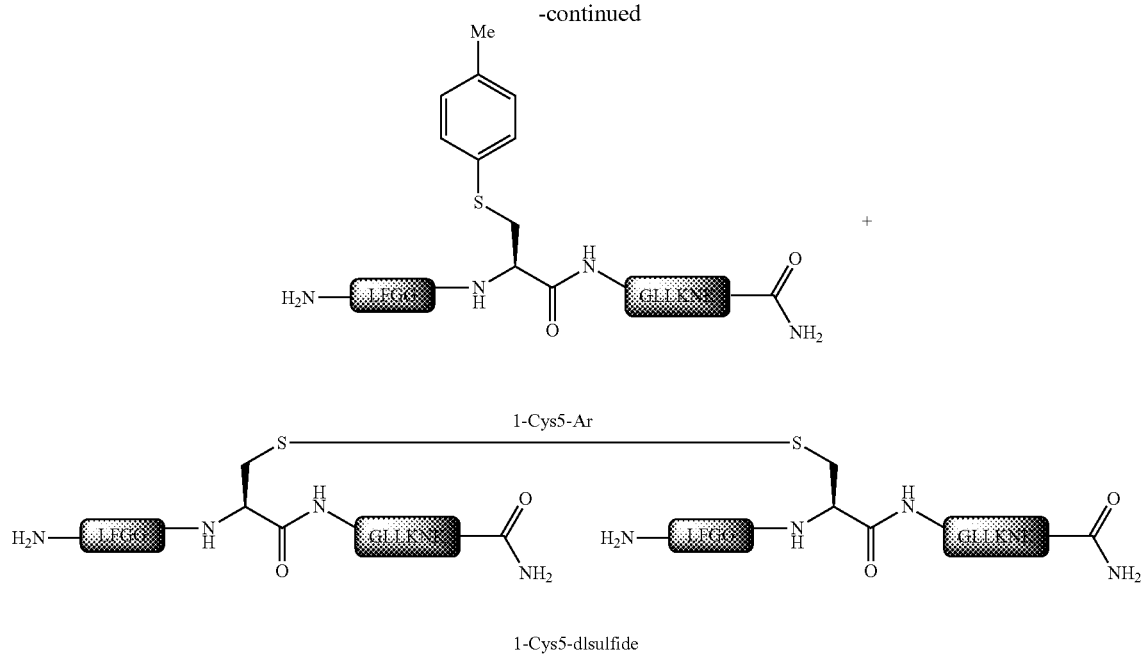
Cysteine-TNP Control Reaction (all Peptides Disclosed as SEQ ID NO: 5)
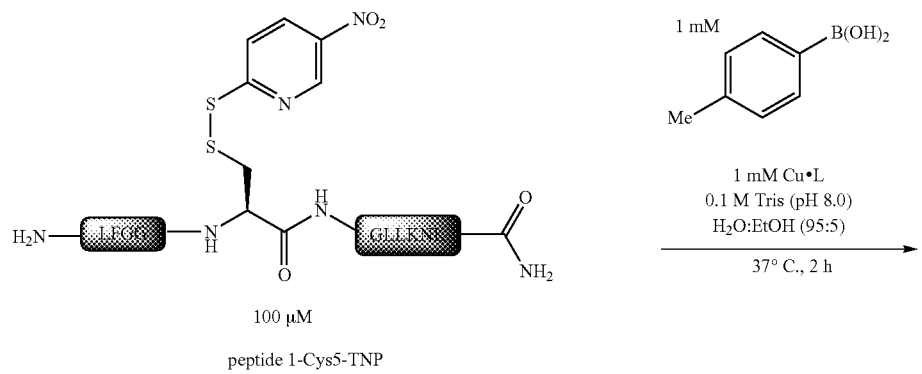
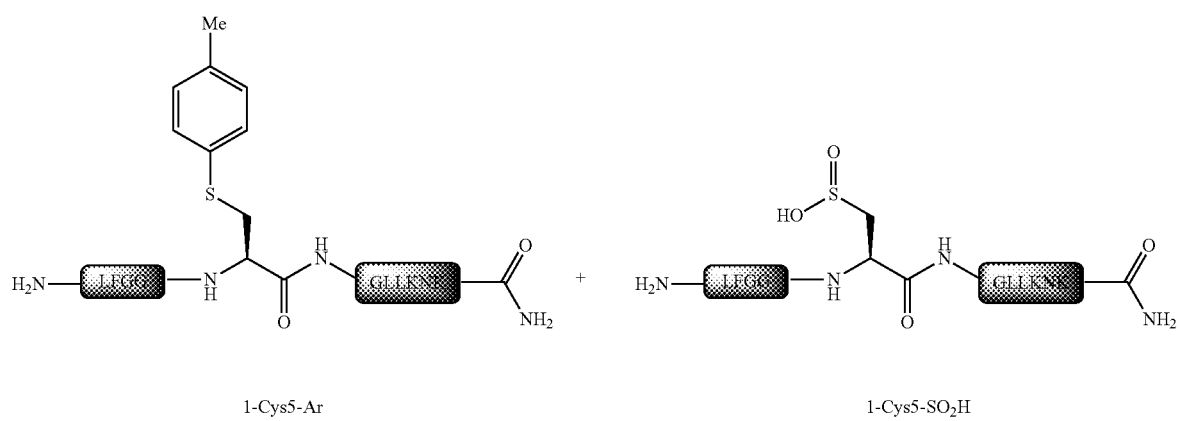

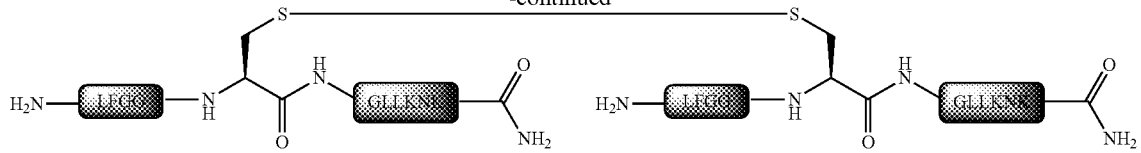

1-Cys5-disulfide

Methionine Control Reaction (SEQ ID NO: 6)

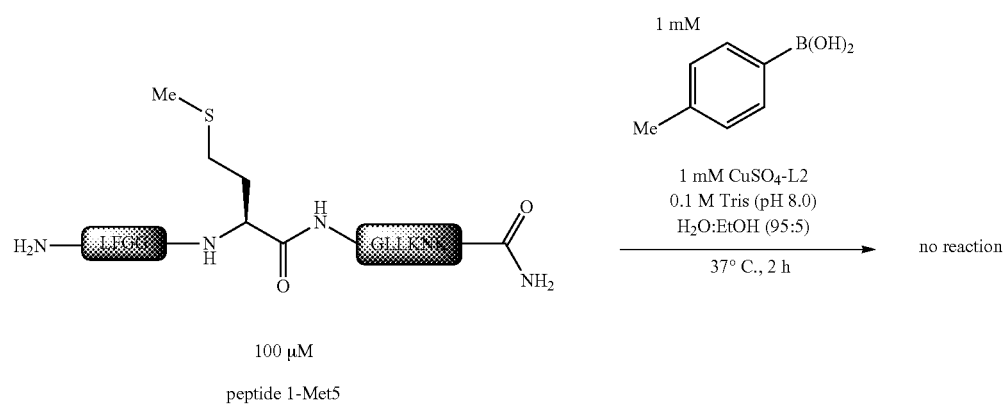

LC-MS Analysis of Arylation Reactions for Substrate Scope

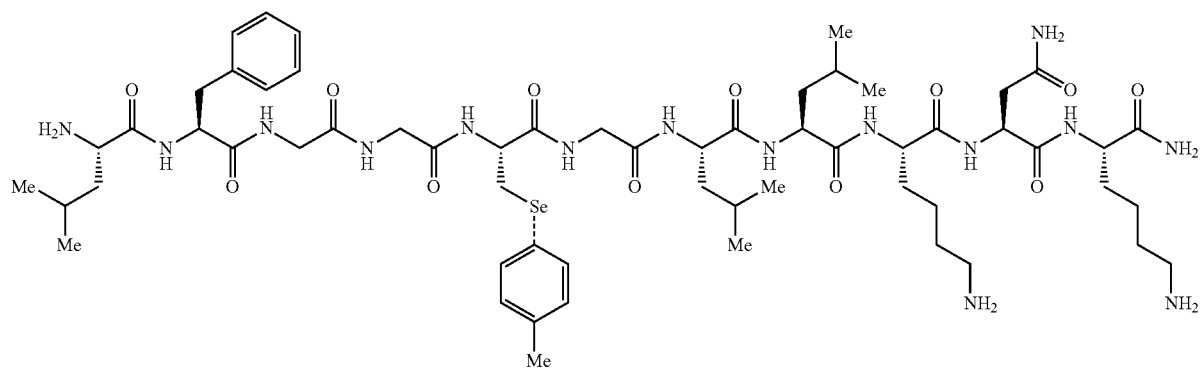

(4a): Prepared according to the general procedure (A) using peptide 1 (100 μM) and CuSO$_4$, L2, and p-tolylboronic acid stock solution (1 mM) at 37° C. for 2 h. The quenched reaction mixture was analyzed using LC-MS Method A. Analytical data for 4a: HRMS (ESI) Mass. calcd. for $C_{59}H_{97}N_{15}O_{12}Se$ [M+2H]$^{2+}$, 643.83. Found [M+21-1]$^{2+}$, 643.84.

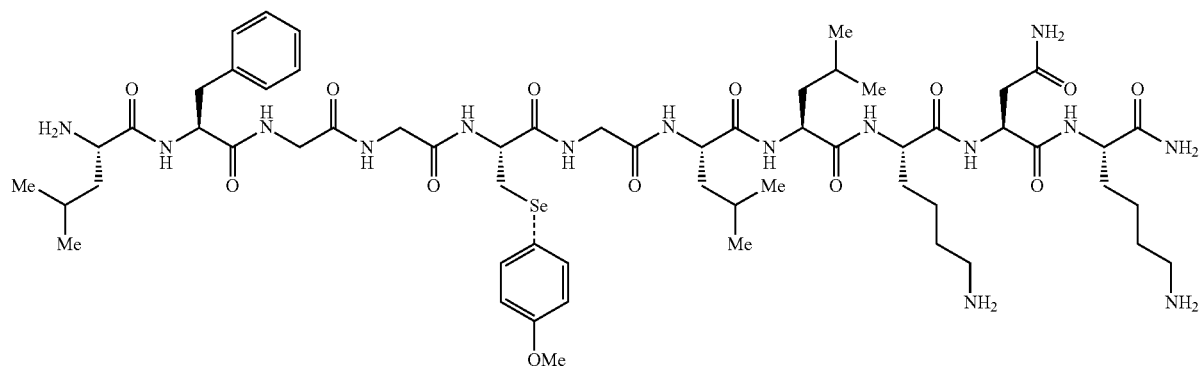

(4b): Prepared according to the general procedure (A) using peptide 1 (100 μM) and CuSO$_4$, L2, and (4-methoxyphenyl) boronic acid stock solution (1 mM) at 37° C. for 1 h. The quenched reaction mixture was analyzed using LC-MS Method A. Analytical data for 4b: HRMS (ESI) Mass. calcd. for C$_{59}$H$_{97}$N$_{15}$O$_{13}$Se [M+2H]$^{2+}$, 651.83. Found [M+2H]$^{2+}$, 651.84.

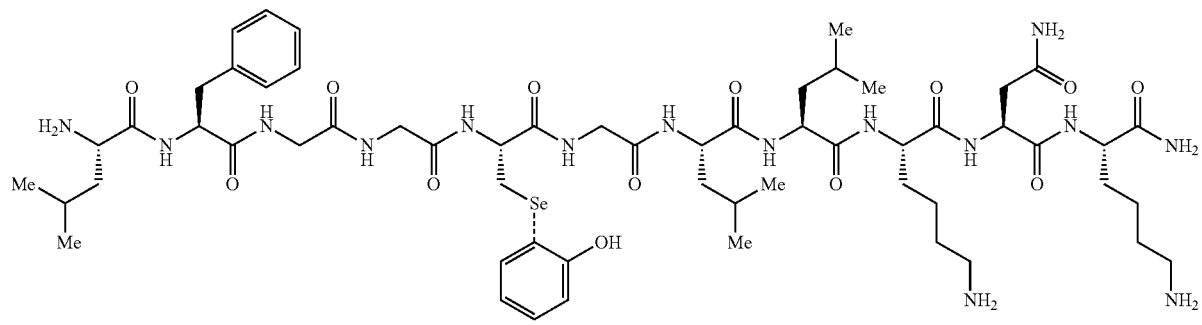

(4c): Prepared according to the general procedure (A) using peptide 1 (100 μM) and CuSO$_4$, L2, and (2-hydroxyphenyl) boronic acid stock solution (1 mM) at 37° C. for 1 h. The quenched reaction mixture was analyzed using LC-MS Method A. Analytical data for 4c: HRMS (ESI) Mass. calcd. for C$_{58}$H$_{94}$N$_{15}$O$_{13}$Se [M+H]$^+$, 1288.63. Found [M+H]$^+$, 1288.61.

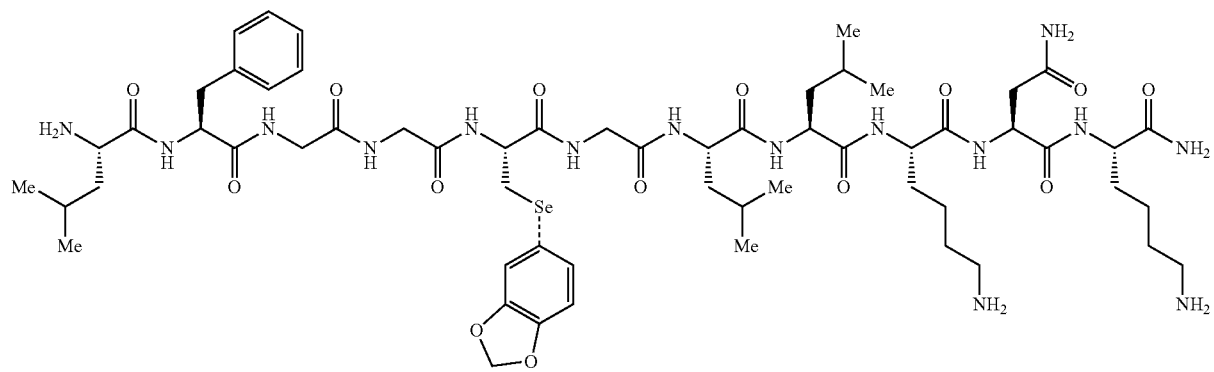

(4d): Prepared according to the general procedure (A) using peptide 1 (100 μM) and CuSO$_4$, L2, and benzo[d][1,3]dioxol-5-ylboronic acid stock solution (1 mM) at 37° C. for 1 h. The quenched reaction mixture was analyzed using LC-MS Method A. Analytical data for 4d: HRMS (ESI) Mass. calcd. for C$_{59}$H$_{95}$N$_{15}$O$_{14}$Se [M+2H]$^{2+}$, 658.82. Found [M+2H]$^{2+}$, 658.81.

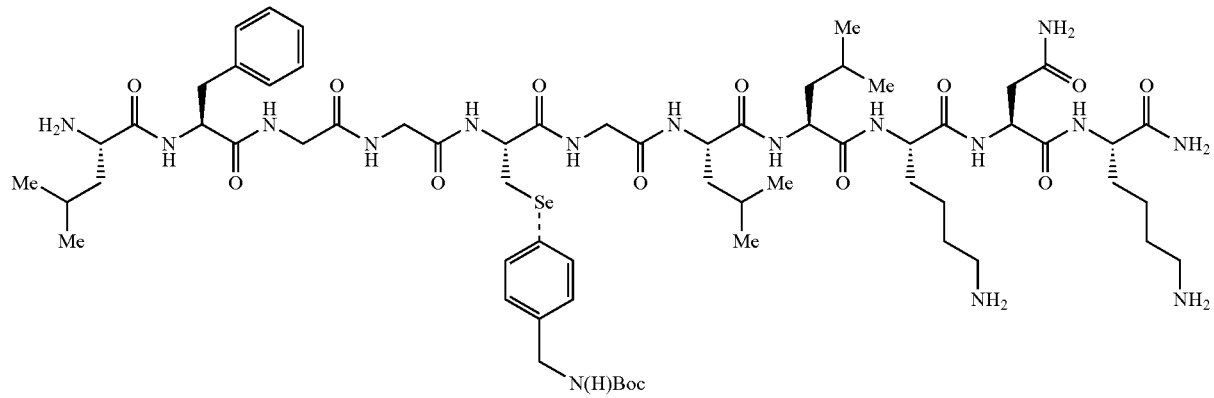

(4e): Prepared according to the general procedure (A) using peptide 1 (100 μM) and CuSO$_4$, L2, and (4-(((tert-butoxycarbonyl)amino)methyl)phenyl)boronic acid stock solution (1 mM) at 37° C. for 1.5 h. The quenched reaction mixture was analyzed using LC-MS Method A. Analytical data for 4e: FIRMS (ESI) Mass. calcd. for C$_{64}$H$_{105}$N$_{16}$O$_{14}$Se [M+H]$^+$, 1401.72. Found [M+H]$^+$, 1401.70.

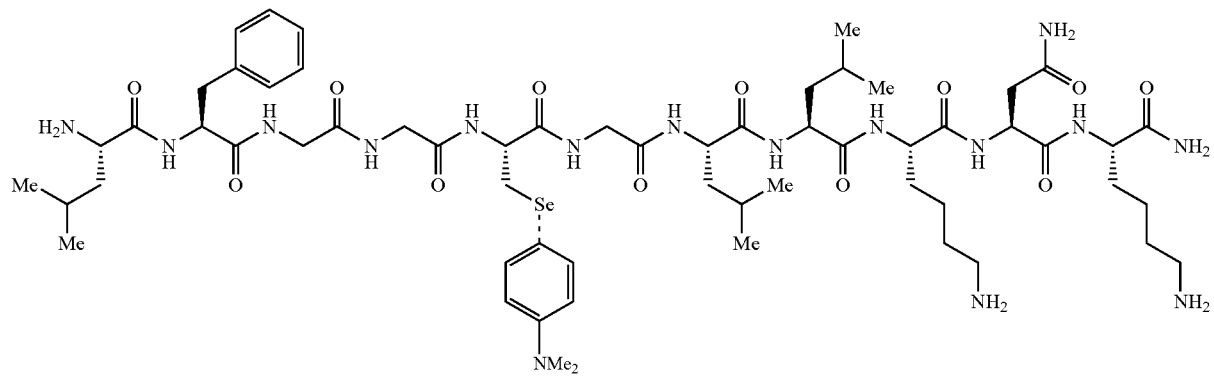

(4f): Prepared according to the general procedure (A) using peptide 1 (100 μM) and CuSO$_4$, L2, and (4-(dimethylamino)phenyl)boronic acid stock solution (1 mM) at 37° C. for 2 h. The quenched reaction mixture was analyzed using LC-MS Method A. Analytical data for 4f: HRMS (ESI) Mass. calcd. for C$_{60}$H$_{99}$N$_{16}$O$_{12}$Se [M+H]$^+$, 1315.68. Found [M+H]$^+$, 1315.69.

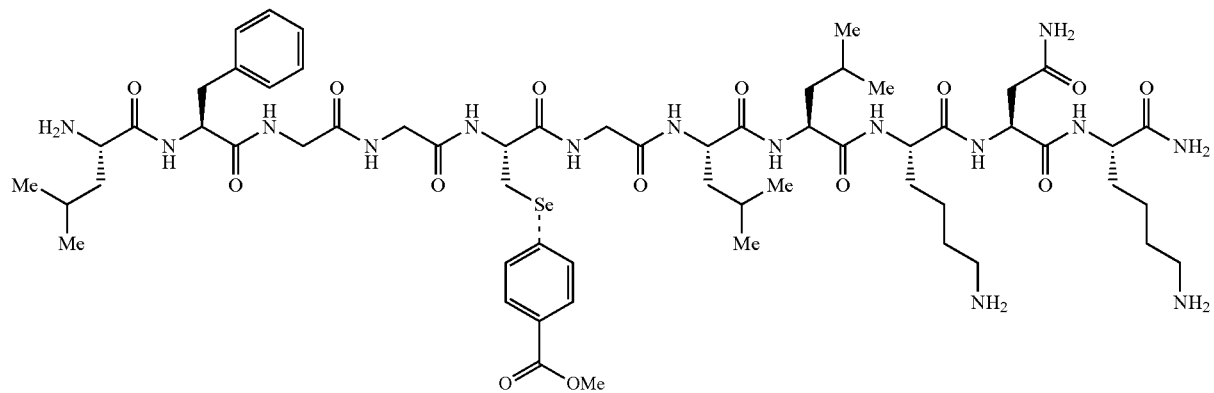

(4g): Prepared according to the general procedure (A) using peptide 1 (100 µM) and CuSO$_4$, L2, and (4-(methoxycarbonyl)phenyl)boronic acid stock solution (2 mM) at 37° C. for 1 h. The quenched reaction mixture was analyzed using LC-MS Method A. Analytical data for 4g: HRMS (ESI) Mass. calcd. for C$_{61}$H$_{100}$N$_{16}$O$_{13}$Se [M+2H]$^{2+}$, 665.82. Found [M+2H]$^{2+}$, 665.82.

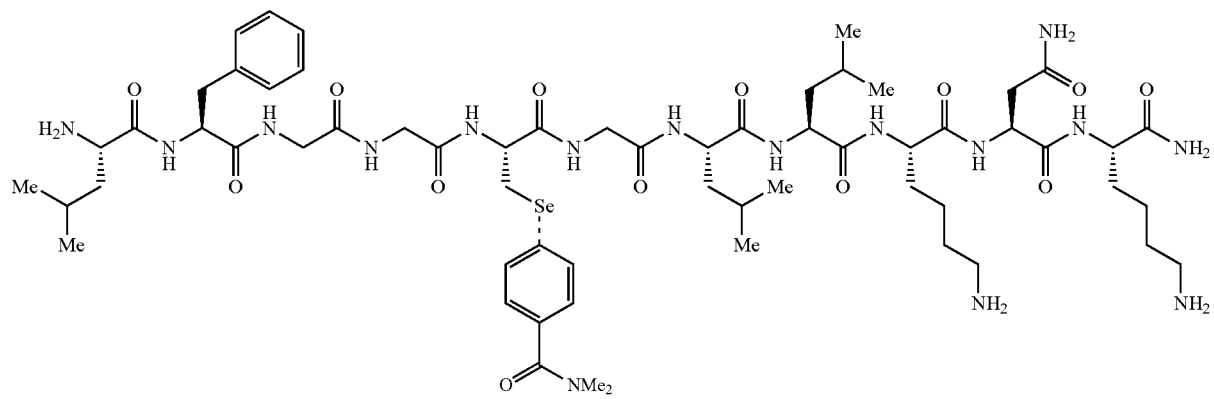

(4h): Prepared according to the general procedure (A) using peptide 1 (100 µM) and CuSO$_4$, L2, and (4-(dimethylcarbamoyl)phenyl)boronic acid stock solution (2 mM) at 37° C. for 1 h. The quenched reaction mixture was analyzed using LC-MS Method A. Analytical data for 4h: HRMS (ESI) Mass. calcd. for C$_{61}$H$_{100}$N$_{16}$O$_{13}$Se [M+2H]$^{2+}$, 672.34. Found [M+2H]$^{2+}$, 672.35.

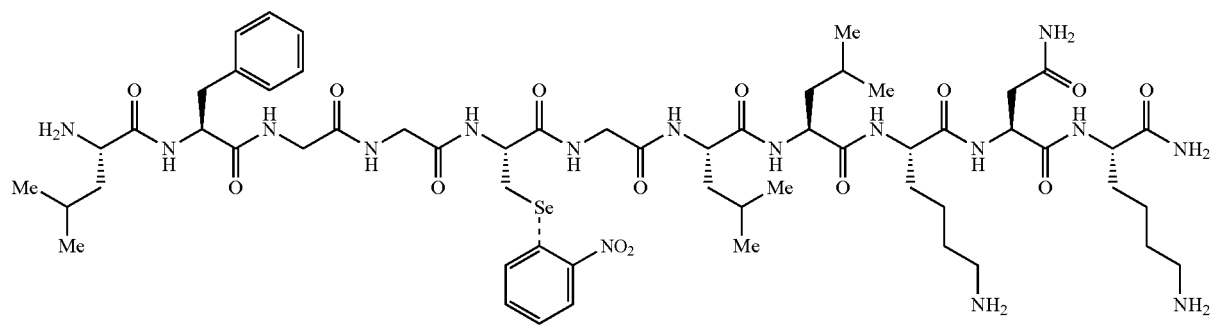

(4i): Prepared according to the general procedure (A) using peptide 1 (100 μM) and CuSO$_4$, L2, and (2-nitrophenyl) boronic acid stock solution (1 mM) at 37° C. for 1 h. The quenched reaction mixture was analyzed using LC-MS Method A. Analytical data for 4i: HRMS (ESI) Mass. calcd. for C$_{58}$H$_{94}$H$_{16}$O$_{14}$Se [M+2H]$^{2+}$, 659.31. Found [M+2H]$^{2+}$, 659.32.

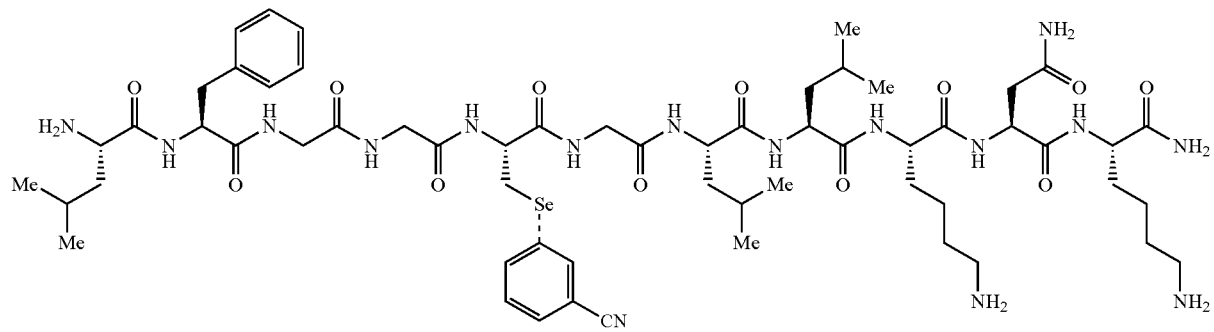

(4j): Prepared according to the general procedure (A) using peptide 1 (100 μM) and CuSO$_4$, L2, and (3-cyanophenyl) boronic acid stock solution (2 mM) at 37° C. for 2 h. The quenched reaction mixture was analyzed using LC-MS Method A. Analytical data for 4j: HRMS (ESI) Mass. calcd. for C$_{58}$H$_{94}$N$_{16}$O$_{14}$Se [M+2H]$^{2+}$, 649.32. Found [M+2H]$^{2+}$, 649.33.

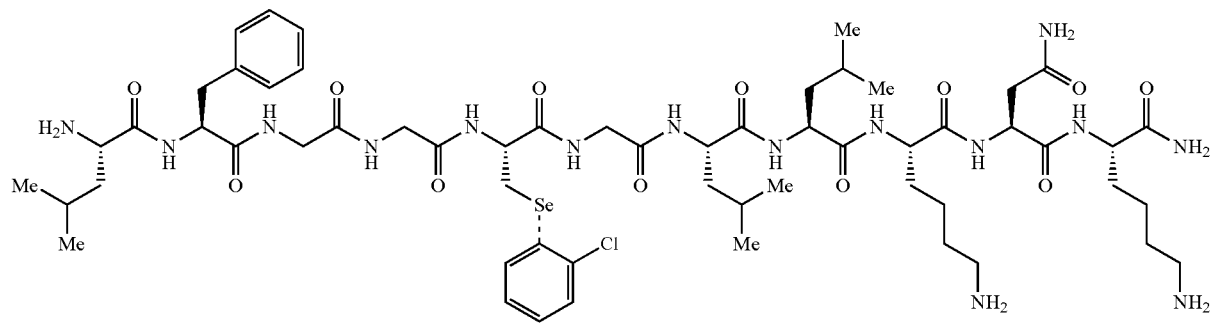

(4k): Prepared according to the general procedure (A) using peptide 1 (100 μM) and CuSO$_4$, L2, and (2-chlorophenyl) boronic acid stock solution (1 mM) at 37° C. for 1 h. The quenched reaction mixture was analyzed using LC-MS Method A. Analytical data for 4k: HRMS (ESI) Mass. calcd. for C$_{58}$H$_{92}$ClN$_{15}$O$_{12}$Se [M+H]$^+$, 1306.59. Found [M+H]$^+$, 1306.58.

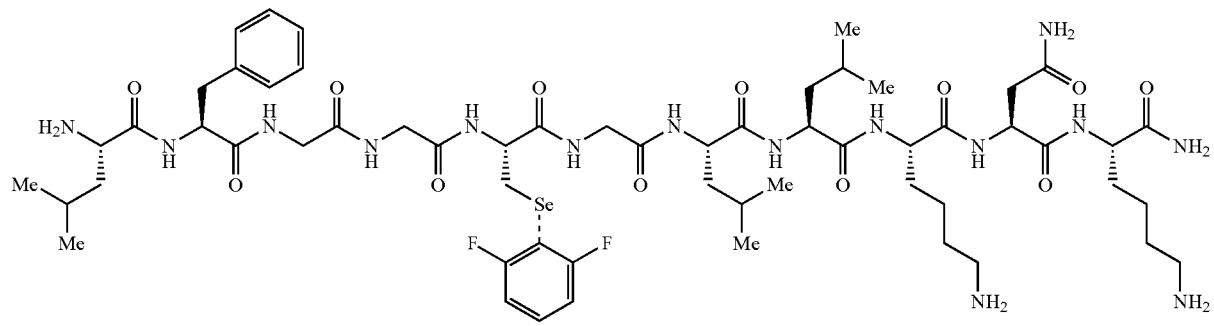

(4l): Prepared according to the general procedure (A) using peptide 1 (100 μM) and CuSO$_4$, L2, and (2,6-difluorophenyl)boronic acid stock solution (1 mM) at 37° C. for 1 h. The quenched reaction mixture was analyzed using LC-MS Method A. Analytical data for 4l: HRMS (ESI) Mass. calcd. for C$_{58}$H$_{91}$F$_2$N$_{15}$O$_{12}$Se [M+2H]$^{2+}$, 654.81. Found [M+2H]$^{2+}$, 654.82.

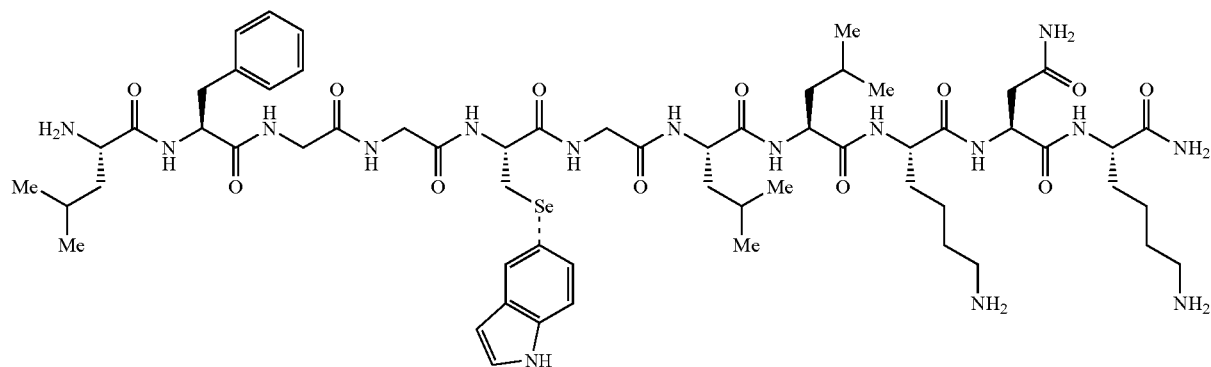

(5a): Prepared according to the general procedure (A) using peptide 1 (100 μM) and CuSO$_4$, L2, and (1H-indol-5-yl) boronic acid stock solution (1 mM) at 37° C. for 1 h. The quenched reaction mixture was analyzed using LC-MS Method A. Analytical data for 5a: HRMS (ESI) Mass. calcd. for C$_{60}$H$_{96}$N$_{16}$O$_{12}$Se [M+2H]$^{2+}$, 656.32. Found [M+2H]$^{2+}$, 656.32.

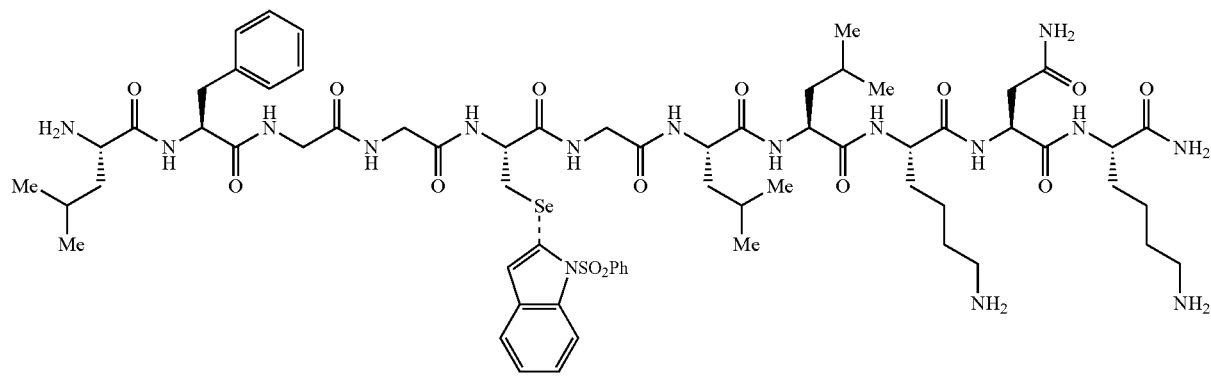

(5b): Prepared according to the general procedure (A) using peptide 1 (100 μM) and CuSO$_4$, L2, and (1-(phenylsulfonyl)-1H-indol-2-yl)boronic acid acid stock solution (1 mM) at 37° C. for 1 h. The quenched reaction mixture was analyzed using LC-MS Method A. Analytical data for 5b: HRMS (ESI) Mass. calcd. for C$_{66}$H$_{100}$N$_{16}$O$_{14}$SSe [M+21-1]$^{2+}$, 726.32. Found [M+2H]$^{2+}$, 726.33.

151 152

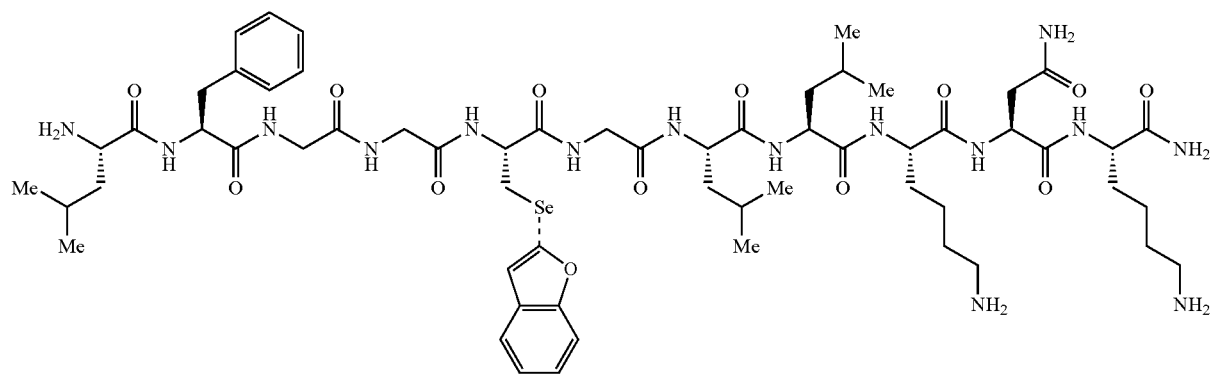

(5c): Prepared according to the general procedure (A) using peptide 1 (100 μM) and CuSO$_4$, L2, and benzofuran-2-ylboronic acid stock solution (1 mM) at 37° C. for 1 h. The quenched reaction mixture was analyzed using LC-MS Method A. Analytical data for 5c: HRMS (ESI) Mass. calcd. for $C_{60}H_{95}N_{15}O_{13}Se$ $[M+2H]^{2+}$, 656.81. Found $[M+2H]^{2+}$, 656.82.

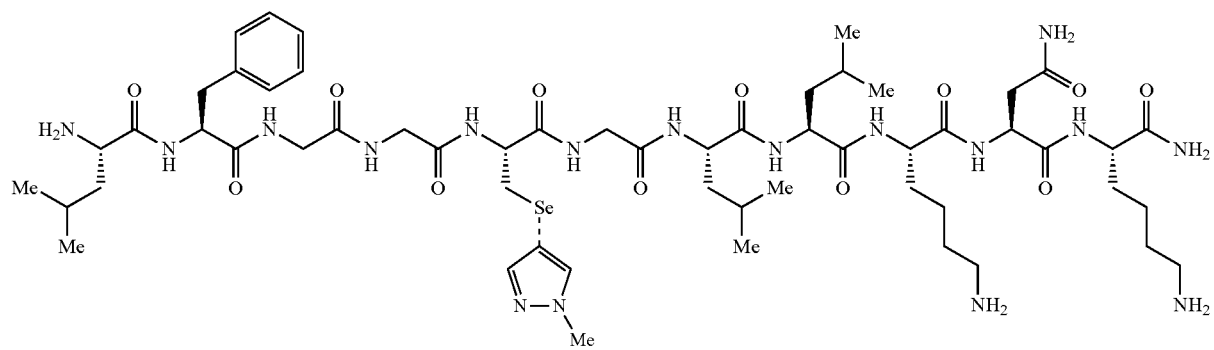

(5d): Prepared according to the general procedure (A) using peptide 1 (100 μM) and CuSO$_4$, L2, and (1-methyl-1H-pyrazol-4-yl)boronic acid stock solution (1 mM) at 37° C. for 1 h. The quenched reaction mixture was analyzed using LC-MS Method A. Analytical data for 5d: HRMS (ESI) Mass. calcd. for $C_{56}H_{94}N_{17}O_{12}Se$ $[M+H]^+$, 1276.64. Found $[M+H]^+$, 1276.63.

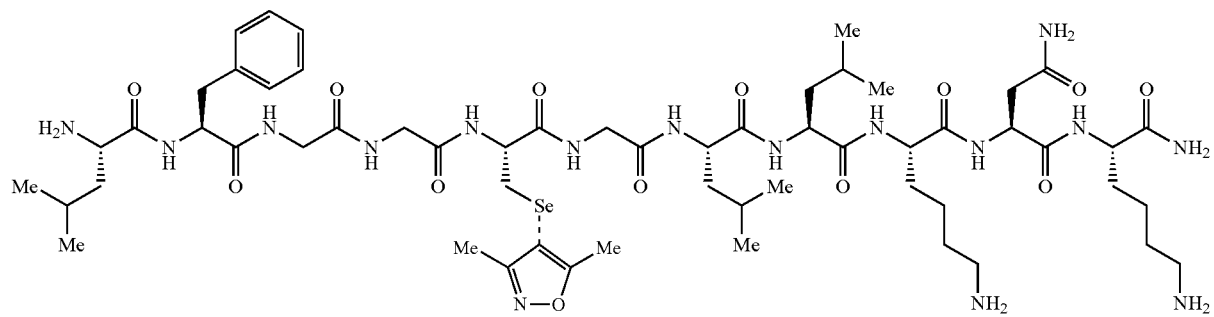

(5e): Prepared according to the general procedure (A) using peptide 1 (100 μM) and CuSO$_4$, L2, and (3,5-dimethylisoxazol-4-yl)boronic acid stock solution (1 mM) at 37° C. for 1 h. The quenched reaction mixture was analyzed using LC-MS Method A. Analytical data for 5e: HRMS (ESI) Mass. calcd. for $C_{57}H_{96}N_{16}O_{13}Se$ $[M+2H]^{2+}$, 646.32. Found $[M+2H]^{2+}$, 646.32.

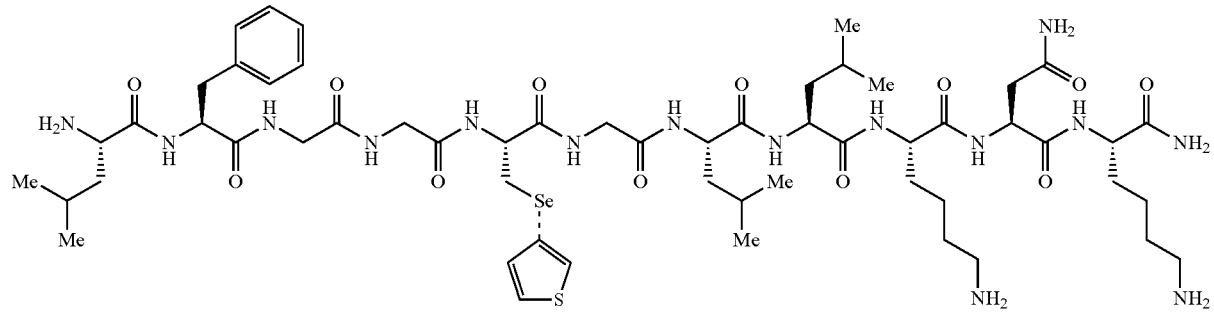

(5f): Prepared according to the general procedure (A) using peptide 1 (100 μM) and CuSO$_4$, L2, and thiophen-3-ylboronic acid stock solution (1 mM) at 37° C. for 1 h. The quenched reaction mixture was analyzed using LC-MS Method A. Analytical data for 5f: HRMS (ESI) Mass. calcd. for $C_{56}H_{93}N_{15}O_{12}SSe$ $[M+2H]^{2+}$, 639.79. Found $[M+2H]^{2+}$, 639.79.

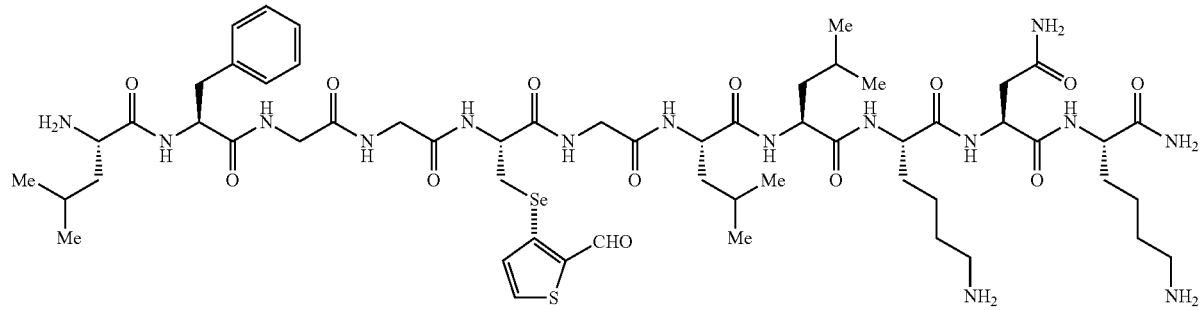

(5g): Prepared according to the general procedure (A) using peptide 1 (100 μM) and CuSO$_4$, L2, and (2-formylthiophen-3-yl)boronic acid stock solution (1 mM) at 37° C. for 1 h. The quenched reaction mixture was analyzed using LC-MS Method A. Analytical data for 5g: HRMS (ESI) Mass. calcd. for $C_{57}H_{93}N_{15}O_{13}SSe$ $[M+2H]^{2+}$, 653.80. Found $[M+2H]^{2+}$, 653.81.

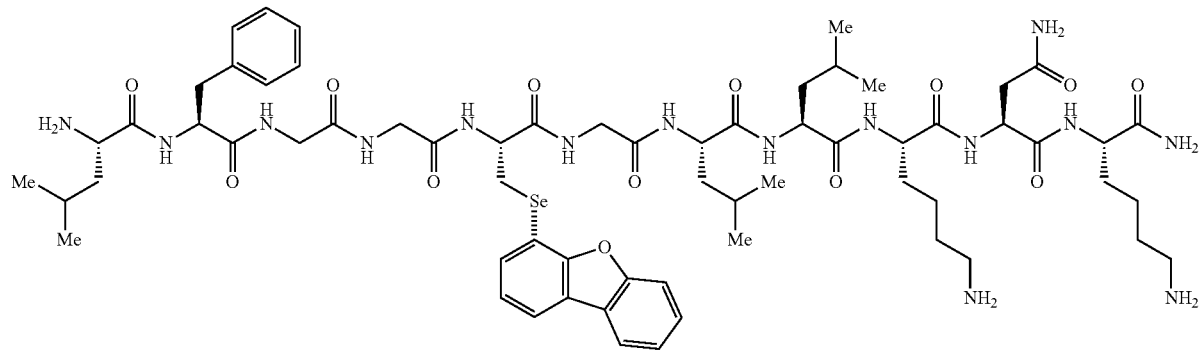

(5h): Prepared according to the general procedure (A) using peptide 1 (100 μM) and CuSO$_4$, L2, and dibenzo[b,d]furan-4-ylboronic acid stock solution (1 mM) at 37° C. for 1 h. The quenched reaction mixture was analyzed using LC-MS Method A. Analytical data for 5h: HRMS (ESI) Mass. calcd. for C$_{64}$H$_{97}$N$_{15}$O$_{13}$Se [M+2H]$^{2+}$, 681.83. Found [M+2H]$^{2+}$, 681.83.

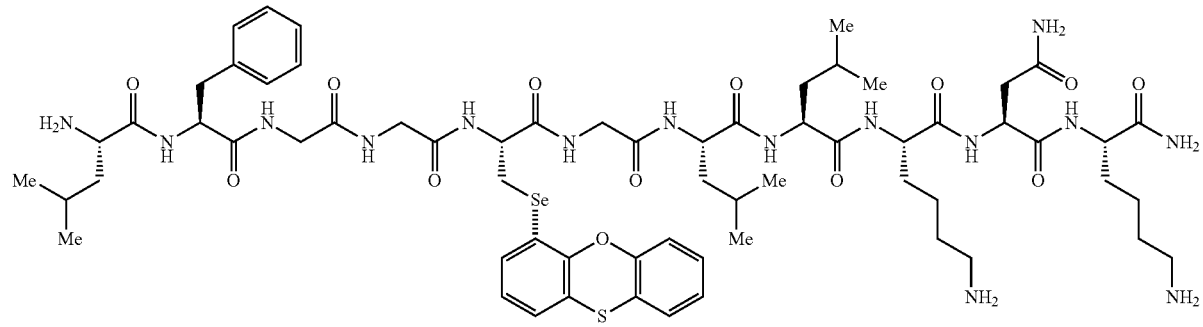

(5i): Prepared according to the general procedure (A) using peptide 1 (100 μM) and CuSO$_4$, L2, and phenoxathiin-4-ylboronic acid stock solution (1 mM) at 37° C. for 1 h. The quenched reaction mixture was analyzed using LC-MS Method C. Analytical data for 5i: HRMS (ESI) Mass. calcd. for C$_{64}$H$_{97}$N$_{15}$O$_{13}$SSe [M+2H]$^{2+}$, 697.81. Found [M+2H]$^{2+}$, 697.82.

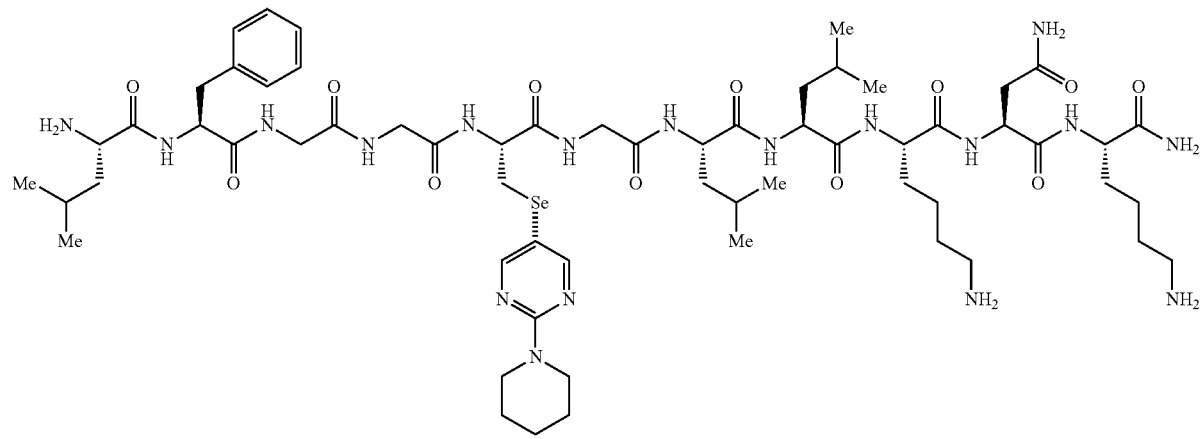

(5j): Prepared according to the general procedure (A) using peptide 1 (100 μM) and CuSO$_4$, L2, and (2-(piperidin-1-yl)pyrimidin-5-yl)boronic acid stock solution (1 mM) at 37° C. for 1 h. The quenched reaction mixture was analyzed using LC-MS Method A. Analytical data for 5j: HRMS (ESI) Mass. calcd. for C$_{61}$H$_{102}$N$_{18}$O$_{12}$Se [M+2H]$^{2+}$, 679.35. Found [M+2H]$^{2+}$, 679.36.

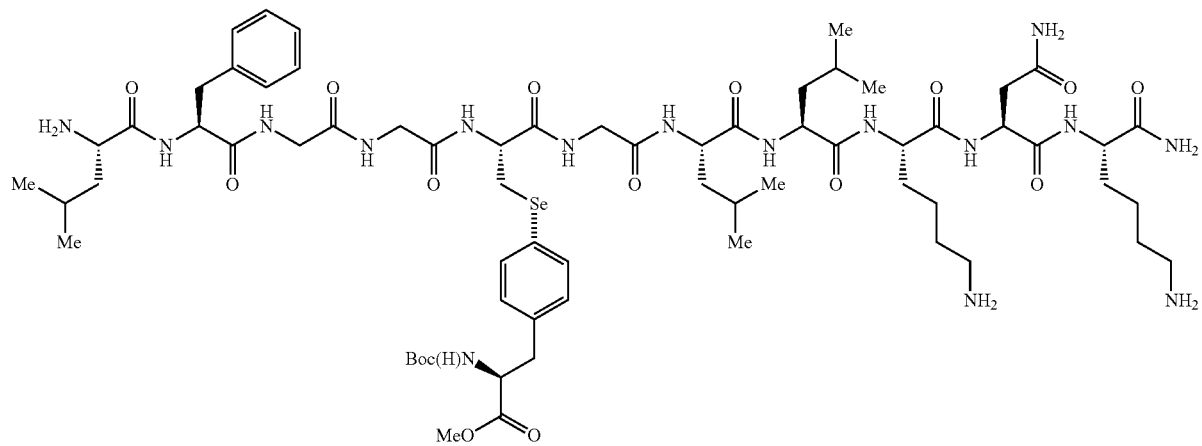

(6a): Prepared according to the general procedure (A) using peptide 1 (100 μM) and CuSO$_4$, L2, and (S)-(4-(2-((tert-butoxycarbonyl)amino)-3-methoxy-3-oxopropyl)phenyl) boronic acid stock solution (2 mM) at 37° C. for 1 h. The quenched reaction mixture was analyzed using LC-MS Method A. Analytical data for 6a: HRMS (ESI) Mass. calcd. for $C_{67}H_{108}N_{16}O_{16}Se$ [M+H]$^+$, 1473.73. Found [M+H]$^+$, 1473.71.

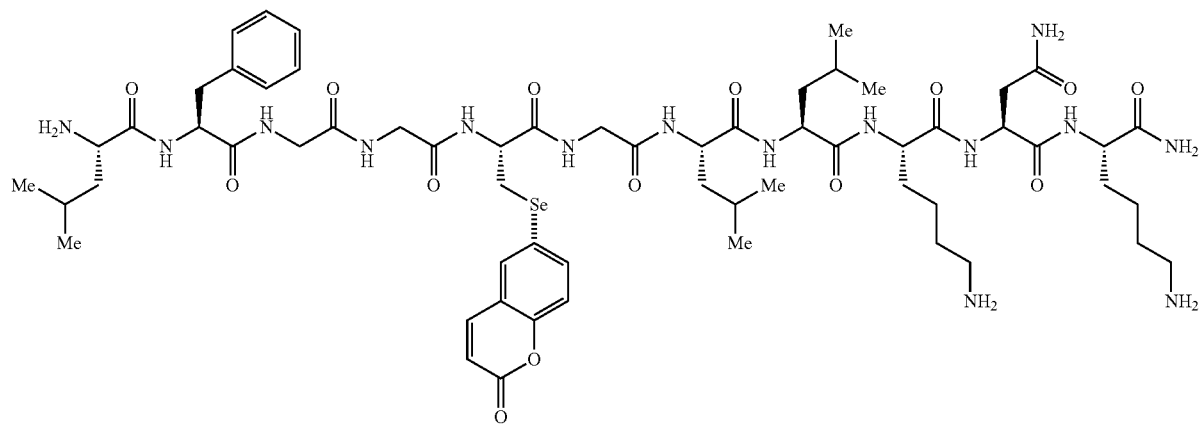

(6b): Prepared according to the general procedure (A) using peptide 1 (100 μM) and CuSO$_4$, L2, and (2-oxo-2H-chromen-6-yl)boronic acid stock solution (2 mM) at 37° C. for 1 h. The quenched reaction mixture was analyzed using LC-MS Method A. Analytical data for 6b: HRMS (ESI) Mass. calcd. for $C_{61}H_{95}N_{15}O_{14}Se$ [M+2H]$^{2+}$, 670.82. Found [M+2H]$^{2+}$, 670.83.

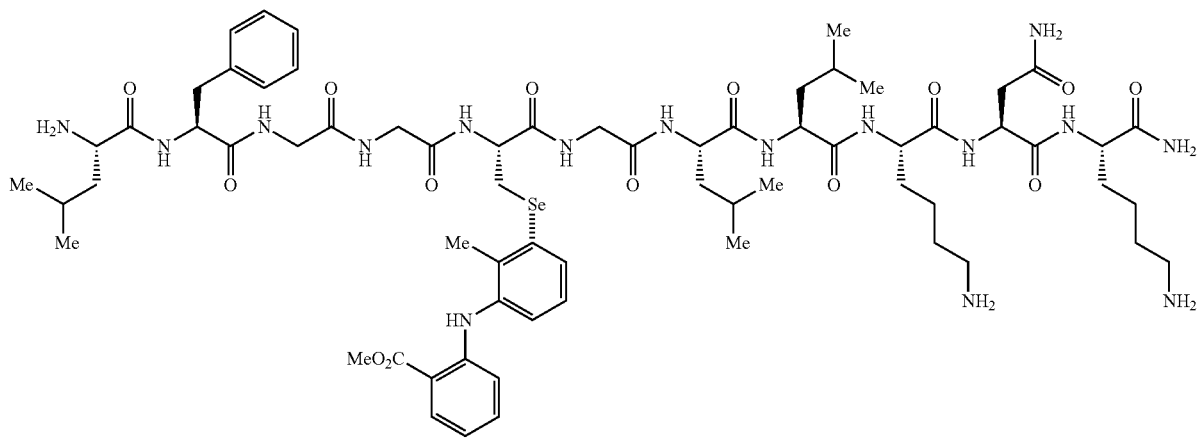

(6c): Prepared according to the general procedure (A) using peptide 1 (100 μM) and CuSO$_4$, L2, and (2-((2-(methoxycarbonyl)phenyl)amino)-6-methylphenyl)boronic acid stock solution (1 mM) at 37° C. for 1 h. The quenched reaction mixture was analyzed using LC-MS Method D. Analytical data for 6c: HRMS (ESI) Mass. calcd. for C$_{58}$H$_{92}$ClN$_{15}$O$_{12}$Se [M+2H]$^{2+}$, 718.35. Found [M+2H]$^{2+}$, 718.36.

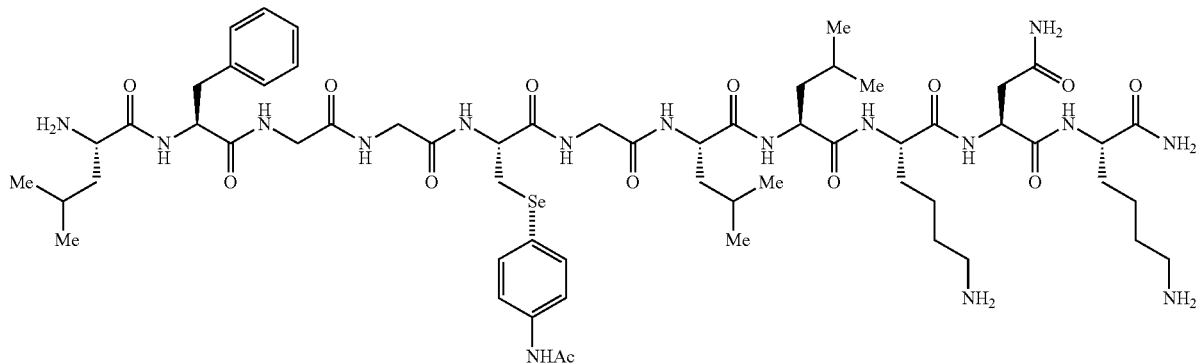

(6d): Prepared according to the general procedure (A) using peptide 1 (100 μM) and CuSO$_4$, L2, and (4-acetamidophenyl)boronic acid stock solution (2 mM) at 37° C. for 1 h. The quenched reaction mixture was analyzed using LC-MS Method A. Analytical data for 6d: HRMS (ESI) Mass. calcd. for C$_{60}$H$_{98}$N$_{16}$O$_{13}$Se [M+2H]$^{2+}$, 665.33. Found [M+2H]$^{2+}$, 665.34.

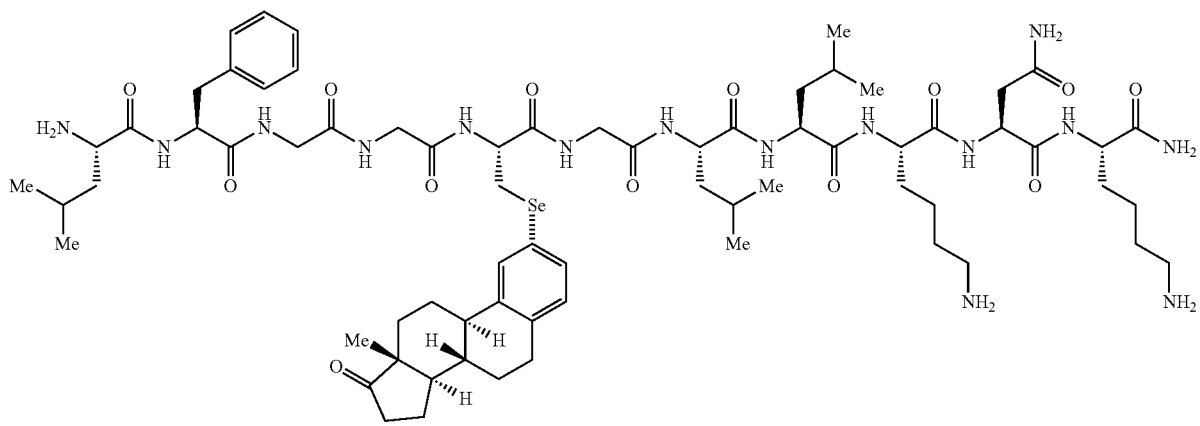

(6e): Prepared according to the general procedure (A) using peptide 1 (100 μM) and CuSO$_4$, L2, and ((8R,9S,13S,14S)-13-methyl-17-oxo-7,8,9,11,12,13,14,15,16,17-decahydro-6H-cyclopenta[a]phenanthren-3-yl)boronic acid solution (2 mM) at 37° C. for 3 h. The only exception is 10% DMF was used instead of 5% EtOH. The quenched reaction mixture was analyzed using LC-MS Method B. Analytical data for 6e: HRMS (ESI) Mass. calcd. for $C_{70}H_{111}N_{15}O_{13}Se$ [M+2]$^{2+}$, 724.88. Found [M+2H]$^{2+}$, 724.89.

30 sec, and 200 μL of the resulting solution was added to the peptide solution in the 20 mL scintillation vial. The resulting reaction mixture was capped, and stirred at 800 rpm in 37° C. water bath for the indicated time (10-60 min). The reaction mixture was quenched with 4 mL of 100 mM aqueous ETDA. The resulting mixture was centrifuged at 4,000 rpm for 10 min. The supernatant was filtered through a 0.22 μm nylon filter and was subjected to purification by

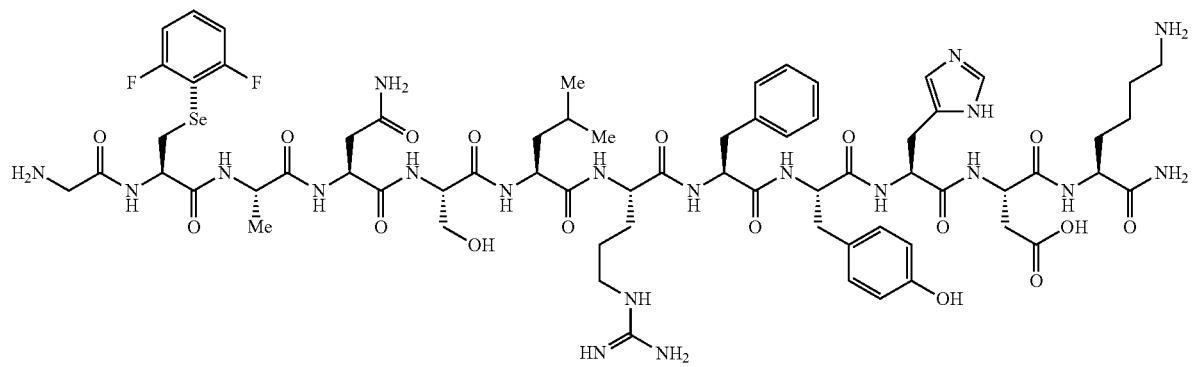

(8): Prepared according to the general procedure (A) using peptide 7 (100 μM) and CuSO$_4$, L2, and (2,6-difluorophenyl)boronic acid stock solution (1 mM) at 37° C. for 1 h. The quenched reaction mixture was analyzed using LC-MS Method A. Analytical data for 8: HRMS (ESI) Mass. calcd. for $C_{67}H_{96}F_2N_{20}O_{17}Se$ [M+H]$^+$, 785.32. Found [M+H]$^+$, 785.32.

Procedure for 1 mM Reactions
General Procedure (B) for Arylation Reactions with Arylboronic Acids

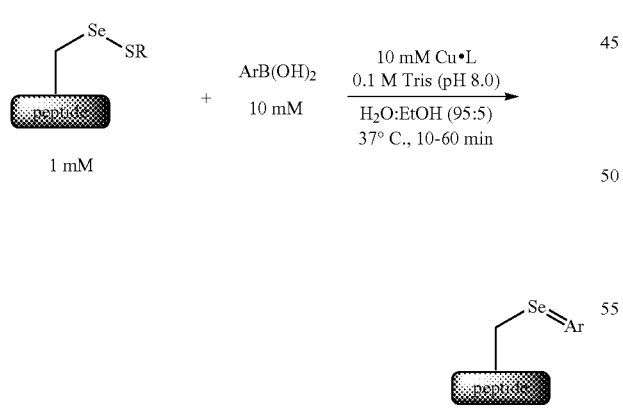

A 20-mL scintillation vial equipped with a stir bar was charged with 3 mL of deionized H$_2$O, 400 μL of 1.0 M Tris Buffer (pH=8.0), 400 μL of peptide 1 (10 mM stock solution). A separate 1.7 mL Eppendorf tube was charged with copper (200 μmop, ligand (200 μmol), arylboronic acid (200 μmol), and 1 mL of 200 proof EtOH. The heterogeneous solution was subjected to sonication for 1 min, vortexed for HPLC. The ligands were completely removed after filtering through nylon filter.
General Procedure for Alkylation of Selenocysteine

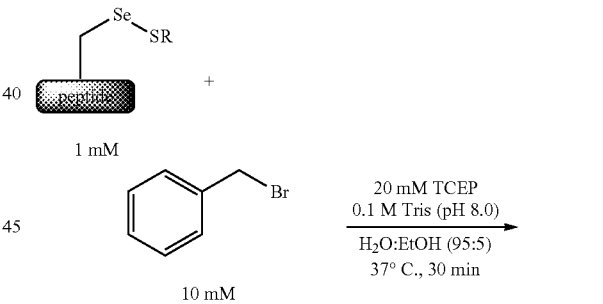

A 20 mL scintillation vial was charged with 3 mL of deionized H$_2$O, 400 μL of 1.0 M Tris Buffer with 200 mM TCEP (pH=8.0), 400 μL of peptide 1 (10 mM stock solution). A separate 1.7 mL Eppendorf tube was charged with benzylbromide (200 μmol) and 1 mL of 200 proof EtOH. 200 μL of the resulting solution was added to the peptide solution in the 20 mL scintillation vial. The resulting reaction mixture was capped, and stirred at 800 rpm in 37° C. water bath for 30 min. The reaction mixture was diluted with 4 mL of deionized water. The resulting solution was filtered through a 0.22 μm nylon filter and was subjected to purification by HPLC.

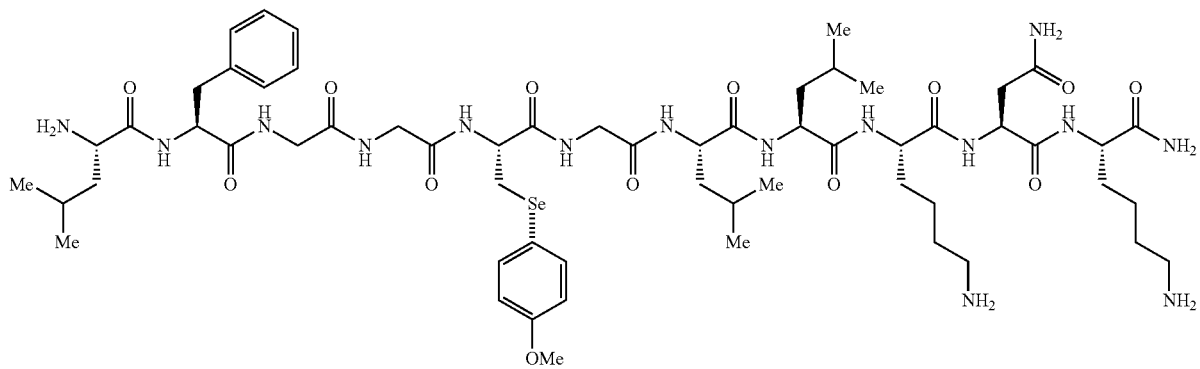

(4b): Prepared according to the general procedure (B) using peptide 1 (1 mM) and CuSO$_4$, L2, and (4-methoxyphenyl)boronic acid (10 mM) at 37° C. for 10 minutes. The quenched reaction mixture was analyzed using LC-MS Method A. Analytical data for 4b: HRMS (ESI) Mass. calcd. for C$_{59}$H$_{97}$N$_{15}$O$_{13}$Se [M+H]$^+$, 1302.64. Found [M+H]$^+$, 1302.64. 4b was obtained as white power (3.55 mg, 68%) after HPLC purification and lyophilization.

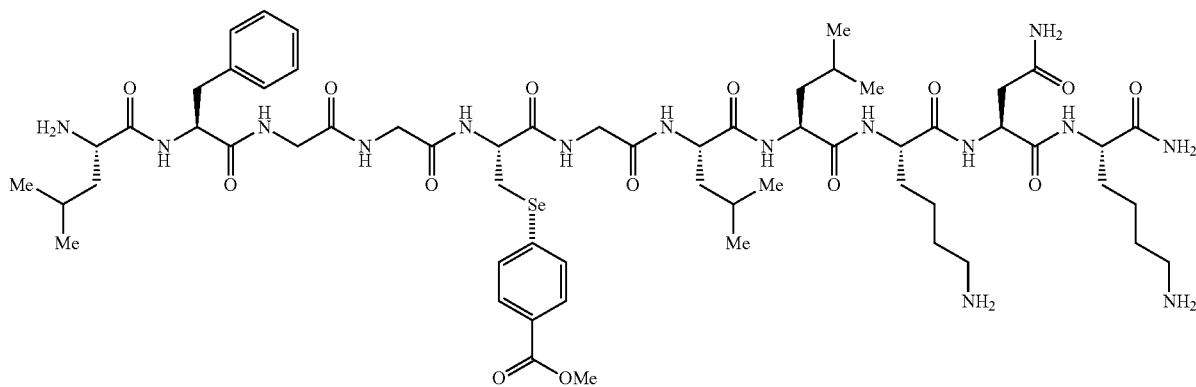

(4g): Prepared according to the general procedure (B) using peptide 1 (1 mM) and CuSO$_4$, L2, and (4-(methoxycarbonyl)phenyl)boronic acid (10 mM) at 37° C. for 1 h. The quenched reaction mixture was analyzed using LC-MS Method A. Analytical data for 4g: HRMS (ESI) Mass. calcd. for C$_6$H$_{100}$N$_{16}$O$_{13}$Se [M+2H]$^{2+}$, 665.82. Found [M+2H]$^{2+}$, 665.82. 4g was obtained as white power (3.91 mg, 74%) after HPLC purification and lyophilization.

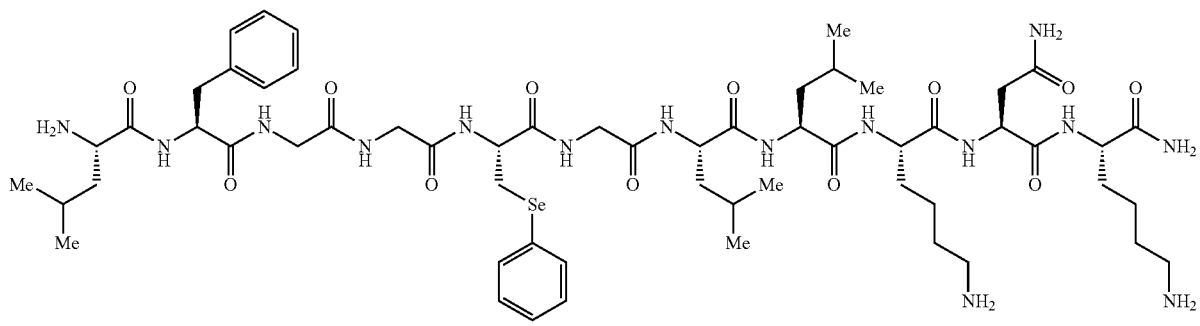 [SMILES: CC(C)C[C@H](NC(=O)CNC(=O)[C@H](C[Se]c1ccccc1)NC(=O)CNC(=O)CNC(=O)[C@H](Cc1ccccc1)NC(=O)[C@@H](N)CC(C)C)C(=O)N[C@@H](CC(C)C)C(=O)N[C@@H](CCCCN)C(=O)N[C@@H](CC(N)=O)C(=O)N[C@@H](CCCCN)C(N)=O]

(4m): Prepared according to the general procedure (B) using peptide 1 (1 mM) and CuSO₄, L2, and phenylboronic acid (10 mM) at 37° C. for 30 minutes. The quenched reaction mixture was analyzed using LC-MS Method A. Analytical data for 4m: HRMS (ESI) Mass. calcd. for $C_{58}H_{93}N_{15}O_{12}Se$ [M+H]⁺, 1272.63. Found [M+H]⁺, 1272.63. 4m was obtained as white power (3.54 mg, 70%) after HPLC purification and lyophilization.

A 0.6 mL tube was charged with 178 μL of deionized H₂O, 20 μL of 1.0 M CAPS Buffer (pH 10.0), 2 μL of peptide (10 mM stock solution). The resulting reaction mixture was capped and incubated in 37° C. water bath or was left at room temperature for 11 hours. 5 μL of the crude reaction was quenched by addition of 200 μL of 50% A: 50% B and was subjected to LC-MS analysis Method E. FIG. 5B.

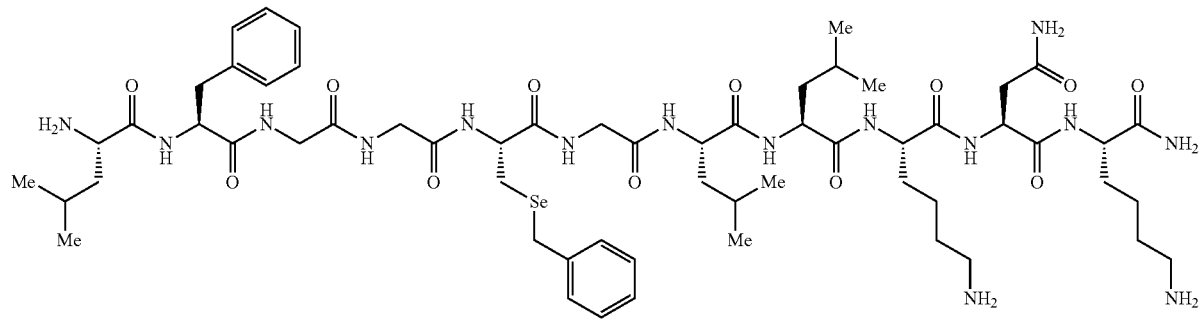 [SMILES: CC(C)C[C@H](NC(=O)CNC(=O)[C@H](C[Se]Cc1ccccc1)NC(=O)CNC(=O)CNC(=O)[C@H](Cc1ccccc1)NC(=O)[C@@H](N)CC(C)C)C(=O)N[C@@H](CC(C)C)C(=O)N[C@@H](CCCCN)C(=O)N[C@@H](CC(N)=O)C(=O)N[C@@H](CCCCN)C(N)=O]

(4n): Prepared according to the alkylation procedure using peptide 1 (1 mM) and benzylbromide (10 mM) at 37° C. for 30 minutes. The reaction mixture was analyzed using LC-MS Method A. Analytical data for 4n: HRMS (ESI) Mass. calcd. for $C_{59}H_{95}N_{15}O_{12}Se$ [M+H]⁺, 1286.65. Found [M+H]⁺, 1286.65. 4n was obtained as white power (3.63 mg, 71%) after HPLC purification and lyophilization.

Stability Studies of Functionalized Selenocysteine Peptides

1) Stability in pH=8.0 Buffer

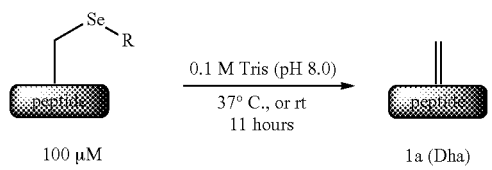

A 0.6 mL tube was charged with 178 μL of deionized H₂O, 20 μL of 1.0 M Tris Buffer (pH 8.0, 2 μL of peptide (10 mM stock solution). The resulting reaction mixture was capped and incubated in 37° C. water bath or was left at room temperature for 11 hours. 5 μL of the crude reaction mixture was quenched by addition of 200 μL of 50% A: 50% B and was subjected to LC-MS analysis Method E. FIG. 5A.

2) Stability in pH=10.0 Buffer

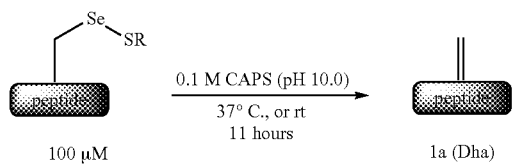

3) Stability Under Oxidative Conditions

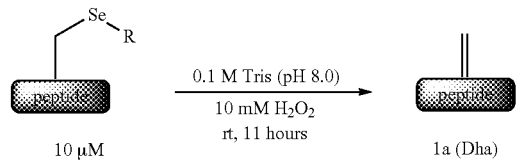

A 300-μL LC-MS vial was charged with 158 μL of deionized H₂O, 20 μL of 1.0 M Tris Buffer (pH=8.0), 2 μL of peptide (1 mM stock solution), 20 μL of H₂O₂ (100 mM stock solution in water). The resulting reaction mixture was capped and was monitored by LC-MS (Method E).

Example 2—Drug Release from Functionalized Selenocysteines

As important as new bioconjugation methods are, it is also important for release of the drug molecule once the bioconjugate is delivered to the treatment site.

Figure 19:
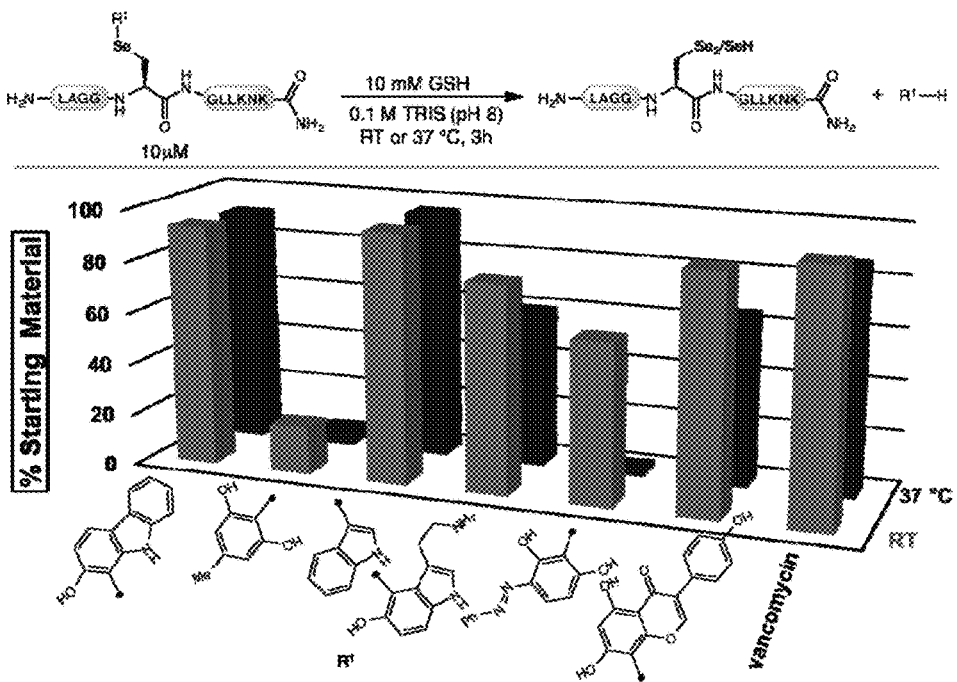
FIG. 19 depicts (top) a reaction scheme showing that glutathione (GSH, a tripeptide), which is found in 5 mM concentration in animal cells, can promote dissociation of the native drug or natural product by reduction of the C—Se bond (SEQ ID NOS 15 and 15, respectively, in order of appearance); (bottom) shows a bar graph depicting the amount of starting material remaining after the exposure to GSH at room temperature or 37° C. for 3 h.

FIG. 19 shows that glutathione (GSH, a tripeptide), which is found in 5 mM concentration in animal cells, can promote dissociation of the native drug or natural product. There is no apparent degradation of the small molecule (LCMS). This is an important breakthrough for the field of drug delivery.

So, selenocysteine peptide conjugates can be delivered to the treatment site and the glutathione found in vivo can promote slow release of the native pharmaceutical.

Example 3—Conjugation of Vancomycin to Peptides

General Procedure

Vancomycin was conjugated to a variety of peptides. As an example: A 20-mL scintillation vial equipped with a stir bar was charged with a peptide (10 mg, 0.00621 mmol), vancomycin hydrochloride (46 mg, 0.031 mmol), DI H₂O (5.6 mL), and 620 μL 1.0 M Tris Buffer (pH=8.0). The reaction mixture was capped, and stirred at 600 rpm in 37° C. water bath for 3 h. Upon consumption of the peptide (monitored by LCMS) the reaction mixture was quenched with 2 mL of 0.1% TFA in 95:5 H2O: MeCN and centrifuged at 4,000 rpm for 4 min. The supernatant was filtered through a 0.22-μm nylon filter and was subjected to purification by HPLC. Analyzed by LC-MS Method D. Analytical data for 11l: HRMS (ESI) Mass. calcd. For $C_{127}H_{167}Cl_2N_{29}O_{41}Se$ $[M+2H]^{2+}$, 1452.52. Found $[M+2H]^{2+}$, 1453.05. The following peptide conjugate (11l) was obtained as white power (7.7 mg, 43%) after HPLC purification and lyophilization.

Eppendorf tube was charged with vancomycin (15 mg, 10 μmol), and 0.25 mL of DI $H_2O$ (making a 80 mM stock solution). The heterogeneous solution was subjected to sonication for 1 min, vortexed for 30 sec, and 2.5 μL of the resulting solution was added to the peptide solution in the 0.6 mL Eppendorf tube. The resulting reaction mixture was capped, vortexed for 30 seconds, and placed in a 37° C.

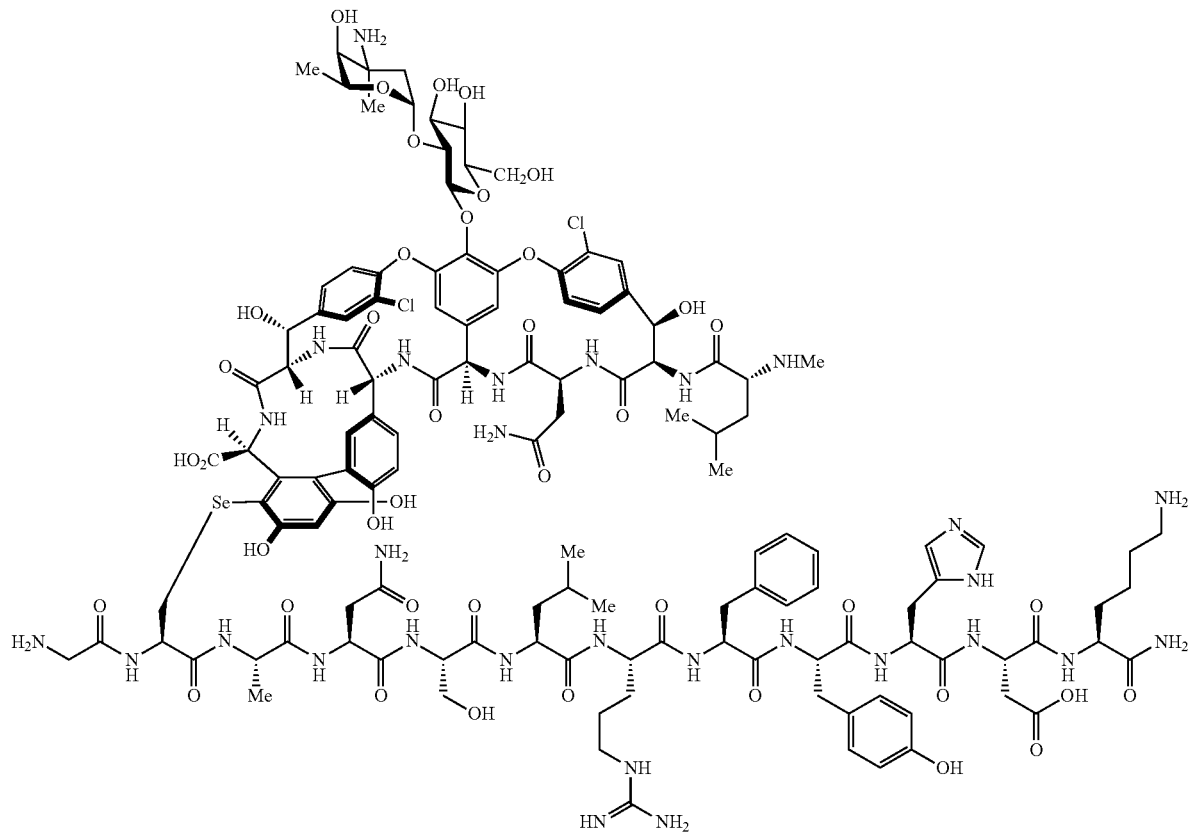

111

With Copper and Ligand

A 0.6 mL Eppendorf tube was charged with 32.5 μL of deionized $H_2O$, 5 μL of 1.0 M Tris Buffer (pH=8.0), 10 μL of peptide (1 mM stock solution in $H_2O$). A separate 0.6 mL Eppendorf tube was charged with copper (0.80 mg, 5 μmol), ligand (1.4 mg, 5 μmol), vancomycin (15 mg, 10 μmol), and 0.25 mL of 200 proof EtOH (making a 40 or 80 mM stock solution, respectively). The heterogeneous solution was subjected to sonication for 1 min, vortexed for 30 sec, and 2.5 μL of the resulting solution was added to the peptide solution in the 0.6 mL Eppendorf tube. The resulting reaction mixture was capped, vortexed for 30 seconds, and placed in a 37° C. water bath for the indicated time (3 h). The reaction mixture was quenched with 5 μL of EDTA (200 mM in $H_2O$), 145 μL of 0.1% TFA in 1:1 $H_2O$:MeCN. The quenched reaction mixture was subjected to immediate LC-MS analysis using LC-MS Method D (injection: 1 μL). Analytical data for 11l: HRMS (ESI) Mass. calcd. for $C_{127}H_{168}Cl_2N_{29}O_{41}Se$ $[M+3H]^{2+}$, 968.68. Found [M+3H]$^{3+}$, 969.04.

Without Copper and Ligand

A 0.6 mL Eppendorf tube was charged with 32.5 μL of deionized $H_2O$, 5 μL of 1.0 M Tris Buffer (pH=8.0), 10 μL of peptide (1 mM stock solution in $H_2O$). A separate 0.6 mL water bath for the indicated time (3 h). The reaction mixture was quenched with 150 μL of 0.1% TFA in 1:1 $H_2O$:MeCN. The quenched reaction mixture was subjected to immediate LC-MS analysis using LC-MS Method D (injection: 1 μL). Analytical data for 11l: HRMS (ESI) Mass. calcd. for $C_{127}H_{168}Cl_2N_{29}O_{41}Se$ $[M+3H]^{2+}$, 968.68. Found [M+3H]$^{3+}$, 969.03.

Example 4—Functionalized Selenocysteines as Antibacterial Agents

Many bacteria have developed a resistance to previously used antibacterial pharmaceuticals.

Vancomycin has been shown to be active against a few strains of gram-positive bacteria by inhibiting the peptidoglycan synthesis. However, vancomycin is not active against gram-negative bacteria due to the bacterium's outer cell membrane. Additionally several strains of gram-positive bacteria have developed resistance towards vancomycin.

Figure 20:
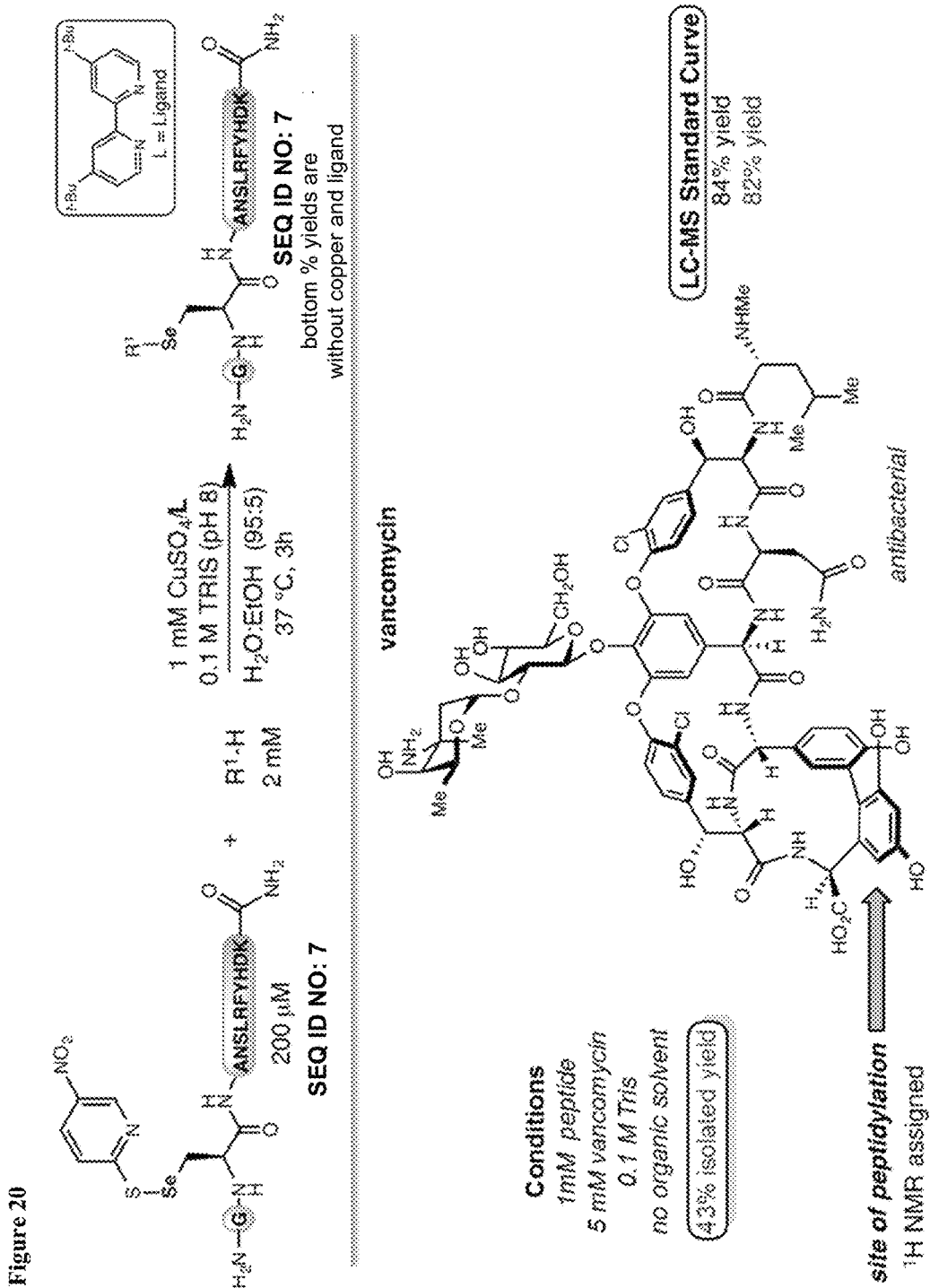
FIG. 20 depicts (top) a reaction scheme showing the conditions for conjugating vancomycin to a model peptide (SEQ ID NOS 7 and 7, respectively, in order of appearance), and (bottom) the reaction conditions, structure of vancomycin, and reaction yield by LC-MS.
Figure 22A:
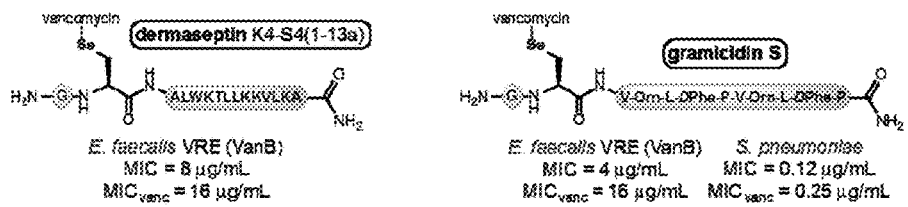
FIG. 22A depicts various antibacterial sequences conjugated to vancomycin, and the results of screening the conjugates against gram-positive strains (SEQ ID NO: 21).
Figure 22B:
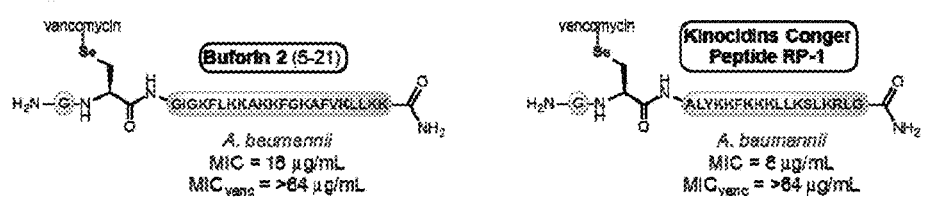
FIG. 22B depicts various antibacterial sequences conjugated to vancomycin, and the results of screening the conjugates against gram-negative strains (SEQ ID NOS 19 and 24, respectively, in order of appearance).

Vancomycin was conjugated to a variety of antibacterial peptides and screened against (a) resistant strains of gram-positive bacteria and b) gram-negative bacteria. See FIG. 20, FIG. 21, FIG. 22, and Table 3.

While there was some modest increase in activity for a few examples it is also important to point out that the MIC values are based on mass and the mass of the peptide conjugates are doubled (sometimes more) relative to vancomycin. This means that the conjugates of the invention are an order of magnitude more active than vancomycin.

Example 8—Copper-free Synthesis of Arylated Selenocysteine

A 0.6 mL Eppendorf tube was charged with 32.5 μL of deionized $H_2O$, 5 μL of 1.0 M Tris Buffer (pH=8.0), 10 μL of peptide (1 mM stock solution in $H_2O$). A separate 0.6 mL Eppendorf tube was charged with (hetero)aryl nucleophile (40 or 80 μmol) and 0.5 mL or 0.25 mL of 200 proof EtOH (making a 40 or 80 mM stock solution, respectively). The heterogeneous solution was subjected to sonication for 1 min, vortexed for 30 sec, and 2.5 μL of the resulting solution was added to the peptide solution in the 0.6 mL Eppendorf tube. The resulting reaction mixture was capped, vortexed for 30 seconds, and placed in a 37° C. water bath for the indicated time (3 h). The reaction mixture was quenched with 50 μlL of $H_2O$ and 100 μL of 0.2% TFA in MeCN. The quenched reaction mixture was subjected to immediate LC-MS analysis.

TABLE 3

MIC of vancomycin alone as compared to vancomycin/peptide conjugates.

| Organism | Phenotype | MMX or ATCC No. | vancomycin | DTC-09-167 | DTC-09-190 | DTC-09-236 | DTC-09-255 | DTC-09-256 | DTC-09-262 | DTC-09-263 | DTC-09-264 | DTC-09-271 | DTC-09-272 | DTC-09-282 | DTC-09-283 | Gentamicin |
|---|---|---|---|---|---|---|---|---|---|---|---|---|---|---|---|---|
| S. aureus | MSSA: QC | 100 29213 | 1 | 64 | 32 | 8 | 64 | 4 | 8 | 8 | 4 | 8 | 8 | 4 | 4 | 0.25 (0.12-1)[1] |
| S. aureus | MRSA | 7778 | 1 | >64 | 32 | 8 | 64 | 4 | 4 | 8 | 4 | 8 | 8 | 4 | 4 | 0.25 |
| E. faecalis | VSE: QC | 101 29212 | 4 | 32 | 16 | 16 | 32 | 16 | 16 | 32 | 8 | 16 | 16 | 4 | 16 | 8 (4-16)[1] |
| E. faecalis | VRE (Van A) | 486 | >64 | >64 | >64 | >64 | >64 | >64 | 32 | >64 | >64 | >64 | >64 | >64 | >64 | >64 |
| E. faecalis | VRE (Van B) | 202 51299 | 16 | >64 | 64 | 32 | >64 | 64 | 16 | 64 | 8 | >64 | >64 | 4 | 16 | >64 |
| K. pneumoniea | PSSP | 1195 49619 | 0.25 | 4 | 2 | 4 | 4 | 8 | 4 | 4 | 1 | 4 | 8 | 0.12 | 4 | 8 |
| E. coli | QC | 102 25922 | >64 | >64 | >64 | >64 | >64 | >64 | 32 | 64 | >64 | >64 | >64 | >64 | 32 | 0.5 (0.25-1)[1] |
| K. pneumoniea | KPC-1 | 6902 BAA-1705 | >64 | >64 | >64 | >64 | >64 | >64 | 32 | >64 | >64 | >64 | >64 | >64 | 64 | 1 |
| P. aeruginosa | QC | 103 27853 | >64 | >64 | >64 | >64 | >64 | >64 | 64 | >64 | >64 | >64 | >64 | >64 | >64 | 1 (0.5-2)[1] |
| A. baumannii | Wild-type | 1630 19606 | >64 | >64 | >64 | >64 | >64 | >64 | 16 | 32 | 64 | 64 | >64 | >64 | 8 | 16 |

[1] CLSI QC range shown in parentheses

Example 5—Selenocysteine Antibody-Drug Conjugates

Figure 23:
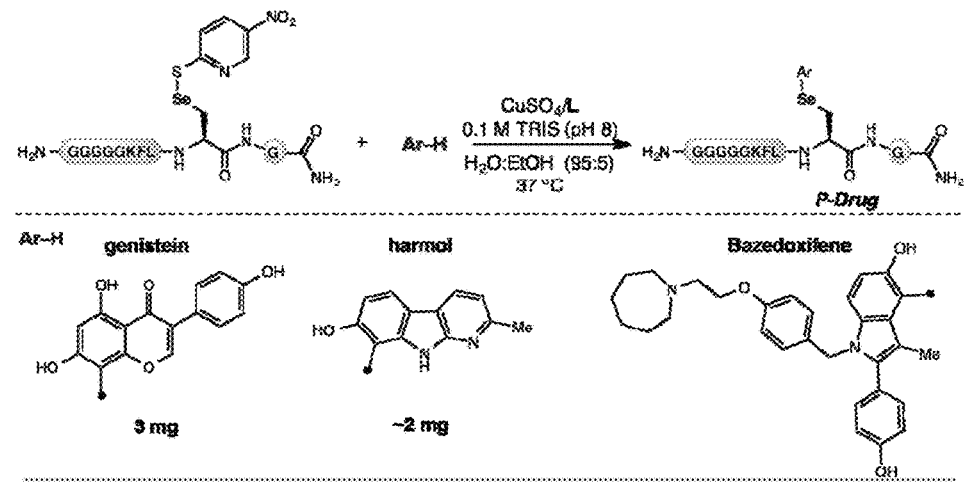
FIG. 23 depicts (top) a reaction scheme showing the conditions for conjugating small molecules to a polyglycine-containing peptide (SEQ ID NOS 25 and 25, respectively, in order of appearance), and (bottom) various Ar—H moieties to be conjugated.
Figure 24:
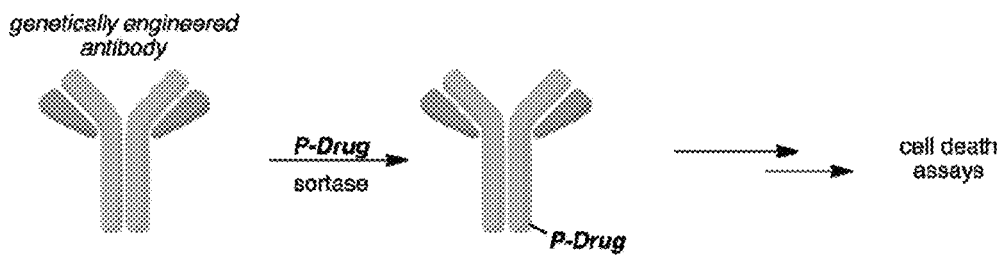
FIG. 24 depicts a schematic representation of the process of sortase-tagging an antibody with a peptide-drug conjugate.
Figure 25:
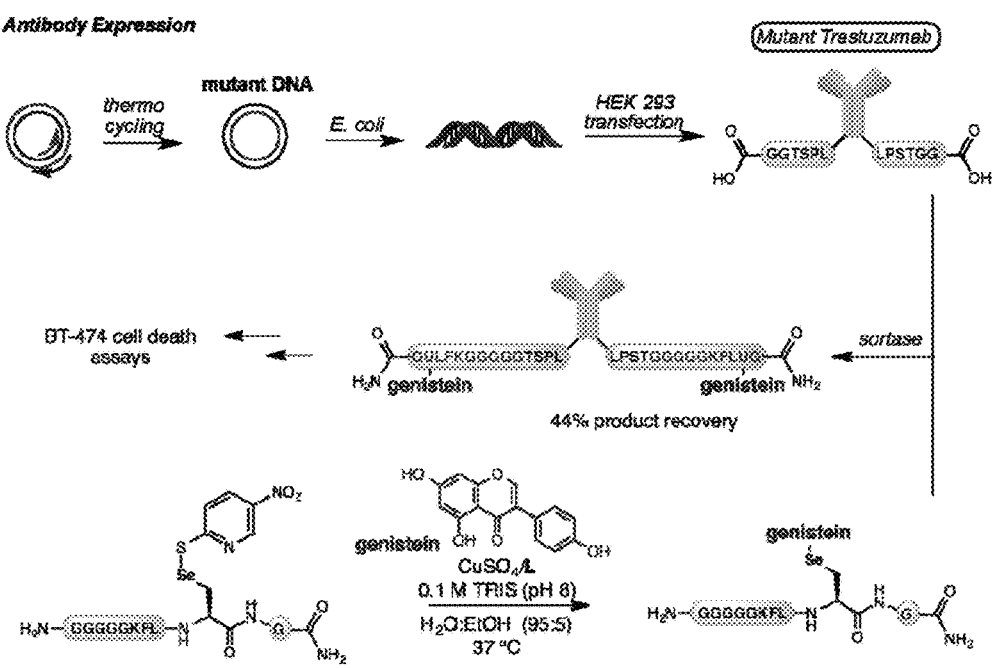
FIG. 25 depicts a schematic representation of making a peptide-drug conjugate and then sortase-tagging an antibody with the peptide-drug conjugate (SEQ ID NOS 26, 26, 27, 27, 28 and 28, respectively, in order of appearance).
Figure 26:
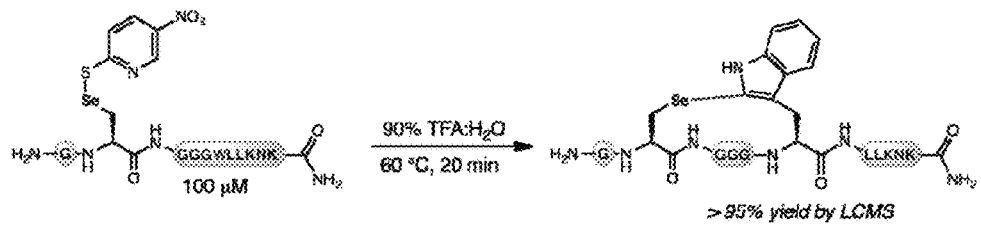
FIG. 26 depicts a reaction scheme showing the conditions for cyclizing a model peptide (SEQ ID NOS 29 and 29, respectively, in order of appearance).
Figure 27:
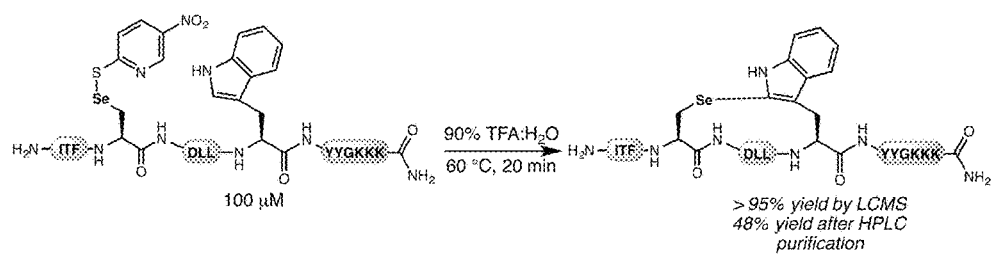
FIG. 27 depicts a reaction scheme showing the conditions for cyclizing an HIV-1 capsid with selenocysteine (SEQ ID NOS 30 and 30, respectively, in order of appearance).
Figure 28:
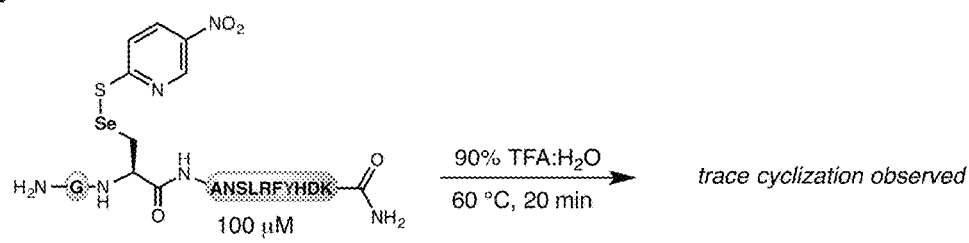
FIG. 28 a reaction scheme showing the conditions for attempting to cyclize a peptide lacking tryptophan (SEQ ID NO: 7).
Figure 29:
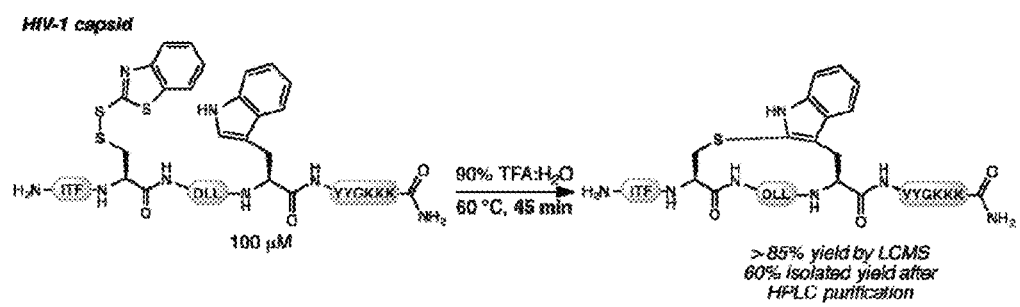
FIG. 29 depicts a reaction scheme showing the conditions for cyclizing an HIV-1 capsid with cysteine (SEQ ID NOS 31 and 31, respectively, in order of appearance).
Figure 30:
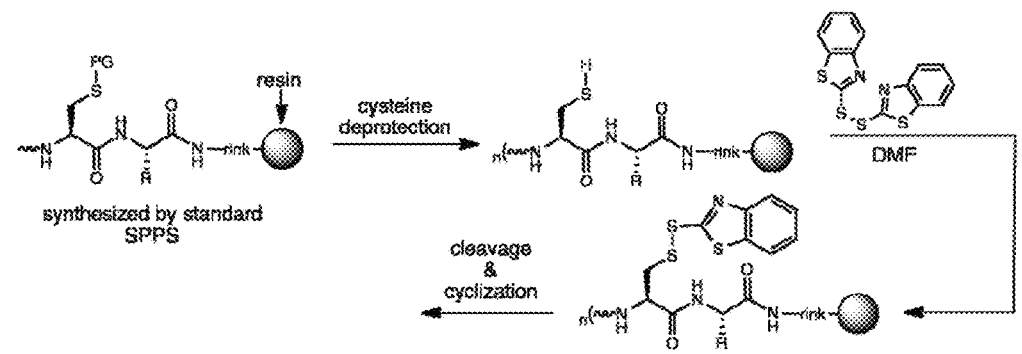
FIG. 30 depicts a reaction scheme showing the formation of disulfide starting material (e.g., the disulfide shown in FIG. 29) on a resin. Cleavage with 95:5 TFA:H$_2$O at 60° C. for 45 min provides completely cyclized material in 60% yield after HPLC purification.
Figure 31A:
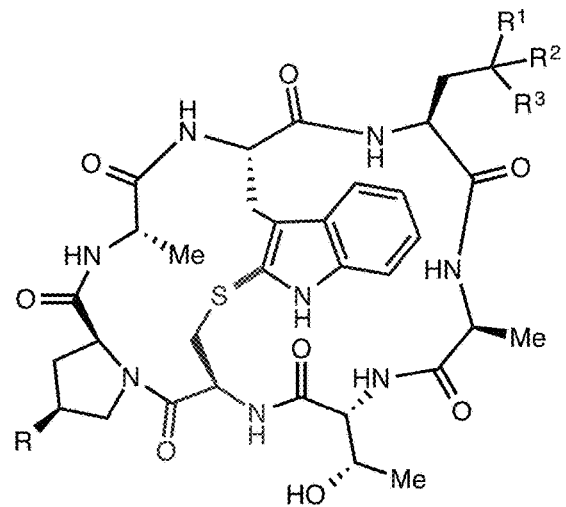
FIG. 31A depicts the structure of the phallotoxins.
Figure 31B:
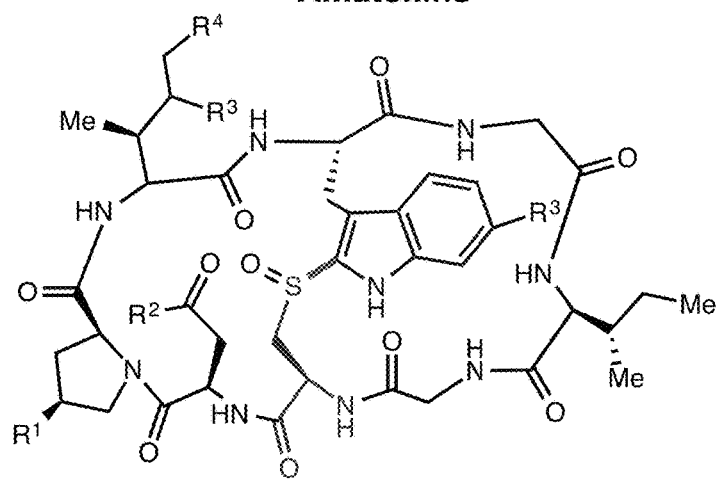
FIG. 31B depicts the structure of the amatoxins.
Figure 33:
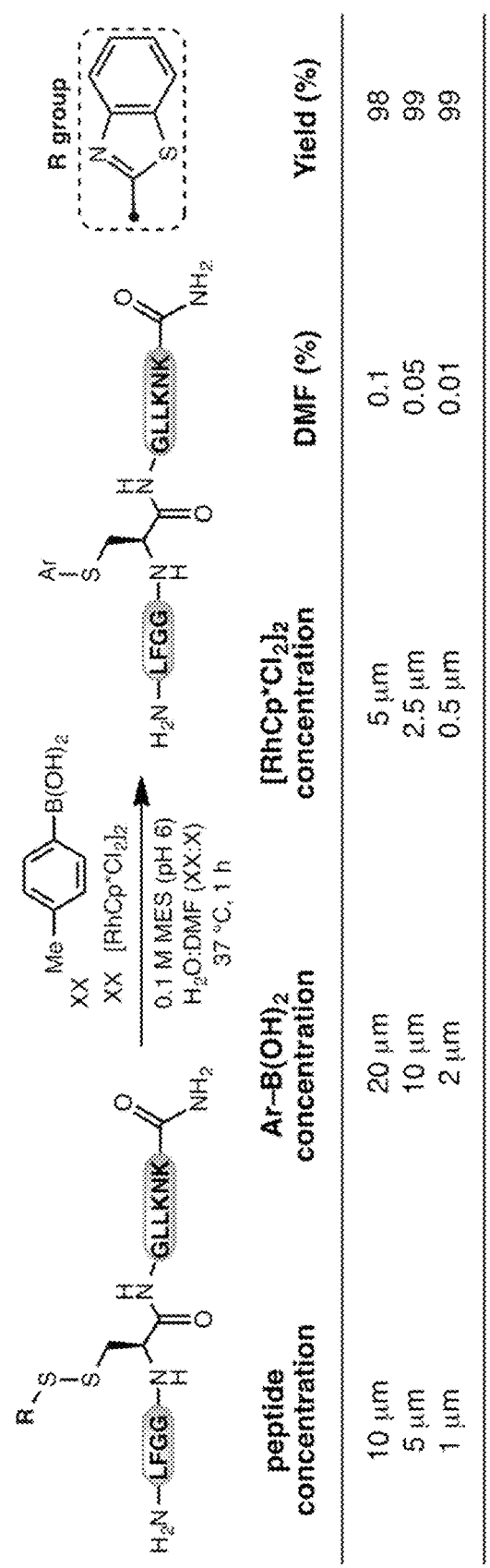
FIG. 33 depicts a reaction scheme and concentrations of reactants for rhodium-catalyzed arylation of a disulfide-containing peptide (SEQ ID NOS 5 and 5, respectively, in order of appearance).
Figure 34:
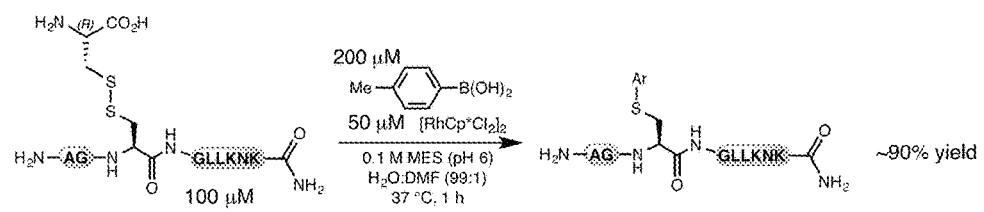
FIG. 34 depicts a reaction scheme showing the arylation of a cysteine disulfide. The ability to affect functionalization with only one equivalent of rhodium has important implications for functionalization of antibodies without prior reduction (SEQ ID NOS 32 and 32, respectively, in order of appearance).
Figure 35:
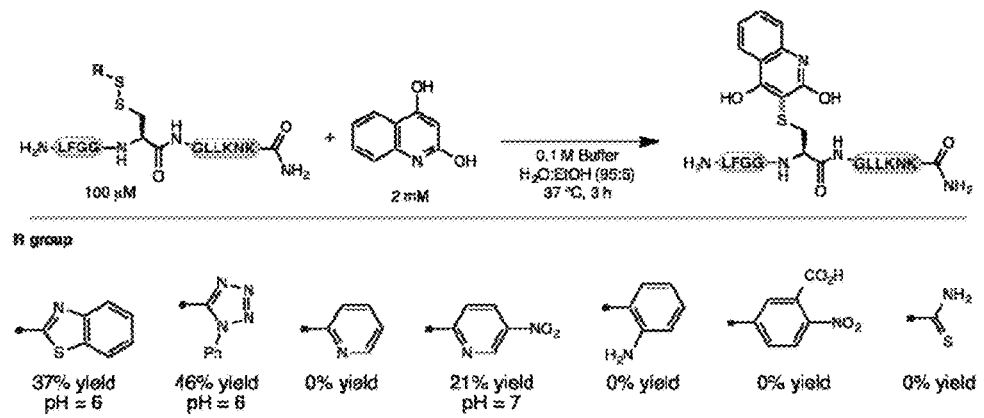
FIG. 35 depicts (top) a reaction scheme showing the metal-free arylation of mixed disulfides (SEQ ID NOS 5 and 5, respectively, in order of appearance), and (bottom) various reagents and yields.
Figure 36:
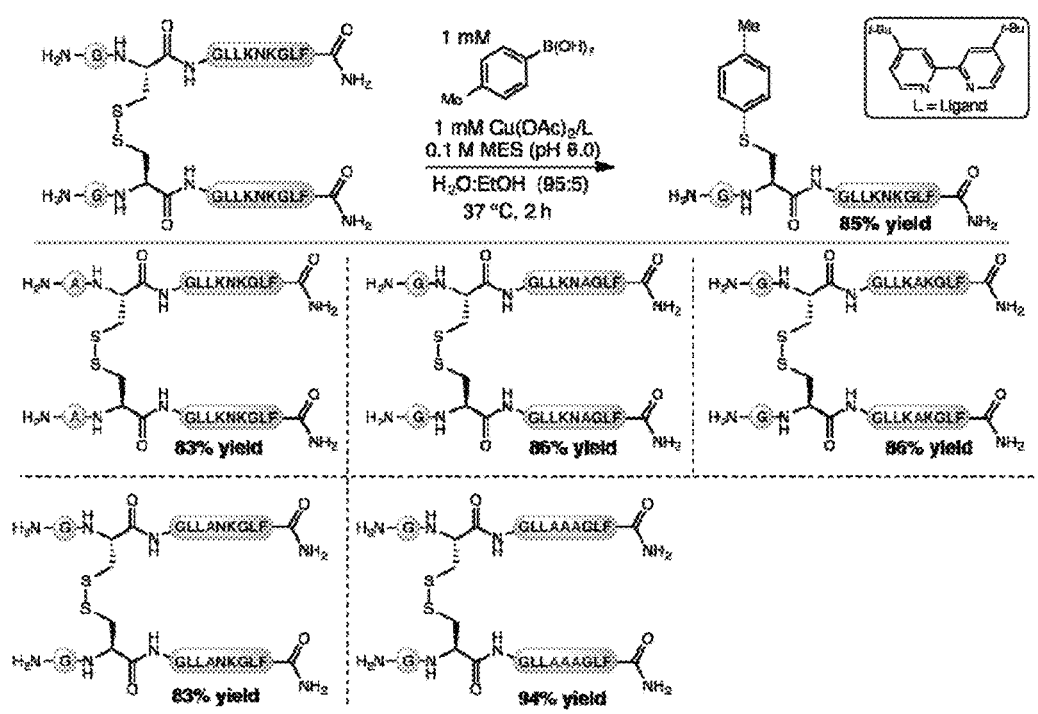
FIG. 36 depicts (top) a reaction scheme showing the copper-catalyzed arylation of a disulfide (SEQ ID NOS 14, 14 and 14, respectively, in order of appearance), and (bottom) the results of this reaction with disulfides having varying sequences (SEQ ID NOS 33-35, 33-37 and 36-37, respectively, in order of appearance).
Figure 37:
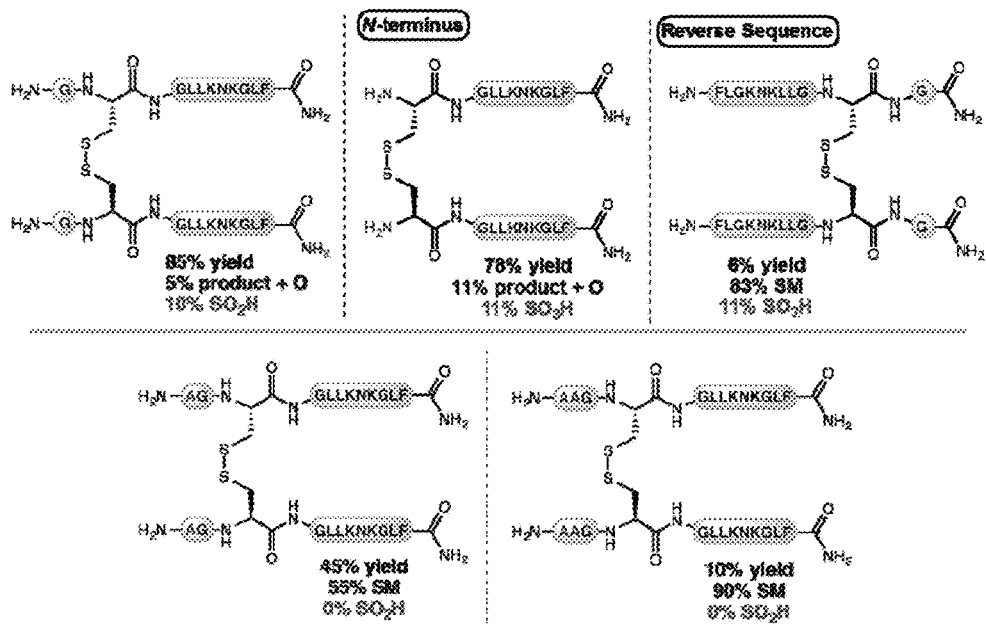
FIG. 37 depicts the results of the reaction depicted in FIG. 36 when the position of the disulfide is varied within the peptide (SEQ ID NOS 14, 38-39, 14, 38-39, 40-41 and 40-41, respectively, in order of appearance).
Figure 38:
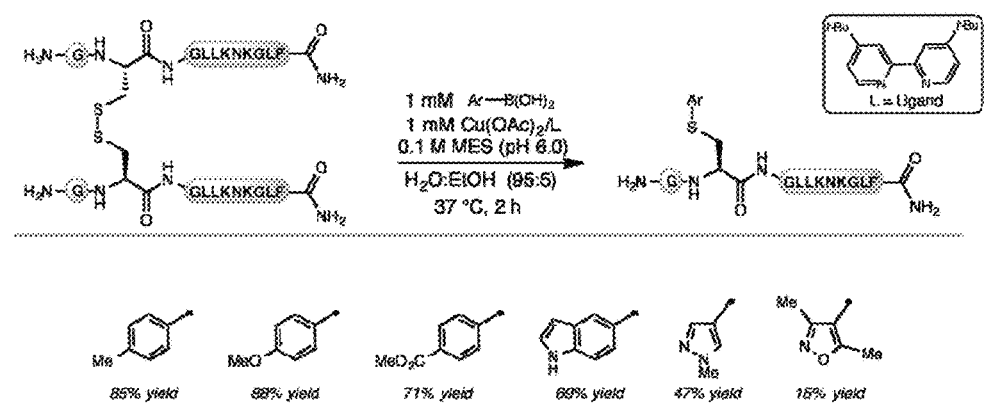
FIG. 38 depicts (top) a reaction scheme showing the copper-catalyzed arylation of a disulfide (SEQ ID NOS 14, 14 and 14, respectively, in order of appearance), and (bottom) various boronic acid arylating agents.
Figure 39:
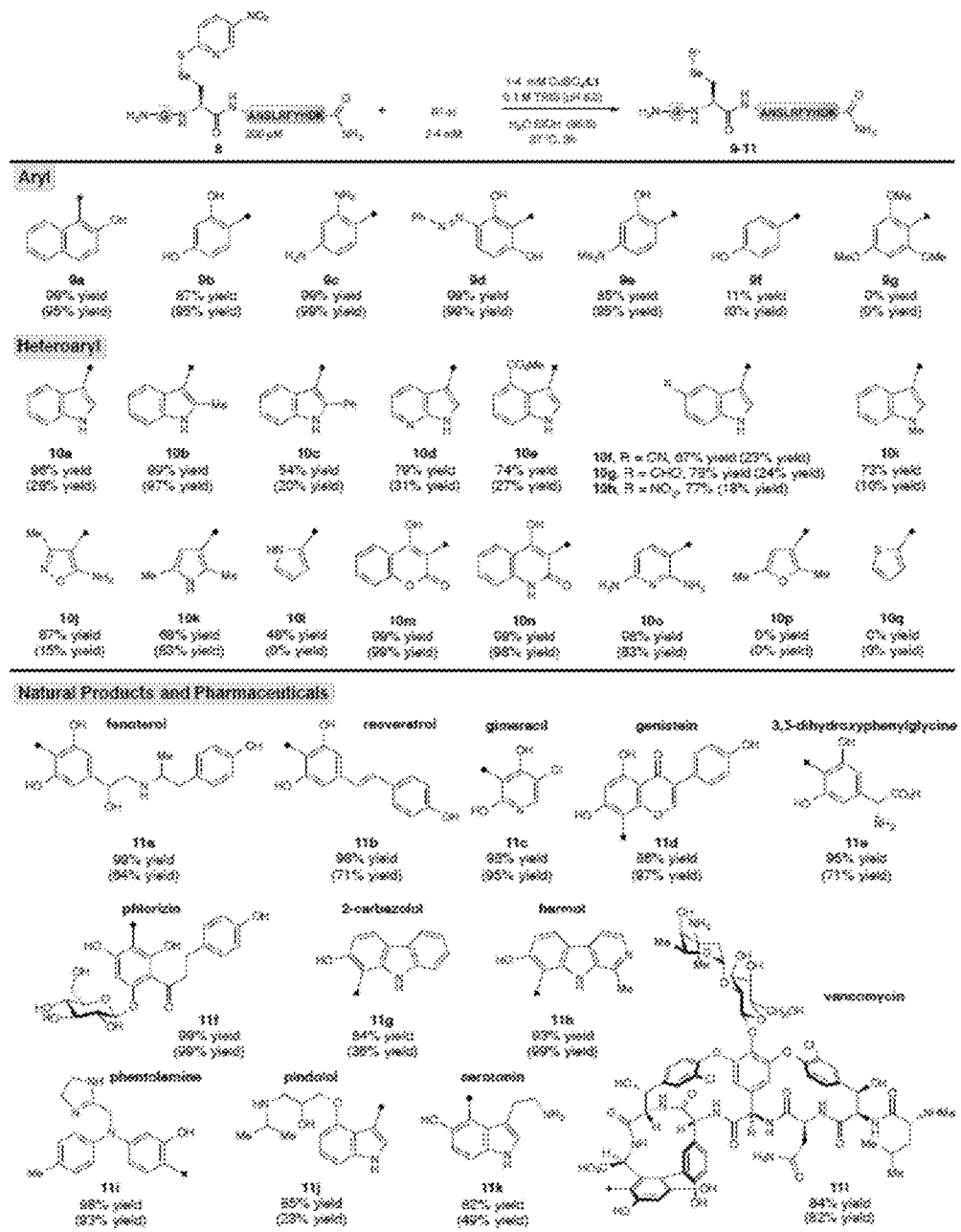
FIG. 39 depicts a reaction scheme and % yield for various arylation reactions using substituted aromatic or heteroaromatic groups in the presence of $CuSO_4$-catalyst (top yields) (peptides disclosed as SEQ ID NOS 7 and 7, respectively, in order of appearance), and in the absence of a metal catalyst and ligand (bottom yields).

Polyglycine peptides with a conjugated small molecule can be effectively sortased onto a mutant trastuzumab antibody. See FIG. 23, FIG. 24, and FIG. 25.

An antibody-drug conjugate (ADC) of genistein was screened against BT-474 cells (mammary gland cancer cells). These results show that selenocysteine is not toxic to cells and can be used as a handle in bioconjugation.

Example 6—Selenocysteine or Cysteine Macrocyclization

Phallotoxins and amatoxins are classes of highly cytotoxic macrocyclic natural products that have a cysteine/tryptophan linkage. These classes of natural products have been isolated from the poisonous mushrooms 1937-1941. Previous strategies to synthesize these natural products required two steps (Savige-Fontana reaction) or monomer synthesis to introduce the cysteine/tryptophan linkage.

However, the selenocysteine or cysteine conjugates described herein may be cyclized to form the required linkage. See FIGS. 26-31B.

Example 7—Cysteine Arylation

Various disulfides, mixed or symmetrical, were arylated with a variety of arylating agents. Variations in the peptide sequence were also investigated to determine their influence on the success of the arylation reaction. Copper-catalyzed, rhodium-catalyzed, or metal-free conditions were used. See FIGS. 32A-38.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound comprising (a) substructure I:

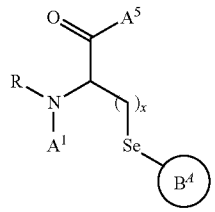

wherein, independently for each occurrence, $A^1$ is H, an amine protecting group, a natural or unnatural amino acid, a peptide, an oligopeptide, a polypeptide, or a protein;

$A^5$ is OH, —O(carboxylate protecting group), a natural or unnatural amino acid, a peptide, an oligopeptide, a polypeptide, or a protein;

$B^4$ is a substituted phenyl radical selected from the group consisting of

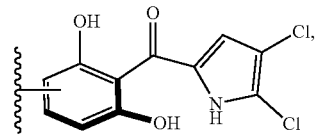

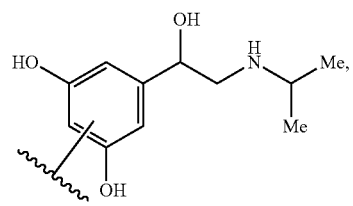

-continued
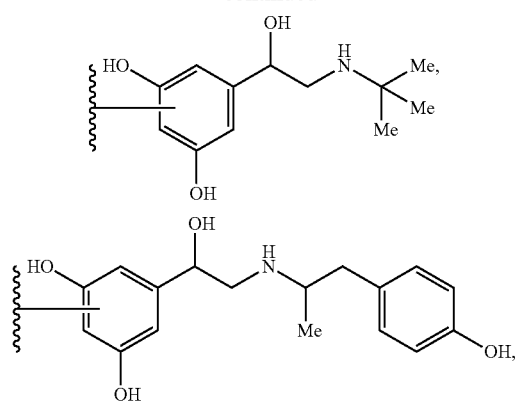
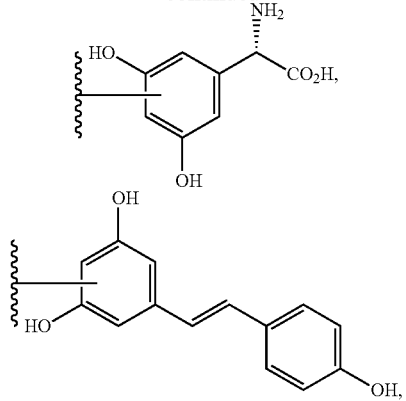
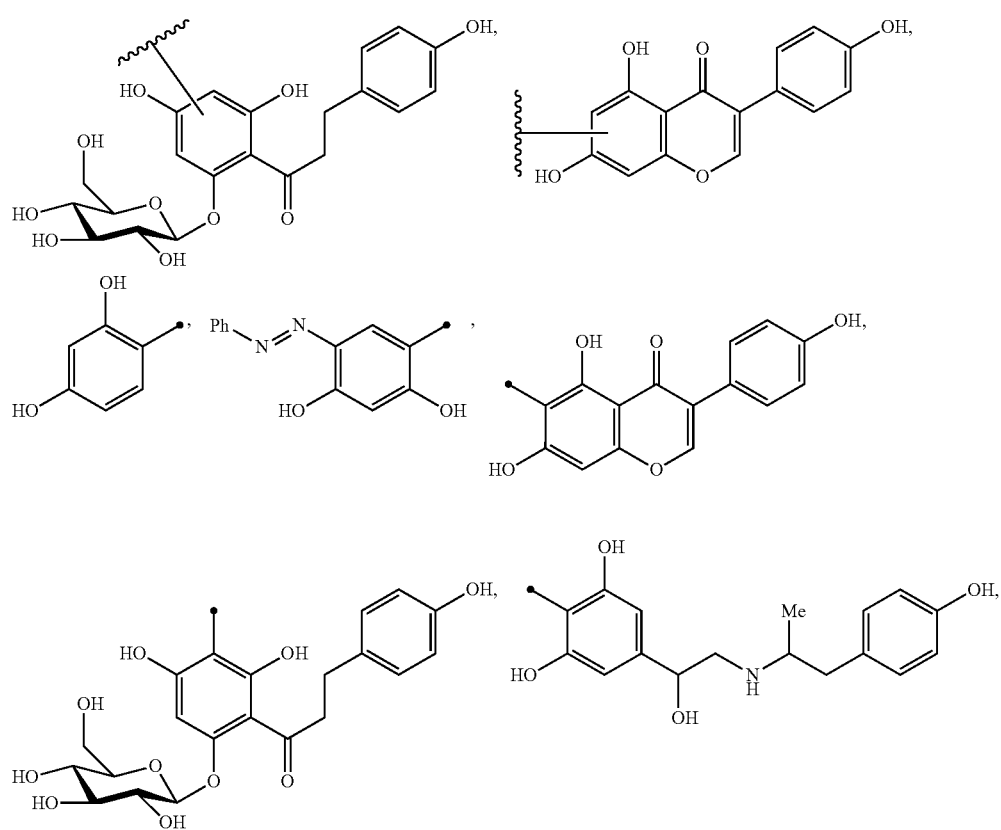
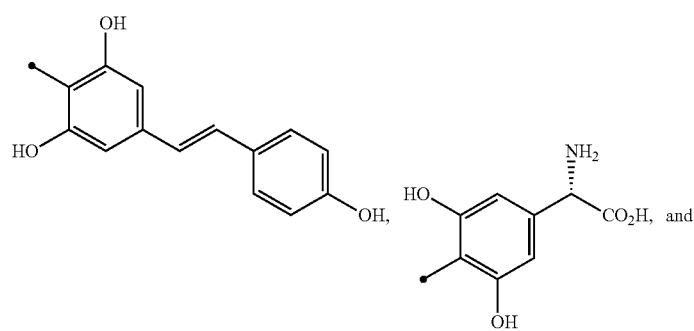

-continued

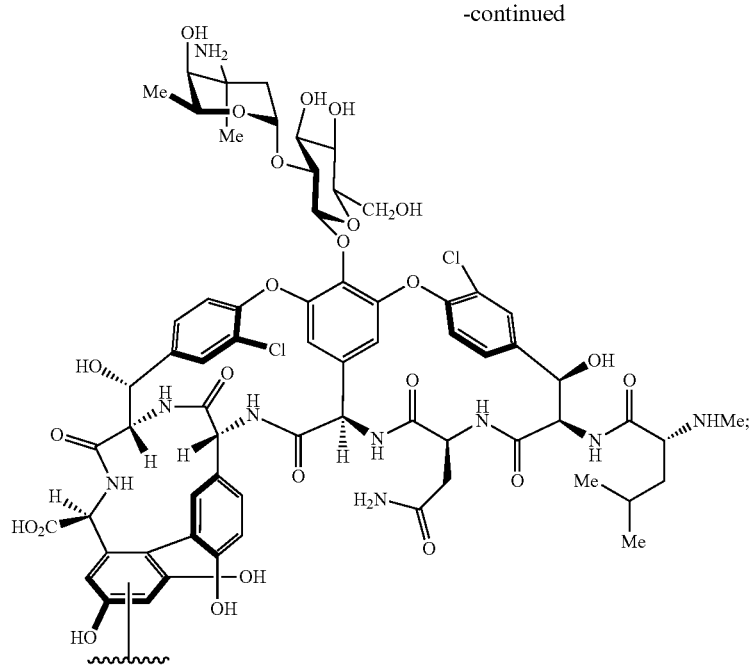

x is 0, 1, 2, 3, 4, 5, or 6; and
R is H or alkyl; or
(b) substructure II:

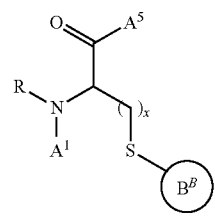
II wherein, independently for each occurrence,
- $A^1$ is H, an amine protecting group, a natural or unnatural amino acid, a peptide, an oligopeptide, a polypeptide, or a protein;
- $A^5$ is OH, —O(carboxylate protecting group), a natural or unnatural amino acid, a peptide, an oligopeptide, a polypeptide, or a protein;

is a substituted phenyl radical selected from the group consisting of

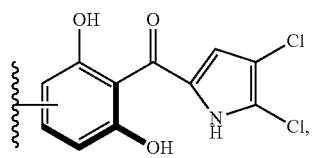

-continued

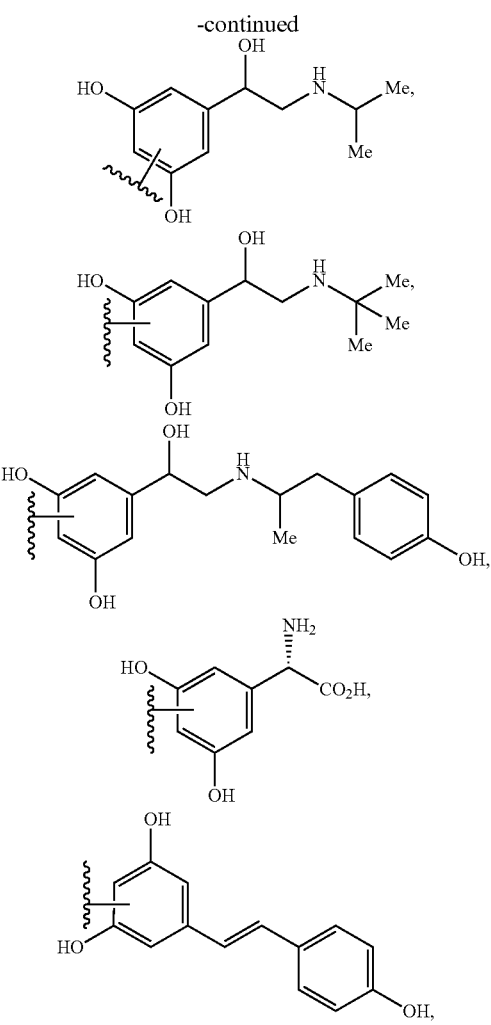

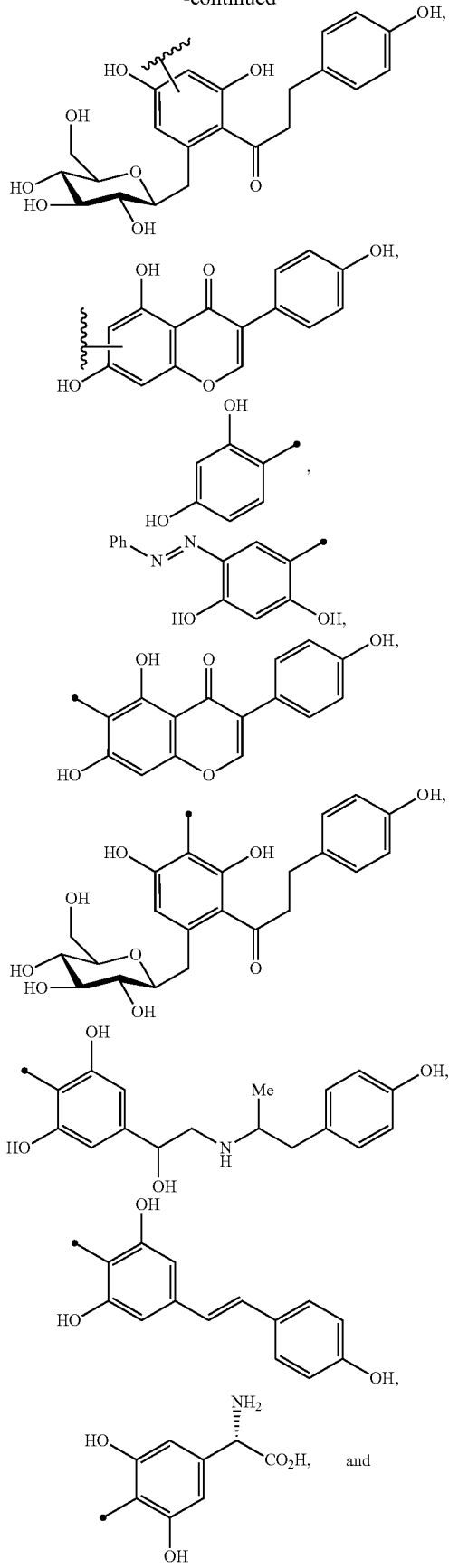

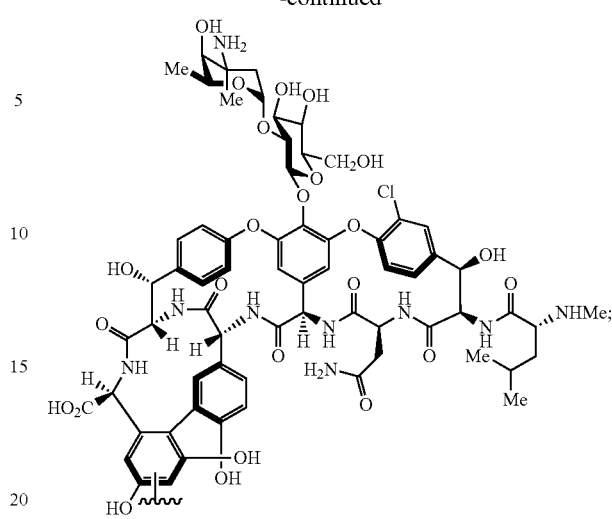

x is 0, 1, 2, 3, 4, 5, or 6; and
R is H or alkyl.

2. A method
(a) according to Scheme 1:

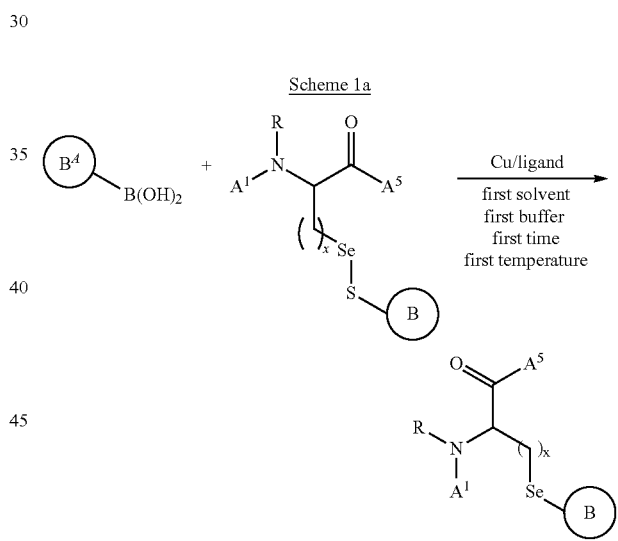

wherein, independently for each occurrence, $A^1$ is H, an amine protecting group, a natural or unnatural amino acid, a peptide, an oligopeptide, a polypeptide, or a protein;

$A^5$ is OH, —O(carboxylate protecting group), a natural or unnatural amino acid, a peptide, an oligopeptide, a polypeptide, or a protein;

$B^A$ is a substituted phenyl radical selected from the group consisting of

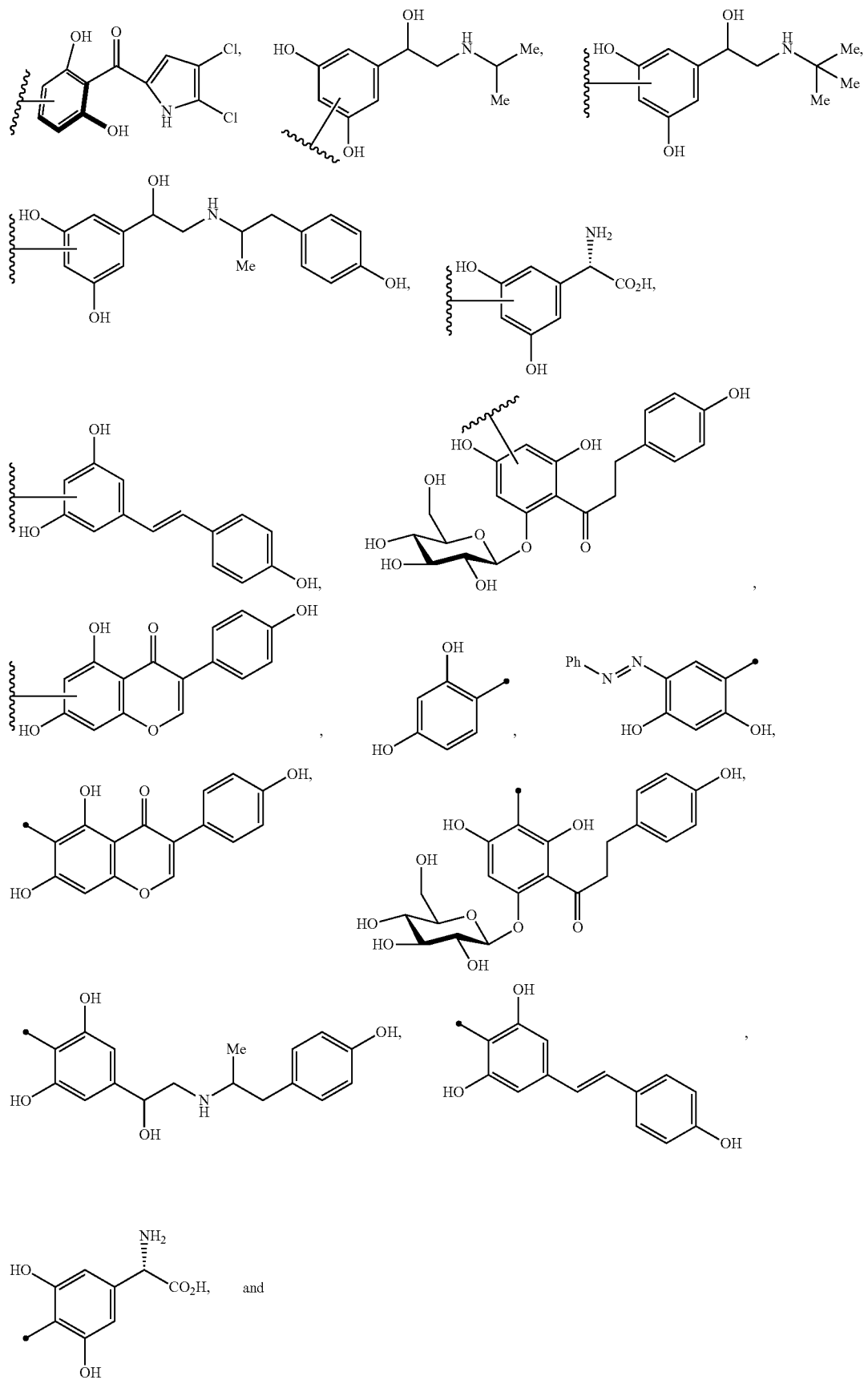

-continued

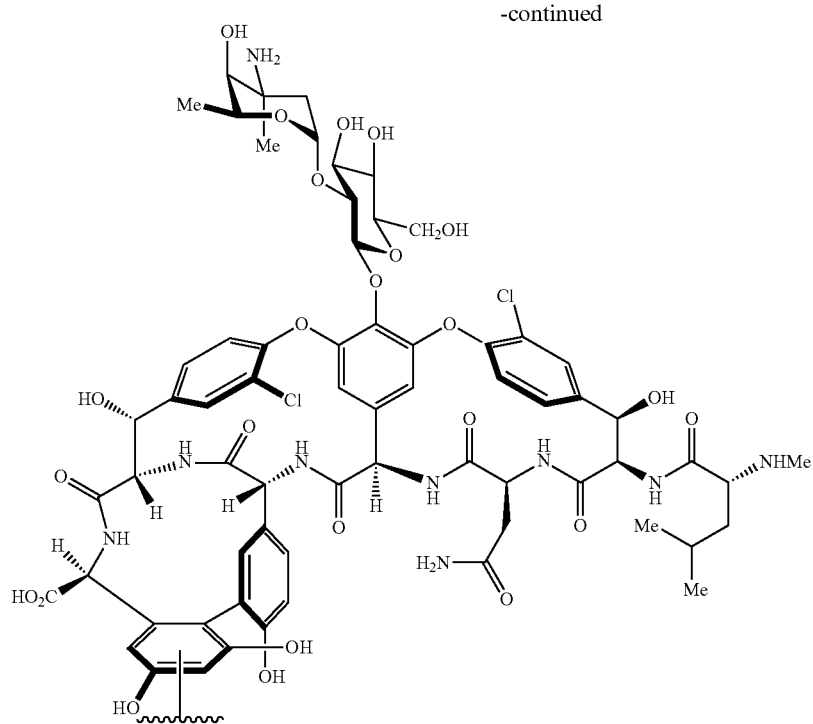

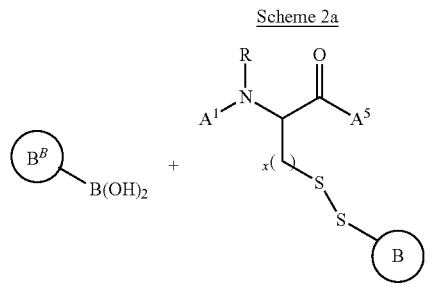

B is a heteroaromatic moiety substituted with an electron withdrawing group;
x is 0, 1, 2, 3, 4, 5, or 6; and
R is H or alkyl;

(b) according to Scheme 2:

Scheme 2a

-continued

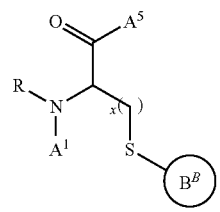

wherein, independently for each occurrence,
$A^1$ is H, an amine protecting group, a natural or unnatural amino acid, a peptide, an oligopeptide, a polypeptide, or a protein;
$A^5$ is OH, —O(carboxylate protecting group), a natural or unnatural amino acid, a peptide, an oligopeptide, a polypeptide, or a protein;

$B^B$ is a substituted phenyl radical selected from the group consisting of

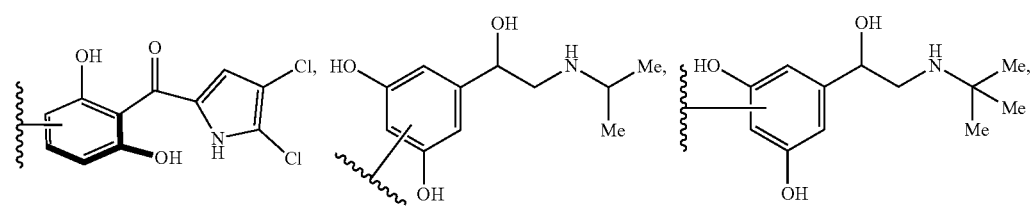

-continued
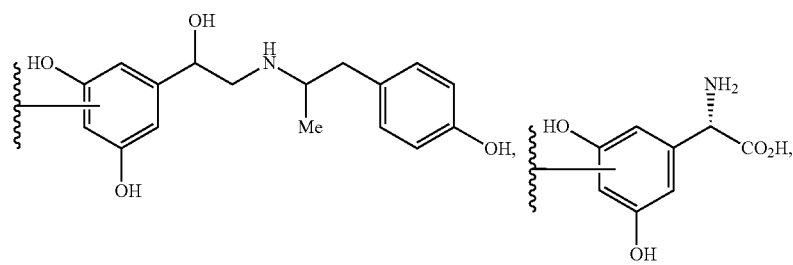
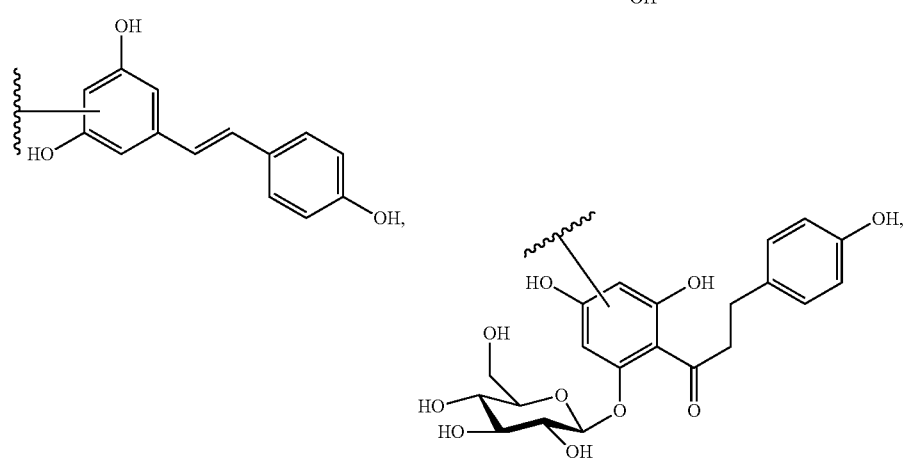
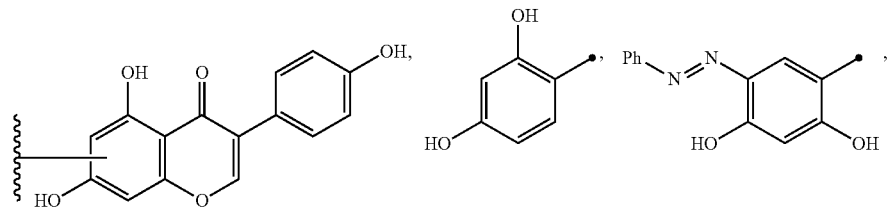
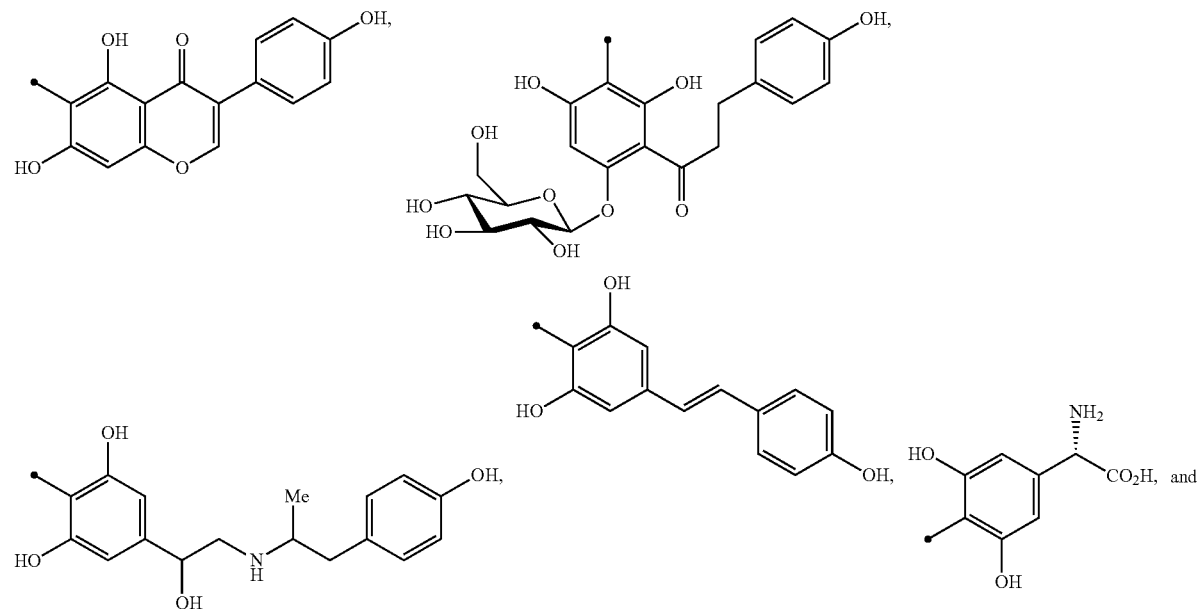

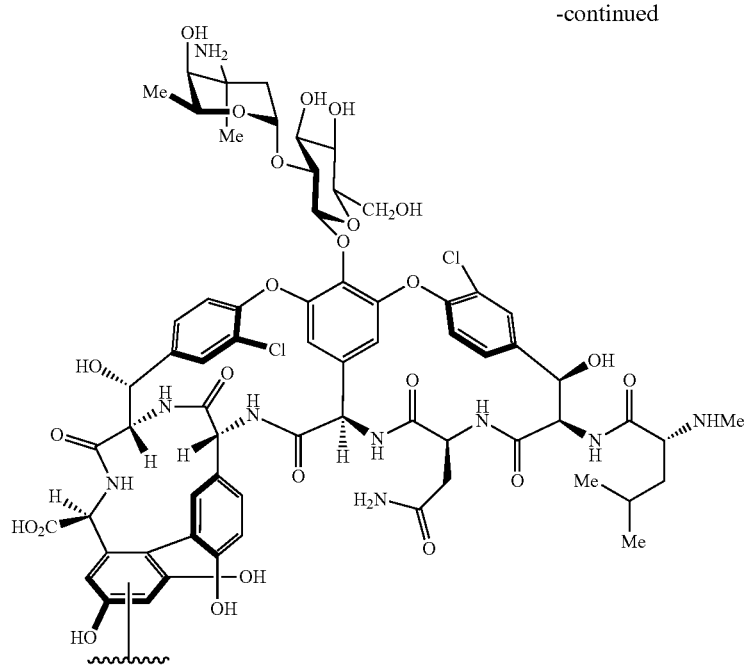
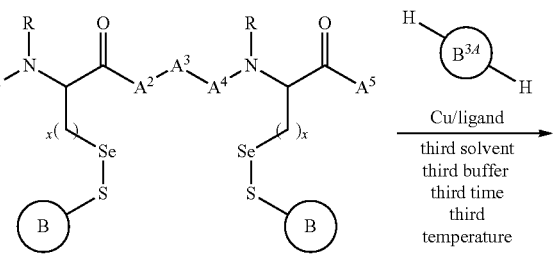
B is a heteroaromatic moiety substituted with an electron withdrawing group;
x is 0, 1, 2, 3, 4, 5, or 6; and
R is H or alkyl;
(c) according to Scheme 3:
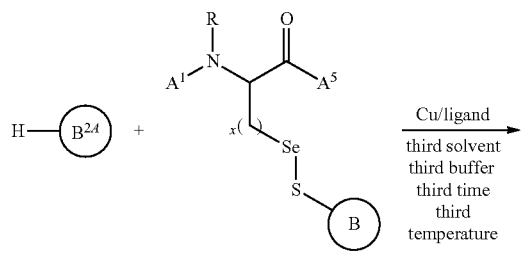
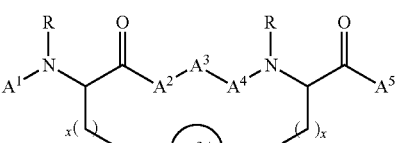
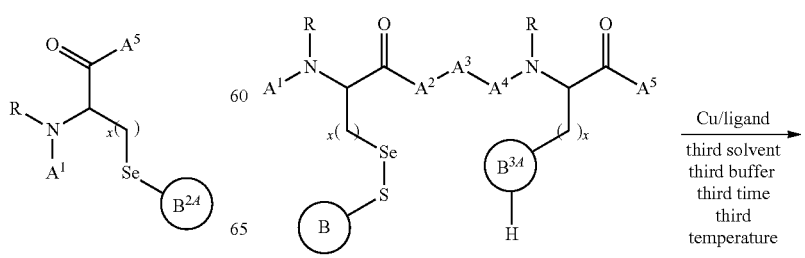

203

-continued

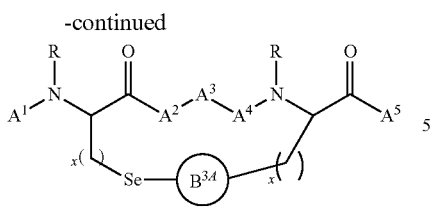

Scheme 3d

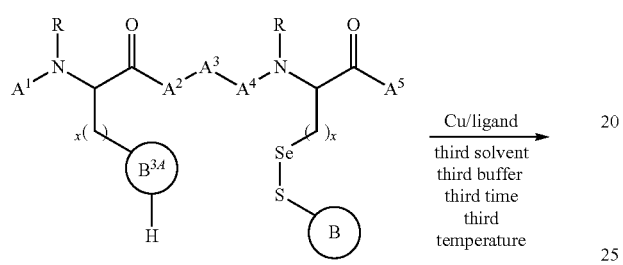 

204

-continued

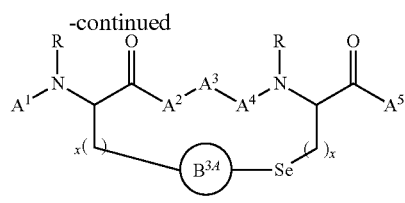

wherein, independently for each occurrence,
  $A^1$ is H, an amine protecting group, a natural or unnatural amino acid, a peptide, an oligopeptide, a polypeptide, or a protein;
  $A^2$, $A^3$, and $A^4$ are selected from the group consisting of a natural amino acid, an unnatural amino acid, and a plurality of natural amino acids or unnatural amino acids;
  $A^5$ is OH, —O(carboxylate protecting group), a natural or unnatural amino acid, a peptide, an oligopeptide, a polypeptide, or a protein;

$B^{2A}$ is a phenyl radical selected from the group consisting of

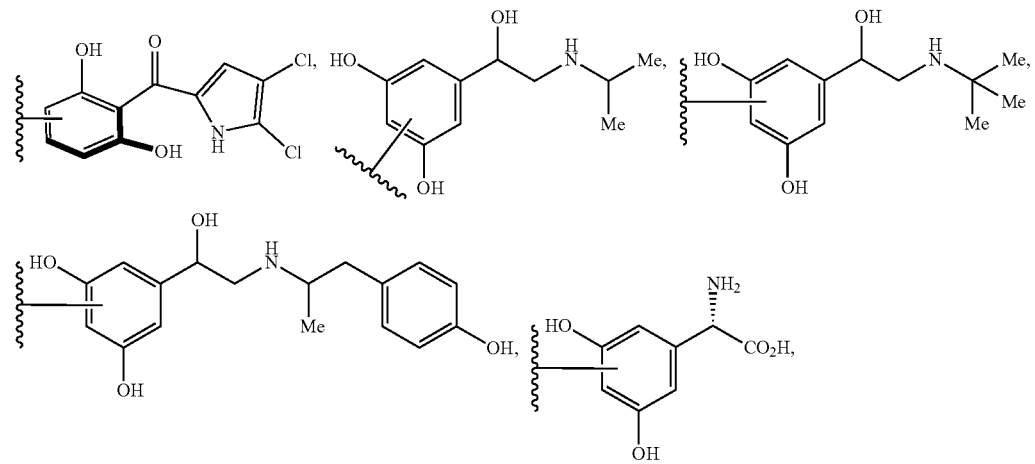

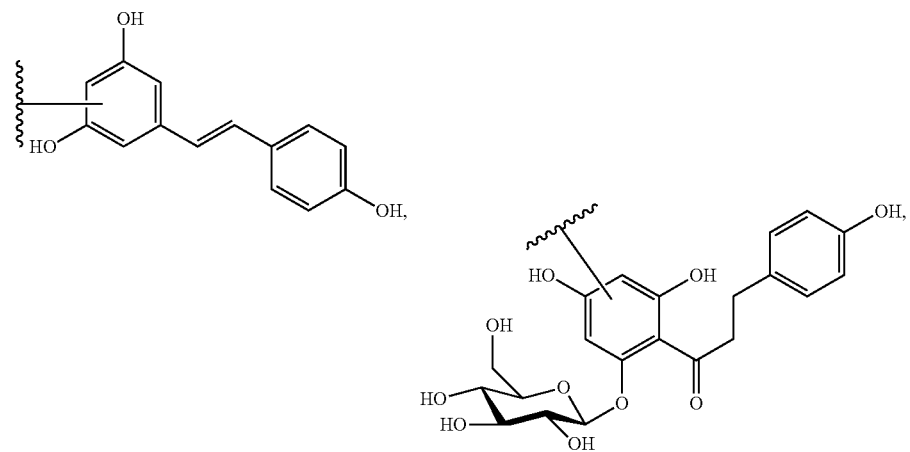

-continued
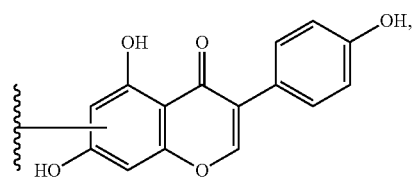
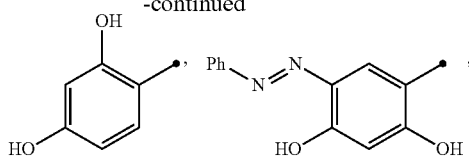
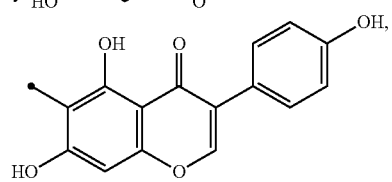
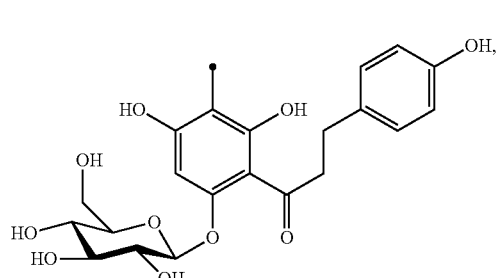
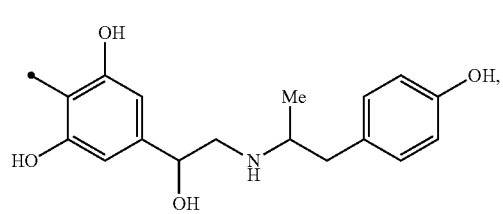
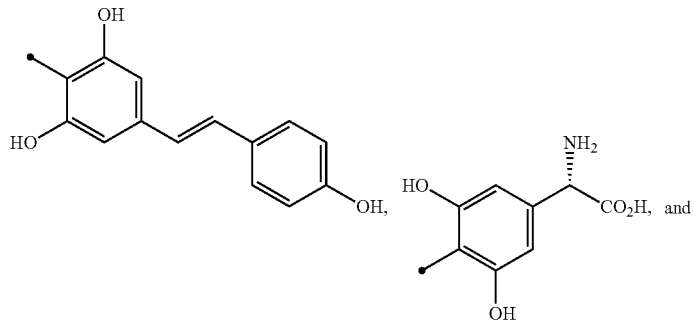
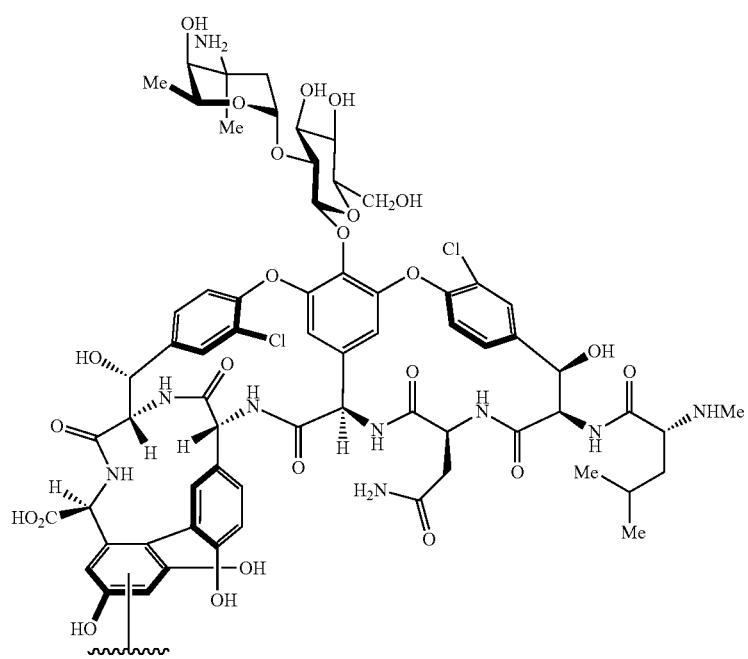
is a substituted phenyl diradical selected from the group consisting of

207
208
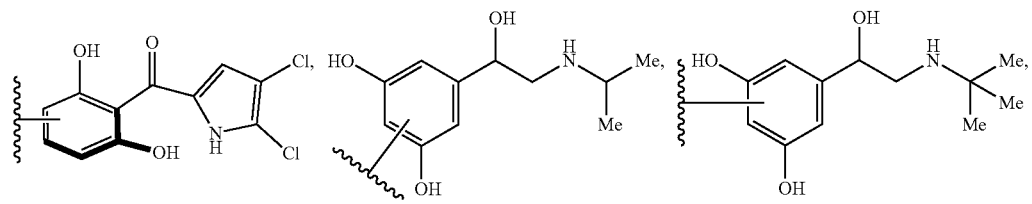
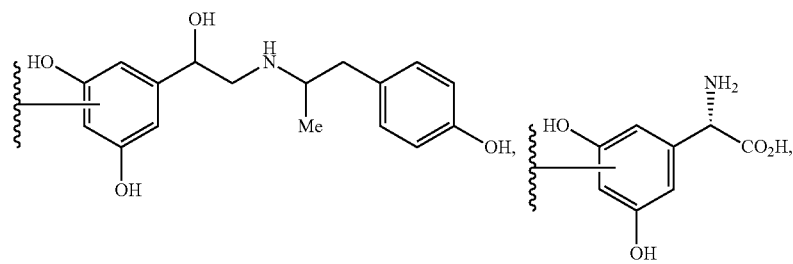
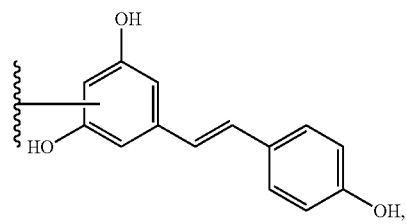
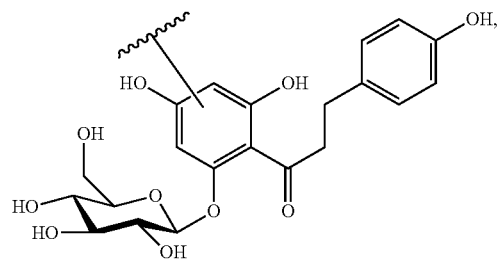
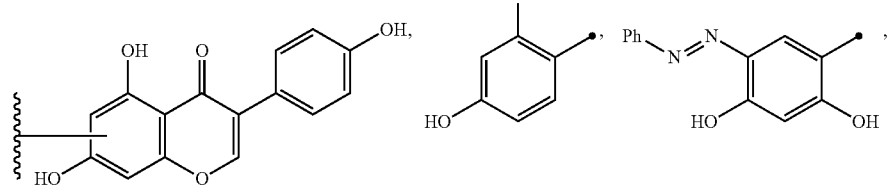
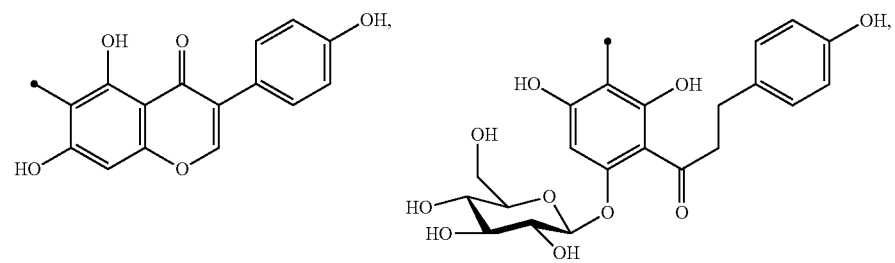
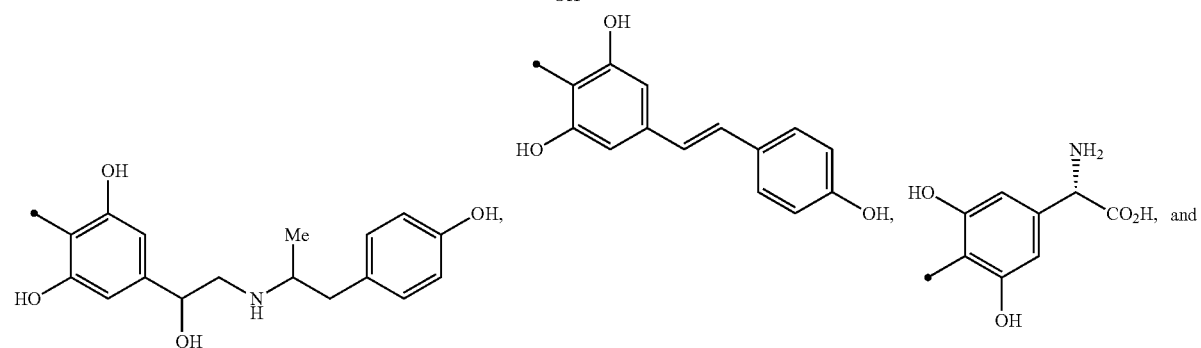

-continued
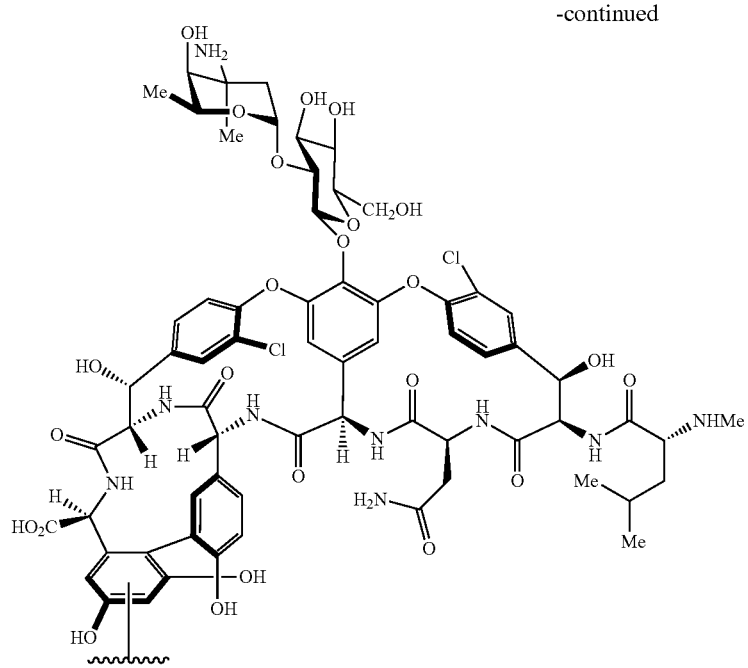
B is a heteroaromatic moiety substituted with an electron withdrawing group;
x is 0, 1, 2, 3, 4, 5, or 6; and
R is H or alkyl;
(d) according to Scheme 4:
Scheme 4a
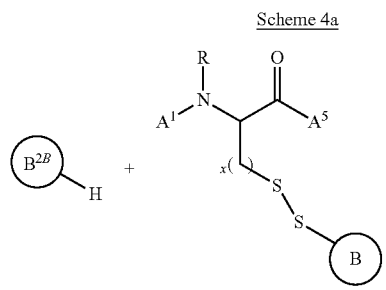
Scheme 4b
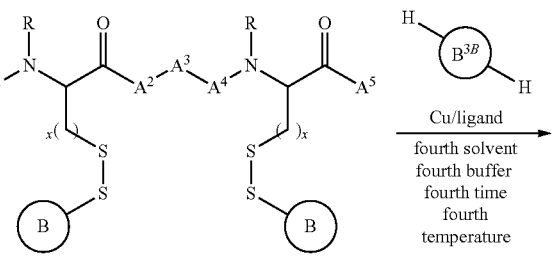
Scheme 4c
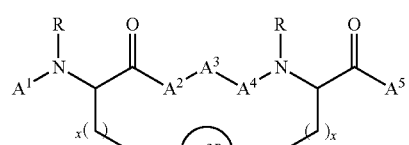
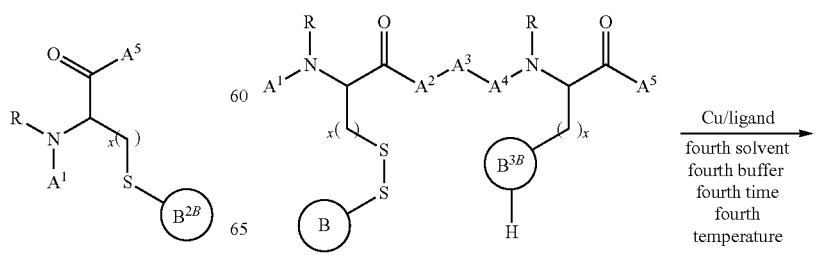

211
-continued

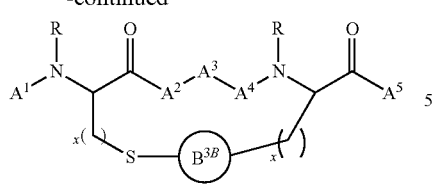

Scheme 4d

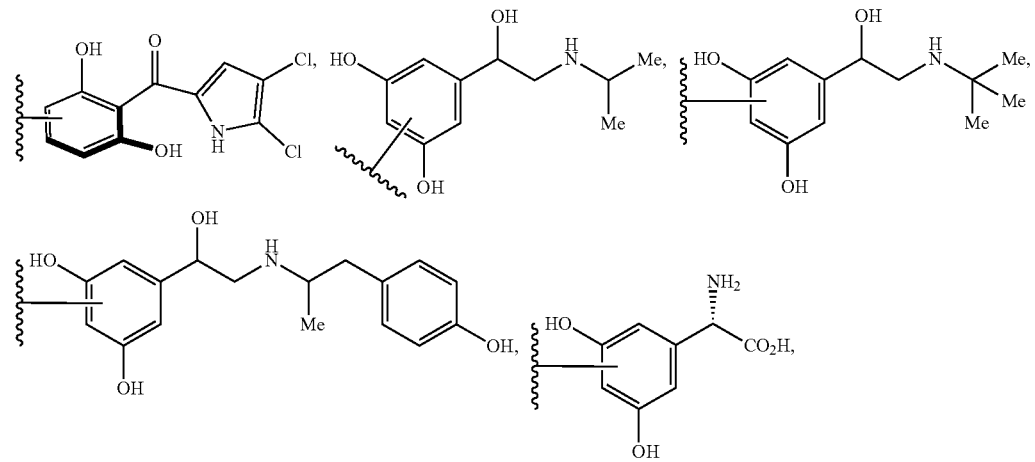

212
-continued

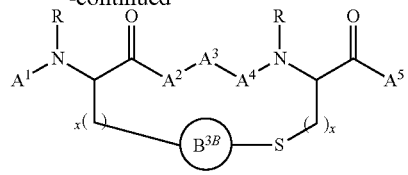

wherein, independently for each occurrence,
  $A^1$ is H, an amine protecting group, a natural or unnatural amino acid, a peptide, an oligopeptide, a polypeptide, or a protein;
  $A^2$, $A^3$, and $A^4$ are selected from the group consisting of a natural amino acid, an unnatural amino acid, and a plurality of natural amino acids or unnatural amino acids;
  $A^5$ is OH, —O(carboxylate protecting group), a natural or unnatural amino acid, a peptide, an oligopeptide, a polypeptide, or a protein;

$B^{2B}$ is a phenyl radical selected from the group consisting of

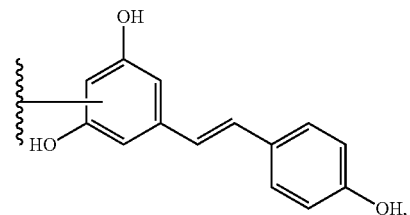

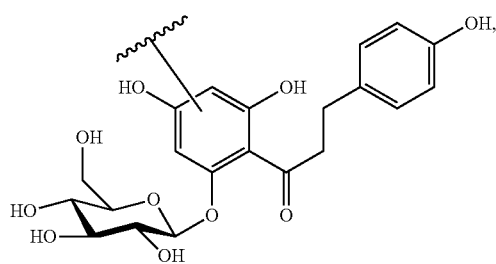

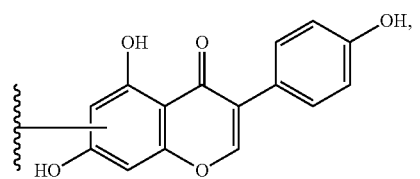
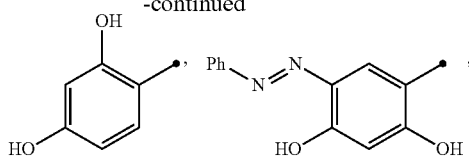
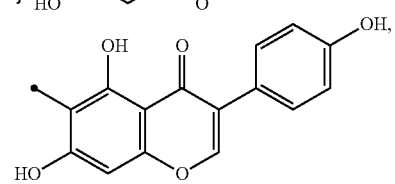
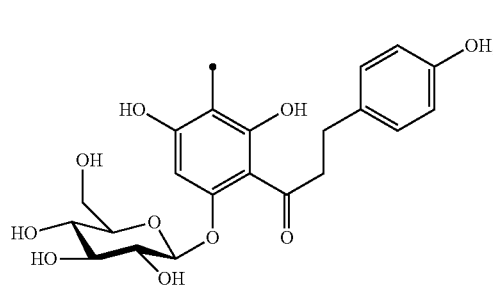
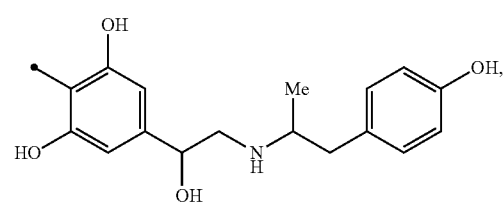
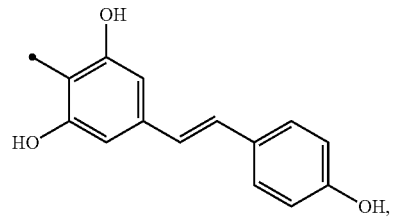
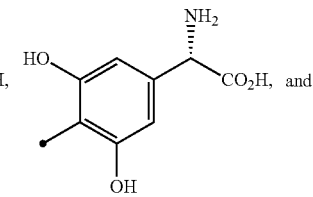
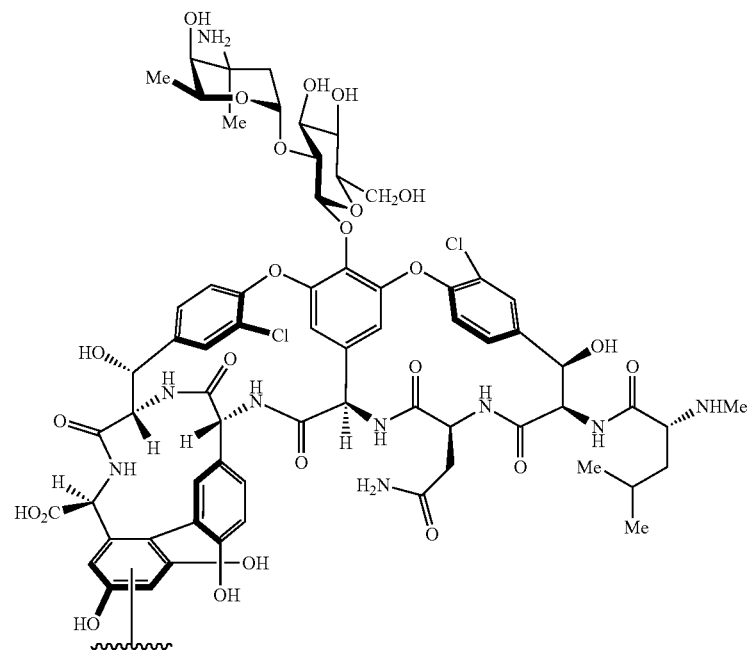
$B^{3B}$ is a phenyl radical selected from the group consisting of
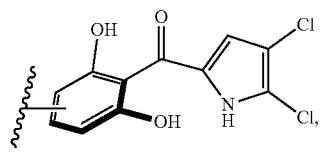

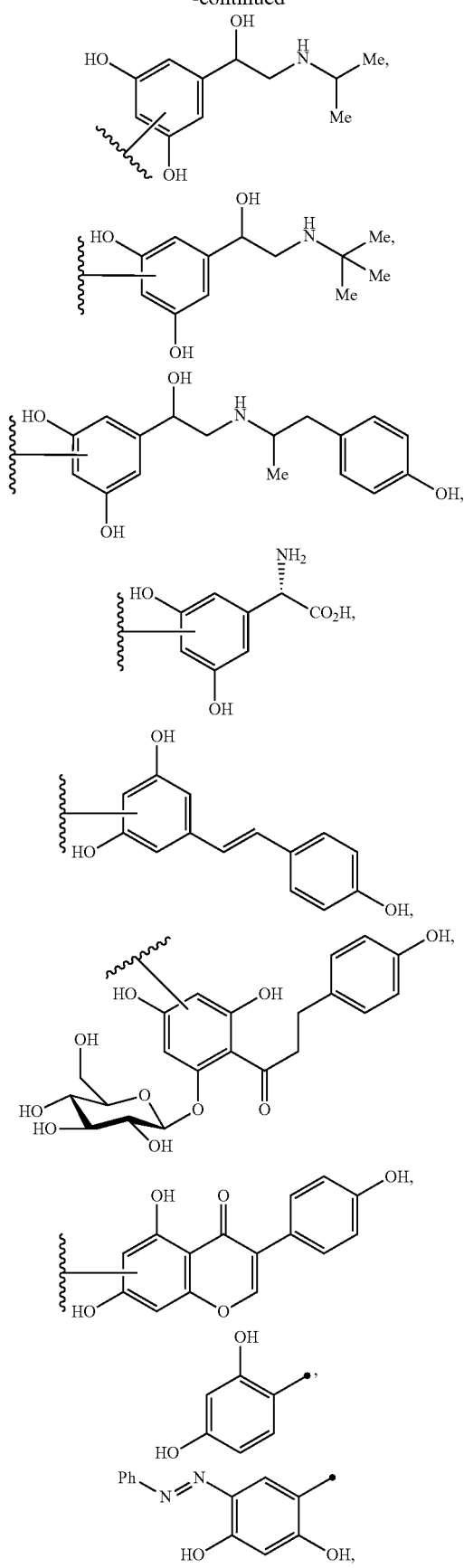
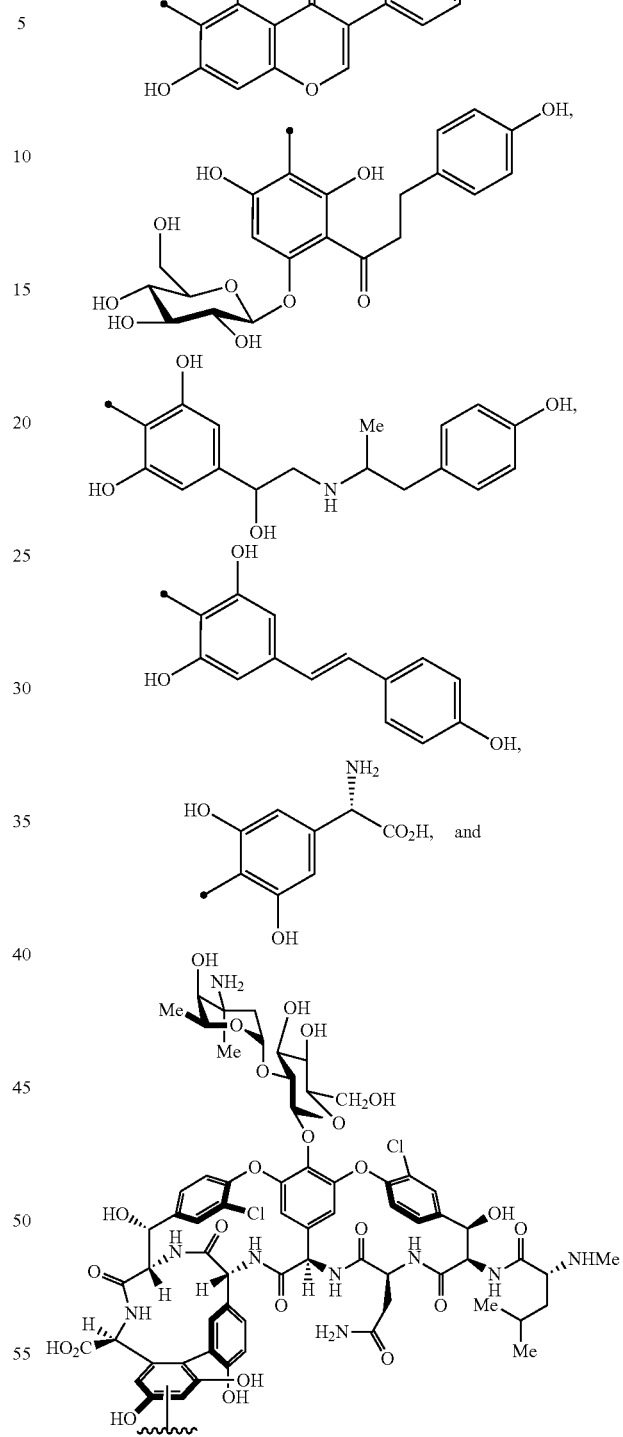
is a heteroaromatic moiety substituted with an electron withdrawing group;

x is 0, 1, 2, 3, 4, 5, or 6; and

R is H or alkyl;

(e) according to Scheme 5:

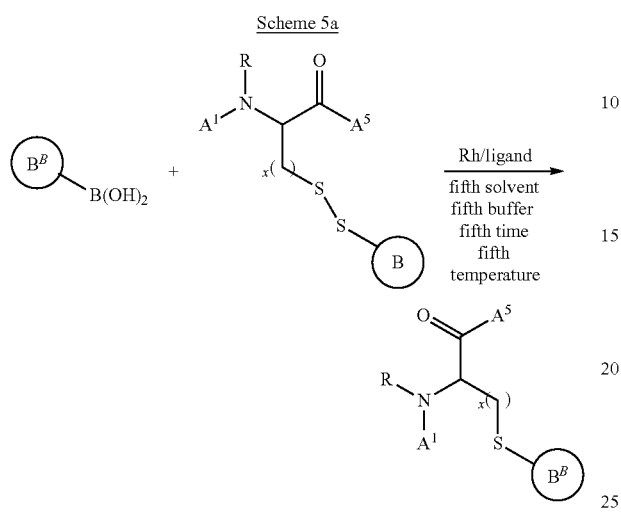

wherein, independently for each occurrence, $A^1$ is H, an amine protecting group, a natural or unnatural amino acid, a peptide, an oligopeptide, a polypeptide, or a protein;

$A^5$ is OH, —O(carboxylate protecting group), a natural or unnatural amino acid, a peptide, an oligopeptide, a polypeptide, or a protein;

is a substituted phenyl radical selected from the group consisting of

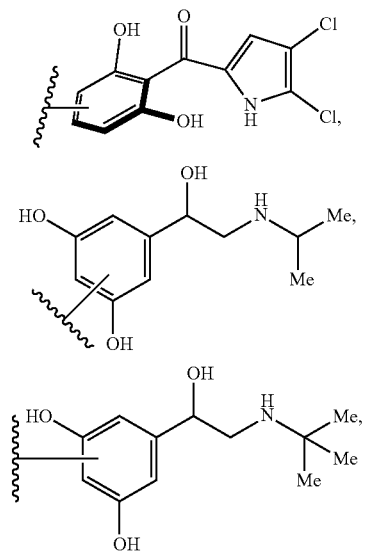

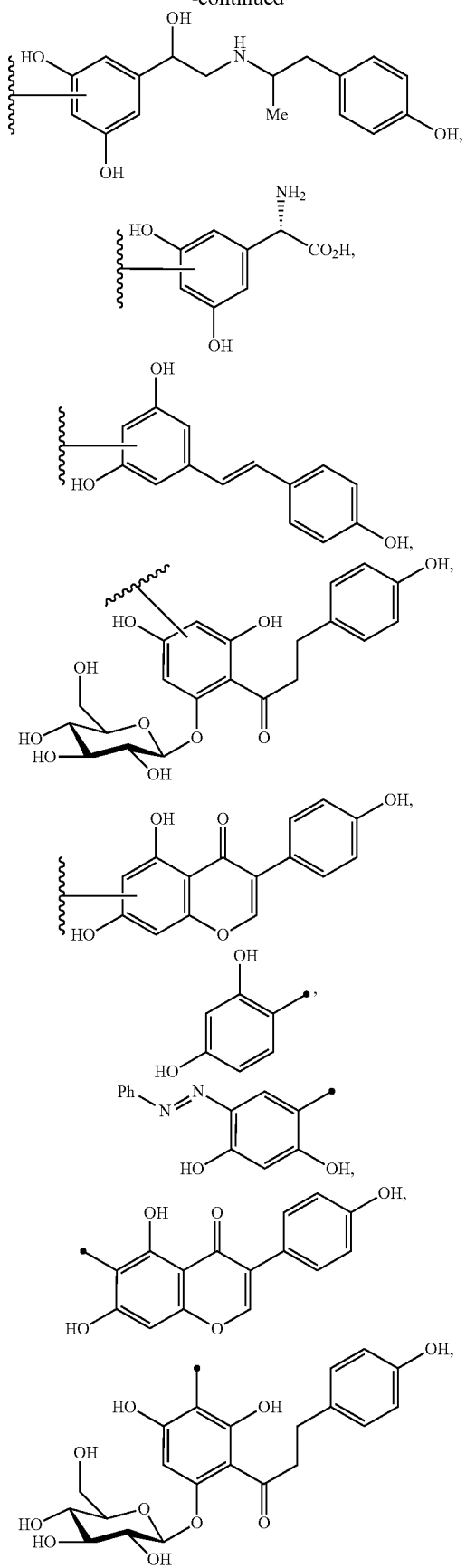

219
-continued
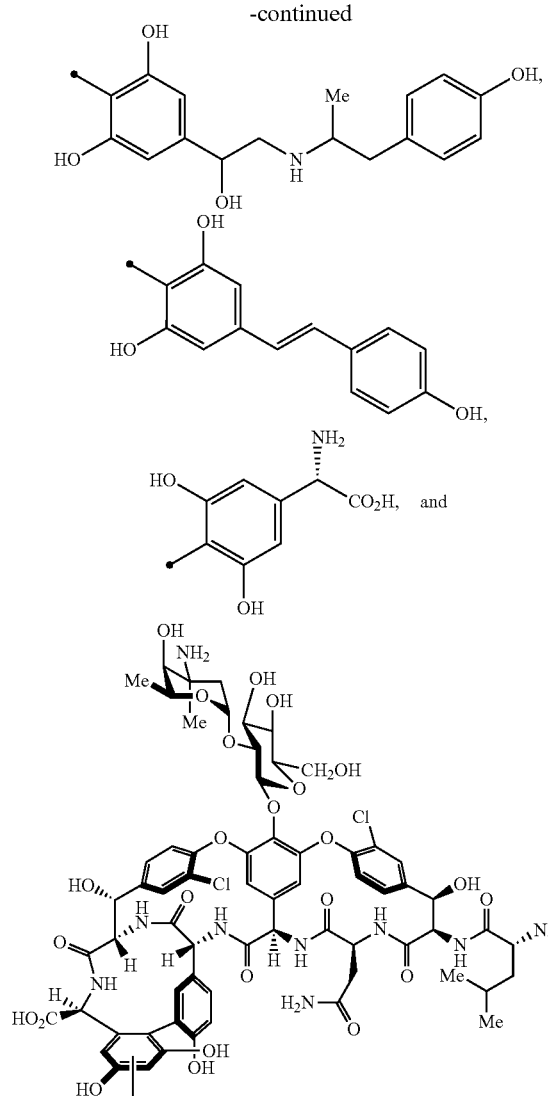
B is a heteroaromatic moiety substituted with an electron withdrawing group;
x is 0, 1, 2, 3, 4, 5, or 6; and
R is H or alkyl;
(f) according to Scheme 6:
Scheme 6a
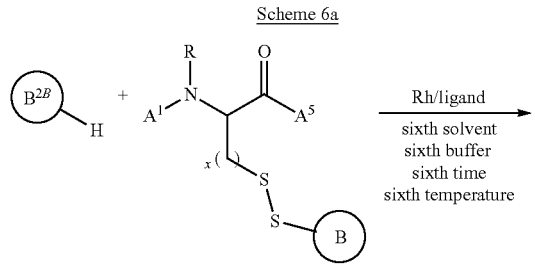
220
-continued
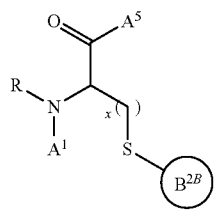
Scheme 6b
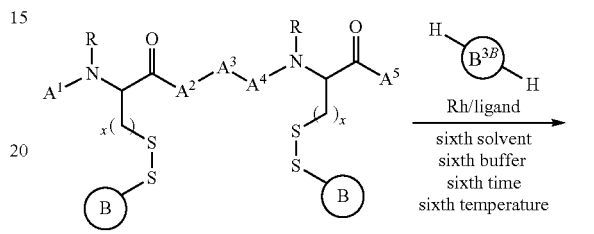
Scheme 6c
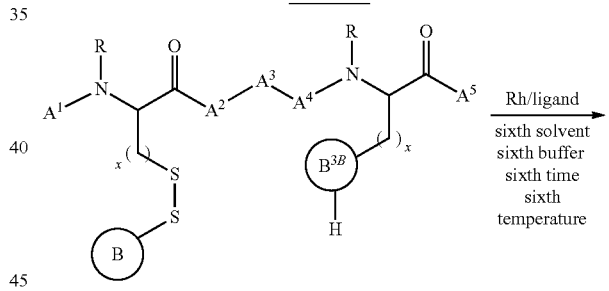
Scheme 6d
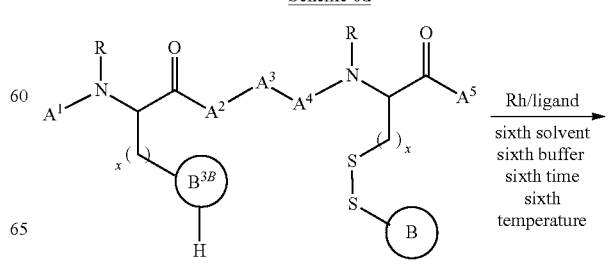

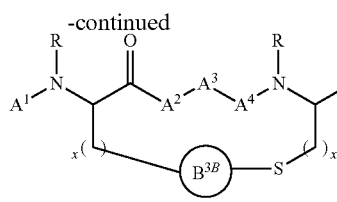

wherein, independently for each occurrence, $A^1$ is H, an amine protecting group, a natural or unnatural amino acid, a peptide, an oligopeptide, a polypeptide, or a protein;

$A^2$, $A^3$, and $A^4$ are selected from the group consisting of a natural amino acid, an unnatural amino acid, and a plurality of natural amino acids or unnatural amino acids;

$A^5$ is OH, —O(carboxylate protecting group), a natural or unnatural amino acid, a peptide, an oligopeptide, a polypeptide, or a protein;

$B^{2B}$ is a phenyl radical selected from the group consisting of

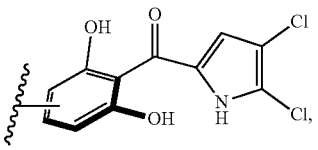

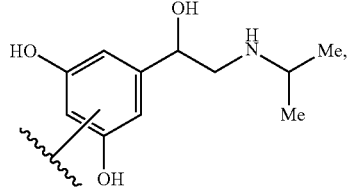

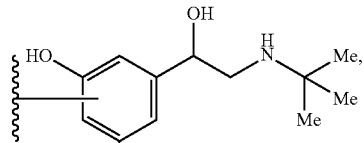

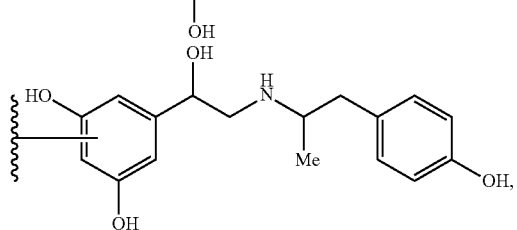

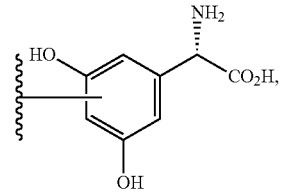

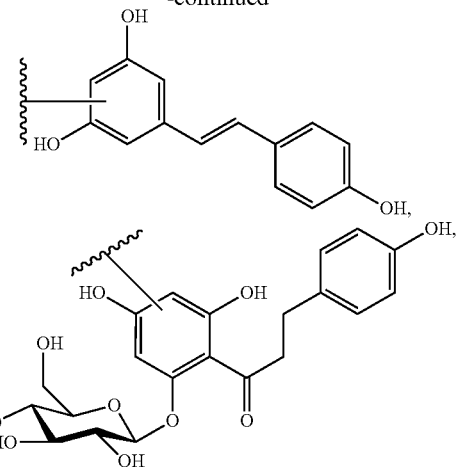

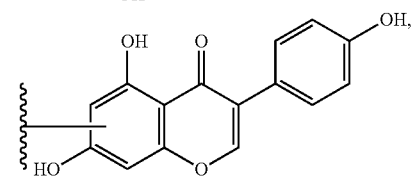

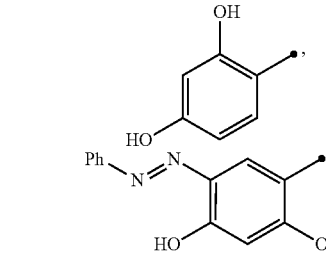

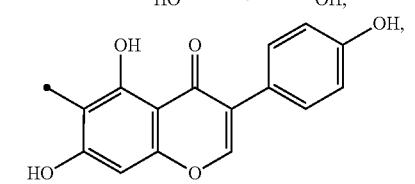

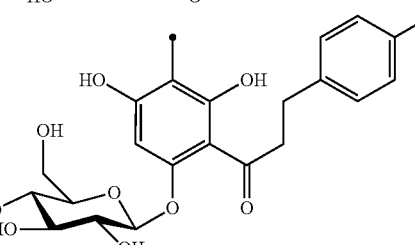

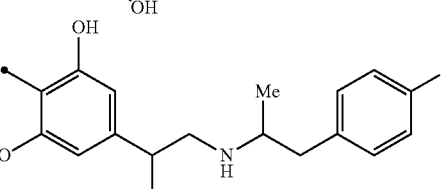

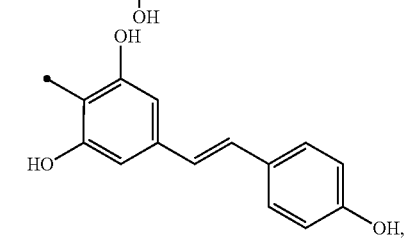

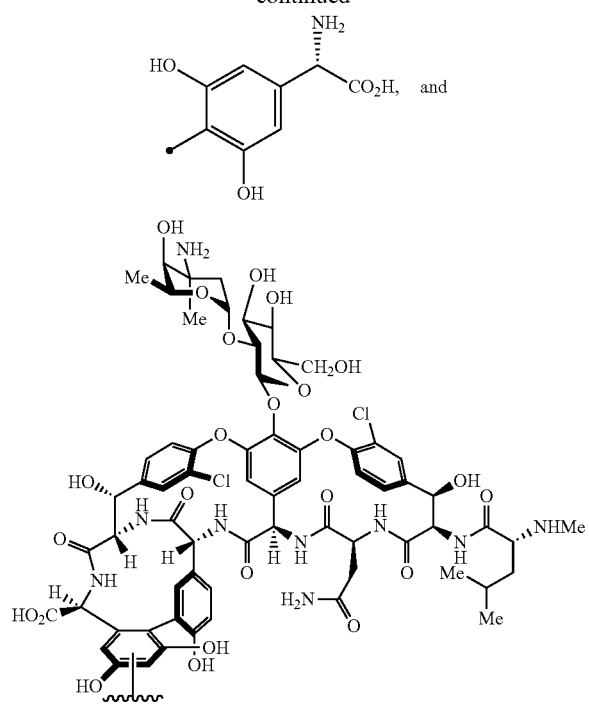
is a phenyl radical selected from the group consisting of
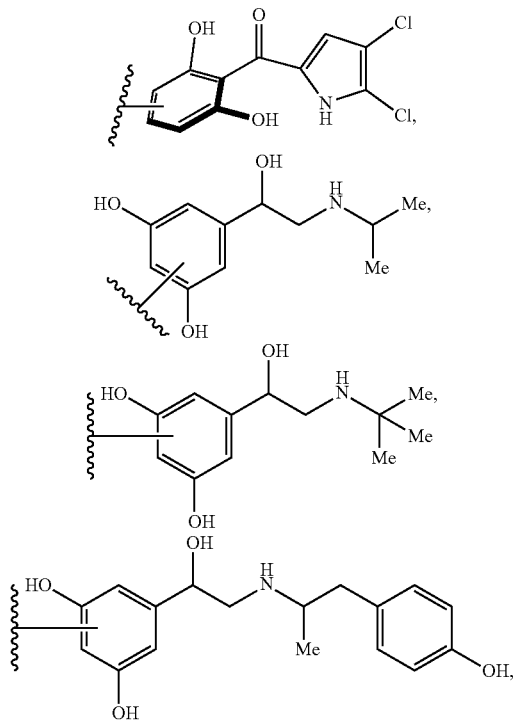

225
-continued
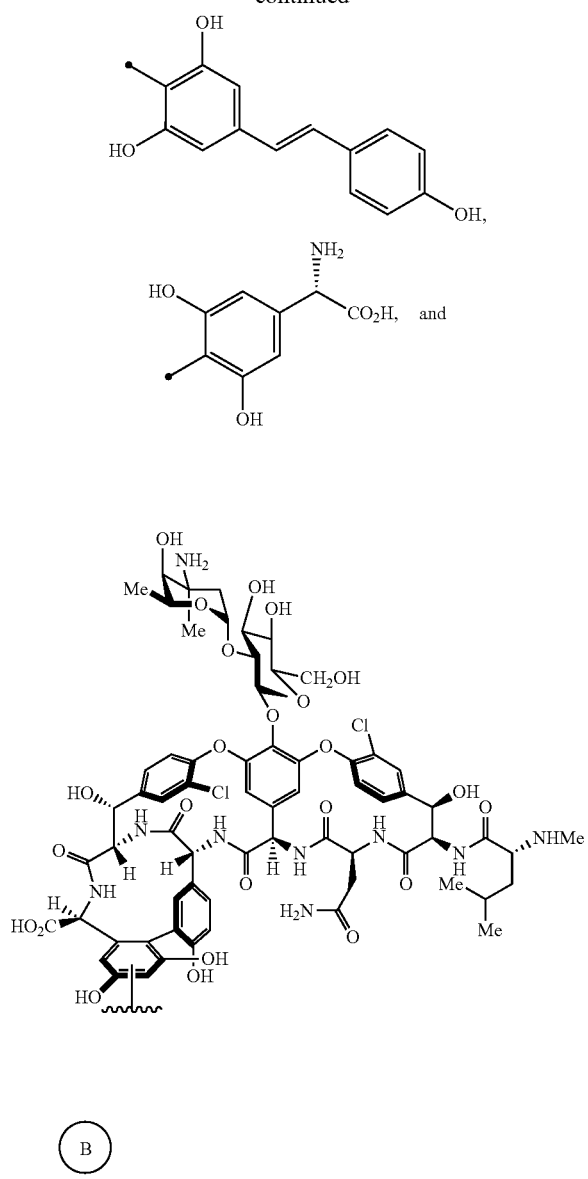
B is a heteroaromatic moiety substituted with an electron withdrawing group;
x is 0, 1, 2, 3, 4, 5, or 6; and
R is H or alkyl;
(g) according to Scheme 7:
Scheme 7a
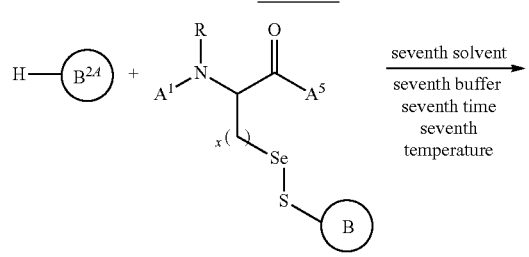
226
-continued
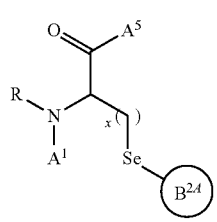
Scheme 7b
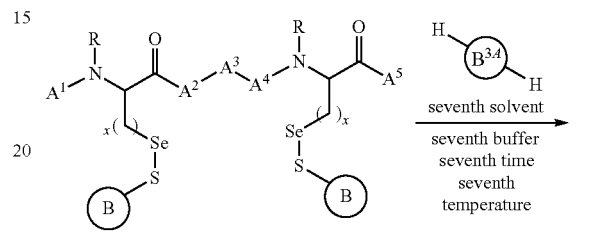
Scheme 7c
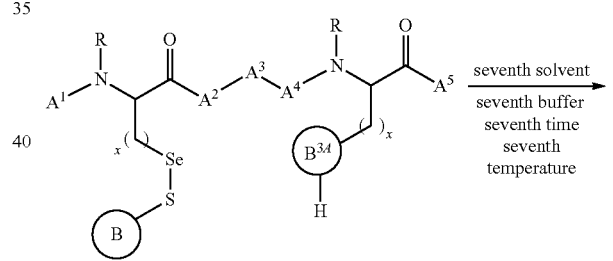
Scheme 7d
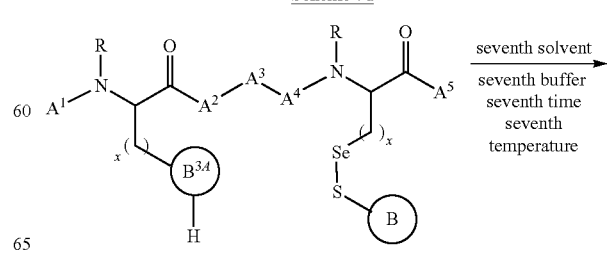

227

-continued

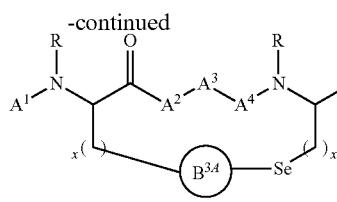

wherein, independently for each occurrence,
- $A^1$ is H, an amine protecting group, a natural or unnatural amino acid, a peptide, an oligopeptide, a polypeptide, or a protein;
- $A^2$, $A^3$, and $A^4$ are selected from the group consisting of a natural amino acid, an unnatural amino acid, and a plurality of natural amino acids or unnatural amino acids;
- $A^5$ is OH, —O(carboxylate protecting group), a natural or unnatural amino acid, a peptide, an oligopeptide, a polypeptide, or a protein;

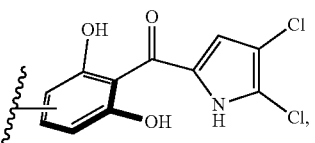

is a phenyl radical selected from the group consisting of

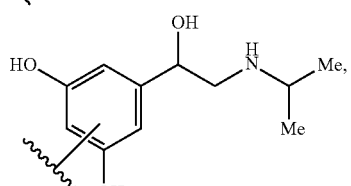

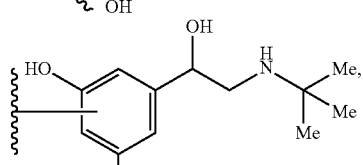

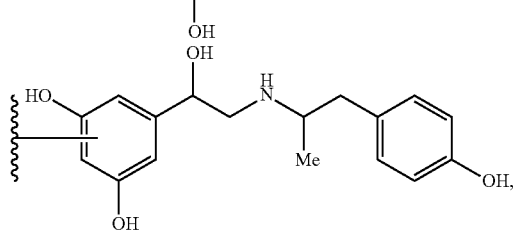

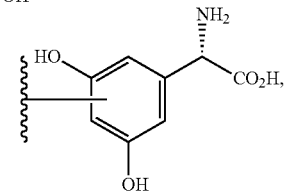
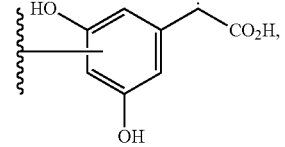
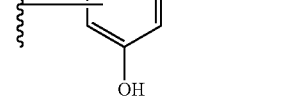

228

-continued

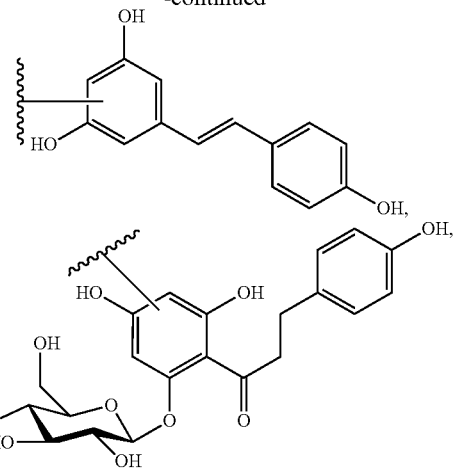

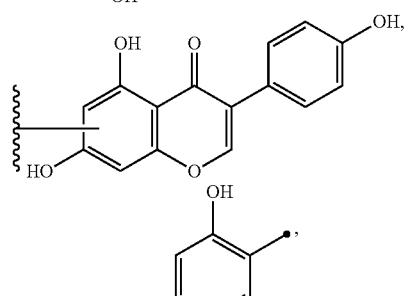

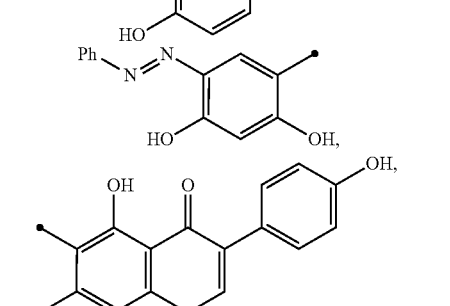

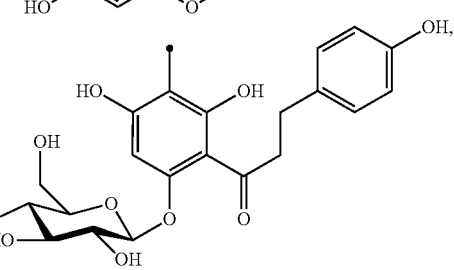

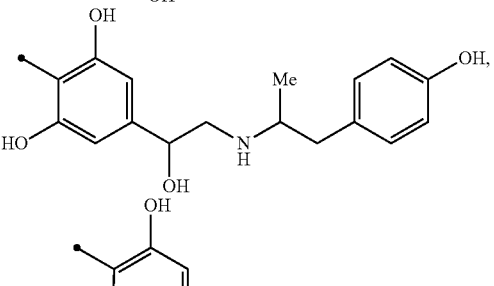

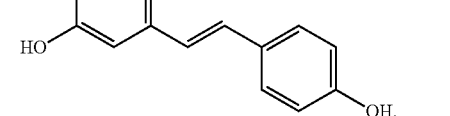

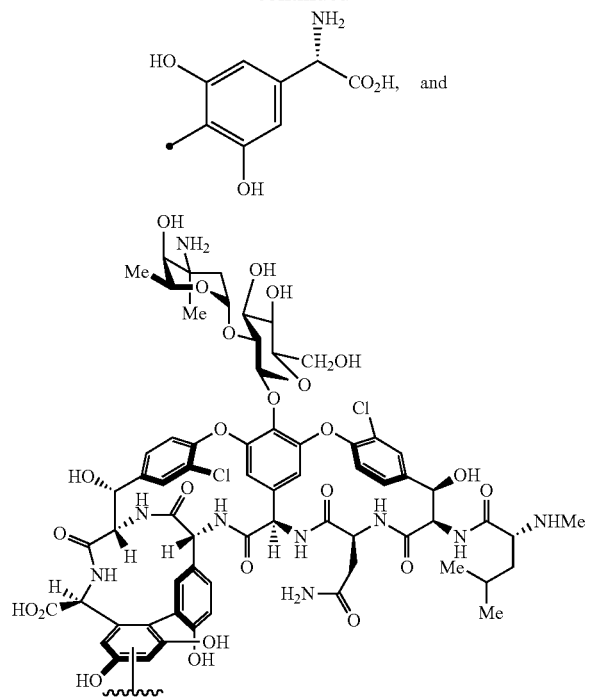
is a substituted phenyl diradical selected from the group consisting of
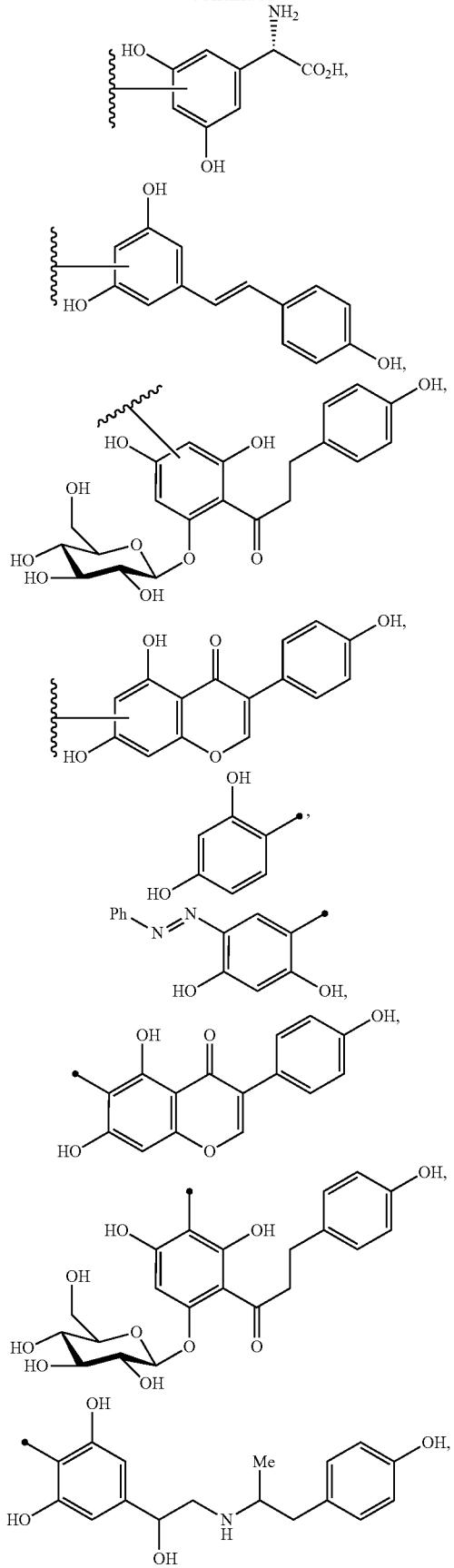

231 -continued
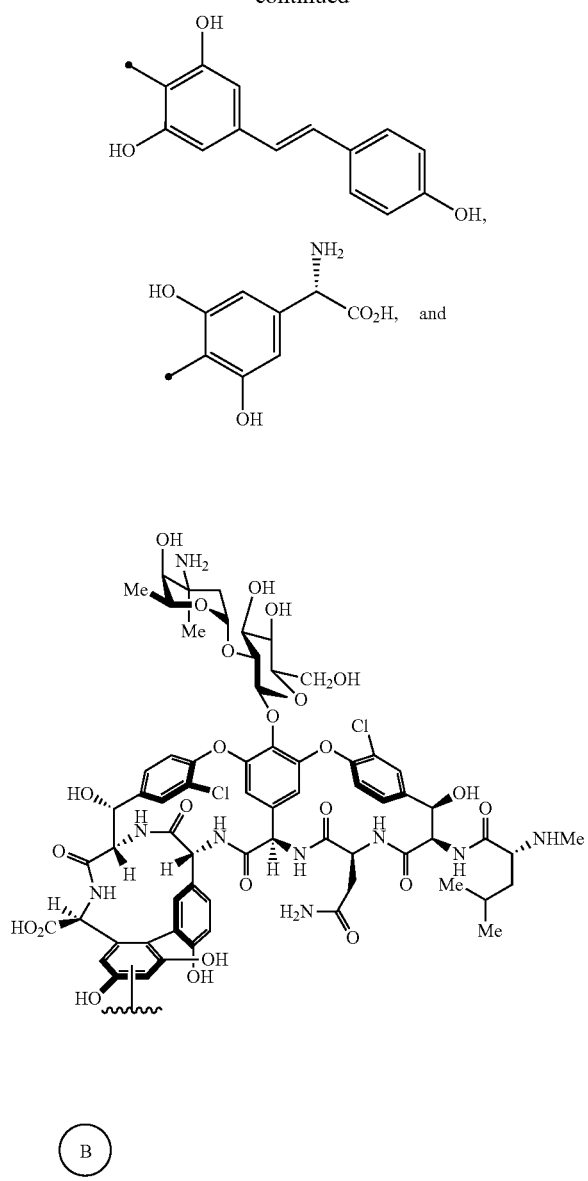
B is a heteroaromatic moiety substituted with an electron withdrawing group;
x is 0, 1, 2, 3, 4, 5, or 6; and
R is H or alkyl; or
(h) according to Scheme 8:
232 -continued
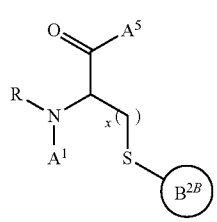
Scheme 8b
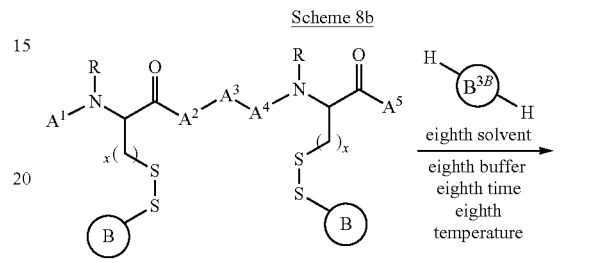
Scheme 8c
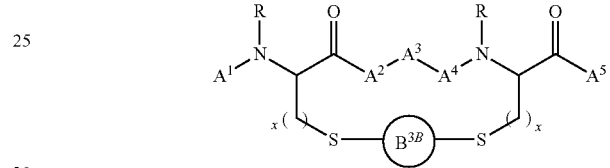
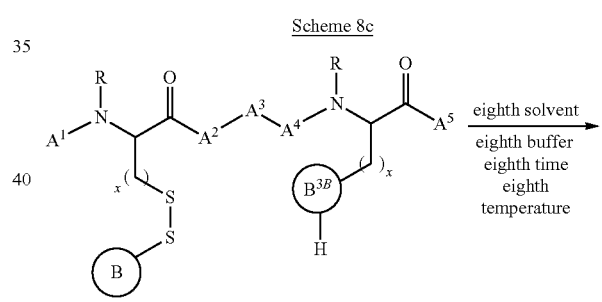
Scheme 8d
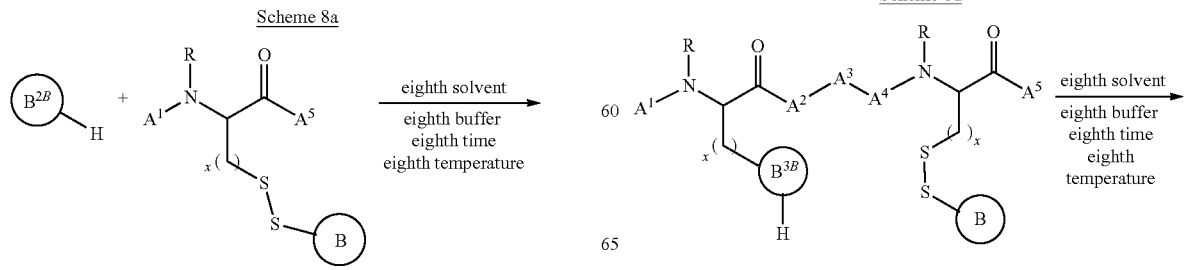
Scheme 8a
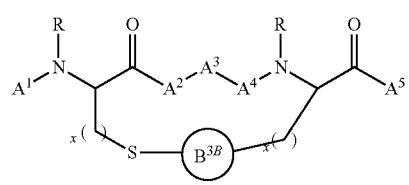

233

-continued

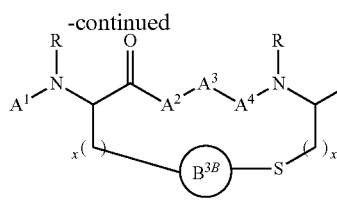

wherein, independently for each occurrence,

A¹ is H, an amine protecting group, a natural or unnatural amino acid, a peptide, an oligopeptide, a polypeptide, or a protein;

A², A³, and A⁴ are selected from the group consisting of a natural amino acid, an unnatural amino acid, and a plurality of natural amino acids or unnatural amino acids;

A⁵ is OH, —O(carboxylate protecting group), a natural or unnatural amino acid, a peptide, an oligopeptide, a polypeptide, or a protein;

$\boxed{B^{2B}}$ is a phenyl radical selected from the group consisting of

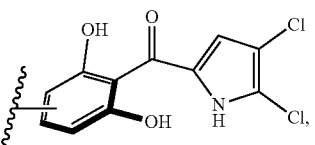

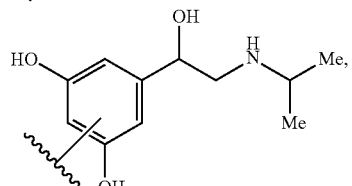

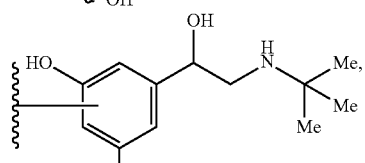

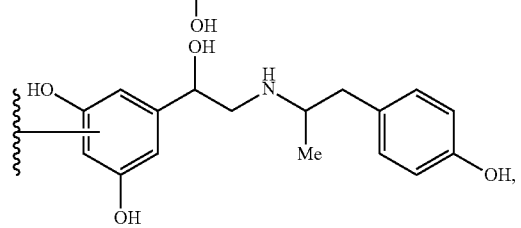

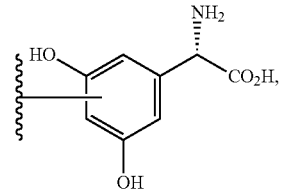

234

-continued

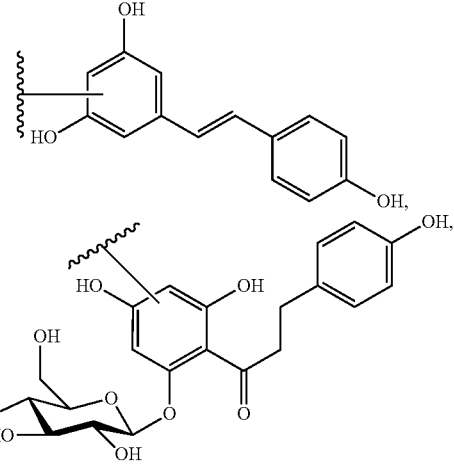

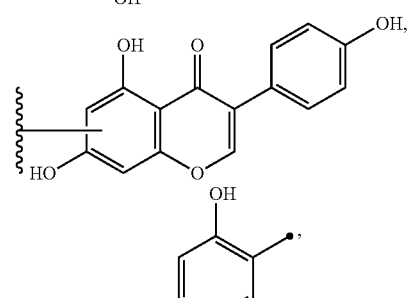

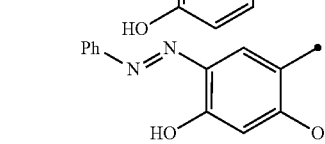

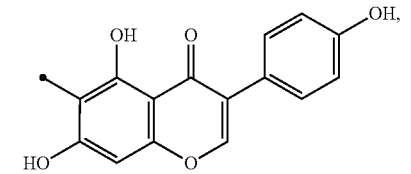

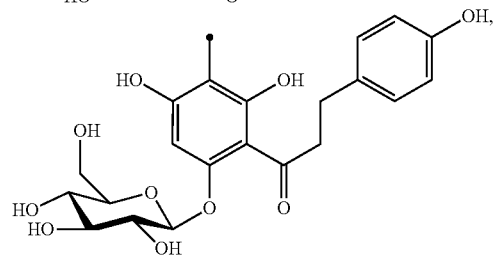

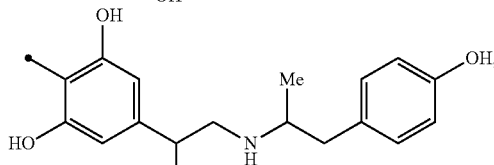

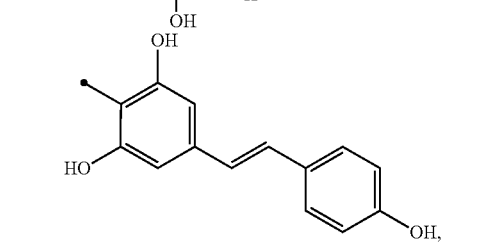

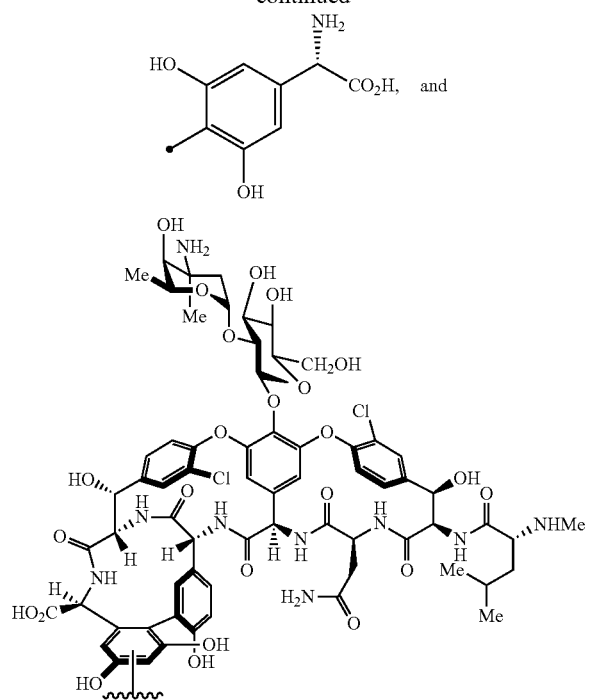
$B^{3B}$ is a phenyl radical selected from the group consisting of
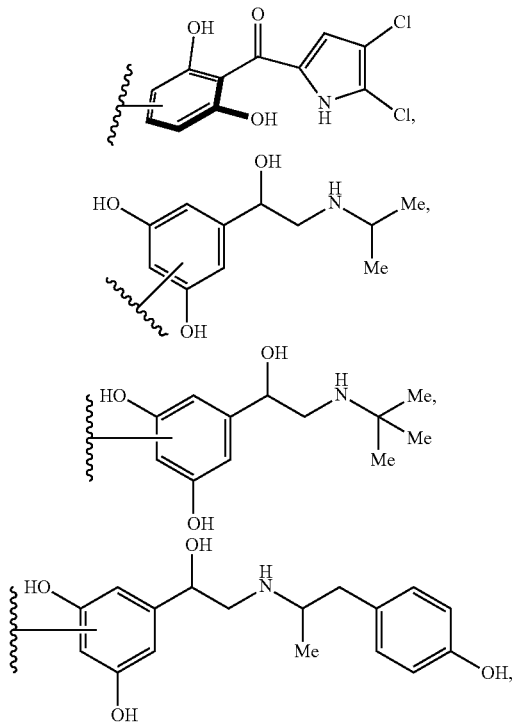
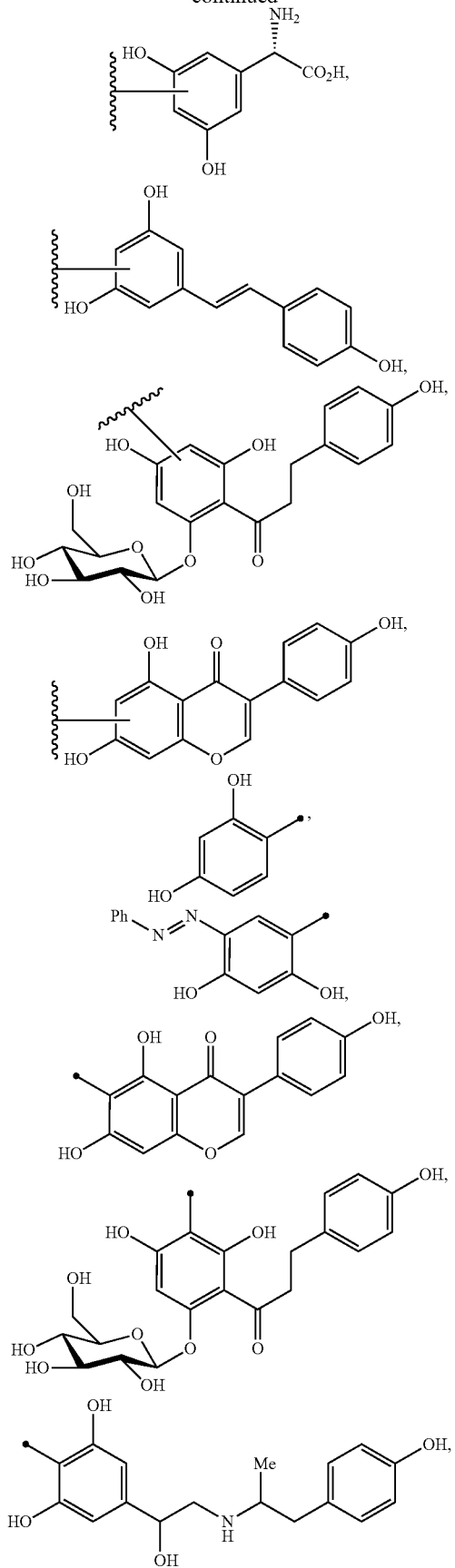

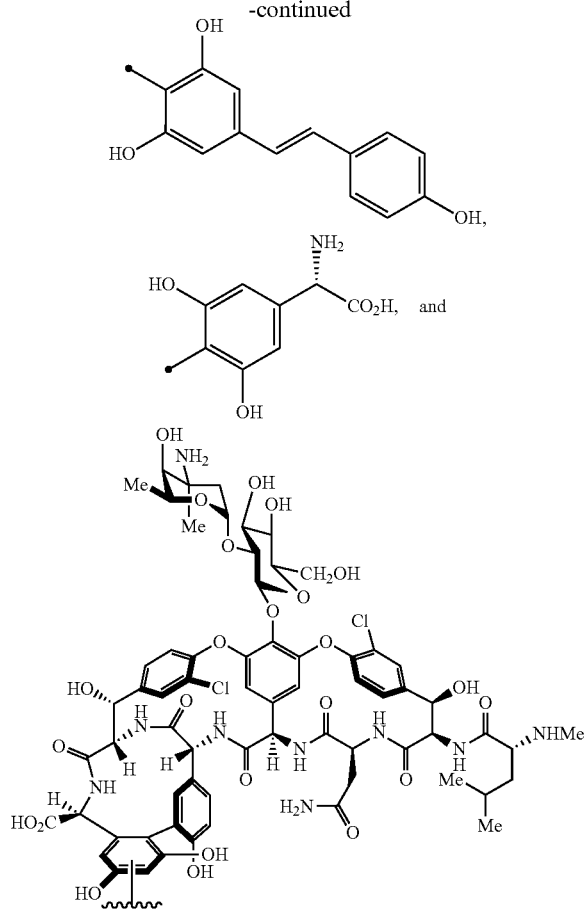

is a heteroaromatic moiety substituted with an electron withdrawing group;

x is 0, 1, 2, 3, 4, 5, or 6; and

R is H or alkyl.

3. A method of treating, killing or inhibiting the growth or proliferation of a bacterium, a fungus, a virus, or a parasite, comprising the step of:

contacting with the bacterium, fungus, virus, or parasite an effective amount of a compound of claim 1, thereby treating killing or inhibiting the growth or proliferation of the bacterium, fungus, virus, or parasite.

4. A method of treating a disease in a subject in need thereof comprising the step of:

administering to the subject an effective amount of a compound of claim 1, thereby treating the disease.

5. The compound of claim 1 comprising substructure I.

6. The compound of claim 1, wherein is a substituted phenyl radical selected from the group consisting of

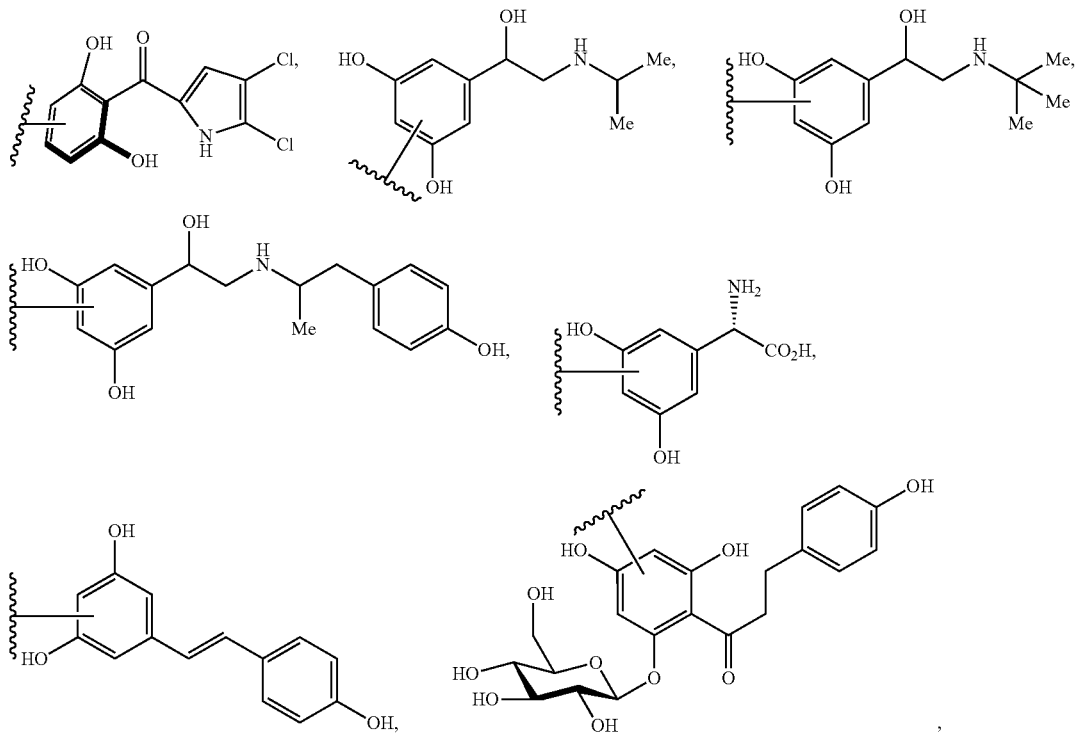

239
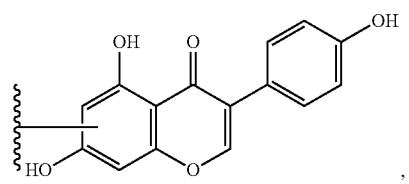
-continued
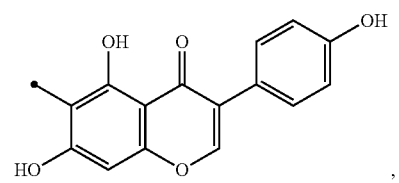
240
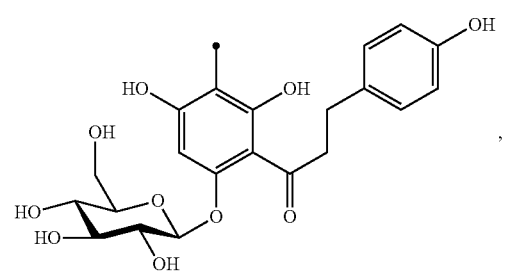
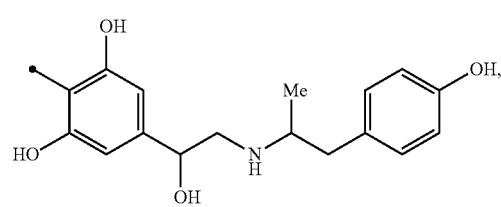
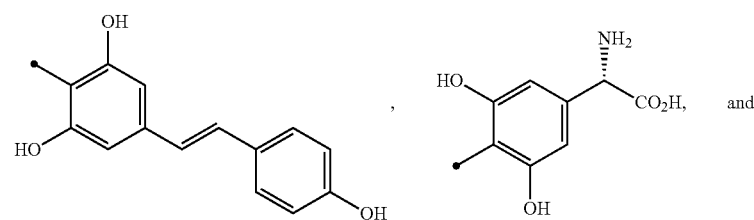
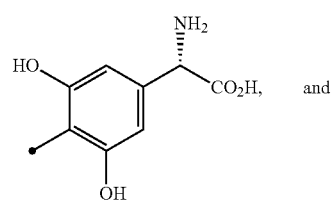
and
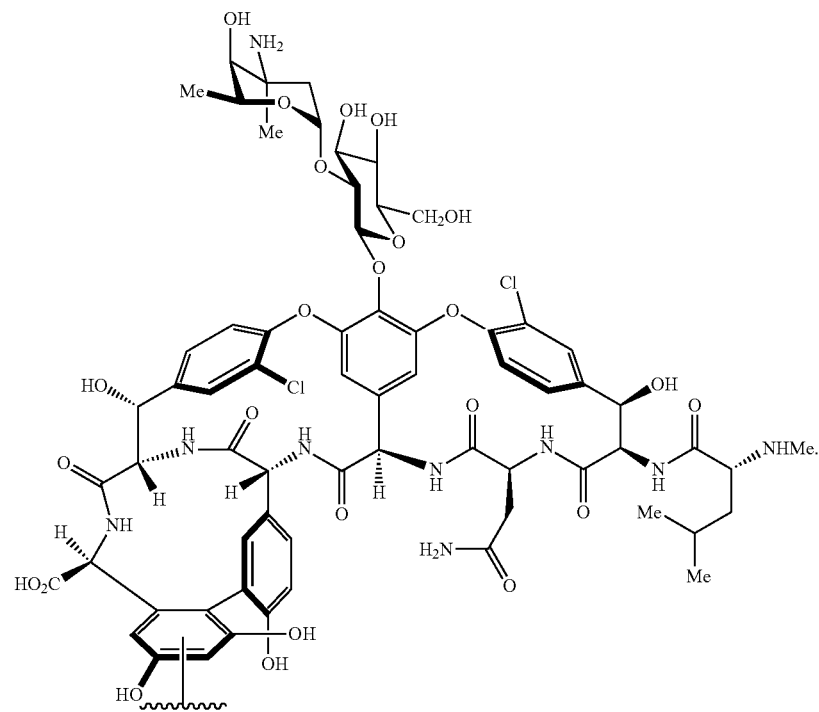

7. The compound of claim 1, wherein
 is
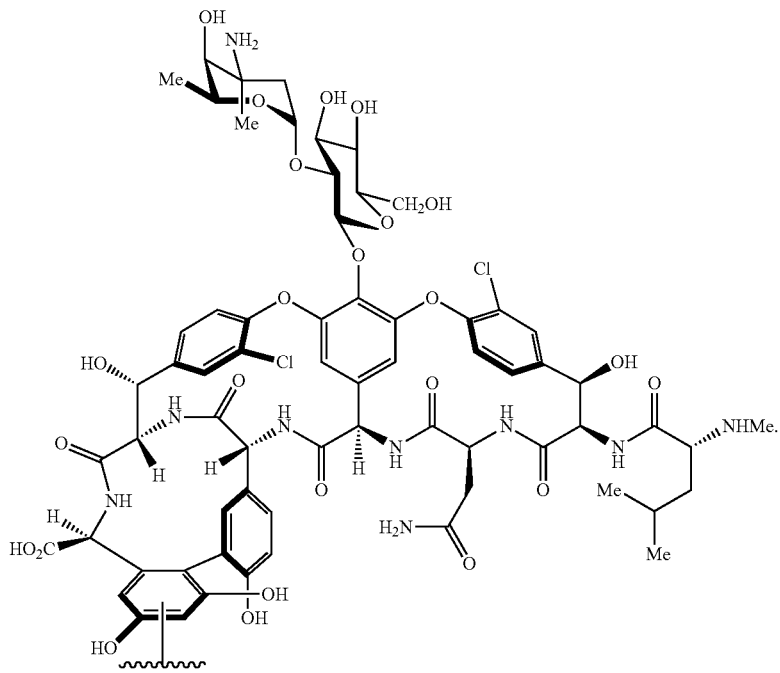
8. The compound of claim 1 comprising substructure II.
9. The compound of claim 1, wherein is a substituted phenyl radical selected from the group consisting of
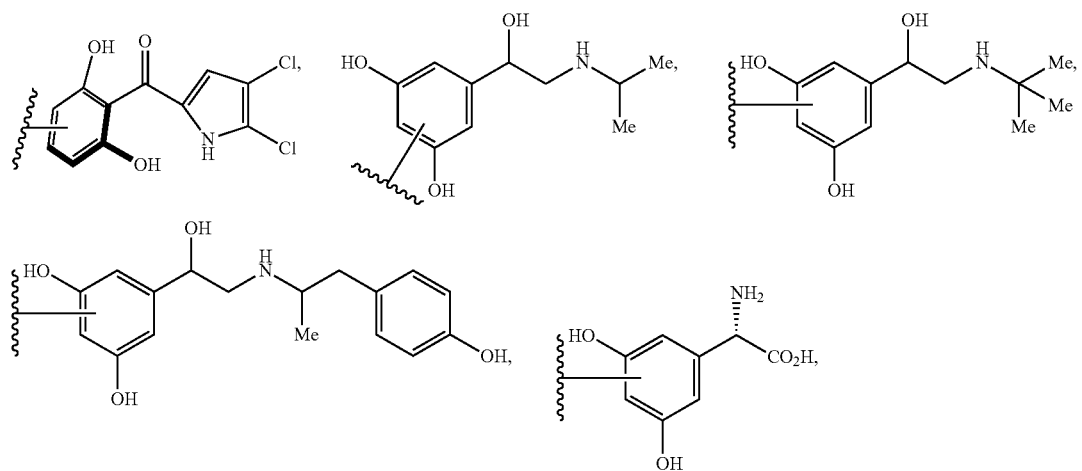

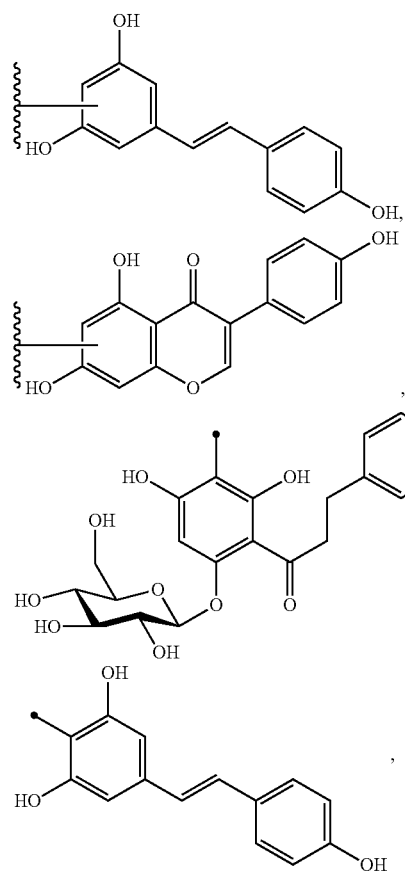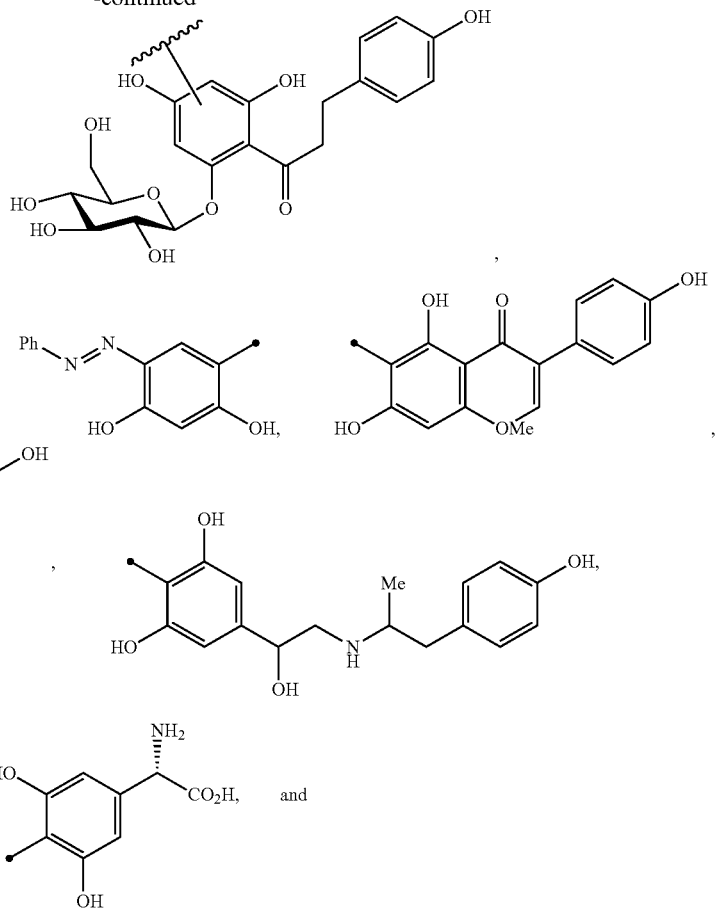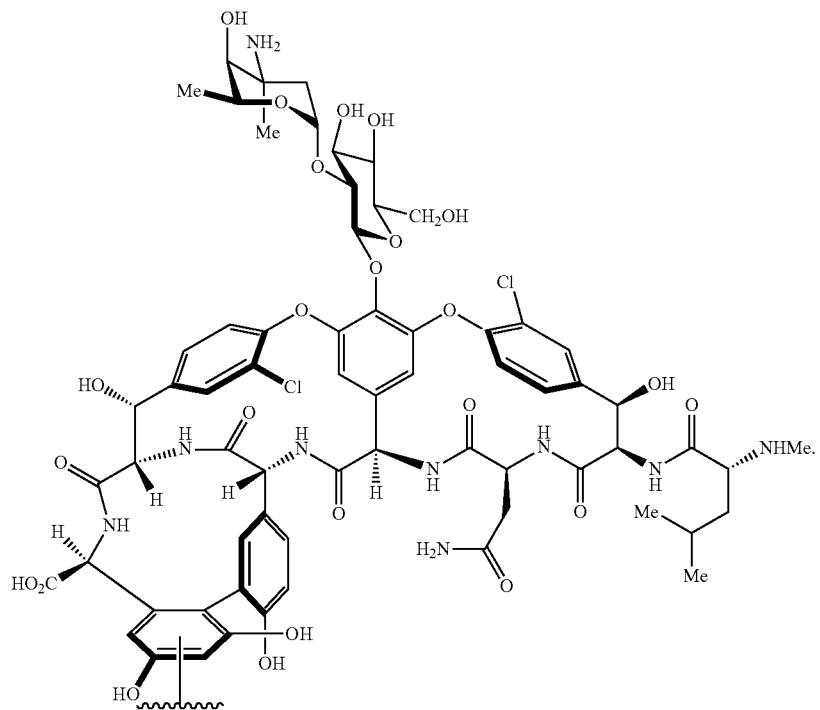

10. The compound of claim 1, wherein
$B^B$ is
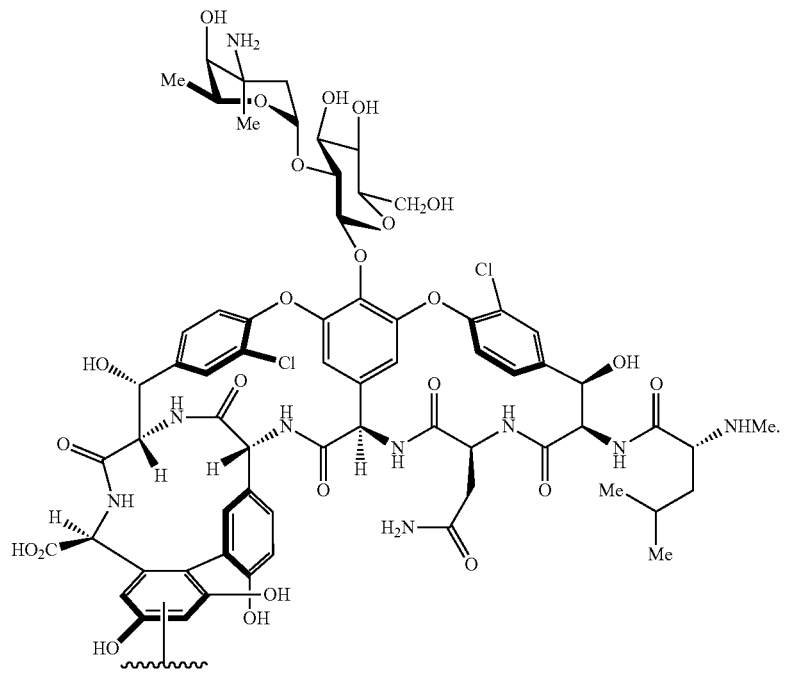
* * * * *